US008710045B2

(12) United States Patent
Marks et al.

(10) Patent No.: US 8,710,045 B2
(45) Date of Patent: *Apr. 29, 2014

(54) AGENTS FOR PREVENTING AND TREATING DISORDERS INVOLVING MODULATION OF THE RYANODINE RECEPTORS

(75) Inventors: Andrew Robert Marks, Larchmont, NY (US); Donald W. Landry, New York, NY (US); Shixian Deng, White Plains, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 390 days.

This patent is subject to a terminal disclaimer.

(21) Appl. No.: 12/938,098

(22) Filed: Nov. 2, 2010

(65) Prior Publication Data

US 2011/0172190 A1     Jul. 14, 2011

Related U.S. Application Data

(63) Continuation-in-part of application No. 11/506,285, filed on Aug. 17, 2006, now Pat. No. 7,879,840, and a continuation-in-part of application No. 11/809,470, filed on Jun. 1, 2007, now abandoned, which is a continuation-in-part of application No. 11/212,309, filed on Aug. 25, 2005, now Pat. No. 8,022,058, which is a continuation-in-part of application No. 10/809,089, filed on Mar. 25, 2004, now Pat. No. 7,718,644, which is a continuation-in-part of application No. 10/763,498, filed on Jan. 22, 2004, now abandoned, said application No. 11/506,285 is a continuation-in-part of application No. 11/212,309, which is a continuation-in-part of application No. 10/809,089, which is a continuation-in-part of application No. 10/763,498.

(60) Provisional application No. 60/810,748, filed on Jun. 2, 2006, provisional application No. 60/904,348, filed on Feb. 28, 2007.

(51) Int. Cl.
*A61P 9/00* (2006.01)
*A61K 31/553* (2006.01)
*A61K 31/554* (2006.01)
*C07D 281/02* (2006.01)

(52) U.S. Cl.
USPC .......... 514/211.05; 514/211.09; 540/490; 540/552

(58) Field of Classification Search
USPC .......... 514/211.05, 211.09; 540/490, 552
See application file for complete search history.

(56) References Cited

U.S. PATENT DOCUMENTS

| | | | |
|---|---|---|---|
| 3,362,962 A * | 1/1968 | Reeder et al. | 540/548 |
| 3,367,930 A | 2/1968 | Schmutz et al. | |
| 3,519,647 A | 7/1970 | Krapcho | |
| 4,567,254 A | 1/1986 | Kataoka et al. | |
| 4,658,055 A | 4/1987 | Onuki et al. | |
| 4,723,012 A | 2/1988 | Matsumoto et al. | |
| 4,841,055 A | 6/1989 | Matsumoto et al. | |
| 4,845,065 A | 7/1989 | Sugimori et al. | |
| 4,849,535 A | 7/1989 | Naora et al. | |
| 4,888,418 A | 12/1989 | Kawai et al. | |
| 4,963,671 A | 10/1990 | Krapcho | |
| 4,990,707 A | 2/1991 | Mais et al. | |
| 5,064,810 A | 11/1991 | Askanazi et al. | |
| 5,075,293 A | 12/1991 | Reifschneider et al. | |
| 5,142,647 A | 8/1992 | Nakagawa et al. | |
| 5,153,184 A | 10/1992 | Reifschneider et al. | |
| 5,166,347 A | 11/1992 | Izawa et al. | |
| 5,179,125 A | 1/1993 | Mimura et al. | |
| 5,180,720 A | 1/1993 | Husa et al. | |
| 5,182,272 A | 1/1993 | Hallinan et al. | |

(Continued)

FOREIGN PATENT DOCUMENTS

DE    38 37 575 A1    5/1990
EP    0 467 325 A2    1/1992

(Continued)

OTHER PUBLICATIONS

CAPLUS printout of Besanty et al., Synthesis of Nitrated Benzo- and Dibenzothiazepines as Possible Antiparasitic Agents, European Journal of Medicinal Chemistry, vol. 23, No. 4, pp. 403-405, 1988.*
CAPLUS printout of JP 3093419, Oct. 3, 2000.*

(Continued)

*Primary Examiner* — Brenda Coleman
(74) *Attorney, Agent, or Firm* — Winston & Strawn LLP

(57) ABSTRACT

The present invention provides compounds of Formula I

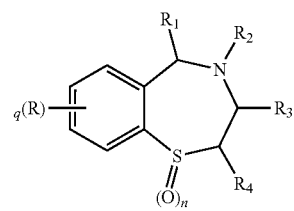

and salts, hydrates, solvates, complexes, and prodrugs thereof. The present invention further provides methods for synthesizing compounds of Formula I. The invention additionally provides pharmaceutical compositions comprising the compounds of Formula I and methods of using the pharmaceutical compositions of Formula I to treat and prevent disorders and diseases associated with the RyR receptors that regulate calcium channel functioning in cells.

20 Claims, 79 Drawing Sheets

(56) References Cited

U.S. PATENT DOCUMENTS

| | | |
|---|---|---|
| 5,204,462 A | 4/1993 | Kobayashi et al. |
| 5,210,266 A | 5/1993 | Mimura et al. |
| 5,214,056 A | 5/1993 | Haruta et al. |
| 5,221,681 A | 6/1993 | Kabbe et al. |
| 5,223,508 A | 6/1993 | Izawa et al. |
| 5,260,286 A | 11/1993 | Lawson et al. |
| 5,272,164 A | 12/1993 | Izawa et al. |
| 5,304,380 A | 4/1994 | Miyajima et al. |
| 5,304,558 A | 4/1994 | Kaneko et al. |
| 5,304,644 A | 4/1994 | Husa et al. |
| 5,324,722 A | 6/1994 | Hagen et al. |
| 5,332,734 A | 7/1994 | Kobayashi et al. |
| 5,354,747 A | 10/1994 | Hansen, Jr. et al. |
| 5,354,758 A | 10/1994 | Lawson et al. |
| 5,387,684 A | 2/1995 | Inoue et al. |
| 5,413,929 A | 5/1995 | Ishizaki et al. |
| 5,416,066 A | 5/1995 | Kaneko et al. |
| 5,449,675 A | 9/1995 | Chandrakumar et al. |
| 5,453,282 A | 9/1995 | Kanauchi et al. |
| 5,457,182 A | 10/1995 | Wiederrecht et al. |
| 5,461,047 A | 10/1995 | Hansen, Jr. et al. |
| 5,476,780 A | 12/1995 | Watanabe et al. |
| 5,478,832 A | 12/1995 | Inoue et al. |
| 5,508,293 A | 4/1996 | Okawara et al. |
| 5,523,410 A | 6/1996 | Kagara et al. |
| 5,580,866 A | 12/1996 | Housley et al. |
| 5,593,988 A | 1/1997 | Tahara et al. |
| 5,624,961 A | 4/1997 | Ban et al. |
| 5,654,001 A | 8/1997 | Kanauchi et al. |
| 5,665,881 A | 9/1997 | Inoue et al. |
| 5,719,155 A | 2/1998 | Cho et al. |
| 5,723,458 A | 3/1998 | Brieaddy et al. |
| 5,750,696 A | 5/1998 | Shibata et al. |
| 5,753,649 A | 5/1998 | Tahara et al. |
| 5,767,247 A | 6/1998 | Kaneko et al. |
| 5,780,441 A | 7/1998 | Higa et al. |
| 5,792,655 A | 8/1998 | Watanabe et al. |
| 5,807,850 A | 9/1998 | Nakamura et al. |
| 5,817,652 A | 10/1998 | Brieaddy et al. |
| 5,824,862 A | 10/1998 | Hiyoshi et al. |
| 5,859,240 A | 1/1999 | Brieaddy |
| 5,866,341 A | 2/1999 | Spinella et al. |
| 5,906,819 A | 5/1999 | Kaibuchi et al. |
| 5,910,494 A | 6/1999 | Brieaddy |
| 6,013,499 A | 1/2000 | Narumiya et al. |
| 6,111,072 A | 8/2000 | Narumiya et al. |
| 6,130,060 A | 10/2000 | Nakamura et al. |
| 6,143,784 A | 11/2000 | Greenhaff et al. |
| 6,184,352 B1 | 2/2001 | Nakamura et al. |
| 6,235,730 B1 | 5/2001 | Sato et al. |
| 6,255,472 B1 | 7/2001 | Tokino et al. |
| 6,271,353 B1 | 8/2001 | Nakamura et al. |
| 6,313,113 B1 | 11/2001 | Lohray et al. |
| 6,316,485 B1 | 11/2001 | Nakamura et al. |
| 6,338,955 B2 | 1/2002 | Oguri et al. |
| 6,348,334 B1 | 2/2002 | Nagata et al. |
| 6,362,231 B1 | 3/2002 | Sakai et al. |
| 6,391,595 B1 | 5/2002 | Kato et al. |
| 6,403,830 B2 | 6/2002 | Webber et al. |
| 6,410,561 B1 | 6/2002 | Shinkai et al. |
| 6,426,365 B1 | 7/2002 | Shinkai et al. |
| 6,465,518 B2 | 10/2002 | Hansen, Jr. et al. |
| 6,465,686 B2 | 10/2002 | Grapperhaus et al. |
| 6,489,125 B1 | 12/2002 | Marks et al. |
| 6,495,544 B2 | 12/2002 | Moormann et al. |
| 6,500,816 B1 | 12/2002 | Ekimoto et al. |
| 6,506,745 B1 | 1/2003 | Aisaka et al. |
| 6,545,170 B2 | 4/2003 | Pitzele et al. |
| 6,562,618 B1 | 5/2003 | Tamatani et al. |
| 6,562,828 B1 | 5/2003 | Katoh et al. |
| 6,583,157 B2 | 6/2003 | McGee et al. |
| 6,586,474 B2 | 7/2003 | Webber et al. |
| 6,632,976 B1 | 10/2003 | Tomizuka et al. |
| 6,649,366 B2 | 11/2003 | Chubinskaya et al. |
| 6,660,837 B1 | 12/2003 | Kaibuchi et al. |
| 6,673,904 B2 | 1/2004 | Nishikawa et al. |
| 6,683,083 B1 | 1/2004 | Kaneko et al. |
| 6,750,255 B2 | 6/2004 | Sakai et al. |
| 6,753,346 B2 | 6/2004 | Shinkai et al. |
| 6,756,406 B2 | 6/2004 | Durley et al. |
| 6,780,608 B1 | 8/2004 | Hakamata et al. |
| 6,787,668 B2 | 9/2004 | Pitzele et al. |
| 6,787,688 B2 | 9/2004 | Harmos et al. |
| 6,803,039 B2 | 10/2004 | Tsuji et al. |
| 6,808,873 B2 | 10/2004 | Murphy et al. |
| 6,812,252 B2 | 11/2004 | Ikawa et al. |
| 6,821,987 B2 | 11/2004 | Kubo et al. |
| 6,824,973 B2 | 11/2004 | Tang et al. |
| 6,828,456 B2 | 12/2004 | Hansen, Jr. et al. |
| 6,830,896 B2 | 12/2004 | Kaneko et al. |
| 6,852,753 B2 | 2/2005 | Koeller et al. |
| 6,869,975 B2 | 3/2005 | Abe et al. |
| 6,890,531 B1 | 5/2005 | Horie et al. |
| 6,897,295 B1 | 5/2005 | Nagata et al. |
| 6,906,072 B1 | 6/2005 | Yamamoto et al. |
| 6,914,158 B2 | 7/2005 | Webber et al. |
| 6,939,895 B2 | 9/2005 | Sakai et al. |
| 6,951,889 B2 | 10/2005 | Hansen, Jr. et al. |
| 6,962,926 B2 | 11/2005 | Laborde et al. |
| 6,964,975 B2 | 11/2005 | Ueno et al. |
| 6,977,252 B1 | 12/2005 | Kaneko et al. |
| 6,989,275 B2 | 1/2006 | Waggoner |
| 6,998,469 B2 | 2/2006 | Tandon et al. |
| 7,005,450 B2 | 2/2006 | Durley et al. |
| 7,029,671 B1 | 4/2006 | Koezuka et al. |
| 7,030,225 B1 | 4/2006 | Tamatani et al. |
| 7,041,870 B2 | 5/2006 | Tomizuka et al. |
| 7,045,615 B2 | 5/2006 | Tamatani et al. |
| 7,064,194 B2 | 6/2006 | Misawa et al. |
| 7,102,013 B2 | 9/2006 | Webber et al. |
| 7,112,655 B1 | 9/2006 | Tamatani et al. |
| 7,135,466 B2 | 11/2006 | Sakai et al. |
| 7,163,952 B2 | 1/2007 | Inaba et al. |
| 7,312,044 B2 | 12/2007 | Marks |
| 7,393,652 B2 | 7/2008 | Marks |
| 8,148,391 B2 * | 4/2012 | Ahmed et al. ............ 514/275 |
| 2002/0042405 A1 | 4/2002 | Schuh |
| 2002/0052358 A1 | 5/2002 | Chubinskaya et al. |
| 2002/0107406 A1 | 8/2002 | Sakai et al. |
| 2002/0115831 A1 | 8/2002 | Tamatani et al. |
| 2002/0132001 A1 | 9/2002 | Garthwaite et al. |
| 2002/0151685 A1 | 10/2002 | Tamatani et al. |
| 2002/0156242 A1 | 10/2002 | Tamatani et al. |
| 2002/0199213 A1 | 12/2002 | Tomizuka et al. |
| 2003/0022911 A1 | 1/2003 | Smith et al. |
| 2003/0044845 A1 | 3/2003 | Jenkins et al. |
| 2003/0054531 A1 | 3/2003 | Gretarsdottir et al. |
| 2003/0055027 A1 | 3/2003 | Schuh |
| 2003/0055087 A1 | 3/2003 | Shinkai et al. |
| 2003/0064406 A1 | 4/2003 | Kaneko et al. |
| 2003/0083472 A1 | 5/2003 | Tamatani et al. |
| 2003/0087907 A1 | 5/2003 | Kubo et al. |
| 2003/0092708 A1 | 5/2003 | Shinkai et al. |
| 2003/0124637 A1 | 7/2003 | Kaneko et al. |
| 2003/0134331 A1 | 7/2003 | Marks et al. |
| 2003/0144271 A1 | 7/2003 | Shulman |
| 2003/0144526 A1 | 7/2003 | Sakai et al. |
| 2003/0176485 A1 | 9/2003 | Sakai et al. |
| 2003/0181764 A1 | 9/2003 | Ikawa et al. |
| 2003/0186885 A1 | 10/2003 | Tandon et al. |
| 2003/0191323 A1 | 10/2003 | Ikawa et al. |
| 2003/0195218 A1 | 10/2003 | Koeller et al. |
| 2003/0199482 A1 | 10/2003 | Seibert et al. |
| 2003/0199701 A1 | 10/2003 | Webber et al. |
| 2003/0220310 A1 | 11/2003 | Schuh |
| 2003/0220312 A1 | 11/2003 | Schuh |
| 2003/0232855 A1 | 12/2003 | Iwamura et al. |
| 2004/0006099 A1 | 1/2004 | Katoh et al. |
| 2004/0017409 A1 | 1/2004 | Mizutani et al. |
| 2004/0048780 A1 | 3/2004 | Marks |
| 2004/0053919 A1 | 3/2004 | Chubinskaya et al. |
| 2004/0073012 A1 | 4/2004 | Tamatani et al. |
| 2004/0073957 A1 | 4/2004 | Tomizuka et al. |
| 2004/0082653 A1 | 4/2004 | Nonaka et al. |

(56) References Cited

U.S. PATENT DOCUMENTS

| | | |
|---|---|---|
| 2004/0120945 A1 | 6/2004 | Tamatani et al. |
| 2004/0132658 A1 | 7/2004 | Tamatani et al. |
| 2004/0132727 A1 | 7/2004 | Sakai et al. |
| 2004/0146506 A1 | 7/2004 | Tamatani et al. |
| 2004/0146991 A1 | 7/2004 | Tsuji et al. |
| 2004/0151669 A1 | 8/2004 | Tamatani et al. |
| 2004/0151718 A1 | 8/2004 | Tamatani et al. |
| 2004/0151720 A1 | 8/2004 | Tamatani et al. |
| 2004/0171613 A1 | 9/2004 | Iwamura et al. |
| 2004/0173802 A1 | 9/2004 | Yukimoto |
| 2004/0175814 A1 | 9/2004 | Kato et al. |
| 2004/0180052 A1 | 9/2004 | Tsuji et al. |
| 2004/0186178 A1 | 9/2004 | Webber et al. |
| 2004/0192584 A1 | 9/2004 | McMahon et al. |
| 2004/0198719 A1 | 10/2004 | Laborde et al. |
| 2004/0209871 A1 | 10/2004 | Fox et al. |
| 2004/0220193 A1 | 11/2004 | Yamamoto et al. |
| 2004/0224368 A1 | 11/2004 | Marks |
| 2004/0225018 A1 | 11/2004 | Sunami et al. |
| 2004/0229781 A1 | 11/2004 | Marks et al. |
| 2004/0229788 A1 | 11/2004 | Tamatani et al. |
| 2004/0229790 A1 | 11/2004 | Tezuka et al. |
| 2004/0229803 A1 | 11/2004 | Stephenson et al. |
| 2004/0229876 A1 | 11/2004 | Kubo et al. |
| 2004/0229957 A1 | 11/2004 | Shinkai et al. |
| 2004/0235162 A1 | 11/2004 | Sato |
| 2004/0242683 A1 | 12/2004 | Urata et al. |
| 2005/0009733 A1 | 1/2005 | Stephenson et al. |
| 2005/0020668 A1 | 1/2005 | Urata et al. |
| 2005/0032210 A1 | 2/2005 | Sato et al. |
| 2005/0035939 A1 | 2/2005 | Akiyama |
| 2005/0051181 A1 | 3/2005 | Okamoto |
| 2005/0059655 A1 | 3/2005 | Garvey et al. |
| 2005/0059810 A1 | 3/2005 | Maeda et al. |
| 2005/0070543 A1 | 3/2005 | Stephenson |
| 2005/0070545 A1 | 3/2005 | Fox et al. |
| 2005/0074762 A1 | 4/2005 | Nakamura et al. |
| 2005/0113451 A1 | 5/2005 | Hansen et al. |
| 2005/0159365 A1 | 7/2005 | Serizawa et al. |
| 2005/0159403 A1 | 7/2005 | Stephenson et al. |
| 2005/0165106 A1 | 7/2005 | Webber et al. |
| 2005/0171196 A1 | 8/2005 | Fujii et al. |
| 2005/0177884 A1 | 8/2005 | Tomizuka et al. |
| 2005/0186640 A1 | 8/2005 | Marks et al. |
| 2005/0187221 A1 | 8/2005 | Matsuda et al. |
| 2005/0187386 A1 | 8/2005 | Marks et al. |
| 2005/0192259 A1 | 9/2005 | Garthwaite et al. |
| 2005/0213426 A1 | 9/2005 | Midas et al. |
| 2005/0215540 A1 | 9/2005 | Marks et al. |
| 2005/0255546 A1 | 11/2005 | Nishikawa |
| 2005/0256199 A1 | 11/2005 | Durley et al. |
| 2005/0277649 A1 | 12/2005 | DeGraffenreid et al. |
| 2006/0011375 A1 | 1/2006 | Sugimoto et al. |
| 2006/0014768 A1 | 1/2006 | Kawasaki et al. |
| 2006/0026698 A1 | 2/2006 | Tomizuka et al. |
| 2006/0030565 A1 | 2/2006 | Shinkai et al. |
| 2006/0035882 A1 | 2/2006 | Koga et al. |
| 2006/0037093 A1 | 2/2006 | Tomizuka et al. |
| 2006/0041945 A1 | 2/2006 | Robl et al. |
| 2006/0059575 A1 | 3/2006 | Kusunoki et al. |
| 2006/0078992 A1 | 4/2006 | Misawa et al. |
| 2006/0084658 A1 | 4/2006 | Yamamoto et al. |
| 2006/0100195 A1 | 5/2006 | Maruyama et al. |
| 2006/0122181 A1 | 6/2006 | Ikemoto et al. |
| 2006/0123490 A1 | 6/2006 | Kakitani et al. |
| 2006/0135506 A1 | 6/2006 | Stephenson et al. |
| 2006/0167043 A1 | 7/2006 | Iwakubo et al. |
| 2006/0185025 A1 | 8/2006 | Oshimura et al. |
| 2006/0189603 A1 | 8/2006 | Garvey et al. |
| 2006/0194767 A1 | 8/2006 | Marks et al. |
| 2006/0205731 A1 | 9/2006 | Kodama et al. |
| 2006/0211717 A1 | 9/2006 | Sakai et al. |
| 2006/0217426 A1 | 9/2006 | Eto et al. |
| 2006/0223133 A1 | 10/2006 | Tamatani et al. |
| 2006/0233902 A1 | 10/2006 | Yajima et al. |
| 2006/0258701 A1 | 11/2006 | Mitsuya et al. |
| 2006/0270705 A1 | 11/2006 | Yonemori et al. |
| 2006/0293266 A1 | 12/2006 | Marks |
| 2007/0010571 A1 | 1/2007 | Garvey et al. |
| 2007/0010670 A1 | 1/2007 | Hirata et al. |
| 2007/0049572 A1 | 3/2007 | Marks et al. |
| 2007/0173482 A1 | 7/2007 | Marks et al. |
| 2009/0227788 A1* | 9/2009 | Deng et al. ............ 540/547 |
| 2010/0087418 A1 | 4/2010 | Shirai et al. |
| 2011/0263569 A1 | 10/2011 | Corey |
| 2012/0101085 A1* | 4/2012 | Abramson et al. ....... 514/211.09 |

FOREIGN PATENT DOCUMENTS

| | | |
|---|---|---|
| EP | 0 565 721 A1 | 10/1993 |
| EP | 0 718 261 A1 | 6/1996 |
| EP | 1 147 772 A1 | 10/2001 |
| EP | 1 254 898 | 11/2002 |
| EP | 1 369 129 A1 | 12/2003 |
| EP | 1 439 221 A1 | 7/2004 |
| EP | 1 447 096 A1 | 8/2004 |
| EP | 1 731 529 A1 | 12/2006 |
| EP | 1 743 895 A1 | 1/2007 |
| FR | 2 709 753 A1 | 3/1995 |
| JP | 03-093419 A | 4/1991 |
| JP | 04-230681 A | 8/1992 |
| JP | 05-271208 A | 10/1993 |
| JP | 10-045706 A | 2/1998 |
| JP | 11-199574 A | 7/1999 |
| JP | 2010195759 * | 9/2010 |
| WO | WO 91/04328 A1 | 4/1991 |
| WO | WO 92/12148 A1 | 7/1992 |
| WO | WO 92/19617 A2 | 11/1992 |
| WO | WO 93/00095 A2 | 1/1993 |
| WO | WO 93/04053 A1 | 3/1993 |
| WO | WO 93/09104 A1 | 5/1993 |
| WO | WO 93/13082 A1 | 7/1993 |
| WO | WO 94/11360 A1 | 5/1994 |
| WO | WO 94/18183 A1 | 8/1994 |
| WO | WO 94/29286 A1 | 12/1994 |
| WO | WO 96/08228 A2 | 3/1996 |
| WO | WO 96/18629 A1 | 6/1996 |
| WO | WO 97/03986 A1 | 2/1997 |
| WO | WO 97/17344 A1 | 5/1997 |
| WO | WO 98/01417 A1 | 1/1998 |
| WO | WO 98/05657 A1 | 2/1998 |
| WO | WO 98/45291 A1 | 10/1998 |
| WO | WO 99/16758 A1 | 4/1999 |
| WO | WO 99/26921 A1 | 6/1999 |
| WO | WO 99/32115 A1 | 7/1999 |
| WO | WO 00/38688 | 7/2000 |
| WO | WO 01/00185 A2 | 1/2001 |
| WO | WO 01/47510 A2 | 7/2001 |
| WO | WO 01/55118 | 8/2001 |
| WO | WO 02/08211 A2 | 1/2002 |
| WO | WO 02/14245 A1 | 2/2002 |
| WO | WO 02/14246 A1 | 2/2002 |
| WO | WO 02/051232 A2 | 7/2002 |
| WO | WO 02/051838 A1 | 7/2002 |
| WO | WO 02/053548 A1 | 7/2002 |
| WO | WO 02/056790 A2 | 7/2002 |
| WO | WO 02/072145 A1 | 9/2002 |
| WO | WO 03/034980 A2 | 5/2003 |
| WO | WO 03/043655 A2 | 5/2003 |
| WO | WO 2004/022057 A1 | 3/2004 |
| WO | WO 2004/023030 A1 | 3/2004 |
| WO | WO 2004/042389 A2 | 5/2004 |
| WO | WO 2004/080283 A2 | 9/2004 |
| WO | WO 2004/104895 A2 | 12/2004 |
| WO | WO 2005/002518 A2 | 1/2005 |
| WO | WO 2005/026177 A1 | 3/2005 |
| WO | WO 2005/037195 A2 | 4/2005 |
| WO | WO 2005/094457 A2 | 10/2005 |
| WO | WO 2005/105793 A1 | 11/2005 |
| WO | WO 2006/071603 A2 | 7/2006 |
| WO | WO 2006/101496 A1 | 9/2006 |
| WO | WO 2006/101497 A1 | 9/2006 |
| WO | WO 2007/024717 A2 | 3/2007 |
| WO | WO 2007/127145 A2 | 11/2007 |

(56) References Cited

FOREIGN PATENT DOCUMENTS

| | | | |
|---|---|---|---|
| WO | WO 2007/143112 A2 | | 12/2007 |
| WO | WO 2008/021432 A2 | | 2/2008 |
| WO | WO 2008/021439 A2 | | 2/2008 |
| WO | WO-2008/051547 | * | 5/2008 |
| WO | WO 2008/060332 A2 | | 5/2008 |
| WO | WO 2008/121602 A1 | | 10/2008 |
| WO | WO 2008/140592 A2 | | 11/2008 |
| WO | WO 2008/144483 A2 | | 11/2008 |
| WO | WO 2009/080730 A1 | | 7/2009 |
| WO | WO-2010/098080 | * | 9/2010 |
| WO | WO-2010/114563 | * | 10/2010 |
| WO | WO 2011/002520 A2 | | 1/2011 |

OTHER PUBLICATIONS

Mishra et al., Diversity-Oriented Synthetic Approach to Naturally Abundant S-Amino Acid Based Benzannulated Enantiomerically Pure Medium Ring Heterocyclic Scaffolds Employing Inter- and Intramolecular Mitsunobu Reations, Journal of Combinatorial Chemistry, vol. 9, No. 2, pp. 321-338, 2007.*
Thevis et al., Doping Control Analysis of Emerging Drugs in Human Plasma—Identification of GW501516, S-107, JTV-519, and S40503, Rapid Communications in Mass Spectrometry, vol. 23, No. 8, pp. 1139-1146, 2009.*
Saruta et al., Traceless Solid-Phase Synthesis of Multiple Sulfonamide-Containing Cyclic Sulfides Exploiting Microwave Irradiation, Tetrahedron Letters, vol. 50, No. 30, pp. 4364-4367, 2009.*
Incerti et al., Synthesis and NMR Spectral Assignments of Novel 1,4-Benzothiazepin-5-one Derivatives, Tetrahedron, vol. 65, No. 36, pp. 7487-7490, 2009.*
Rujirawanich et al., Substituted 1,4-Benzoxazepines, 1,5-Benzoxazocines and N- and S-Variants, Organic Letters, vol. 11, No. 23, pp. 5494-5496, 2009.*
CAPLUS printout Wang et al., Synthesis of a Novel Conformational Restricted Amino Acid for Potential Use in Peptide Chemistry, Heterocyclic Communications, vol. 15, No. 6, pp. 397-400, Dec. 2009.*
Ackerman, "Cardiac Channelopathies: it's in the genes," Nature Medicine, 10(5): 463-464 (2004).
Ahern et al., "Intramembrane charge movements and excitation—contraction coupling expressed by two-domain fragments of the $Ca^{2+}$ channel," Proc Natl Acad Sci USA, 98(12):6935-6940 (2001).
Ahern et al., "Subconductance States in Single-Channel Activity of Skeletal Muscle Ryanodine Receptors After Removal of FKBP12," Biophys J, 72(1):146-162 (1997).
Ahmmed et al., "Changes in $Ca^{2+}$ Cycling Proteins Underlie Cardiac Action Potential Prolongation in a Pressure-Overloaded Guinea Pig Model With Cardiac Hypertrophy and Failure," Circ Res, 86:558-570 (2000).
Altamura et al., "Investigation on the flexibility of chiral tricyclic derivatives," New J. Chem., 32:1617-1627 (2008).
Alvarez et al., "Late Post-myocardial Infarction Induces a Tetrodotoxin-resistant $Na^+$ Current in Rat Cardiomyocytes," J Mol Cell Cardiol, 32(7):1169-1179 (2000).
Antos et al., "Dilated Cardiomyopathy and Sudden Death Resulting From Constitutive Activation of Protein Kinase A," Circ Res, 89:997-1004 (2001).
Baillie et al., "β-Arrestin-mediated PDE4 cAMP phosphodiesterase recruitment regulates β-adrenoceptor switching from $G_S$ to $G_i$," Proc Natl Acad Sci USA, 100(3):940-945 (2003).
Bangur et al., "Mutational Analysis of the D1/E1 Core Helices and the Conserved N-Terminal Region of Yeast Transcription Factor IIB (TFIIB): Identification of an N-Terminal Mutant That Stabilizes Tata-Binding Protein—TFIIB—DNA Complexes," Mol Cell Biol, 17(12): 6784-6793 (1997).
Barbone et al., "Comparison of Right and Left Ventricular Responses to Left Ventricular Assist Device Support in Patients With Severe Heart Failure. A Primary Role of Mechanical Unloading Underlying Reverse Remodeling," Circulation, 104:670-675 (2001).
Barnes, "Theophylline: New Perspectives for an Old Drug," Am J Respir Crit Care Med, 167:813-818 (2003).
Basso et al., "Arrhythmogenic Right Ventricular Cardiomyopathy Causing Sudden Cardiac Death in Boxer Dogs. A New Animal Model of Human Disease," Circulation, 109:1108-1185 (2004).
Behr et al., "Cardiological assessment of first-degree relatives in sudden arrhythmic death syndrome," Lancet, 362:1457-1459 (2003).
Bellinger et al., "Remodeling of ryanodine receptor complex causes 'leaky' channels: A molecular mechanism for decreased exercise capacity," Proc Natl Acad Sci USA, 105(6):2198-2202 (2008).
Bellinger et al., "Hypernitrosylated ryanodine receptor calcium release channels are leaky in dystrophic muscle," Nat Med, 15(3):325-330 (2009).
Bennett et al., "The Pattern of Onset and Spontaneous Cessation of Artial Fibrillation in Man," Circulation, 41:981-988 (1970).
Bennett et al., "Synthesis of 2-methoxydibenzo [b,f] (1,4)-thiazepin-11(10H)-one-5,5-dioxide," Organic Preparations and Procedures International: The New Journal for Organic Synthesis, 6(6):287-293 (1974).
Bennett et al., "Identification and characterization of the murine FK506 binding protein (FKBP) 12.6 gene," Mammalian Genome, 9:1069-1071 (1998).
Beuckelmann et al., "Intracellular Calcium Handling in Isolated Ventricular Myocytes From Patients With Terminal Heart Failure," Circulation, 85:1046-1055 (1992).
Bezprozvanny et al., "Bell-shaped calcium-response curves of $Ins(1,4,5)P_3$- and calcium-gated channels from endoplasmic reticulum of cerebellum," Nature, 351:751-754 (1991).
Bidasee et al., "Chronic Diabetes Increases Advanced Glycation End Products on Cardiac Ryanodine Receptors/Calcium-Release Channels," Diabetes, 52:1825-1836 (2003).
Bidasee et al., "Diabetes Increases Formation of Advanced Glycation End Products on Sarco(endo)plasmic Reticulum $Ca^{2+}$-ATPase," Diabetes, 53:463-473 (2004).
Bittar et al., "The Arrhythmogenicity of Theophyilline. A Multivariate Analysis of Clinical Determinants," Chest, 99:1415-1420 (1991).
Blayney et al., "Ryanodine receptor-mediated arrhythmias and sudden cardiac death," Pharmacol Ther, 123(2):151-177 (2009).
Bohm et al., "cAMP concentrations, cAMP dependent protein kinase activity, and phospholamban in non-failing and failing myocardium," Cardiovasc Res, 28(11):1713-1719 (1994).
Bolger et al., "Characterization of five different proteins produced by alternatively spliced mRNAs from the human cAMP-specific phosphodiesterase PDE4D gene," Biochem. J., 328:539-548 (1997).
Boyden et al., "2APB- and JTV519(K201)-sensitive micro $Ca^{2+}$ waves in arrhythmogenic Purkinje cells that survive in infarcted canine heart," Heart Rhythm, 1(2):218-226 (2004).
Brillantes et al., "Stabilization of Calcium Release Channel (Ryanodine Receptor) Function by FK506-binding Protein," Cell, 77(4):513-523 (1994).
Brillantes et al., "Developmental and Tissue-Specific Regulation of Rabbit Skeletal and Cardiac Muscle Calcium Channels Involved in Excitation-Contraction Coupling," Circ Res, 75:503-510 (1994).
Brillantes et al., "Differences in Cardiac Calcium Release Channel (Ryanodine Receptor) Expression in Myocardium From Patients With End-Stage Heart Failure Caused by Ischemic Versus Dilated Cardiomyopathy," Circ Res, 71:18-26 (1992).
Bristow et al., $β_1$- and $β_2$-Adrenergic-Receptor Subpopulations in Nonfailing and Failing Human Ventricular Myocardium: Coupling of Both Receptor Subtypes to Muscle Contraction and Selective $β_1$-Receptor Down-Regulation in Heart Failure, Circ Res, 59:297-309 (1986).
Bristow et al., "Carvedilol Produces Dose-Related Improvements in Left Ventricular Function and Survival in Subjects With Chronic Heart Failure," Circulation, 94:2807-2816 (1996).
Bristow et al., "β-Adrenergic Neuroeffector Abnormalities in the Failing Human Heart are Produced by Local Rather than Systemic Mechanisms," J. Clin. Invest., 89:803-815 (1992).
Bristow et al., "Decreased Catecholamine Sensitivity and β-Adrenergic-Receptor Density in Failing Human Hearts," N Engl J Med, 307:205-211 (1982).
Bruton et al., "Ryanodine receptors of pancreatic β-cells mediate a distinct context-dependent signal for insulin secretion," The FASEB Journal, 17:301-303 (2002).

(56) References Cited

OTHER PUBLICATIONS

Buijs et al., "β-Adrenergic activation reveals impaired cardiac calcium handling at early stage of diabetes," Life Sciences, 76:1083-1098 (2005).
Burashnikov et al., "Reinduction of Atrial Fibrillation Immediately After Termination of the Arrhythmia Is Mediated by Late Phase 3 Early Afterdepolarization—Induced Triggered Activity," Circulation, 107:2355-2360 (2003).
Callaway et al., "Localization of the High and Low Affinity [$^3$H]Ryanodine Binding Sites on the Skeletal Muscle $Ca^{2+}$ Release Channel," J Biol Chem, 269(22):15876-15884 (1994).
Cameron et al., "FKBP12 Binds the Inositol 1,4,5-Trisphosphate Receptor at Leucine-Proline (1400-1401) and Anchors Calcineurin to this FK506-like Domain," J Biol Chem, 272(44):27582-27588 (1997).
Carlisle et al., "PKA-phosphorylation of PDE4D3 facilitates recruitment of the mAKAP signalling complex," Biochem. J., 381:587-592 (2004).
Catsoulacos, "Synthesis of Substituted Dihydrobenzothiazepines and Related Compounds," Journal of Heterocyclic Chemistry, 7(2):409-411 (1970).
Cerrone et al., "Bidirectional Ventricular Tachycardia and Fibrillation Elicited in a Knock-In Mouse Model Carrier of a Mutation in the Cardiac Ryanodine Receptor," Circ Res, 96:e77-e82 (2005).
Chatrath et al., "β-Blocker Therapy Failures in Symptomatic Probands with Genotyped Long-QT Syndrome," Pediatr Cardiol, 25:459-465 (2004).
Che et al., "Reversal of P-glycoprotein mediated multidrug resistance by a newly synthesized 1,4-benzothiazipine derivative, JTV-519," Cancer Letters, 187(1):111-119 (2002).
Chen et al., "Mechanism of TGFbeta receptor inhibition by FKBP12," EMBO J, 16(13):3866-3876 (1997).
Cheng et al., "Amplitude Distribution of Calcium Sparks in Confocal Images: Theory and Studies with an Automatic Detection Method," Biophysical Journal, 76:606-617 (1999).
Chidsey et al., "Augmentation of the Plasma Nor-Epinephrine Response to Exercise in Patients with Congestive Heart Failure," N Engl J Med, 267:650-654 (1962).
Choi et al., "Spectrum and Frequency of Cardiac Channel Defects in Swimming-Triggered Arrhythmia Syndromes," Circulation, 110:2119-2124 (2004).
Choi et al., "Sudden Cardiac Death and Channelopathies: A Review of Implantable Defibrillator Therapy," Pediatr Clin North Am, 51(5):1289-1303 (2004).
Chugh et al., "Epidemiology and Natural History of Atrial Fibrillation: Clinical Implications," J Am Coll Cardiol, 37(2):371-378 (2001).
CIBIS-II Investigators and Committees, "The Cardiac Insufficiency Bisoprolol Study II (CIBIS-II): A Randomised Trial," The Lancet, 353(9146):9-13 (1999).
Cohn et al., "Plasma Norepinephrine as a Guide to Prognosis in Patients with Chronic Congestive Heart Failure," N Engl J Med, 311(13):819-823 (1984).
Conti et al., "Cyclic AMP-specific PDE4 Phosphodiesterases as Critical Components of Cyclic AMP Signaling,;" J Biol Chem, 278(8):5493-5496 (2003).
Cranefield, "Action Potentials, Afterpotentials, and Arrhythmias," Circ Res, 41(4):415-423 (1977).
Culligan et al., "Drastic reduction of calsequestrin-like proteins and impaired calcium binding in dystrophic *mdx* muscle," J Appl Physiol, 92:435-445 (2002).
Czollner et al., "Synthesis of 1,4-Benzothiazepines and investigation of their reactions," Magyar Kemiai Folyoirat, Kiralyi Magy. Termtud. Tars. Chem. Szakoszt, Budapest, HU, 94:332-335 (1998).
Daoud et al., "Effect of Verapamil and Procainamide on Atrial Fibrillation-Induced Electrical Remodeling in Humans," Circulation, 96:1542-1550 (1997).
Dietz et al., "Epinephrine Regulation of Skeletal Muscle Glycogen Metabolism: Studies Utilizing the Perfused Rat Hindlimb Preparation," J Biol Chem, 255(6):2301-2307 (1980).

Dodge et al., "mAKAP assembles a protein kinase A/PDE4 phosphodiesterase cAMP signaling module," EMBO Journal, 20(8):1921-1930 (2001).
Doi et al., "Propranolol Prevents the Development of Heart Failure by Restoring FKBP12.6—Mediated Stabilization of Ryanodine Receptor," Circulation, 105:1374-1379 (2002).
Dorian , "Antiarrhythmic action of beta-blockers: potential mechanisms," J Cardiovasc Pharmacol Ther, 10(Suppl 1):515-22 (2005).
Drexler et al., "Contrasting Peripheral Short-term and Long-term Effects of Converting Enzyme Inhibition in Patients with Congestive Heart Failure. A Double-Blind, Placebo-Controlled Trial," Circulation, 79:491-502 (1989).
Duddeck et al., "Oxazepines and Thiazepines, XVI. $^1$H and $^{13}$C-NMR spectroscopic Investigations of the Structure of Benzothiazepinone Derivatives," Liebigs Ann. Chem., 869-876 (1985).
Dun et al., "Chronic atrial fibrillation does not further decrease outward currents. It increases them.," Am J Physiol Heart Circ Physiol, 285:H1378-H1384 (2003).
Dyachok et al., "$Ca^{2+}$-induced $Ca^{2+}$ release by activation of inositol 1,4,5-triphosphate receptors in primary pancreatic β-cells," Cell Calcium, 36:1-9 (2004).
Dyachok et al., "$Ca^{2+}$-induced $Ca^{2+}$ Release via Inositol 1,4,5-triphosphate Receptors is Amplified by Protein Kinase A and Triggers Exocytosis in Pancreatic β-Cells," J Biol Chem, 279(44):45455-45461 (2004).
Echt et al., "Mortality and morbidity in patients receiving encainide, flecainide, or placebo. The Cardiac Arrhythmia Suppression Trial.," N Engl J Med, 324(12):781-788 (1991).
Eichhorn et al., "Medical Therapy Can Improve the Biological Properties of the Chronically Failing Heart," Circulation, 94:2285-2296 (1996).
Eisner et al., "The Ryanodine Receptor: Cause or Consequence of Diabetic Heart Failure?," J Mol Cell Cardiol, 32:1377-1378 (2000).
Ellison et al., "Acute β-Adrenergic Overload Produces Myocyte Damage through Calcium Leakage from the Ryanodine Receptor 2 but Spares Cardiac Stem Cells," J Biol Chem, 282(15):11397-11409 (2007).
Elvan et al., "Pacing-Induced Chronic Atrial Fibrillation Impairs Sinus Node Function in Dogs," Circulation, 94:2953-2960 (1996).
Exhibit A: Chemical Structure (2006).
Fabiato, "Calcium-induced release of calcium from the cardiac sarcoplasmic reticulum," Am. J. Physiol., 245:C1-C14 (1983).
Falk, "Atrial Fibrillation," N Engl J Med, 344:1067-1078 (2001).
Farr et al., "Sparking the Failing Heart," N Engl J Med, 351:185-187 (2004).
Feldman et al., "Deficient production of cyclic AMP: pharmacologic evidence of an important cause of contractile dysfunction in patients with end-stage heart failure," Circulation, 75(2):331-339 (1987).
Fisher et al., "Familial Polymorphic Ventricular Arrhythmias. A Quarter Century of Successful Medical Treatment Based on Serial Exercise-Pharmacologic Testing," J Am Coll Cardiol, 34(7):2015-2022 (1999).
Fitzgerald et al., "Reduced ryanodine receptor content in isolated neonatal cardiomyocytes compared with the intact tissue," J Mol Cell Cardiol, 26(10):1261-1265 (1994).
Fodor et al., "New convenient synthesis of 1,4-benzothiazepines," Tetrahedron Letters, 36(5):753-756 (1995).
Fox et al., "Spontaneously Occurring Arrhythmogenic Right Ventricular Cardiomyopathy in the Domestic Cat. A New Animal Model Similar to the Human Disease," Circulation, 102:1863-1870 (2000).
Fozzard, "Afterdepolarizations and triggered activity," Basic Res Cardiol, 87 (Suppl 2):105-113 (1992).
Franzen et al., "Cloning of a TGF beta type I receptor that forms a heteromeric complex with the TGF beta type II receptor," Cell, 75(4):681-692 (1993).
Franzini-Armstrong et al., "Alternate disposition of tetrads in peripheral couplings of skeletal muscle," Journal of Muscle Research and Cell Motility, 16:319-324 (1995).
Fraser et al., "Modulation of ion channels: a 'current' view of AKAPs," Neuron, 23(3):423-426 (1999).

(56) References Cited

OTHER PUBLICATIONS

Frazier, "First Use of an Untethered, Vented Electric Left Ventricular Assist Device for Long-term Support," Circulation, 89:2908-2914 (1994).
Gaburjakova et al., "FKBP12 Binding Modulates Ryanodine Receptor Channel Gating," J Biol Chem, 276(20):16931-16935 (2001).
Gailly, "New aspects of calcium signaling in skeletal muscle cells: implications in Duchenne muscular dystrophy," Biochimica et Biophysica Acta, 1600:38-44 (2002).
Garofalo et al., "Polycondensed Heterocycles. X. A New Method for the Preparation of Pyrrolo[2,1-c][1,4]benzothiazepines by Intramolecular Mitsunobu Cyclisation," Tetrahedron, 55:1479-1490 (1999).
Gaspo et al., "Functional Mechanisms Underlying Tachycardia-Induced Sustained Atrial Fibrillation in a Chronic Dog Model," Circulation, 96:4027-4035 (1997).
Giembycz, "Development status of second generation PDE4 inhibitors for asthma and COPD: The story so far," Monaldi Arch Chest Dis, 57(1):48-64 (2002).
Gillian et al., "Analysis of expression of the human ryanodine receptor gene in malignant hyperthermia skeletal muscle tissue," Biochem Soc Trans, 19(1):46S (1991).
Gillo et al., "Calcium Influx in Induced Differentiation of Murine Erythroleukemia Cells," Blood, 81(3):783-792 (1993).
Giordano et al., "Rapamycin antagonizes NF-κB nuclear translocation activated by TNF-α in primary vascular smooth muscle cells and enhances apoptosis," Am J Physiol Heart Circ Physiol, 290:H2459-H2465 (2006).
Go et al., "Differential Regulation of Two Types of Intracellular Calcium Release Channels During End-Stage Heart Failure," J. Clin. Invest., 95:888-894 (1995).
Goette et al., "Electrical Remodeling in Atrial Fibrillation. Time Course and Mechanisms," Circulation, 94:2968-2974 (1996).
Gómez et al., "Defective Excitation-Contraction Coupling in Experimental Cardiac Hypertrophy and Heart Failure," Science, 276:800-806 (1997).
Gong et al., "Persistent improvement in synaptic and cognitive functions in an Alzheimer mouse model after rolipram treatment," J. Clin. Invest., 114(11): 1624-1634 (2004).
González et al., "Involvement of multiple intracellular release channels in calcium sparks of skeletal muscle," Proc Natl Acad Sci USA, 97(8):4380-4385 (2000).
Gretarsdottir et al., "The gene encoding phosphodiesterase 4D confers risk of ischemic stroke," Nature Genetics, 35(2):131-138 (2003).
Gullestad et al., "Effect of metoprolol CR/XL on exercise tolerance in chronic heart failure—a substudy to the MERIT-HF trial," European Journal of Heart Failure, 3:463-468 (2001).
Gwathmey et al., "Abnormal Intracellular Calcium Handling in Myocardium from Patients with End-Stage Heart Failure," Circ Res, 61:70-76 (1987).
Hachida et al, "Protective Effect of JTV519 on Prolonged Myocardial Preservation," Transplantation Proceedings, 31:1094 (1999).
Hachida et al., "Significant Effect of 1,4-Benzothiazepine Derivative (K2) in Improving Myocardial Preservation," Transplantation Proceedings, 29:1346-1348 (1997).
Hachida et al., "Protective Effect of JTV519, A New 1,4-Benzothiazepine Derivative, on Prolonged Myocardial Preservation," J Card Surg, 14:187-193 (1999).
Hachida et al., "Protective Effect of JTV519 (K201), a New 1,4-Benzothiazepine Derivative, on Prolonged Myocardial Preservation," Transplantation Proceedings, 31:996-1000 (1999).
Hain et al., "Phosphorylation Modulates the Function of the Calcium Release Channel of Sarcoplasmic Reticulum from Skeletal Muscle," Biophysical Journal, 67:1823-1833 (1994).
Hain et al., "Phosphorylation Modulates the Function of the Calcium Release Channel of Scarcoplasmic Reticulum from Cardiac Muscle," J Biol Chem, 270(5):2074-2081 (1995).
Hara et al., "Steady-state and nonsteady-state action potentials in fibrillating canine atrium: abnormal rate adaptation and its possible mechanisms," Cardiovascular Research, 42:455-469 (1999).
Harnick et al., "The Human Type 1 Inositol 1,4,5-Trisphosphate Receptor from T Lymphocytes," J Biol Chem, 270(6):2833-2840 (1995).
Harrington, "Mechanisms of exercise intolerance in congestive heart failure," Current Opinion in Cardiology, 12:224-232 (1997).
Hasenfuss et al., "Treatment of Heart Failure Through Stabilization of the Cardiac Ryanodine Receptor," Circulation, 107:378-380 (2003).
Haut Donahue et al., "Annexin V disruption impairs mechanically induced calcium signaling in osteoblastic cells," Bone, 35:656-663 (2004).
Hirai, "Reactivity of Some Benzothiazepine Derivatives," Annu. Rep. Sankyo Res. Lab., 44:141-150 (1992).
Holz et al., "cAMP-dependent Mobilization of Intracellular $Ca^{2+}$ Stores by Activation of Ryanodine Receptors in Pancreatic β-Cells," J Biol Chem, 274(20):14147-14156 (1999).
Houslay et al., "PDE4 cAMP phosphodiesterases: modular enzymes that orchestrate signaling cross-talk, desensitization and compartmentalization," Biochem. J., 370:1-18 (2003).
Huse et al., "Crystal Structure of the Cytoplasmic Domain of the Type 1 TGFβ Receptor in Complex with FKBP12," Cell, 96:425-436 (1999).
Ikemoto et al., "Regulation of Calcium Release by Interdomain Interaction within Ryanodine Receptors," Frontiers in Bioscience, 7:d671-683 (2002).
Inagaki et al., "Anti-Ischemic Effect of a Novel Cardioprotective Agent, JTV519, is Mediated Through Specific Activation of δ-Isoform of Protein Kinase C in Rat Ventricular Myocardium," Circulation, 101:797-804 (2000).
Inagaki et al., "The Cardioprotective Effects of a New 1,4-Benzothiazepine Derivative, JTV519, on Ischemia/Reperfusion-Induced $Ca^{2+}$ Overload in Isolated Rat Hearts," Cardiovascular Drugs and Therapy, 14:489-495 (2000).
Ishii et al., "JTV-519, a new cardioprotective drug, and cariporide, synergistically improved post-ischemic contractile recovery in rat," Journal of Molecular and Cellular Cardiology, 34(6):A29 (2002).
Islam et al., "Effects of caffeine on cytoplasmic free $Ca^{2+}$ concentration in pancreatic β-cells are mediated by interaction with ATP-sensitive $K^+$ channels and L-type voltage-gated $Ca^{2+}$ channels but not the ryanodine receptor," Biochem. J., 306:679-686 (1995).
Islam et al., "In situ activation of the type 2 ryanodine receptor in pancreatic beta cells requires cAMP-dependent phosphorylation," Proc. Natl. Acad. Sci. USA, 95:6145-6150 (1998).
Islam, "Perspectives in Diabetes. The Ryanodine Receptor Calcium Channel of β-cells. Molecular Regulation and Physiological Significance," Diabetes, 51:1299-1309 (2002).
Isselbacher et al., "Harrison's Principles of Internal Medicine," 13th Edition, 1:1022-1024 (1994).
Ito et al., "JTV-519, a novel cardioprotective agent, improves the contractile recovery after ischaemia-reperfusion in coronary perfused guinea-pig ventricular muscles," British Journal of Pharmacology, 130:767-776 (2000).
Jayaraman et al., "Regulation of the Inositol 1,4,5-Trisphosphate Receptor by Tyrosine Phosphorylation," Science, 272:1492-1494 (1996).
Jayaraman et al., FK506 Binding Protein Associated with the Calcium Release Channel (Ryanodine Receptor), J Biol Chem, 267(14):9474-9477 (1992).
Jiang et al., "Abnormal $Ca^{2+}$ Release, but Normal Ryanodine Receptors, in Canine and Human Heart Failure," Circ Res, 91:1015-1022 (2002).
Jiang et al , "Enhanced Basal Activity of a Cardiac $Ca^{2+}$ Release Channel (Ryanodine Receptor) Mutant Associated with Ventricular Tachycardia and Sudden Death," Circ Res, 91:218-225 (2002).
Jin et al., "Impaired growth and fertility of cAMP-specific phosphodiesterase PDE4D-deficient mice," Proc. Natl. Acad. Sci. USA, 96(21):11998-12003 (1999).
Johansson, "Adams-Stokes Syndrome. A Review and Follow-up Study of Forty-two Cases," The American Journal of Cardiology, pp. 76-93 (Jul. 1961).

(56) References Cited

OTHER PUBLICATIONS

Johnson et al., "Ryanodine receptors in human pancreatic β cells: localization and effects on insulin secretion," The FASEB Journal, 18:878-880 (2004).
Johnson et al., "RyR2 and Calpain-10 Delineate a Novel Apoptosis Pathway in Pancreatic Islets," J Biol Chem, 279(23):24794-24802 (2004).
Kaftan et al., "Effects of Rapamycin on Ryanodine Receptor/$Ca^{2+}$-Release Channels from Cardiac Muscle," Circ Res, 78:990-997 (1996).
Kaneko et al., "Crystal Structure of Annexin V with its Ligand K-201 as a Calcium Channel Activity Inhibitor," J. Mol. Biol., 274:16-20 (1997).
Kaneko et al, "Inhibition of annexin V-dependent $Ca^{2+}$ movement in large unilamellar vesicles by K201, a new 1,4-benzothiazepine derivative," Biochimica et Biophysica Acta, 1330:1-7 (1997).
Kaneko, "New 1,4-Benzothiazepine Derivative, K201, Demonstrates Cardioprotective Effects Against Sudden Cardiac Cell Death and Intracellular Calcium Blocking Action," Drug Development Research, 33:429-438 (1994).
Kang et al., "A cAMP and $Ca^{2+}$ coincidence detector in support of $Ca^{2+}$-induced $Ca^{2+}$ release in mouse pancreatic β cells," J Physiol, 566(1):173-188 (2005).
Kang et al., "cAMP-regulated guanine nucleotide exchange factor II (Epac2) mediates $Ca^{2+}$-induced $Ca^{2+}$ release in INS-1 pancreatic β cells," J Physiol, 536(2):375-385 (2001).
Kapiloff et al., "mAKAP and the ryanodine receptor are part of a multi-component signaling complex on the cardiomyocyte nuclear envelope," Journal of Cell Science, 114:3167-3176 (2001).
Kapiloff et al., "mAKAP: an A-kinase anchoring protein targeted to the nuclear membrane of differentiated myocytes," Journal of Cell Science, 112:2725-2736 (1999).
Katritzky et al., "$^1H$ and $^{13}C$ NMR study of tetrahydro-1,4-benzothiazepine conformations," J. Chem. Soc., Perkin Trans. 2, 1816-1822 (2002).
Katritzky et al., "Convenient syntheses of 2,3,4,5-tetrahydro-1,4-benzothiazepines, -1,4-benzoxazepines and -1,4-benzodiazepines," J. Chem. Soc., Perkin Trans. 1, 592-598 (2002).
Katz et al., "Lactate turnover at rest and during submaximal exercise in patients with heart failure," J. Appl. Physiol., 75(5):1974-1979 (1993).
Kawabata et al., "A Novel Cardioprotective Agent, JTV-519, is Abolished by Nitric Oxide Synthase Inhibitor on Myocardial Metabolism in Ischemia-Reperfused Rabbit Hearts," Hypertens Res., 25:303-309 (2002).
Kawabata et al., "Effect of a Novel Cardioprotective Agent, JTV-519, on Metabolism, Contraction and Relaxation in the Ischemia-Reperfused Rabbit Heart," Jpn Circ J, 64:772-776 (2000).
Kimura et al., "Effects of a Novel Cardioprotective Drug, JTV-519, on Membrane Currents of Guinea Pig Ventricular Myocytes," Jpn. J. Pharmacol., 79:275-281 (1999).
Kirchhefer et al., "Activity of cAMP-dependent protein kinase and $Ca^{2+}$/calmodulin-dependent protein kinase in failing and nonfailing human hearts," Cardiovascular Research, 42:254-261 (1999).
Kiriyama et al., "Effects of JTV-519, a novel anti-ischaemic drug, on the delayed rectifier $K^+$ current in guinea-pig ventricular myocytes," Naunyn-Schmiedeberg's Arch Pharmacol., 361(6):646-653 (2000).
Kirsch et al., "Spark- and ember-like elementary $Ca^{2+}$ release events in skinned fibres of adult mammalian skeletal muscle," Journal of Physiology, 537(2):379-389 (2001).
Kirsch et al., "The Roles of Annexins and Types II and X Collagen in Matrix Vesicle-mediated Mineralization of Growth Plate Cartilage," J Biol Chem, 275(45):35577-35583 (2000).
Kiryu et al., "Pathologic and Electrocardiographic Findings in Sudden Cardiac Death in Racehorses," J. Vet. Med. Sci., 61(8):921-928 (1999).
Kittleson et al., "Familial Hypertrophic Cardiomyopathy in Main Coon Cats. an Animal Model of Human Disease," Circulation, 99:3172-3180 (1999).

Klein et al., "Voltage dependence of the pattern and frequency of discrete $Ca^{2+}$ release events after brief repriming in frog skeletal muscle," Proc. Natl. Acad. Sci. USA, 94:11061-11066 (1997).
Kneller et al., "Remodeling of $Ca^{2+}$-handling by atrial tachycardia: evidence for a role in loss of rate-adaptation," Cardiovascular Research, 54:416-426 (2002).
Kobrinsky et al., "Expressed Ryanodine Receptor can Substitute for the Inositol 1,4,5-Trisphosphate Receptor in *Xenopus laevis* Oocytes during Progesterone-Induced Maturation," Developmental Biology, 172:531-540 (1995).
Kohno et al., "A new cardioprotective agent, JTV519, improves defective channel gating of ryanodine receptor in heart failure," Am J Physiol Heart Circ Physiol, 284:H1035-H1042 (2003).
Kukin et al., "Prospective, Randomized Comparison of Effect of Long-Term Treatment with Metoprolol or Carvedilol on Symptoms, Exercise, Ejection Fraction, and Oxidative Stress in Heart Failure," Circulation, 99:2645-2651 (1999).
Kumagai et al., "Antiarrhythmic Effects of JTV-519, a Novel Cardioprotective Drug, on Atrial Fibrillation/Flutter in a Canine Sterile Pericarditis Model," J Cardiovasc Electrophysiol, 14:880-884 (2003).
Lacampagne et al., "Modulation of the Frequency of Spontaneous Sarcoplasmic Reticulum $Ca^{2+}$ Release Events ($CA^{2+}$ Sparks) by Myoplasmic [$Mg^{2+}$] in Frog Skeletal Muscle," J. Gen. Physiol, 111:207-224 (1998).
LaFerla, "Calcium Dyshomeostasis and Intracellular Signalling in Alzheimer's Disease," Nat Rev Neurosci, 3(11):862-872 (2002).
Laflamme et al., "$G_S$ and adenylyl cyclase in transverse tubules of heart: implications for cAMP-dependent signaling," Am. J. Physiol., 277:H1841-H1848 (1999).
Lai et al., "The Ryanodine Receptor-$Ca^{2+}$ Release Channel Complex of Skeletal Muscle Sarcoplasmic Reticulum," J Biol Chem, 264(28):16776-16785 (1989).
Laitinen et al., "Mutations of the Cardiac Ryanodine Receptor (RyR2) Gene in Familial Polymorphic Ventricular Tachycardia," Circulation, 103:485-490 (2001).
Lamb et al., "Effects of FK506 and rapamycin on excitation—contraction coupling in skeletal muscle fibres of the rat," Journal of Physiology, 494(2):569-576 (1996).
Lauffenburger et al., "Receptors. Models for Binding, Trafficking and Signaling," Oxford University Press, Chapter 2, pp. 9-12 (1996).
Laver et al., "Inactivation of $Ca^{2+}$ Release Channels (Ryanodine Receptors RyR1 and RyR2) with Rapid Steps in [$Ca^{2+}$] and Voltage," Biophysical Journal, 74:2352-2364 (1998).
Lee et al., "Sudden unexplained death: evaluation of those left behind," The Lancet, 362(9394):1429-1430 (2003).
Leenhardt et al., "Catecholaminergic Polymorphic Ventricular Tachycardia in Children," Circulation, 91:1512-1519 (1995).
Lehnart et al., "Cardiac Ryanodine Receptor Function and Regulation in Heart Disease," Ann. N.Y. Acad. Sci., 1015:144-159 (2004).
Lehnart et al., "Defective Ryanodine Receptor Interdomain Interactions May Contribute to Intracellular $Ca^{2+}$ Leak. A Novel Therapeutic Target in Heart Failure," Circulation, 111:3342-3346 (2005).
Lehnart et al., "Phosphodiesterase 4D Deficiency in the Ryanodine-Receptor Complex Promotes Heart Failure and Arrhythmias," Cell, 123:25-35 (2005).
Lehnart et al., "Sudden Death in Familial Polymorphic Ventricular Tachycardia Associated with Calcium Release Channel (Ryanodine Receptor) Leak," Circulation, 109:3208-3214 (2004).
Lehnart et al., "Calstabin deficiency, ryanodine receptors, and sudden cardiac death," Biochemical and Biophysical Research Communications, 322:1267-1279 (2004).
Lehnart et al., "Immunophilins and Coupled Gating of Ryanodine Receptors," Current Topics in Medicinal Chemistry, 3:1383-1391 (2003).
Lehnart et al., "Phosphodiesterase 4D Associates with the Cardiac Calcium Release Channel (Ryanodine Receptor) and Protects from Hypertrophy and Heart Failure," Circulation, 110(17) Suppl. S:227-228 (2004).
Lehnart et al., "Leaky $Ca^{2+}$ release channel/ryanodine receptor 2 causes seizures and sudden cardiac death in mice," J. Clin. Invest., 118(6):2230-2245 (2008).

(56) References Cited

OTHER PUBLICATIONS

Leistad et al., "Atrial Contractile Dysfunction After Short-term Atrial Fibrillation is Reduced by Verapamil but Increased by BAY K8644," Circulation, 93:1747-1754 (1996).
Lesh et al., "Anti-Ryanodine Receptor Antibody Binding Sites in Vascular and Endocardial Endothelium," Circ Res, 72:481-488 (1993).
Lévai, "Oxazepines and Thiazepines, VI. A Convenient Synthesis of Benzothiazepine Sulfoxides," Acta Chim. Acad. Sci. Hung., 102:141-142 (1979).
Levin et al., "Reversal of Chronic Ventricular Dilation in Patients with End-Stage Cardiomyopathy by Prolonged Mechanical Unloading," Circulation, 91:2717-2720 (1995).
Levy et al., "Long-Term Trends in the Incidence of and Survival with Heart Failure," N Engl J Med, 347(18):1397-1402 (2002).
Lisy et al., "New Cardioprotective Agent K201 is Natriuretic and Glomerular Filtration Rate Enhancing," Circulation, 113:246-251 (2006).
Liu et al., "Crosstalk between the cAMP and Inositol Trisphosphate-Signalling Pathways in Pancreatic β-Cells," Arch Biochem Biophys, 334(2):295-302 (1996).
Lorenz et al., "TOR Mutations Confer Rapamycin Resistance by Preventing Interaction with FKBP12-Rapamycin," J Biol Chem, 270(46):27531-27537 (1995).
Loughrey et al., "K201 modulates excitation—contraction coupling and spontaneous $Ca^{2+}$ release in normal adult rabbit ventricular cardiomyocytes," Cardiovascular Research, 76:236-246 (2007).
Lunde et al., "Contraction and Intracellular $Ca^{2+}$ Handling in Isolated Skeletal Muscle of Rats with Congestive Heart Failure," Circ Res, 88:1299-1305 (2001).
Lunde et al., "Contractile properties of in situ perfused skeletal muscles from rats with congestive heart failure," Journal of Physiology, 540(2):571-580 (2002).
MacDougall et al., "Identification of the major protein phosphatases in mammalian cardiac muscle which dephosphorylate phospholamban," Eur. J. Biochem., 196:725-734 (1991).
MacFarlane et al., "Cellular basis for contractile dysfunction in the diaphragm from a rabbit infarct model of heart failure," Am J Physiol Cell Physiol 278:C739-C746 (2000).
Mackenzie et al., "The role of inositol 1,4,5-triphosphate receptors in $Ca^{2+}$ signaling and the generation of arrhythmias in rat atrial myocytes," J. Physiol, 541(2):395-409 (2002).
Mancini et al., "Contribution of Skeletal Muscle Atrophy to Exercise Intolerance and Altered Muscle Metabolism in Heart Failure," Circulation, 85:1364-1373 (1992).
Manzur et al., "A severe clinical and pathological variant of central core disease with possible autosomal recessive inheritance," Neuromuscular Disorders, 8:467-473 (1998).
Marban et al., "Mechanisms of Arrhythmogenic Delayed and Early Afterdepolarizations in Ferret Ventricular Muscle," J. Clin. Invest., 78:1185-1192 (1986).
Marks, "Clinical Implications of Cardiac Ryanodine Receptor/Calcium Release Channel Mutations Linked to Sudden Cardiac Death," Circulation, 106:8-10 (2002).
Marks et al., "Involvement of the Cardiac Ryanodine Receptor/Calcium Release Channel in Catecholaminergic Polymorphic Ventricular Tachycardia," Journal of Cellular Physiology, 190:1-6 (2002).
Marks et al., "Progression of Heart Failure. Is Protein Kinase a Hyperphosphorylation of the Ryanodine Receptor a Contributing Factor?," Circulation, 105:272-275 (2002).
Marks, "Ryanodine Receptors, FKBP12, and Heart Failure," Frontiers in Bioscience, 7:d970-977 (2002).
Marks, "A Guide for the Perplexed. Towards an Understanding of the Molecular Basis of Heart Failure," Circulation, 107:1456-1459 (2003).
Marks, "Cardiac Intracellular Calcium Release Channels. Role in Heart Failure," Circulation Research, 87:8-11 (2000).
Marks, "Cellular Functions of Immunophilins," Physiological Reviews, 76(3):631-649 (1996).
Marks, "Ryanodine Receptors/Calcium Release Channels in Heart Failure and Sudden Cardiac Death," J Mol Cell Cardiol, 33:615-624 (2001).
Marks, "Arrhythmias of the heart: beyond ion channels," Nature Medicine, 9(3):263-264 (2003).
Marks, "Calcium and the heart: a question of life and death," J. Clin. Invest., 111(5):597-600 (2003).
Marks, "Calcium Channels Expressed in Vascular Smooth Muscle," Circulation, 86(Suppl III):III-61-III-67 (1992).
Marks, "Immunophilin Modulation of Calcium Channel Gating," Methods, 9:177-187 (1996).
Marks, "Intracellular calcium-release channels: regulators of cell life and death," Am. J. Physiol., 272:H597-H605 (1997).
Marks et al., "Molecular cloning and characterization of the ryanodine receptor/junctional channel complex cDNA from skeletal muscle sarcoplasmic reticulum," Proc. Natl. Acad. Sci. USA, 86:8683-8687 (1989).
Marks et al., "Regulation of Ryanodine Receptors via Macromolecular Complexes: A Novel Role for Leucine/Isoleucine Zippers," Trends Cardiovascular Med, 12:166-170 (2002).
Marks et al., "Surface Topography Analysis of the Ryanodine Receptor/Junctional Channel Complex Based on Proteolysis Sensitivity Mapping," J Biol Chem, 265(22):13143-13149 (1990).
Marks et al., "The Ryanodine Receptor/Junctional Channel Complex is Regulated by Growth Factors in a Myogenic Cell Line," The Journal of Cell Biology, 114(2):303-312 (1991).
Maron et al., "Recommendations for Physical Activity and Recreational Sports Participation for Young Patients with Genetic Cardiovascular Diseases," Circulation, 109:2807-2816 (2004).
Marx et al., "Requirement of a Macromolecular Signaling Complex for β Adrenergic Receptor Modulation of the KCNQ1-KCNE1 Potassium Channel," Science, 295:496-499 (2002).
Marx et al., "Coupled Gating Between Cardiac Calcium Release Channels (Ryanodine Receptors)," Circ Res, 88:1151-1158 (2001).
Marx et al., "Regulation of the ryanodine receptor in heart failure," Basic Res Cardiol, 97 Suppl. 1:1/49-1/51 (2002).
Marx et al., "Phosphorylation-dependent Regulation of Ryanodine Receptors: A Novel Role for Leucine/Isoleucine Zippers," The Journal of Cell Biology, 153(4):699-708 (2001).
Marx et al., "PKA Phosphorylation Dissociates FKBP12.6 from the Calcium Release Channel (Ryanodine Receptor): Defective Regulation in Failing Hearts," Cell, 101:365-376 (2000).
Marx et al., "Coupled Gating Between Individual Skeletal Muscle $Ca^{2+}$ Release Channels (Ryanodine Receptors)," Science, 281(5378):818-821 (1998).
Masumiya et al., "Localization of the 12.6-kDa FK506-binding Protein (FKBP12.6) Binding Site to the NH2-terminal Domain of the Cardiac $Ca^{2+}$ Release Channel (Ryanodine Receptor)," J Biol Chem, 278(6):3786-3792 (2003).
McCartney et al., "Cloning and Characterization of A-kinase Anchor Protein 100 (AKAP100)," J Biol Chem, 270(16):9327-9333 (1995).
McPhie et al., "Structure of the Hormone Binding Domain of Human β1 Thyroid Hormone Nuclear Receptor: Is it an α/β Barrell?," Biochemistry, 32:7460-7465 (1993).
Meissner, "Ryanodine Receptor/$Ca^{2+}$ Release Channels and Their Regulation by Endogenous Effectors," Annu. Rev. Physiol., 56:485-508 (1994).
Merit-HF Study Group, "Effect of metoprolol CR/XL in chronic heart failure: Metoprolol CR/XL Randomised Intervention Trial in Congestive Heart Failure (MERIT-HF)," The Lancet, 353:2001-2007 (1999).
Meurs et al., "A cardiac myosin binding protein C mutation in the Main Coon cat with familial hypertrophic cardiomyopathy," Human Molecular Genetics, 14(23):3587-3593 (2005).
Meurs, "Boxer dog cardiomyopathy: an update," Vet Clin Small Anim, 34:1235-1244 (2004).
Miller et al., "Manganese alters mitochondrial integrity in the hearts of swine marginally deficient in magnesium," BioFactors, 20:85-96 (2004).
Minotti et al., "Impaired Skeletal Muscle Function in Patients with Congestive Heart Failure," J. Clin. Invest., 88:2077-2082 (1991).
Mitchell et al., "Measurement of heart rate and Q-T interval in the conscious mouse," Am. J. Physiol., 274:H747-H751 (1998).

(56) References Cited

OTHER PUBLICATIONS

Mitchell et al., "Ryanodine Receptor Type I and Nicotinic Acid Adenine Dinucleotide Phosphate Receptors Mediate $Ca^{2+}$ Release from Insulin-containing Vesicles in Living Pancreatic β-Cells (MIN6)," J Biol Chem, 278(13):11057-11064 (2003).
Moghadam, "Heritability of sudden death syndrome and its associated correlations to ascites and body weight in broilers," British Poultry Science, 46(1):54-57 (2005).
Mohler et al., "Ankyrin-B mutation causes type 4 long-QT cardiac arrhythmia and sudden cardiac death," Nature, 421:634-639 (2003).
Moise, "Inherited arrhythmias in the dog: potential experimental models of cardiac disease," Cardiovascular Research, 44(1):37-46 (1999).
Mongillo et al., "Fluorescence Resonance Energy Transfer-Based analysis of cAMP dynamics in Live Neonatal Rat Cardiac Myocytes Reveals Distinct Functions of Compartmentalized Phosphodiesterases," Cir. Res. 95:67-75 (2004).
Morgan et al., "Abnormal Intracellular Calcium Handling, a Major Cause of Systolic and Diastolic Dysfunction in Ventricular Myocardium from Patients with Heart Failure," Circulation, 81(Suppl. II):III-21-III-32 (1990).
Morillo et al., "Chronic Rapid Atrial Pacing. Structural, Functional, and Electrophysiological Characteristics of a New Model of Sustained Atrial Fibrillation," Circulation. 91:1588-1595 (1995).
Morita et al., "Ca channel blocking activity of JTV-519, a novel protective drug to cytotoxicity," Neuroscience Research 31, Suppl. 1:S65-S65 (1998).
Moschella et al., "Inositol 1,4,5-Trisphosphate Receptor Expression in Cardiac Myocytes," J Cell Biol, 120(5):1137-1146 (1993).
Most et al., "Sealing the leak, healing the heart," Nature Medicine, 9(8):993-994 (2003).
Näbauer et al., "Regulation of Calcium Release is Gated by Calcium Current, not Gating Charge, in Cardiac Myocytes," Science, 244(4906):800-803 (1989).
Nair et al., "Synthesis & Reactions of Benz[1,4]thiazepine Derivatives," Indian Journal of Chemistry, 7:862-865 (1969).
Nakai et al., "Functional nonequality of the cardiac and skeletal ryanodine receptors," Proc. Natl. Acad. Sci. USA, 94:1019-1022 (1997).
Nakamura et al., "Reversal of Cisplatin Resistance by the 1,4-Benzothiazepine Derivative, JTV-519," Jpn. J. Cancer Res., 92:597-602 (2001).
Nakamura et al., "Parasitic Females of *Strongyloides papillosus* as a Pathogenetic Stage for Sudden Cardiac Death in Infected Lambs," J. Vet. Med. Sci., 56(4):723-727 (1994).
Nakaya et al., "Inhibitory effects of JTV-519, a novel cardioprotective drug, on potassium currents and experimental atrial fibrillation in guinea-pig hearts," British Journal of Pharmacology, 131:1363-1372 (2000).
Neumann et al., "Increased Expression of Cardiac Phosphatases in Patients with End-Stage Heart Failure," J Mol Cell Cardiol, 29:265-272 (1997).
Nousiainen et al., "Cardiac arrhythmias in the differential diagnosis of epilepsy," J Neurol, 236:93-96 (1989).
Ondrias et al., "FKBP12 Modulates Gating of the Ryanodine Receptor/Calcium Release Channel," Ann N.Y. Acad. Sci., 853:149-56 (1998).
Ondrias et al., "Single Channel Properties and Calcium Conductance of the Cloned Expressed Ryanodine Receptor/Calcium-Release Channel," Soc Gen Physiol Ser., 51:29-45 (1996).
Ono et al., "Altered interaction of FKBP12.6 with ryanodine receptor as a cause of abnormal $Ca^{2+}$ release in heart failure," Cardiovascular Research, 48:323-331 (2000).
Otsu et al., "Molecular Cloning of cDNA Encoding the $Ca^{2+}$ Release Channel (Ryanodine Receptor) of Rabbit Cardiac Muscle Sarcoplasmic Reticulum," J Biol Chem, 265(23):13472-13483 (1990).
Oyama et al., "Genomic expression patterns of cardiac tissues from dogs with dilated cardiomyopathy," Am J Vet Res, 66(7): 1140-1155 (2005).
Oyama et al., "Arrhythmogenic right ventricular cardiomyopathy in Boxer dogs is associated with calstabin 2 deficiency," Journal of Veterinary Cardiology, 10:1-10 (2008).
Packer et al., "Effect of Oral Milrinone on Mortality in Severe Chronic Heart Failure," N Engl J Med, 325:1468-1475 (1991).
Paul-Pletzer et al., "Identification of a Dantrolene-binding Sequence on the Skeletal Muscle Ryanodine Receptor," J Biol Chem, 277(38):34918-34923 (2002).
Pereira et al., "Mechanisms of $[Ca2^{2+}]$;Transient Decrease in Cardiomyopathy of *db/db* Type 2 . Diabetic Mice," Diabetes, 55:608-615 (2006).
Perreault et al., "Alterations in Contractility and Intracellular $Ca^{2+}$ Transients in Isolated Bundles of Skeletal Muscle Fibers from Rats with Chronic Heart Failure," Circ Res, 73:405-412 (1993).
Perry et al., "Targeting of Cyclic AMP Degradation to $β_2$-Adrenergic Receptors by β-Arrestins," Science, 298:834-836 (2002).
Pfammatter et al., "Cardiac arrhythmias mimicking primary neurological disorders: a difficult diagnostic situation," Acta Paediatr, 84:569-572 (1995).
Pieske et al., "$Ca^{2+}$ Handling and Sarcoplasmic Reticulum $Ca^{2+}$ Content in Isolated Failing and Nonfailing Human Myocardium," Circ Res, 85:38-46 (1999).
Pogwizd et al., "Mechanisms Underlying Spontaneous and Induced Ventricular Arrhythmias in Patients with Idiopathic Dilated Cardiomyopathy," Circulation, 98:2404-2414 (1998).
Pogwizd et al., "Arrhythmogenesis and Contractile Dysfunction in Heart Failure. Roles of Sodium-Calcium Exchange, Inward Rectifier Potassium Current, and Residual β-Adrenergic Responsiveness," Circ Res, 88:1159-1167 (2001).
Priori et al., "Clinical and Molecular Characterization of Patients with Catecholaminergic Polymorphic Ventricular Tachycardia," Circulation, 106:69-74 (2002).
Priori et al., "Mutations in the Cardiac Ryanodine Receptor Gene (*hRyR2*) Underlie Catecholaminergic Polymorphic Ventricular Tachycardia," Circulation, 103:196-200 (2001).
Protas et al., "Regional dispersion of L-type calcium current in ventricular myocytes of German shepherd dogs with lethal cardiac arrhythmias," Heart Rhythm, 2:172-176 (2005).
Ramirez et al., "Mathematical analysis of canine atrial action potentials: rate, regional factors, and electrical remodeling," Am J Physiol Heart Circ Physiol, 279:H1767-H1785 (2000).
Regitz-Zagrosek et al., "Myocardial cyclic AMP and norepinephrine content in human heart failure," European Heart Journal, 15 (Suppl. D):7-13 (1994).
Reiken et al., "PKA phosphorylation activates the calcium release channel (ryanodine receptor) in skeletal muscle: defective regulation in heart failure," The Journal of Cell Biology, 160(6):919-928 (2003).
Reiken et al., "Protein Kinase a Phosphorylation of the Cardiac Calcium Release Channel (Ryanodine Receptor) in Normal and Failing Hearts. Role of Phosphatases and Response to Isoproterenol," The Journal of Biological Chemistry, 278(1):444-453 (2003).
Reiken et al., "A Novel Excitation-Contraction (EC) Coupling Myopathy in Heart Failure Involving Both Cardiac and Skeletal Muscles," Supplement to Circulation, 104(17):II-131 (2001).
Reiken et al., "β-Blockers Restore Calcium Release Channel Function and Improve Cardiac Muscle Performance in Human Heart Failure," Circulation, 107:2459-2466 (2003).
Reiken et al., "Defective Skeletal Muscle Calcium Release Channel Function During Heart Failure," Circulation, 106(19) Supplement: II-225 (2002).
Reiken et al., "β-Adrenergic Receptor Blockers Restore Cardiac Calcium Release Channel (Ryanodine Receptor) Structure and Function in Heart Failure," Circulation, 104:2843-2848 (2001).
Reiken et al., "PKA phosphorylation of the cardiac calcium release channel (ryanodine receptor) in normal and failing hearts: role of phosphatases and response to isoproterenol," The Journal of Biological Chemistry (2002).
Reiner et al., "Skeletal Muscle Sarcoplasmic Calcium Regulation and Sudden Death Syndrome in Chickens," Br Poult Sci., 36(4):667-75 (1995).
Rensma et al., "Length of Excitation Wave and Susceptibility to Reentrant Atrial Arrhythmias in Normal Conscious Dogs," Cir. Res. 62:395-410 (1988).

(56) References Cited

OTHER PUBLICATIONS

Richter et al., "Splice variants of the cyclic nucleotide phosphodiesterase PDE4D are differentially expressed and regulated in rat tissue," Biochem. J., 388:803-811 (2005).
Rios et al., "Charge Movement and the Nature of Signal Transduction in Skeletal Muscle Excitation-Contraction Coupling," Annu. Rev. Physiol., 54:109-133 (1992).
Rios et al., "Involvement of dihydropyridine receptors in excitation-contraction coupling in skeletal muscle," Nature, 325:717-720 (1987).
Rosemblit et al., "Intracellular Calcium Release Channel Expression during Embryogenesis," Developmental Biology, 206:163-177 (1999).
Ruehr et al., "Targeting of Protein Kinase a by Muscle a Kinase-anchoring Protein (mAKAP) Regulates Phosphorylation and Function of the Skeletal Muscle Ryanodine Receptor," the Journal of Biological Chemistry, 278(27):24831-24836 (2003).
Salama et al., "Mouse models of long QT syndrome," J Physiol, 578(1): 43-53 (2007).
Schneider et al., "Voltage Dependent Charge Movement in Skeletal Muscle: a Possible Step in Excitation-Contraction Coupling," Nature, 242:244-246 (1973).
Schoenmakers et al., "Chelator: An Improved Method for Computing Metal Ion Concentrations in Physiological Solutions," BioTechniques, 12(6):870-879 (1992).
Schott et al., "Cardiac arrhythmias that masquerade as epilepsy," British Medical Journal, 1:1454-1457 (1977).
Schotten et al., "Electrical and Contractile Remodeling During the First Days of Atrial Fibrillation Go Hand in Hand," Circulation, 107:1433-1439 (2003).
Semsarian et al., "The L-type calcium channel inhibitor diltiazem prevents cardiomyopathy in a mouse model," J. Clin. Invest., 109(8):1013-1020 (2002).
Sen et al., "Inotropic and Calcium Kinetic Effects of Calcium Channel Agonist and Antagonist in Isolated Cardiac Myocytes From Cardiomyopathic Hamsters," Cir. Res., 67:599-608 (1990).
Sette et al., "Phosphorylation and Activation of a cAMP-specific Phosphodiesterase by the cAMP-dependent Protein Kinase," The Journal of Biological Chemistry, 271(28):16526-16534 (1996).
Sette et al., "The ratPDE3/IVd Phosphodiesterase Gene Codes for Multiple Proteins Differentially Activated by cAMP-dependent Protein Kinase," The Journal of Biological Chemistry, 269(28):18271-18274 (1994).
Shannon et al., "Elevated Sarcoplasmic Reticulum $Ca^{2+}$ Leak in Intact Ventricular Myocytes From Rabbits in Heart Failure," Cir. Res., 93:592-594 (2003).
Shao et al., "Dyssynchronous (non-uniform) $Ca^{2+}$ release in myocytes from streptozotocin-induced diabetic rats," J Mol Cell Cardiol, 42(1):234-246 (2007).
Shibata, "264W94 Glaxo Wellcome," Current Opinion in Cardiovascular, Pulmonary & Renal Investigational Drugs, 1(2):276-278 (1999).
Shinohara et al., "A Synthesis of Mono- and Dimethoxy-1,2,3,4-tetrahydroisoquinolines via Pummerer Reaction: Effects of Methoxyl Groups on Intramolecular Cyclization," Chem. Pharm. Bull., 46(6):918-927 (1998).
Shirokova et al., "Local calcium release in mammalian skeletal muscle," Journal of Physiology, 512(2):377-384 (1998).
Shiroshita-Takeshita et al., "Atrial Fibrillation: Basic Mechanisms, Remodeling and Triggers," J Interv Card Electrophysiol., 13(3):181-193 (2005).
Shou et al., "Cardiac defects and altered ryanodine receptor function in mice lacking FKBP12," Nature, 391:489-492 (1998).
Shridhar et al., "Antiinflammatory Agents: Part VII—Synthesis of Some New Methyl 2,3-Dihydro-1,4- & -1,5-benzothiazepinone-2-acetates," Indian Journal of Chemistry, 22B:300-302 (1983).
Shtifman et al., "Interdomain Interactions within Ryanodine Receptors Regulate $Ca^{2+}$ Spark Frequency in Skeletal Muscle," J. Gen. Physiol., 119:15-31 (2002).
Song et al., "ATP promotes development of afterdepolarizations and triggered activity in cardiac myocytes," Am J Physiol Heart Circ Physiol, 267:H2005-H2011 (1994).
Sonnleitner et al., "Gating of the skeletal calcium release channel by ATP is inhibited by protein phosphatase 1 but not by $Mg^{2+}$," Cell Calcium, 21(4):283-290 (1997).
Sorensen et al., "Exercise blood flow and microvascular distensibility in skeletal muscle normalize after heart transplantation," Clin Transplantation, 13:410-419 (1999).
Special Report, "Preliminary Report: Effect of Encainide and Flecainide on Mortality in a Randomized Trial of Arrhythmia Suppression after Myocardial Infarction," N Engl J Med, 321:406-412 (1989).
Stevenson et al., "Sudden Death Prevention in Patients with Advanced Ventricular Dysfunction," Circulation, 88(6):2953-2961 (1993).
Still et al., "The Behavior of Thiochromanone and Isothiochromanone Sulfoxides in the Schmidt Reaction: Isolation of a Novel Azide Product from Thiochromone Sulfone," Can. J. Chem., 53:276-282 (1975).
Stratton et al., "Effects of Cardiac Transplantation on Bioenergetic Abnormalities of Skeletal Muscle in Congestive Heart Failure," Circulation, 89:1624-1631 (1994).
Suissa et al., "Bronchodilators and Acute Cardiac Death," Am. J. Respir. Crit. Care Med., 154(6):1598-1602 (1996).
Suko et al., "Phosphorylation of serine 2843 in ryanodine receptor-calcium release channel of skeletal muscle by cAMP-, cGMP- and CaM-dependent protein kinase," Biochim Biophys Acta., 1175(2):193-206 (1993).
Sullivan et al., "Exercise Intolerance in Patients with Chronic Heart Failure," Progress in Cardiovascular Diseases, 38(1):1-22 (1995).
Sun et al., "Cellular Mechanisms of Atrial Contractile Dysfunction Caused by Sustained Atrial Tachycardia," Circulation, 98:719-727 (1998).
Swan et al., "Calcium Channel Antagonism Reduces Exercise-Induced Ventricular Arrhythmias in Catecholaminergic Polymorphic Ventricular Tachycardia Patients with RyR2 Mutations," J Cardiovasc Electrophysiol, 16:162-166 (2005).
Swan et al., "Arrhythmic Disorder Mapped to Chromosome 1q42-q43 Causes Malignant Polymorphic Ventricular Tachycardia in Structurally Normal Harts," J Am Coll Cardiol, 34:2035-2042 (1999).
Szabó et al., "Synthesis and spectroscopic investigations of 1,4-benzothiazephine derivatives," Magyar Kemiai Folyoirat, 93(6):269-276 (1987) (in Hungarian and English).
Szabó et al., "Synthesis and Transformation of 4,5-Dihydro-1,4-benzothiazepin-3(2H)—one Derivatives," Magyar Kemiai Folyoirat, 93(3):139-144 (1987) (in Hungarian and English).
Szabó et al., "Synthesis and Transformations of 4,5-Dihydro-1,4-benzothiazepin-3(2H)-one Derivatives," Chemische Berichte, 119(9):2904-2913 (1986).
Szabó et al., Synthesis and spectroscopic investigations of 1,4-benzothiazepine derivatives, Can. J. Chem., 65:175-181 (1987).
Takasawa et al., "Cyclic ADP-ribose and Inositol 1,4,5-Trisphosphate as Alternate Second Messengers for Intracellular $Ca^{2+}$ Mobilization in Normal and Diabetic β-Cells," J Biol Chem, 273(5):2497-2500 (1998).
Takeshima et al., "Primary structure and expression from complementary DNA of skeletal muscle ryanodine receptor," Nature, 339:439-445 (1989).
Tanabe et al., "Regions of the skeletal muscle dihydropyridine receptor critical for excitation-contraction coupling," Nature, 346:567-569 (1990).
Taskén et al., "Phosphodiesterase 4D and Protein Kinase A Type II Constitute a Signaling Unit in the Centrosomal Area," The Journal of Biological Chemistry, 276(25):21999-22002 (2001).
Taur et al., "The Cardiac Ryanodine Receptor (RyR2) and its Role in Heart Disease," Cardiology in Review, 13:142-146 (2005).
Tester et al., "Compendium of cardiac channel mutations in 541 consecutive unrelated patients referred for long QT syndrome genetic testing," Heart Rhythm, 2:507-517 (2005).
Tester et al., "Targeted Mutational Analysis of the *RyR2*-Encoded Cardiac Ryanodine Receptor in Sudden Unexplained Death: A

(56) References Cited

OTHER PUBLICATIONS

Molecular Autopsy of 49 Medical Examiner/Coroner's Cases," Mayo Clin Proc., 79(11):1380-1384 (2004).
Tieleman et al., "Verapamil Reduces Tachycardia-Induced Electrical Remodeling of the Atria," Circulation, 95:1945-1953 (1997).
Timerman et al., "The Calcium Release Channel of Sarcoplasmic Reticulum is Modulated by FK-506-binding Protein," the Journal of Biological Chemistry, 268(31):22992-22999 (1993).
Timerman et al., "The Ryanodine Receptor from Canine Heart Sarcoplasmic Reticulum is Associated with a Novel FK-506 Binding Protein," Biochem. Biophys. Res. Commun., 198(2):701-706 (1994).
Timmermans et al, "Immediate Reinitiation of Atrial Fibrillation Following Internal Atrial Defibrillation," J Cardiovasc Electrophysiol, 9:122-128 (1998).
Tipton et al., "My Child Just Fainted: no. Big Deal or Sudden-Death Warning?," Emerg Med Serv. 33(7):41-45 (2004).
Tomaselli et al., "What Causes Sudden Death in Heart Failure?," Circ Res, 95:754-763 (2004).
Tse et al., "JTV-519 Japan Tobacco," Curr Opin Investig Drugs, 2(7):936-939 (2001).
Tsuji et al., "Sudden Cardiac Death in Calves with Experimental Heavy Infection of *Strongyloides papillosus*," J. Vet. Med. Sci., 54(6):1137-1143 (1992).
Tunwell et al., "H. Sapiens mRNA for ryanodine Receptor 2," GenBank Database, Accession No. X98330 (Sep. 9, 1996).
Tunwell et al., "The Human Cardiac Muscle Ryanodine Receptor-Calcium Release Channel: Identification, Primary Structure and Topological Analysis," Biochem. J., 318(2):477-487 (1996).
Valdivia et al., "Rapid Adaptation of Cardiac Ryanodine Receptors: Modulation by $Mg^{2+}$ and Phosphorylation," Science, 267:1997-2000 (1995).
van Rooij et al., "MCIP1 Overexpression Suppresses Left Ventricular Remodeling and Sustains Cardiac Function After Myocardial Infarction," Circ Res., 94:e18-e26 (2004).
Varadi et al., "Dynamic Imaging of Endoplasmic Reticulum $Ca^{2+}$ Concentration in Insulin-Secreting MIN6 Cells Using Recombinant Targeted Cameleons. Roles of Sarco(endo)plasmic Reticulum $Ca^{2+}$-ATPase (SERCA)-2 and Ryanodine Receptors," Diabetes, 51 (Suppl 1):S190-201 (2002).
Verde et al., "Characterization of the cyclic nucleotide phosphodiesterase subtypes involved in the regulation of the L-type $Ca^{2+}$ current in rat ventricular myocytes," Br J Pharmacol, 127(1):65-74 (1999).
Vest et al., "Defective Cardiac Ryanodine Receptor Regulation During Atrial Fibrillation," Circulation, 111:2025-2032 (2005).
Vignola, "PDE4 inhibitors in COPD—a more selective approach to treatment," Respir Med, 98(6):495-503 (2004).
von Altrock et al., "Sudden Deaths in Taking Blood Samples from Fattening Swine Herds—Experiences from Practice," Berl Munch Tierarztl Wochenschr, 112(3):86-90 (1999).
Wang et al., "Regional and functional factors determining induction and maintenance of atrial fibrillation in dogs," Am. J. Physiol., 271:H148-H158 (1996).
Wang et al., "Cloning and characterization of novel PDE4D isoforms PDE4D6 and PDE4D7," Cellular Signalling, 15:883-891 (2003).
Wang et al., "Retinoic acid stimulates annexin-mediated growth plate chondrocyte mineralization," The Journal of Cell Biology, 157(6):1061-1069 (2002).
Wang et al., "Physical Training Alters the Pathogenesis of Pacing-Induced Heart Failure through Endothelium-Mediated Mechanisms in Awake Dogs," Circulation, 96:2683-2692 (1997).
Wang et al., "Annexin-mediated $Ca^{2+}$ Influx Regulates Growth Plate Chondrocyte Maturation and Apoptosis," J Biol Chem, 278(6):3762-3769 (2003).
Wang et al., "Effects of Flecainide and Quinidine on Human Atrial Action Potentials," Circulation, 82:274-283 (1990).
Ward et al., "Defects in ryanodine receptor calcium release in skeletal muscle from post-myocardial infarct rats," The FASEB Journal, 17:1517-1519 (2003).

Wehrens et al., "$Ca^{2+}$/Calmodulin-Dependent Protein Kinase II Phosphorylation Regulates the Cardiac Ryanodine Receptor," Circ Res., 94:e61-e70 (2004).
Wehrens et al., "Enhancing calstabin binding to ryanodine receptors improves cardiac and skeletal muscle function in heart failure," Proc Natl Acad Sci USA, 102(27):9607-9612 (2005).
Wehrens et al., "FKBP12.6 Deficiency and Defective Calcium Release Channel (Ryanodine Receptor) Function Linked to Exercise-Induced Sudden Cardiac Death," Cell, 113:829-840 (2003).
Wehrens et al., "Molecular determinants of altered contractility in heart failure," Ann Med, 36 (Suppl 1):70-80 (2004).
Wehrens et al., "Novel Therapeutic Approaches for Heart Failure by Normalizing Calcium Cycling," Nature Reviews Drug Discovery, 3:565-574 (2004).
Wehrens et al., "Protection from Cardiac Arrhythmia Through Ryanodine Receptor-Stabilizing Protein Calstabin2," Science, 304:292-296 (2004).
Wehrens et al., "Ryanodine Receptor-Targeted Anti-Arrhythmic Therapy," Ann N Y Acad Sci, 1047:366-375 (2005).
Wehrens et al., "Sudden Unexplained Death Caused by Cardiac Ryanodine Receptor (*RyR2*) Mutations," Mayo Clin Proc, 79(11):1367-1371 (2004).
Wehrens et al., "Altered function and regulation of cardiac ryanodine receptors in cardiac disease," Trends Biochem Sci, (12):671-678 (2003).
Wehrens et al., "Intracellular Calcium Release and Cardiac Disease," Annu. Rev. Physiol., 67:69-98 (2005).
Wehrens et al., "Myocardial Disease in Failing Hearts: Defective Excitation-Contraction Coupling," Cold Spring Harb Symp Quant Biol, 67:533-541 (2002).
Wehrens et al., "Ryanodine receptor/calcium release channel PKA phosphorylation: A critical mediator of heart failure progression," Proc Natl Acad Sci USA, 103(3):511-518 (2006).
Wehrens et al., "Regulation of RYRs by phosphorylation/Dephosphorylation," Ryanodine Receptors. Structure, Function and Dysfunction in Clinical Disease, Edited by Xander H.T. Wehrens and Andrew R. Marks, Springer, pp. 155-260 (2005).
Wellens et al., "Atrioverter: An Implantable Device for the Treatment of Atrial Fibrillation," Circulation, 98:1651-1656 (1998).
Westphal et al., "Regulation of NMDA Receptors by an Associated Phosphatase-Kinase Signaling Complex," Science, 285:93-96 (1999).
Wijffels et al., "Atrial Fibrillation Begets Atrial Fibrillation," Circulation, 92:1954-1968 (1995).
Wilde et al., "Ion Channels, the QT Interval, and Arrhythmias," PACE, 20(Pt. II):2048-2051 (1997).
Wilson et al., "Exertional Fatigue Due to Skeletal Muscle Dysfunction in Patients with Heart Failure," Circulation, 87:470-475 (1993).
Wilson, "Exercise Intolerance in Heart Failure. Importance of Skeletal Muscle," Circulation, 91:559-561 (1995).
Wit et al., "Pathophysiologic mechanisms of cardiac arrhythmias," Am Heart J, 106:798-811 (1983).
Woolcott et al., "Arachidonic acid is a physiological activator of the ryanodine receptor in pancreatic β-cells," Cell Calcium, 39:529-537 (2006).
Wünsch et al., "Benzokondensierte 7-Ring-Heterocyclen, I. 2.3.4.5-Tetrahydro-1.4-benzothiazepinone-(5)," Chemische Berichte, 102:1618-1625 (1969) (English abstract).
Wünsch et al., "Benzokondensierte 7-Ring-Heterocyclen, VI. Schmidt-Reaktion an 1-Thio-chromanonen-(4) and 1-Thio-chromanon-(4)-1.1-dioxiden," Chemische Berichte, 103: 2302-2307 (1970) (English abstract).
Xiang et al., "Phosphodiesterase 4D is required for $β_2$ adrenoceptor subtype-specific signaling in cardiac myocytes," Proc Natl Acad Sci USA, 102(3):909-914 (2005).
Xin et al., "Oestrogen protects FKBP12.6 null mice from cardiac hypertrophy," Nature, 416:334-337 (2002).
Yamamoto et al., "Abnormal $Ca^{2+}$ release from cardiac sarcoplasmic reticulum in tachycardia-induced heart failure," Cardiovascular Research, 44:146-155 (1999).
Yamamoto et al., "$Ca^{2+}$-dependent dual functions of peptide C. The peptide corresponding to the $Glu^{724}$-$Pro^{760}$ region (the so-called

(56) References Cited

OTHER PUBLICATIONS determinant of excitation-contraction coupling) of the dihydropyridine receptor alpha 1 subunit II-III loop," J Biol Chem, 277(2):993-1001 (2002).
Yamamoto et al., "Peptide Probe Study of the Critical Regulatory Domain of the Cardiac Ryanodine Receptor," Biochem Biophys Res Commun, 291(4):1102-1108 (2002).
Yamamoto et al., "Spectroscope Monitoring of Local Conformational Changes during the Intramolecular Domain—Domain Interaction of the Ryanodine Receptor," Biochemistry, 41:1492-1501 (2002).
Yamamoto et al., "T-tubule Depolarization-induced Local Events in the Ryanodine Receptor, as Monitored with the Fluorescent Conformational Probe Incorporated by Mediation of Peptide A," J Biol Chem, 277(2):984-992 (2002).
Yamamoto-Hino et al., "Cloning and Characterization of Hunan Type 2 and Type 3 Inositol 1,4,5-Trisphosphate Receptors," Receptors Channels, 2:9-22 (1994).
Yamazawa et al., "Subtype specificity of the ryanodine receptor for $Ca^{2+}$ signal amplification in excitation-concentration coupling," The EMBO Journal, 15(22):6172-6177 (1996).
Yang et al., "A-kinase Anchoring Protein 100 (AKAP100) is Localized in Multiple Subcellular Compartments in the Adult Rat Heart," J Cell Biol, 142(2):511-522 (1998).
Yano et al., "Altered Stoichiometry of FKBP12.6 Versus Ryanodine Receptor as a Cause of Abnormal $Ca^{2+}$ Leak Through Ryanodine Receptor in Heart Failure," Circulation, 102:2131-2136 (2000).
Yano et al., "RyR-bound FKBP12.6 and the Modulation," Clin Calcium, 11(6):743-748 (2001).
Yano et al., "FKBP12.6-Mediated Stabilization of Calcium-Release Channel (Ryanodine Receptor) as a Novel Therapeutic Strategy Against Heart Failure," Circulation, 107:477-484 (2003).
Yaras et al., "Effects of Diabetes on Ryanodine Receptor Ca Release Channel (RyR2) and $Ca^{2+}$ Homeostasis in Rat Heart," Diabetes, 54:3082-3088 (2005).
Yaras et al., "Restoration of diabetes-induced abnormal local $Ca^{2+}$ release in cardiomyocytes in angiotensin II receptor blockade," Am J Physiol Heart Circ Physiol, 292:H912-H920 (2007).
Yu et al., "Tachycardia-Induced Change of Atrial Refractory Period in Humans: Rate Dependency and Effects of Antiarrhythmic Drugs," Circulation, 97:2331-2337 (1998).
Yue et al., "Ionic Remodeling Underlying Action Potential Changes in a Canine Model of Atrial Fibrillation," Circ Res, 81:512-525 (1997).
Zaccolo et al., "Discrete Microdomains with High Concentration of cAMP in Stimulated Rat Neonatal Cardiac Myocytes," Science, 295:1711-1715 (2002).
Zahradka et al., "Activation of MMP-2 in response to vascular injury is mediated by phosphatidylinositol 3-kinase-dependent expression of MT1-MMPp," Am J Physiol Heart Circ Physiol, 287:H2861-H2870 (2004).
Zhang et al., "Growth Hormone Promotes $Ca^{2+}$-Induced $Ca^{2+}$ Release in Insulin-Secreting Cells by Ryanodine Receptor Tyrosine Phosphorylation," Molecular Endocrinology, 18(7):1658-1669 (2004).
Zucchi et al., "The Sarcoplasmic Reticulum $Ca^{2+}$ Channel/Ryanodine Receptor: Modulation by Endogenous Effectors, Drugs and Disease States," Pharmacological Reviews, 49(1):1-51 (1997).
Non-Final Office Action mailed Aug. 7, 2001, U.S. Appl. No. 09/568,474, filed May 10, 2000.
Non-Final Office Action mailed Jan. 14, 2002, U.S. Appl. No. 09/568,474, filed May 10, 2000.
Non-Final Office Action mailed May 4, 2004, U.S. Appl. No. 10/288,606, filed Nov. 5, 2002.
Final Office Action mailed Nov. 22, 2004, U.S. Appl. No. 10/288,606, filed Nov. 5, 2002.
Non-Final Office Action mailed Jul. 11, 2005, U.S. Appl. No. 10/288,606, filed Nov. 5, 2002.
Final Office Action mailed Jan. 5, 2006, U.S. Appl. No. 10/288,606, filed Nov. 5, 2002.
Non-Final Office Action mailed Jan. 26, 2007, U.S. Appl. No. 10/288,606, filed Nov. 5, 2002.
Final Office Action mailed Oct. 5, 2007, U.S. Appl. No. 10/288,606, filed Nov. 5, 2002.
Non-Final Office Action mailed Mar. 25, 2008, U.S. Appl. No. 10/288,606, filed Nov. 5, 2002.
Non-Final Office Action mailed Apr. 27, 2005, U.S. Appl. No. 10/608,723, filed Jun. 26, 2003.
Final Office Action mailed Dec. 29, 2005, U.S. Appl. No. 10/608,723, filed Jun. 26, 2003.
Non-Final Office Action mailed Aug. 23, 2006, U.S. Appl. No. 10/608,723, filed Jun. 26, 2003.
Final Office Action mailed Feb. 16, 2007, U.S. Appl. No. 10/608,723, filed Jun. 26, 2003.
Non-Final Office Action mailed Oct. 30, 2007, U.S. Appl. No. 10/608,723, filed Jun. 26, 2003.
Final Office Action mailed Mar. 20, 2008, U.S. Appl. No. 10/608,723, filed Jun. 26, 2003.
Non-Final Office Action mailed Feb. 27, 2007, U.S. Appl. No. 10/680,988, filed Oct. 7, 2003.
Final Office Action mailed Nov. 29, 2007, U.S. Appl. No. 10/680,988, filed Oct. 7, 2003.
Non-Final Office Action mailed Mar. 19, 2008, U.S. Appl. No. 10/680,988, filed Oct. 7, 2003.
Non-Final Office Action mailed May 3, 2005, U.S. Appl. No. 10/794,218, filed Mar. 5, 2004.
Non-Final Office Action mailed Jan. 9, 2006, U.S. Appl. No. 10/794,218, filed Mar. 5, 2004.
Final Office Action mailed Aug. 23, 2006, U.S. Appl. No. 10/794,218, filed Mar. 5, 2004.
Non-Final Office Action mailed Nov. 27, 2007, U.S. Appl. No. 10/809,089, filed Mar. 25, 2004.
Non-Final Office Action mailed Sep. 4, 2008, U.S. Appl. No. 10/809,089, filed Mar. 25, 2004.
Non-final Office Action mailed Feb. 5, 2009, U.S. Appl. No. 10/809,089, filed Mar. 25, 2004.
Final Office Action mailed Aug. 5, 2009, U.S. Appl. No. 10/809,089, filed Mar. 25, 2004.
Non-Final Office Action mailed Aug. 29, 2006, U.S. Appl. No. 11/088,123, filed Mar. 23, 2005.
Final Office Action mailed Mar. 27, 2007, U.S. Appl. No. 11/088,123, filed Mar. 23, 2005.
Non-Final Office Action mailed Oct. 20, 2008, U.S. Appl. No. 11/212,309, filed Aug. 25, 2005.
Final Office Action mailed Jun. 5, 2009, U.S. Appl. No. 11/212,309, filed Aug. 25, 2005.
Non-Final Office Action mailed Oct. 20, 2008, U.S. Appl. No. 11/212,413, filed Aug. 25, 2008.
Non-Final Office Action mailed Sep. 17, 2008, U.S. Appl. No. 11/305,528, filed Dec. 16, 2005.
Supplementary European Search Report, Application. No. 04756121.2, Dec. 21, 2007.
Supplementary European Search Report, Application No. 04794052.3, Nov. 5, 2008.
Supplementary European Search Report, Application No. 05732932.8, Mar. 18, 2009.
Extended European Search Report, Application No. EP 06801887.8, Apr. 21, 2009.
Extended European Search Report, Application No. EP 09166965.5, Oct. 14, 2009.
International Search Report and Written Opinion, Application No. PCT/US2004/20474, Aug. 30, 2005.
International Search Report and Written Opinion, Application No. PCT/US2004/32550, Oct. 18, 2005.
International Search Report and Written Opinion, Application No. PCT/US2004/06971, Jun. 25, 2008.
International Search Report and Written Opinion, Application No. PCT/US2005/09495, Mar. 14, 2006.
International Search Report and Written Opinion, Application No. PCT/US2005/010055, Oct. 27, 2005.
International Preliminary Report on Patentability, Application No. PCT/US2005/010055, Oct. 4, 2007.

(56) References Cited

OTHER PUBLICATIONS

International Search Report and Written Opinion, Application No. PCT/US2005/045914, Aug. 31, 2006.
International Preliminary Report on Patentability, Application No. PCT/US2005/045914, Jun. 28, 2007.
International Search Report and Written Opinion, Application No. PCT/US2005/010056, Jun. 5, 2007.
International Preliminary Report on Patentability, Application No. PCT/US2005/010056, Oct. 4, 2007.
International Search Report and Written Opinion, Application No. PCT/US2006/032405, Dec. 7, 2007.
International Search Report and Written Opinion, Application No. PCT/US2007/009289, Aug. 14, 2008.
International Search Report and Written Opinion, Application No. PCT/US2007/009715, Aug. 21, 2008.
International Search Report and Written Opinion, Application No. PCT/US2007/012936, Oct. 28, 2008.
International Search Report and Written Opinion, Application No. PCT/US2007/012969, Jan. 10, 2008.
International Search Report and Written Opinion, Application No. PCT/US2007/018138, Aug. 26, 2008.
International Search Report and Written Opinion, Application No. PCT/US2007/018147, Sep. 8, 2008.
Non-Final Office mailed May 4, 2009, U.S. Appl. No. 11/506,285, filed Aug. 17, 2006.
International Search Report, PCT/US11/51369, mailed Feb. 2, 2012.
International Search Report, PCT/US11/046704, mailed Nov. 8, 2011.
International Search Report, PCT/US11/046693, mailed Nov. 3, 2011.
James et al., "Inhibition of SR $Ca^{2+}$ uptake: A Novel Action of the RyR2-FKBP12.6 Antagonist K201", Cardiovascular Research, Oxford University Press, GB, vol. 76, No. 2, pp. 199-201, (2007).
Roubenoff, R. "Physical Activity Inflammation and Muscle Loss", Nutrition Reviews, vol. 65, No. 12, pp. S208-S212, (2007).
Andersson D.C. et al., "Ryanodine Receptor Oxidation Causes Intracellular Calcium Leak and Muscle Weakness in Aging", Cell Metabolism, vol. 14, No. 2, pp. 196-207 (2011).
Boudet et al., Studies in the Thiazepin Series. Synthesis and Study of 6, 7-benzo-1,4-Tetrahydrothiazepin, Comptes Rendus des Seances de l'Academie des Sciences, Sede C. Sciences Chimiques, vol. 282, No. 4, pp. 249-251 (1976).
Wuensch,K.H. et al, "2,3-Dihydro-1,4-benzothiazepin-5(4H)-ones", Zeitschrift fuer Chemie, vol. 7, No. 5, p. 185-186 (1967).
J. Fauconnier et al., "Ryanodine receptor leak mediated by caspase-8 activation leads to left: ventriculare injury after myocardial ischemia-reperfusion", Proceedings of the National Academy of Sciences, vol. 108, No. 32, pp. 13258-13263 (2011).

\* cited by examiner

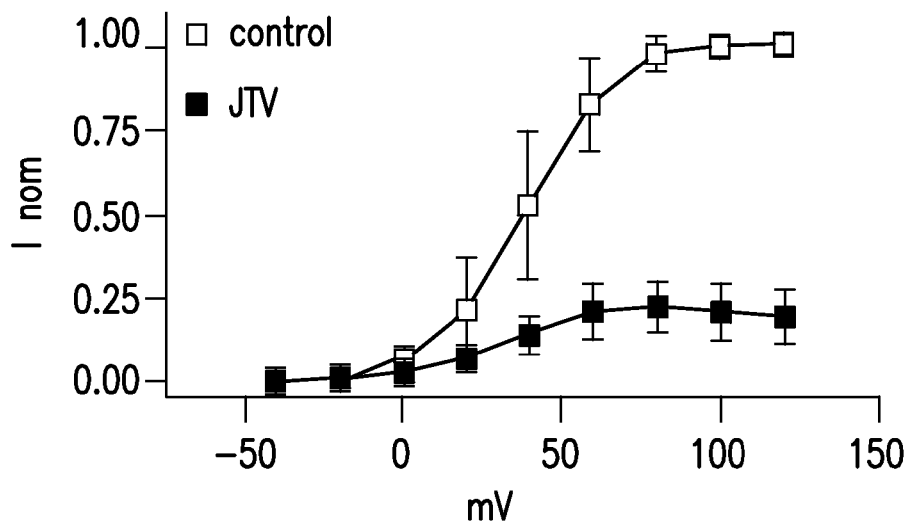
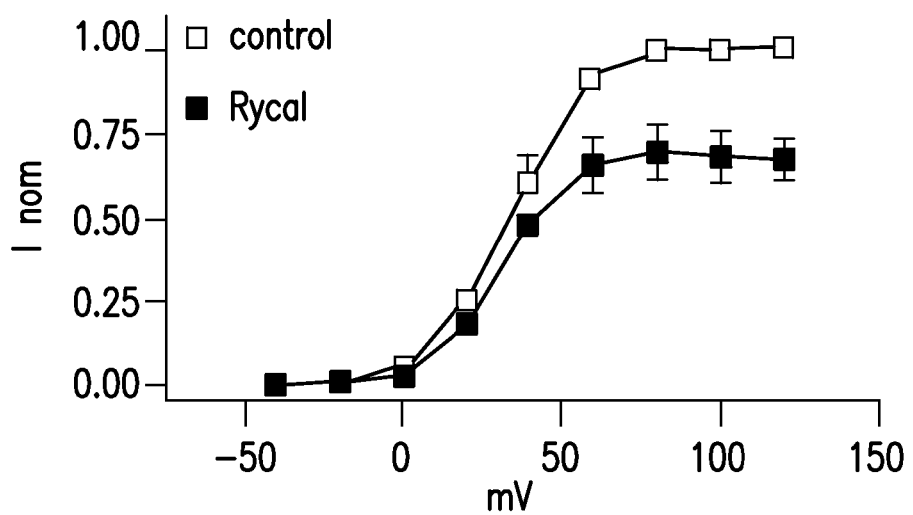
FIG. 1D

A

B

Figure 36
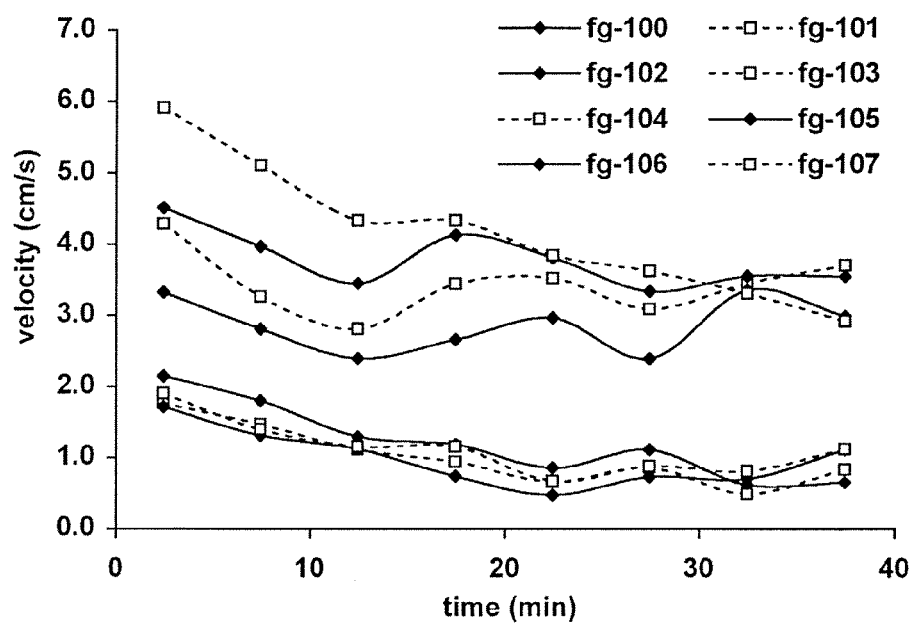
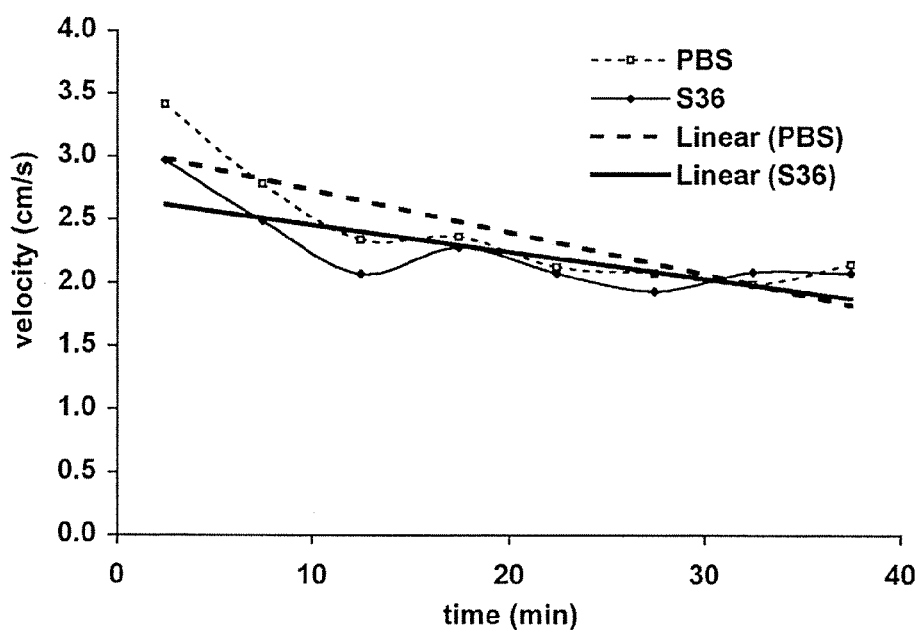

Figure 44
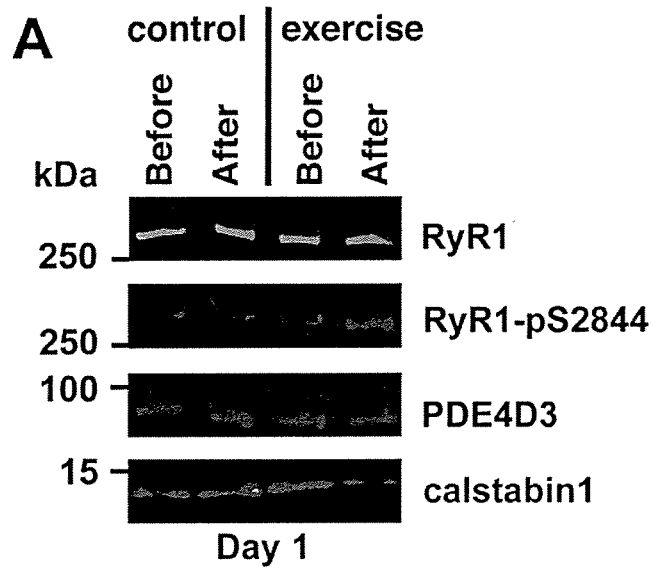
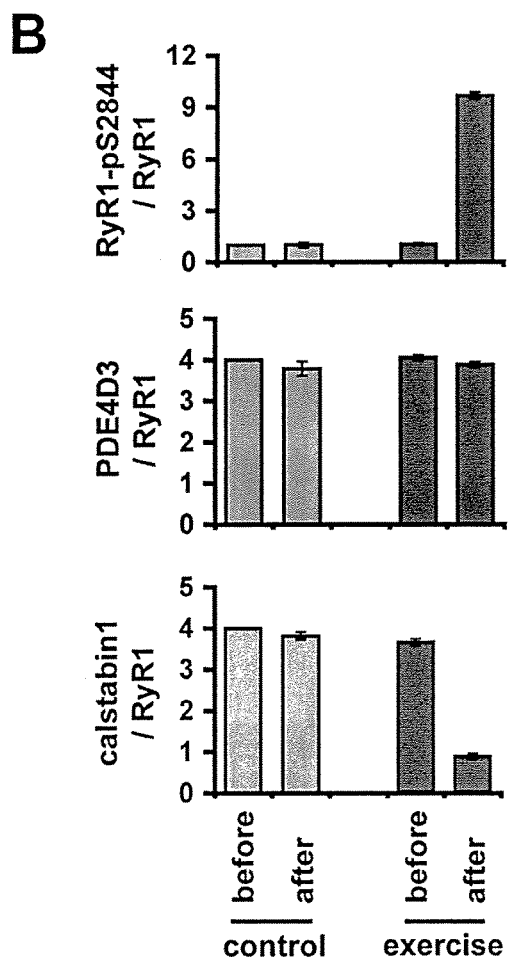

Figure 44
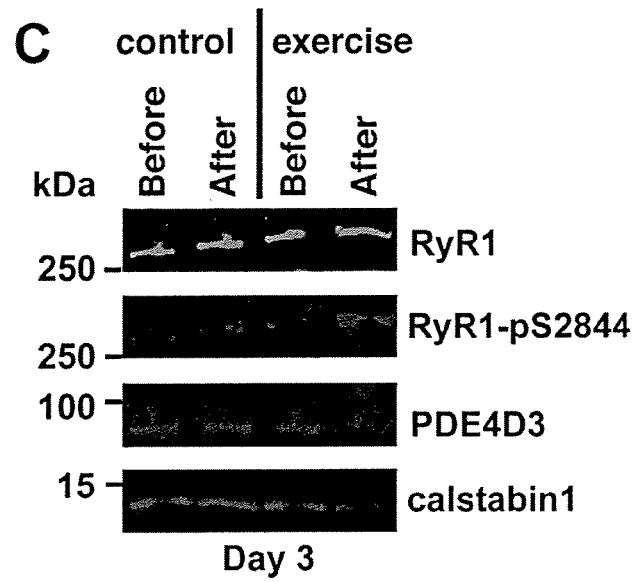
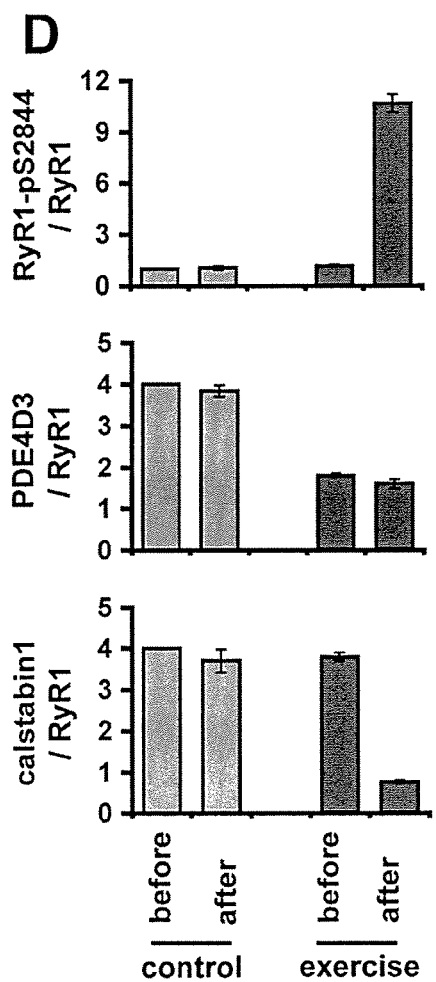

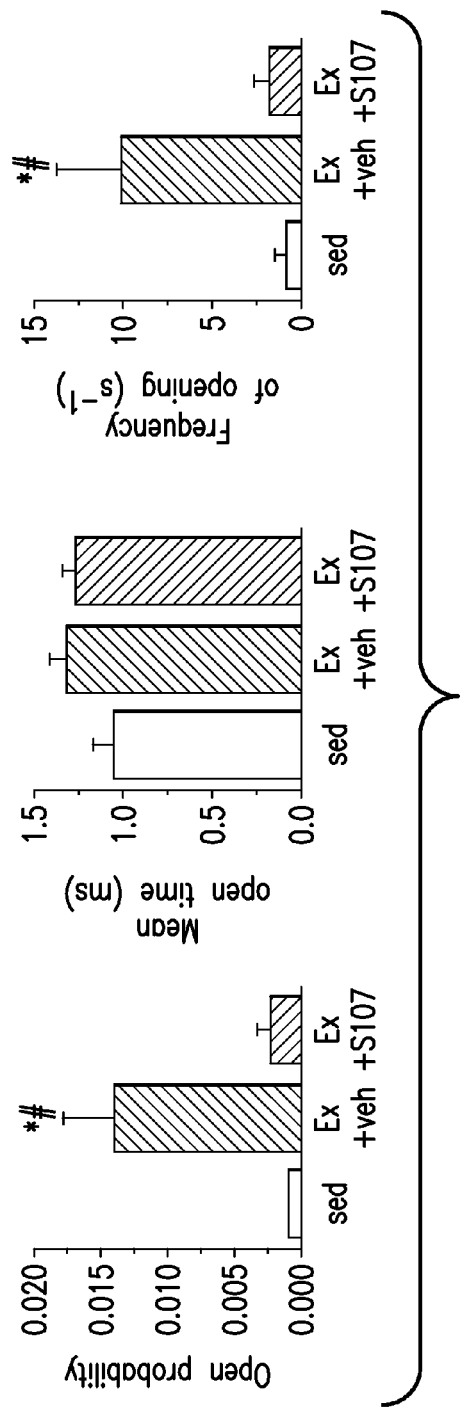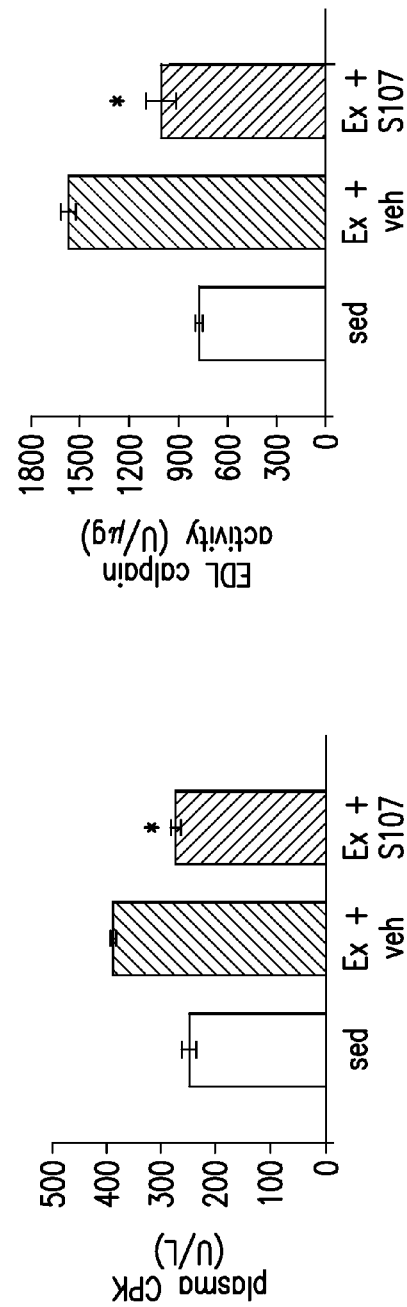

Figure 58
A 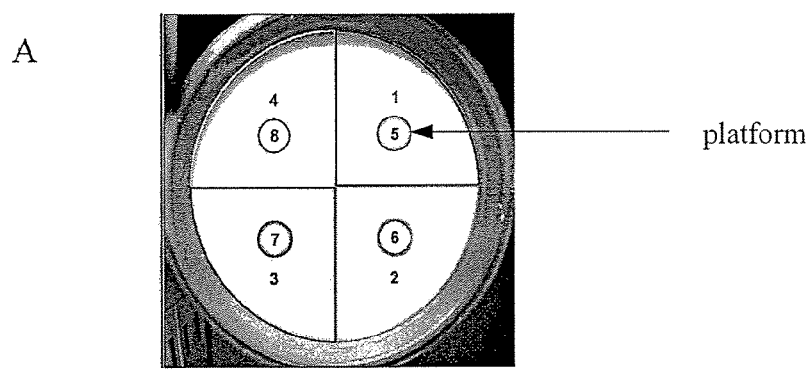
B 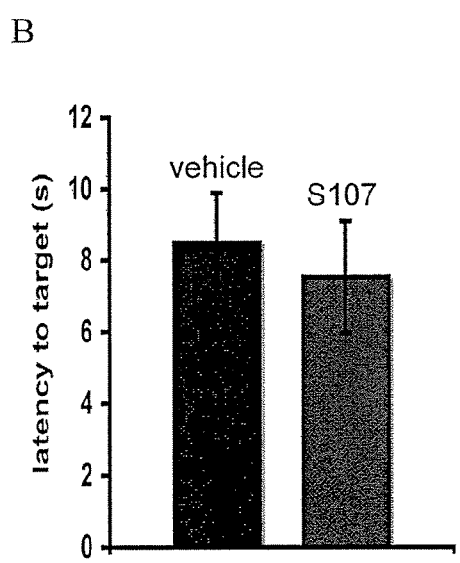
C 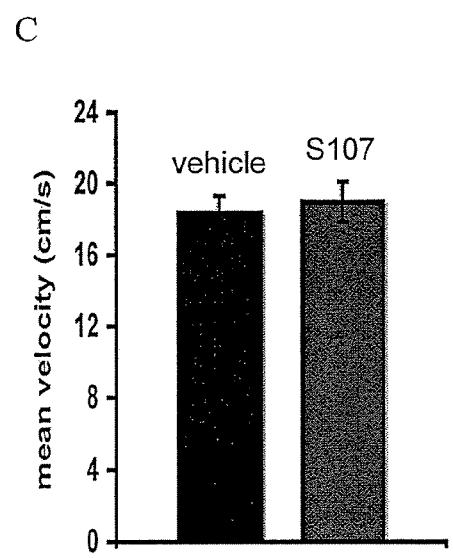

Figure 59
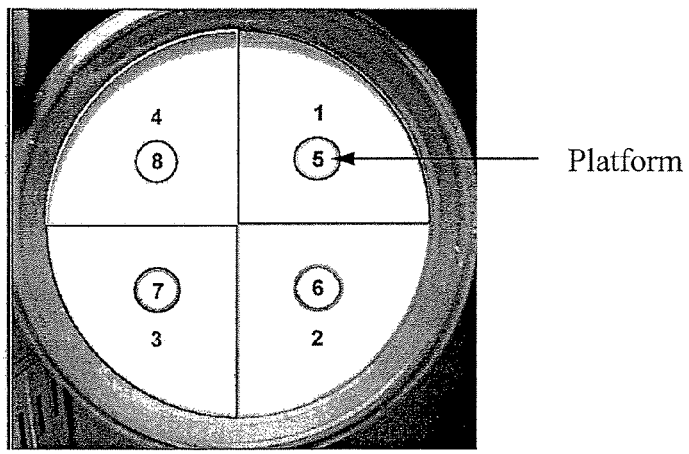
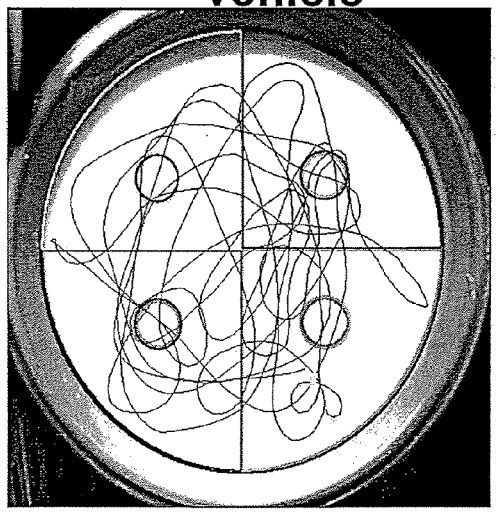
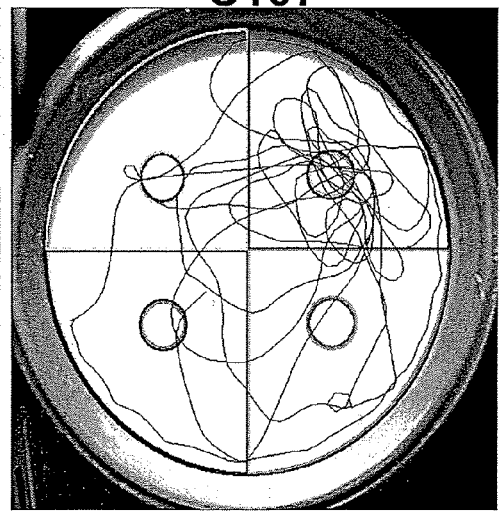

Figure 60
A 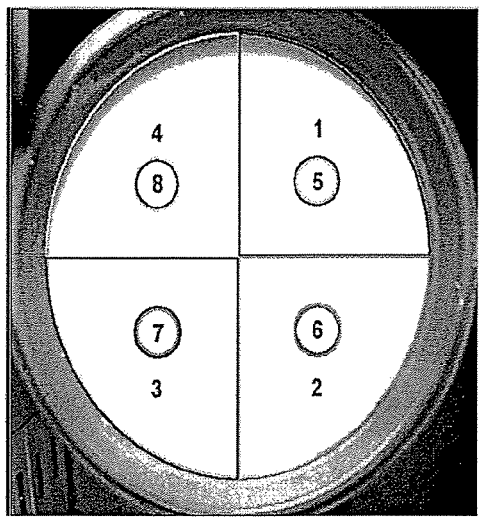
B 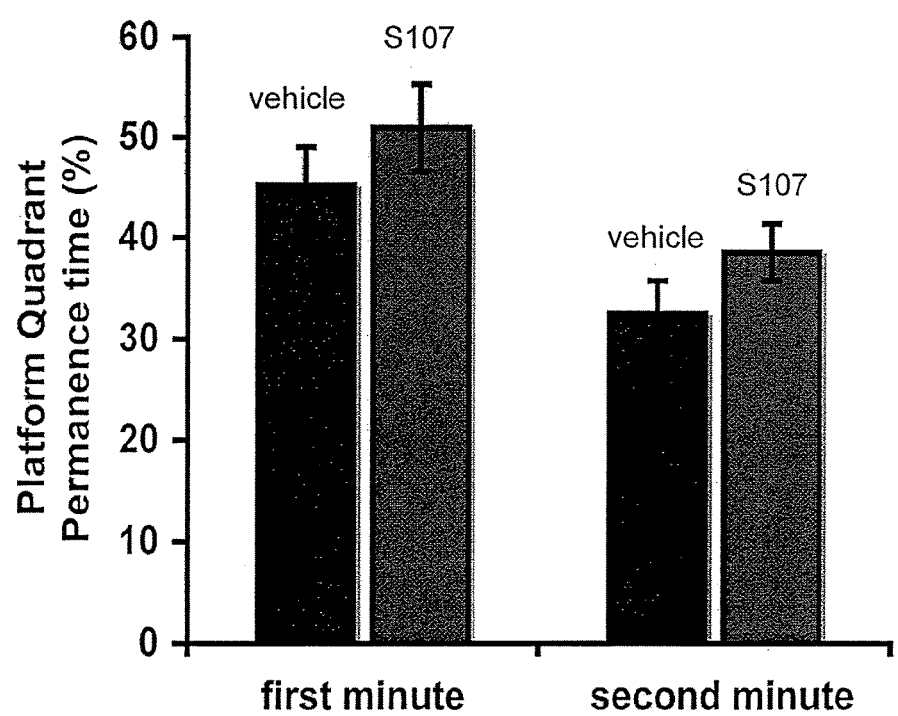

AGENTS FOR PREVENTING AND TREATING DISORDERS INVOLVING MODULATION OF THE RYANODINE RECEPTORS

CROSS-REFERENCE TO RELATED APPLICATIONS

This application is a continuation-in-part of (a) U.S. patent application Ser. No. 11/506,285, filed Aug. 17, 2006 now U.S. Pat. No. 7,879,840 and (b) a continuation-in-part of U.S. patent application Ser. No. 11/809,470, filed Jun. 1, 2007 now abandoned. Each of (a) and (b) is a continuation-in-part of U.S. patent application Ser. No. 11/212,309, filed on Aug. 25, 2005, now U.S. Pat. No. 8,022,058 which is a continuation-in-part of U.S. patent application Ser. No. 10/809,089, filed on Mar. 25, 2004, now U.S. Pat. No. 7,718,644, which is a continuation-in-part of U.S. patent application Ser. No. 10/763,498, filed on Jan. 22, 2004, now abandoned. Application (b) also claims the benefit of U.S. Application Nos. 60/810,748 filed Jun. 2, 2006 and 60/904,348 filed Feb. 28, 2007. The contents of each application mentioned above are expressly incorporated by reference herein.

GOVERNMENT INTERESTS

This invention was made with government support under grant number ARMY W911NF-05-1-0462 awarded by Defense Advanced Research Projects Agency (DARPA), Department of Defense. The government has certain rights in the invention.

FIELD OF THE INVENTION

This invention relates to compounds and their use to treat and prevent disorders and diseases associated with the ryanodine receptors that regulate calcium channel functioning in cells. More particularly, the invention discloses compounds that are related to 1,4-benzothiazepines and are useful to treat cardiac diseases and disorders, skeletal muscle diseases and disorders, as well as diseases, disorders and conditions affecting the nervous system, such as neuropathies, seizures, and disorders affecting cognitive functioning. The invention also discloses pharmaceutical compositions comprising the compounds and articles of manufacture comprising the pharmaceutical compositions.

BACKGROUND OF THE INVENTION

The sarcoplasmic reticulum (SR) functions, among other things, as a specialized intracellular calcium ($Ca^{2+}$) store. Channels in the SR called ryanodine receptors (RyRs) open and close to regulate the release of $Ca^{2+}$ from the SR into the intracellular cytoplasm of the cell. Release of $Ca^{2+}$ into the cytoplasm from the SR increases cytoplasmic $Ca^{2+}$ concentration. Open probability (Po) of the RyR receptor refers to the likelihood that the RyR channel is open at any given moment, and therefore capable of releasing $Ca^{2+}$ into the cytoplasm from the SR.

There are three types of ryanodine receptors, all of which are $Ca^{2+}$ channels: RyR1, RyR2, and RyR3. RyR1 is found predominantly in skeletal muscle as well as other tissues, RyR2 is found predominantly in the heart as well as other tissues, and RyR3 is found in the brain as well as other tissues. The RyR channels are formed by four RyR polypeptides in association with four FK506 binding proteins (FKBPs), specifically FKBP12 (calstabin1) and FKBP12.6 (calstabin2). Calstabin1 binds to RyR1, calstabin2 binds to RyR2, and calstabin1 binds to RyR3. The FKBP proteins (calstabin1 and calstabin2) bind to the RyR channel (one molecule per RyR subunit), stabilize RyR-channel functioning, and facilitate coupled gating between neighboring RyR channels, thereby preventing abnormal activation of the channel during the channel's closed state.

Protein kinase A (PKA) binds to the cytoplasmic surface of the RyR receptors. PKA phosphorylation of the RyR receptors causes partial dissociation of calstabins from RyRs. Dissociation of calstabin from RyR causes increased open probability of RyR, and therefore increased $Ca^{2+}$ release from the SR into the intracellular cytoplasm.

$Ca^{2+}$ release from the SR in skeletal muscle cells and heart cells is a key physiological mechanism that controls muscle performance, because increased concentration of $Ca^{2+}$ in the intracellular cytoplasm causes contraction of the muscle.

Excitation-contraction (EC) coupling in skeletal muscles involves electrical depolarization of the plasma membrane in the transverse tubule (T-tubule), which activates voltage-gated L-type $Ca^{2+}$ channels (LTCCs). LTCCs trigger $Ca^{2+}$ release from the SR through physical interaction with RyR1. The resulting increase in cytoplasmic $Ca^{2+}$ concentration induces actin-myosin interaction and muscle contraction. To enable relaxation, intracellular $Ca^{2+}$ is pumped back into the SR via SR $Ca^{2+}$-ATPase pumps (SERCAs), which is regulated by phospholamban (PLB) depending on the muscle fiber type.

It has been shown that disease forms that result in sustained activation of the sympathetic nervous system and increased plasma catecholamine levels cause maladaptive activation of intracellular stress pathways resulting in destabilization of the RyR1 channel closed state and intracellular $Ca^{2+}$ leak. SR $Ca^{2+}$ leak via RyR1 channels was found to deplete intracellular SR calcium stores, to increase compensatory energy consumption, and to result in significant acceleration of muscle fatigue. The stress-induced muscle defect permanently reduces isolated muscle and in vivo performance particularly in situations of increased demand.

It also has been shown that destabilization of the RyR1 closed state occurs under pathologic conditions of increased sympathetic activation and involves depletion of the stabilizing calstabin1 (FKBP12) channel subunit. Proof-of-principle experiments have shown that PKA activation as an end effector of the sympathetic nervous systems increases RyR1 PKA phosphorylation at Ser-2843 which decreases the binding affinity of calstabin1 to RyR1 and increases channel open probability.

In cardiac striated muscle, RyR2 is the major $Ca^{2+}$-release channel required for EC coupling and muscle contraction. During EC coupling, depolarization of the cardiac-muscle cell membrane during phase zero of the action potential activates voltage-gated $Ca^{2+}$ channels. $Ca^{2+}$ influx through the open voltage-gated channels in turn initiates $Ca^{2+}$ release from the SR via RyR2. This process is known as $Ca^{2+}$-induced $Ca^{2+}$ release. The RyR2-mediated, $Ca^{2+}$-induced $Ca^{2+}$ release then activates the contractile proteins in the cardiac cell, resulting in cardiac muscle contraction.

Phosphorylation of cardiac RyR2 by PKA is an important part of the "fight or flight" response that increases cardiac EC coupling gain by augmenting the amount of $Ca^{2+}$ released for a given trigger. This signaling pathway provides a mechanism by which activation of the sympathetic nervous system, in response to stress, results in increased cardiac output. PKA phosphorylation of RyR2 increases the open probability of the channel by dissociating calstabin2 (FKBP12.6) from the channel complex. This, in turn, increases the sensitivity of RyR2 to $Ca^{2+}$-dependent activation.

Despite advances in treatment, heart failure remains an important cause of mortality in Western countries. An important hallmark of heart failure is reduced myocardial contractility. In heart failure, contractile abnormalities result, in part, from alterations in the signaling pathway that allows the cardiac action potential to trigger $Ca^{2+}$ release via RyR2 channels and muscle contraction. In particular, in failing hearts, the amplitude of the whole-cell $Ca^{2+}$ transient is decreased and the duration prolonged.

Cardiac arrhythmia, a common feature of heart failure, results in many of the deaths associated with the disease. Atrial fibrillation (AF) is the most common cardiac arrhythmia in humans, and represents a major cause of morbidity and mortality. Structural and electrical remodeling—including shortening of atrial refractoriness, loss of rate-related adaptation of refractoriness, and shortening of the wavelength of re-entrant wavelets—accompany sustained tachycardia. This remodeling is likely important in the development, maintenance and progression of atrial fibrillation. Studies suggest that calcium handling plays a role in electrical remodeling in atrial fibrillation.

Approximately 50% of all patients with heart disease die from fatal cardiac arrhythmias. In some cases, a ventricular arrhythmia in the heart is rapidly fatal—a phenomenon referred to as "sudden cardiac death" (SCD). Fatal ventricular arrhythmias and SCD also occur in young, otherwise-healthy individuals who are not known to have structural heart disease. In fact, ventricular arrhythmia is the most common cause of sudden death in otherwise-healthy individuals.

Catecholaminergic polymorphic ventricular tachycardia (CPVT) is an inherited disorder in individuals with structurally normal hearts. It is characterized by stress-induced ventricular tachycardia—a lethal arrhythmia that causes SCD. In subjects with CPVT, physical exertion and/or stress induce bidirectional and/or polymorphic ventricular tachycardias that lead to SCD even in the absence of detectable structural heart disease. CPVT is predominantly inherited in an autosomal-dominant fashion. Individuals with CPVT have ventricular arrhythmias when subjected to exercise, but do not develop arrhythmias at rest. Studies have identified mutations in the human RyR2 gene, on chromosome 1q42-q43, in individuals with CPVT.

Failing hearts (e.g., in patients with heart failure and in animal models of heart failure) are characterized by a maladaptive response that includes chronic hyperadrenergic stimulation. In heart failure, chronic beta-adrenergic stimulation is associated with the activation of beta-adrenergic receptors in the heart, which, through coupling with G-proteins, activate adenylyl cyclase and thereby increase intracellular cAMP concentration. CAMP activates cAMP-dependent PKA, which has been shown to induce hyperphosphorylation of RyR2. Thus, chronic heart failure is a chronic hyperadrenergic state that results in several pathologic consequences, including PKA hyperphosphorylation of RyR2.

The PKA hyperphosphorylation of RyR2 has been proposed as a factor contributing to depressed contractile function and arrhythmogenesis in heart failure. Consistent with this hypothesis, PKA hyperphosphorylation of RyR2 in failing hearts has been demonstrated, in vivo, both in animal models and in patients with heart failure undergoing cardiac transplantation.

In failing hearts, the hyperphosphorylation of RyR2 by PKA induces the dissociation of FKBP12.6 (calstabin2) from the RyR2 channel. This causes marked changes in the biophysical properties of the RyR2 channel, including increased open probability (Po) due to an increased sensitivity to $Ca^{2+}$-dependent activation; destabilization of the channel, resulting in subconductance states; and impaired coupled gating of the channels, resulting in defective EC coupling and cardiac dysfunction. Thus, PKA-hyperphosphorylated RyR2 is very sensitive to low-level $Ca^{2+}$ stimulation, and this manifests itself as a diastolic SR $Ca^{2+}$ leak through the PKA hyperphosphorylated RyR2 channel.

The maladaptive response to stress in heart failure results in depletion of FKBP12.6 from the channel macromolecular complex. This leads to a shift to the left in the sensitivity of RyR2 to $Ca^{2+}$-induced $Ca^{2+}$ release, resulting in channels that are more active at low-to-moderate $Ca^{2+}$ concentrations. Over time, the increased "leak" through RyR2 results in resetting of the SR $Ca^{2+}$ content to a lower level, which in turn reduces EC coupling gain and contributes to impaired systolic contractility.

Additionally, a subpopulation of RyR2 that are particularly "leaky" can release SR $Ca^{2+}$ during the resting phase of the cardiac cycle, diastole. This results in depolarizations of the cardiomyocyte membrane known as delayed after-depolarizations (DADs), which are known to trigger fatal ventricular cardiac arrhythmias.

In patients with CPVT mutations in their RyR2 and otherwise structurally-normal hearts, a similar phenomenon is at work. Specifically, it is known that exercise and stress induce the release of catecholamines that activate beta-adrenergic receptors in the heart. Activation of the beta-adrenergic receptors leads to PKA hyperphosphorylation of RyR2 channels. Evidence also suggests that the PKA hyperphosphorylation of RyR2 resulting from beta-adrenergic-receptor activation renders mutated RyR2 channels more likely to open in the relaxation phase of the cardiac cycle, increasing the likelihood of arrhythmias.

Cardiac arrhythmias are known to be associated with diastolic SR $Ca^{2+}$ leaks in patients with CPVT mutations in their RyR2 and otherwise structurally-normal hearts. In these cases, the most common mechanism for induction and maintenance of ventricular tachycardia is abnormal automaticity. One form of abnormal automaticity, known as triggered arrhythmia, is associated with aberrant release of SR $Ca^{2+}$, which initiates DADs. DADs are abnormal depolarizations in cardiomyocytes that occur after repolarization of a cardiac action potential. The molecular basis for the abnormal SR $Ca^{2+}$ release that results in DADs has not been fully elucidated. However, DADs are known to be blocked by ryanodine, providing evidence that RyR2 plays a key role in the pathogenesis of this aberrant $Ca^{2+}$ release.

It has been shown that exercise-induced arrhythmias and sudden death (in patients with CPVT) result from a reduced affinity of FKBP12.6 (calstabin2) for RyR2. Additionally, it has been demonstrated that exercise activates RyR2 as a result of phosphorylation by adenosine 3',5'-monophosphate (cAMP)-dependent protein kinase (PKA). Mutant RyR2 channels, which had normal function in planar lipid bilayers under basal conditions, were more sensitive to activation by PKA phosphorylation—exhibiting increased activity (open probability) and prolonged open states, as compared with wild-type channels. In addition, PKA-phosphorylated mutant RyR2 channels were resistant to inhibition by $Mg^{2+}$, a physiological inhibitor of the channel, and showed reduced binding to FKBP12.6 (aka calstabin2, which stabilizes the channel in the closed state). These findings indicate that, during exercise, when the RyR2 are PKA-phosphorylated, the mutant CPVT channels are more likely to open in the relaxation phase of the cardiac cycle (diastole), increasing the likelihood of arrhythmias triggered by SR $Ca^{2+}$ leak.

Fatigue is the process whereby skeletal muscles become weaker with repeated or intense use such as exercise, or as a result of an illness, disorder or disease. Fatigue can result in task failure and it can be a pronounced symptom in a variety of medical conditions including heart failure, renal failure, cancer, and various muscular dystrophies. Over the past decade, it has become evident that the two dominant classical explanations of muscle fatigue, namely, accumulation of lactic acid and intracellular acidosis, do not cause fatigue. In fact, both may be protective mechanisms during high intensity exercise to prevent fatigue (Allen and Westerblad 2004; Pedersen, Nielsen et al. 2004).

Muscle contraction depends on the efficient coupling of electrical stimulation of the muscle surface to $Ca^{2+}$ release via the ryanodine receptor, the SR $Ca^{2+}$ release channel, to the generation of actinmyosin cross bridges. It is evident, then, that a defect in excitation-contraction coupling that resulted in a reduction in the amplitude of the $Ca^{2+}$ transient would, among other effects, result in impaired contraction and force generation through ineffective myosin cross bridge formation. Eberstein and Sandow suggested inhibition of $Ca^{2+}$ release as a likely factor in the fatigue process (Eberstein and Sandow 1963). Reductions in the amplitude of $Ca^{2+}$ release evoked during fatiguing stimulation have been reported in multiple muscle preparations (Allen, Lee et al. 1989; Westerblad and Allen 1991; Allen and Westerblad 2001). The time course of recovery from fatigue parallels the time course over which prolonged depression of $Ca^{2+}$ release is observed (Westerblad, Bruton et al. 2000).

SR $Ca^{2+}$ leak was documented in myofibers following intense exercise and in a model of muscular dystrophy (Wang, Weisleder et al. 2005), possibly due to defective skeletal ryanodine receptors (RyR1s). Chronic activation of the sympathetic nervous system (SNS) in the context of heart failure promotes intrinsic skeletal muscle fatigue due to depletion of the phosphodiesterase PDE4D3 from the RyR1 complex, RyR1 PKA hyperphosphorylation at Serine 2844, calstabin1 depletion from the RyR1 complex, and a gain-of-function channel defect (Reiken, Lacampagne et al. 2003). RyR1 dysfunction in the skeletal muscle leads to altered local subcellular $Ca^{2+}$ release events and impaired global calcium transients (Ward, Reiken et al. 2003). JTV-519, (4-[3-(4-benzylpiperidin-1-yl)propionyl]-7-methoxy-2,3,4,5-tetrahydro-1,4-benzothiazepine monohydrochloride-a 1,4-benzothiazepine has been shown to be a modulator of RyR calcium-ion channels, given in the context of a murine model of heart failure, was able to improve skeletal muscle function, as assessed by an ex vivo isolated muscle fatiguing protocol, five weeks after left coronary artery ligation. JTV-519's beneficial effect on muscle fatigue was not solely due to cardiac improvement, as a beneficial effect was still seen when the drug was given to calstabin2 deficient mice which derive no cardiac benefit from treatment with JTV-519. Thus, it has been postulated that JTV-519 directly affects muscle function (Wehrens, Lehnart et al. 2005). In the context of chronic exercise, identical changes in the RyR1 macromolecular complex, namely depletion of PDE4D3 from the RyR1 complex, RyR1 PKA hyperphosphorylation at Serine 2844, and calstabin1 depletion from the RyR1 complex are related in a time-dependent and activity-dependent manner with repeated intense exercise in a mouse model. These biochemical changes in the RyR1 macromolecular complex regulation and function are stable following prolonged exercise and recover slowly over days to weeks. It has therefore been proposed that RyR1 $Ca^{2+}$ leak limits peak muscle performance and mediates muscle damage during prolonged, stressful exercise.

The contraction of striated muscle is initiated when calcium ($Ca^{2+}$) is released from tubules within the muscle cell known as the sarcoplasmic reticulum (SR). Calcium release channels, called ryanodine receptors (RyR), on the SR are required for excitation-contraction (EC) coupling. The type 2 ryanodine receptor (RyR2) is found in the heart, while the type 1 ryanodine receptor (RyR1) is found in skeletal muscle. The RyR1 receptor is a tetramer comprised of four 565,000 dalton RyR1 polypeptides and four 12,000 dalton FK-506 binding proteins (FKBP12). FKBP12s are regulatory subunits that stabilize RyR channel function (Brillantes et al., 1994) and facilitate coupled gating between neighboring RyR channels (Marx et al., 1998); the latter are packed into dense arrays in specialized SR regions that release intracellular stores of $Ca^{2+}$, thereby triggering muscle contraction. In addition to FKBP12, the RyR1 macromolecular complex also includes the catalytic and regulatory subunits of PKA, and the phosphatase PP1 (Marx et al., 2001).

One FKBP12 molecule is bound to each RyR1 subunit. Dissociation of FKBP12 significantly alters the biophysical properties of the channels, resulting in the appearance of subconductance states, and increased open probability ($P_o$) of the channels (Brillantes et al., 1994; Gaburjakova et al., 2001). In addition, dissociation of FKBP12 from RyR1 channels inhibits coupled gating resulting in channels that gate stochastically rather than as an ensemble (Marx et al., 1998). Coupled gating of arrays of RyR channels is thought to be important for efficient EC coupling that regulates muscle contraction (Marx et al., 1998). FKBPs are cis-trans peptidyl-prolyl isomerases that are widely expressed and subserve a variety of cellular functions (Marks, 1996). FKBP12s are tightly bound to and regulate the function of the skeletal (RyR1) (Brillantes et al., 1994; Jayaraman et al., 1992) and cardiac (RyR2) (Kaftan et al., 1996) muscle $Ca^{2+}$ release channels, as well as a related intracellular $Ca^{2+}$ release channel known as the type 1 inositol 1,4,5-triphosphate receptor (IP3R1) (Cameron et al., 1997), and the type I transforming growth factor β (TGFβ) receptor (TβRI) (Chen et al., 1997).

U.S. Pat. No. 7,312,044, the contents of which are hereby incorporated by reference, discloses methods of treating defective skeletal muscle function during heart failure by administering an agent which inhibits dissociation of FKB12 binding protein from RyR1 receptor.

Co-pending U.S. patent application Ser. No. 11/212,309 and U.S. Pat. No. 7,704,990, the contents of which are hereby incorporated by reference, disclose methods of making and using novel benzothiazepine derivatives to treat and prevent disorders and diseases associated with the RyR receptors, including skeletal muscular disorders and diseases such as skeletal muscle fatigue, exercise-induced skeletal muscle fatigue, muscular dystrophy, bladder disorders, and incontinence.

There is a need to identify new agents effective for treating or preventing muscle fatigue that is stress or exercise induced or that results from diseases associated with the RyR receptors that regulate calcium channel functioning in cells, including cardiac disease or disorder, defective skeletal muscle function, HIV Infection, AIDS, muscular dystrophy, cancer, malnutrition, exercise-induced muscle fatigue, age-associated muscle fatigue, renal disease, and renal failure.

SUMMARY OF THE INVENTION

In view of the foregoing, there is a need to identify new agents effective for treating or preventing disorders and diseases associated with the RyRs that regulate calcium channel functioning in cells, including skeletal muscular disorders and diseases and especially cardiac disorders and diseases. More particularly, a need remains to identify new compounds that can be used to treat RyR associated disorders by, for example, repairing the leak in RyR channels, and enhancing binding of FKBP proteins (calstabin1 and calstabin2) to PKA-phosphorylated RyR, and to mutant RyRs that otherwise have reduced affinity for, or do not bind to, FKBP12 and FKBP12.6. Embodiments of the invention solve some or all of these needs.

In one embodiment, the present invention provides a compound represented by the structure of formula I:

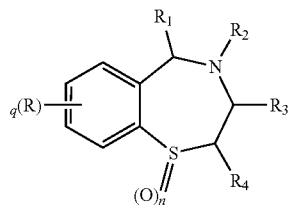

wherein n, q, R, $R_1$, $R_2$, $R_3$ and $R_4$ are as defined herein.

Certain compounds of formula I are defined by any of formulae I-a, I-b, I-c, I-d, I-e, I-f, I-g, I-h, I-i, I-j, I-k, I-k-1, I-l, I-l-1, I-m, I-m-1, I-n, I-o and I-p as defined herein.

Non-limiting examples of compounds of formula I are compounds selected from the group consisting of S1, S2, S3, S4, S5, S6, S7, S9, S11, S12, S13, S14, S19, S20, S22, S23, S36, S37, S38, S40, S43, S44, S45, S46, S47, S48, S49, S50, S51, S52, S53, S54, S55, S56, S57, S58, S59, S60, S61, S62, S63, S64, S66, S67, S69, S71, S72, S73, S74, S75, S76, S77, S78, S79, S80, S81, S82, S83, S84, S85, S86, S87, S88, S89, S90, S91, S92, S93, S94, S95, S96, S97, S98, S99, S100, S101, S102, S103, S104, S107, S108, S109, S110, S111, S112, S113, S114, S117, S118, S119, S120, S121, S122 and S123, and salts thereof.

In other embodiments, the present invention provides methods of treating a disorder or a disease in a subject, or reducing the risk of sudden cardiac death in a subject who is considered to be subject to such risk, comprising administering to the subject a therapeutically effective amount of a compound according to claim 1 to effectuate the treatment, wherein the disorder or disease is selected from the group consisting of cardiac disorders and diseases, skeletal muscular disorders and diseases, cognitive disorders and diseases, malignant hyperthermia, diabetes, and sudden infant death syndrome; wherein the cardiac disorders and diseases are selected from the group consisting of irregular heartbeat disorders and diseases; exercise-induced irregular heartbeat disorders and diseases; heart failure, congestive heart failure; chronic obstructive pulmonary disease; and high blood pressure; wherein the skeletal muscular disorders and diseases are selected from the group consisting of skeletal muscle fatigue, exercise-induced skeletal muscle fatigue, muscular dystrophy, bladder disorders, and incontinence; and wherein the cognitive disorders and diseases are selected from the group consisting of Alzheimer's Disease, forms of memory loss, and age-dependent memory loss.

In one embodiment, the compound is administered to the subject to treat cardiac disorders and diseases selected from the group consisting of irregular heartbeat disorders and diseases; exercise-induced irregular heartbeat disorders and diseases; congestive heart failure; chronic obstructive pulmonary disease; and high blood pressure.

In some embodiments, the irregular heartbeat disorders and diseases and exercise-induced irregular heartbeat disorders and diseases are selected from the group consisting of atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof.

In another embodiment, the compound is administered to the subject to treat skeletal muscular disorders and diseases selected from the group consisting of skeletal muscle fatigue, exercise-induced skeletal muscle fatigue, muscular dystrophy, bladder disorders, and incontinence.

In another embodiment, the compound is administered to the subject to treat cognitive disorders and diseases selected from the group consisting of Alzheimer's Disease, forms of memory loss, and age-dependent memory loss.

Other features and advantages of the present invention will become apparent from the following detailed description. It should be understood, however, that the detailed description and the specific examples while indicating various embodiments of the invention are given by way of illustration only, since various changes and modifications within the spirit and scope of the invention will become apparent to those skilled in the art from this detailed description.

BRIEF DESCRIPTION OF THE FIGURES

FIG. 36 shows tracking data during swimming on the first day of exercise for control vehicle treated (PBS) mice and mice treated with S36. Individual mouse velocities over five minute time intervals are shown in Embodiment A and mean velocities of each treatment group are shown in Embodiment B (n=4 PBS, n=4 S36). After one day of exercise, there is no substantial difference between the treatment groups. Fg-100, fg-103, fg-105, fg-106 indicates mice treated with S36. Fg-101, fg-102, fg-104, fg-107 indicates mice treated with PBS.

FIG. 39 shows that the trend toward improved performance in S36 treated mice continues on page 16.

FIG. 44 shows that high intensity cycling exercise in humans results in PKA phosphorylation of RyR1, and calstabin1 and PDE4D3 depletion. A) Immunoblot of the RyR1 complex immunoprecipitated from 100 ug of muscle homogenate from human thigh biopsies before and after exercise on day 1 and day 3 (C) of a high intensity (three hours at 57% $VO_2$ max) cycling protocol. Control cyclists sat in the exercise room but did not exercise. Immunoblots show total RyR1, RyR1-S2844 PKA phosphorylation, bound calstabin1, and bound PDE4D3. B) and D) Quantification by densitometry of A) and C) respectively. Bar graphs depict PKA phosphorylation, calstabin1, and PDE4D3 levels in the RyR1 complex normalized to total RyR1 from control (n=6) and exercise (n=12) biopsies on each day.

FIG. 50 shows that S107 protects against chronic exercise-induced muscle damage and calpain activation. A) Plasma creatine kinase (CPK) activity levels in sedentary and chronically exercised mice with, and without, calstabin1 rebinding with S107. B) Calpain activity levels in EDL homogenates measured using a fluorogenic calpain substrate assay. *, p<0.01 unpaired t-test, S107 vs vehicle.

FIG. 58 shows the difference in permanence time between S107 and vehicle treated mice. A: schematic representation of platform. B: latency to target(s) for vehicle (veh) and S107 treated mice. C: mean velocity (cm/s) for vehicle (veh) and S107 treated mice.

FIG. 59 shows a trend towards altered behavior consistent with improved learning and persistence in S107-treated mice (C), as compared with vehicle-treated mice (B). Panel A provides a schematic representation of the platform.

FIG. 60B is a bar graph representation showing improved learning or increased persistence with S107 treated mice, as compared with vehicle. FIG. 60A provides a schematic representation of the experimental set-up.

DETAILED DESCRIPTION OF THE INVENTION

Figure 1A:
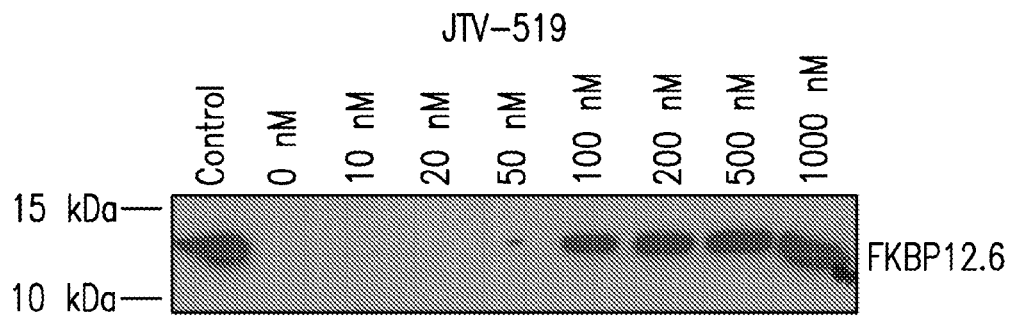
FIG. 1, embodiments A, B, C, and D are, respectively, (A) immunoblots of PKA phosphorylated RyR2 in the presence of FKBP12.6 and increasing JTV-519 concentrations; (B) immunoblots of PKA phosphorylated RyR2 in the presence of 0.5 nM S36; (C) a graph of current through plasma membrane, voltage dependent L-type $Ca^{2+}$ channels which are completely blocked by nifedipine but not by S36 in isolated mouse cardiomyocytes; and (D) a graph of the voltage-dependence of L-type $Ca^{2+}$ current in channels in the presence of JTV-519 and S36.

The following are definitions of terms used in the present specification. The initial definition provided for a chemical group or term herein applies to that group or term throughout the present specification individually or as part of another group, unless otherwise indicated.

As used herein and in the appended claims, the singular forms "a," "an," and "the" include plural references unless the content clearly dictates otherwise. Thus, for example, reference to "an agent" includes a plurality of such agents and equivalents thereof known to those skilled in the art, and reference to "the FKBP12.6 polypeptide" is a reference to one or more FKBP12.6 polypeptides (also known as calstabin2) and equivalents thereof known to those skilled in the art, and so forth. All publications, patent applications, patents, and other references mentioned herein are incorporated by reference in their entirety.

As used herein the term "fatigue" refers to skeletal muscle fatigue and/or weakness. Muscle fatigue can be due to strenuous or repeated physical activity or exercise, chronic stress, disease, disorder, syndrome or any other underlying pathophysiological condition that has symptoms of fatigue, or affects myofibers and/or muscle function. Muscle fatigue is defined as the failure of exercise performance—this can be assessed on an exercise stress test and quantified as the time it takes to fail at the given task (e.g. walking/jogging/running on a treadmill). Failure at the task is defined as termination of the exercise due to inability to continue—this is defined as muscle fatigue.

Sustained or prolonged exercise is defined as exercise performed over a defined and measurable time period.

Strenuous exercise is exercise to evoke muscle fatigue within a defined time period.

Chronic stress is defined as conditions that cause muscle fatigue chronically either due to persistent chronic exercise or stress due to chronic diseases/disorders that are often associated with chronic activation of the sympathetic nervous systems (e.g., chronic activation of the "fight or flight" response). In one embodiment, the subject's defective skeletal muscle function occurs during chronic obstructive pulmonary disease, hypertension, asthma, or hyperthyroidism.

In certain aspects, the present invention is directed to compositions and methods for the treatment and prevention of myopathies. The term "myopathy" as used herein refers to neuromuscular disorders caused by dysfunction in the muscle itself. The term "myopathy", as used herein, encompasses all of the myopathies described herein and also all other myopathies known to those of skill in the art.

Myopathies may be inherited (such as many of the muscular dystrophies) or acquired. Myopathic diseases and disorders include, but are not limited to, congenital myopathies, muscular dystrophies (characterized by progressive weakness in voluntary muscles), mitochondrial myopathies, endocrine myopathies, muscular glycogen storage diseases, myoglobinurias, dermatomyositis, myositis ossificans, familial periodic paralysis, polymyositis, inclusion body myositis, neuromyotonia, stiff-man syndrome, common muscle cramps, and tetany.

Examples of muscular dystrophies include, but are not limited to, Duchenne muscular dystrophy, facioscapulohumeral dystrophy, limb girdle muscular dystrophy, and myotonic muscular dystrophy, Becker's muscular dystrophy, congenital muscular dystrophy, Distal muscular dystrophy, Emery-Dreifuss muscular dystrophy, Facioscapulohumeral muscular dystrophy, Limb-girdle muscular dystrophy, Myotonic muscular dystrophy, and Oculopharyngeal muscular dystrophy. Examples of mitochondrial myopathies include, but are not limited to, Kearns-Sayre syndrome, MELAS and MERRF. MELAS which is an abbreviation of "mitochondrial myopathy, encephalopathy, lactic acidosis, and stroke" is a progressive neurodegenerative disorder. MELAS affects multiple organ systems including the central nervous system (CNS), skeletal muscle, the eye, cardiac muscle, and, more rarely, the gastrointestinal and renal systems. MERFF, which is an abbreviation of "myoclonus epilepsy with ragged-red fibers" may cause epilepsy, coordination loss, dementia and muscle weakness. Examples of glycogen storage diseases of muscle include, but are not limited to, Pompe's disease, Andersen's disease, and Cori's diseases. Examples of myoglobinurias include, but are not limited to McArdle's disease, Tarui disease, and DiMauro disease.

The following are definitions of terms used in the present specification. The initial definition provided for a group or term herein applies to that group or term throughout the present specification individually or as part of another group, unless otherwise indicated.

As used herein, the term "RyCal compounds" refers to compounds of the general Formula I, I-a, I-b, I-c, I-d, I-e, I-f, I-g, I-h, I-j, I-k, I-k-1, I-l, I-l-1, I-m, I-m-1, I-n, I-o, I-p or II as provided by the invention, and herein referred to as "compound(s) of the invention".

The compounds of the invention are referred using a numerical naming system, with compound numbers 1 to 123 provided herein. These numbered compounds are referred to using either the prefix "S" or the prefix "ARM." Thus, the first numbered compound is referred to either as "S1" or "ARM001", the second numbered compound is referred to as either "S2" or "ARM002", the third numbered compound is referred to as either "S3" or "ARM003", and so on. The "S" and the "ARM" nomenclature systems are used interchangeably throughout the specification, the drawings, and the claims.

The term "alkyl" as used herein refers to a linear or branched, saturated hydrocarbon having from 1 to 6 carbon atoms. Representative alkyl groups include, but are not limited to, methyl, ethyl, propyl, isopropyl, butyl, sec-butyl, tert-butyl, pentyl, isopentyl, neopentyl, hexyl, isohexyl, and neohexyl. The term "$C_1$-$C_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl.

The term "alkenyl" as used herein refers to a linear or branched hydrocarbon having from 2 to 6 carbon atoms and having at least one carbon-carbon double bond. In one embodiment, the alkenyl has one or two double bonds. The alkenyl moiety may exist in the E or Z conformation and the compounds of the present invention include both conformations.

The term "alkynyl" as used herein refers to a linear or branched hydrocarbon having from 2 to 6 carbon atoms and having at least one carbon-carbon triple bond.

The term "aryl" as used herein refers to an aromatic group containing 1 to 3 aromatic rings, either fused or linked.

The term "cyclic group" as used herein includes a cycloalkyl group and a heterocyclic group.

The term "cycloalkyl group" as used herein refers to a three- to seven-membered saturated or partially unsaturated carbon ring. Any suitable ring position of the cycloalkyl group may be covalently linked to the defined chemical structure. Exemplary cycloalkyl groups include cyclopropyl, cyclobutyl, cyclopentyl, cyclohexyl, and cycloheptyl.

The term "halogen" as used herein refers to fluorine, chlorine, bromine, and iodine.

The term "heterocyclic group" or "heterocyclic" or "heterocyclyl" or "heterocyclo" as used herein refers to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached to the remainder of the molecule at any heteroatom or carbon atom of the ring or ring system. Exemplary heterocyclic groups include, but are not limited to, azepanyl, azetidinyl, aziridinyl, dioxolanyl, furanyl, furazanyl, homo piperazinyl, imidazolidinyl, imidazolinyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, and triazolyl. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

The term "phenyl" as used herein refers to a substituted or unsubstituted phenyl group.

The aforementioned terms "alkyl," "alkenyl," "alkynyl," "aryl," "phenyl," "cyclic group," "cycloalkyl," "heterocyclyl," "heterocyclo," and "heterocycle" may further be optionally substituted with one or more substituents. Exemplary substituents include but are not limited to one or more of the following groups: hydrogen, halogen, $CF_3$, $OCF_3$, cyano, nitro, $N_3$, oxo, cycloalkyl, alkenyl, alkynyl, heterocycle, aryl, alkylaryl, heteroaryl, $OR_a$, $SR_a$, $S(=O)R_e$, $S(=O)_2R_e$, $P(=O)_2R_e$, $S(=O)_2OR_a$, $P(=O)_2OR_a$, $NR_bR_c$, $NR_bS(=O)_2R_e$, $NR_bP(=O)_2R_e$, $S(=O)_2NR_bR_c$, $P(=O)_2NR_bR_c$, $C(=O)OR_a$, $C(=O)R_a$, $C(=O)NR_bR_C$, $OC(=O)R_a$, $OC(=O)NR_bR_C$, $NR_bC(=O)OR_a$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, alkynyl, alkylaryl, heteroaryl, heterocycle, or aryl; $R_b$, $R_c$ and $R_d$ are independently hydrogen, alkyl, cycloalkyl, alkylaryl, heteroaryl, heterocycle, aryl, or said $R_b$ and $R_c$, together with the N to which they are bonded optionally form a heterocycle; and $R_e$ is alkyl, cycloalkyl, alkenyl, cycloalkenyl, alkynyl, alkylaryl, heteroaryl, heterocycle, or aryl. In the aforementioned exemplary substitutents, groups such as alkyl, cycloalkyl, alkenyl, alkynyl, cycloalkenyl, alkylaryl; heteroaryl, heterocycle and aryl can themselves be optionally substituted.

Exemplary substituents may further optionally include at least one labeling group, such as a fluorescent, a bioluminescent, a chemiluminescent, a colorimetric and a radioactive labeling group. A fluorescent labeling group can be selected from bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, arginine, and variants and derivatives thereof. For example, ARM118 of the present invention contains a labeling group BODIPY, which is a family of fluorophores based on the 4,4-difluoro-4-bora-3a,4a-diaza-s-indacene moiety. For further information on fluorescent label moieties and fluorescence techniques, see, e.g., *Handbook of Fluorescent Probes and Research Chemicals*, by Richard P. Haughland, Sixth Edition, Molecular Probes, (1996), which is hereby incorporated by reference in its entirety. One of skill in the art can readily select a suitable labeling group, and conjugate such a labeling group to any of the compounds of the invention, without undue experimentation.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

Throughout the specification, unless otherwise noted, the nitrogen in the benzothiazepine ring of compounds of the present invention may optionally be a quaternary nitrogen. Non-limiting examples include ARM-113 and ARM-119.

Compounds of the present invention may exist in their tautomeric form (for example, as an amide or imino ether). All such tautomeric forms are contemplated herein as part of the present invention.

The term "prodrug" as employed herein denotes a compound that, upon administration to a subject, undergoes chemical conversion by metabolic or chemical processes to yield compounds of the present invention.

All stereoisomers of the compounds of the present invention (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 99% of the compound ("substantially pure" compound), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Metabolite as used herein refers to a byproduct produced in vivo, for example in a subject, from a chemical compound.

As used herein, the term "RyCal compounds" refers to compounds of the general Formula I or II as provided by the invention, and herein referred to as compound(s) of the invention. Such compounds include, but are not limited to, any one or more of the compounds of formulae including, but not limited to, the compounds of formulae S1, S2, S3, S4, S5, S6, S7, S8, S9, S10, S11, S12, S13, S14, S19, S20, S22, S23, S24, S25, S26, S36, S37, S38, S40, S43, S44, S45, S46, S47, S48, S49, S50, S51, S52, S53, S54, S55, S56, S57, S58, S59, S60, S61, S62, S63, S64, S66, S67, S68, S69, S70, S71, S72, S73, S74, S75, S76, S77, S78, S79, S80, S81, S82, S83, S84, S85, S86, S87, S88, S89, S90, S91, S92, S93, S94, S95, S96, S97, S98, S99, S100, S101, S102, S103, S104, S105, S107, S108, S109, S110, S111, S112, S113, S114, S115, S116, S117, S118, S119, S120, S121, S122, and S123, as herein defined. In certain embodiments, the compounds are isolated and substantially pure.

A subject treated by the methods of the invention can include a mammal. Such a mammal can include a human, primate, canine, equine, feline, porcine, murine, bovine, foul, ungulate or sheep. The terms "animal," "subject" and "patient" as used herein include all members of the animal kingdom including, but not limited to, mammals, animals (e.g., cats, dogs, horses, etc.) and humans.

"PKA phosphorylation" means a reaction in which a phosphate group is substituted for a hydroxyl group by the enzyme protein kinase A (PKA).

"Back-phosphorylation" of RyR1 or RyR2 receptor means the in vitro phosphorylation of receptor by protein kinase A.

A "pharmaceutical composition" refers to a mixture of one or more of the compounds described herein, or pharmaceutically acceptable salts, hydrates, polymorphs, or prodrugs thereof, with other chemical components, such as physiologically acceptable carriers and excipients. The purpose of a pharmaceutical composition is to facilitate administration of a compound to an organism.

A compound of the present invention also can be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

The term "pharmaceutically acceptable acid addition salt" as used herein means any non-toxic organic or inorganic salt of any base compounds represented by Formula I, I-a, I-b, I-c, I-d, I-e, I-f, I-g, I-h, I-j, I-k, I-k-1, I-l, I-l-1, I-m, I-m-1, I-n, I-o, I-p, or Formula II, any of their intermediates. Illustrative inorganic acids which form suitable acid addition salts include hydrochloric, hydrobromic, sulfuric and phosphoric acids, as well as metal salts such as sodium monohydrogen orthophosphate and potassium hydrogen sulfate. Illustrative organic acids that form suitable acid addition salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed and such salts exist in either a hydrated, solvated or substantially anhydrous form. In general, the acid addition salts of compounds of the invention are more soluble in water and various hydrophilic organic solvents, and generally demonstrate higher melting points in comparison to their free base forms.

A compound of the present invention also can be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

The term "pharmaceutically acceptable salt" means a salt that is suitable for, or compatible with, the treatment of a patient or a subject such as a human or animal patient such as a person or dog. The salts can be any non-toxic organic or inorganic salt of any of the compounds represented by Formula I, I-a, I-b, I-c, I-d, I-e, I-f, I-g, I-h, I-j, I-k, I-k-1, I-l, I-l-1, I-m, I-m-1, I-n, I-o, I-p, II or any of the specific compounds described herein, or any of their intermediates. Illustrative salt-forming ions include, but are not limited to, ammonium ($NH_4^+$), calcium ($Ca^{2+}$), iron ($Fe^{2+}$ and $Fe^{3+}$), magnesium ($Mg^{2+}$), potassium ($K^+$), pyridinium ($C_5H_5NH^+$), quaternary ammonium ($NR_4^+$), sodium ($Na^+$), acetate, carbonate, chloride, bromide, citrate, cyanide, hydroxide, nitrate, nitrite, oxide, phosphate, sulfate, maleate, fumarate, lactate, tartrate, gluconate, besylate, and valproate. Illustrative inorganic acids that form suitable salts include, but are not limited to, hydrochloric, hydrobromic, sulfuric and phosphoric acids, as well as metal salts such as sodium monohydrogen orthophosphate and potassium hydrogen sulfate. Illustrative organic acids that form suitable acid addition salts include, but are not limited to, mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either mono or di-acid salts can be formed, and such salts exist in either a hydrated, solvated or substantially anhydrous form. In general, the acid addition salts of compounds of Formula I, I-a, I-b, I-c, I-d, I-e, I-f, I-g, I-h, I-j, I-k, I-k-1, I-l, I-l-1, I-m, I-m-1, I-n, I-o, or I-p, are more soluble in water and various hydrophilic organic solvents, and generally demonstrate higher melting points in comparison to their free base forms. The selection of an appropriate salt can be performed by one skilled in the art. For example, one can select salts in reference to "Handbook of Pharmaceutical Salts: Properties, Selection, and Use" by P. Heinrich Stahl and Camille G. Wermuth, or Berge (1977) "Pharmaceutical Salts" J. Pharm Sci., Vol 66(1), p 1-19. Other non-pharmaceutically acceptable salts (e.g., oxalates) may be used, for example, in the isolation of compounds of the invention for laboratory use or for subsequent conversion to a pharmaceutically acceptable acid addition salt.

The compounds of Formula I, I-a, I-b, I-c, I-d, I-e, I-f, I-g, I-h, I-j, I-k, I-k-1, I-l, I-l-1, I-m, I-m-1, I-n, I-o, I-p, and Formula II of the present invention may form hydrates or solvates, which are included in the scope of the claims. When the compounds of Formula I of the present invention exist as regioisomers, configurational isomers, conformers or diastereoisomeric forms all such forms and various mixtures thereof are included in the scope of Formula I. It is possible to isolate individual isomers using known separation and purification methods, if desired. For example, when a compound of Formula I of the present invention is a racemate, the racemate can be separated into the (S)-compound and (R)-compound by optical resolution. Individual optical isomers and mixtures thereof are included in the scope of Formula I, I-a, I-b, I-c, I-d, I-e, I-f, I-g, I-h, I-j, I-k, I-k-1, I-l, I-l-1, I-m, I-m-1, I-n, I-o, I-p, and Formula II.

The term "solvate" as used herein means a compound of Formula I, I-a, I-b, I-c, I-d, I-e, I-h, I-j, I-k, I-k-1, I-l, I-l-1, I-m, I-m-1, I-n, I-o, I-p, and Formula II or a pharmaceutically acceptable salt of a compound of Formula I, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term "polymorph" refers to a particular crystalline state of a substance, having particular physical properties such as X-ray diffraction, IR spectra, melting point, and the like.

The term an "effective amount," "sufficient amount" or "therapeutically effective amount" of an agent as used herein is that amount sufficient to effect beneficial or desired results, including clinical results and, as such, an "effective amount" depends upon the context in which it is being applied, whether the response is preventative and/or therapeutic. The term "effective amount" also includes that amount of the compound of Formula I which is "therapeutically effective" and which avoids or substantially attenuates undesirable side effects.

As used herein and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

As used herein, the term "inhibiting dissociation" includes blocking, decreasing, inhibiting, limiting or preventing the physical dissociation or separation of an FKBP subunit from an RyR molecule in cells of the subject, and blocking, decreasing, inhibiting, limiting or preventing the physical dissociation or separation of an RyR molecule from an FKBP subunit in cells of the subject.

As used herein, the term "increasing binding" includes enhancing, increasing, or improving the ability of phosphorylated RyR to associate physically with FKBP (e.g., binding of approximately two fold or, approximately five fold, above the background binding of a negative control) in cells of the subject and enhancing, increasing or improving the ability of FKBP to associate physically with phosphorylated RyR (e.g., binding of approximately two fold, or, approximately five fold, above the background binding of a negative control) in cells of the subject.

As used herein, the term "cardiac muscle cell" includes cardiac muscle fibers, such as those found in the myocardium of the heart.

The present invention provides compounds that are capable of treating and preventing disorders and diseases associated with the RyR receptors that regulate calcium channel functioning in cells. More particularly, the present invention provides compounds that are capable of treating or preventing a leak in RyR channels. "Disorders and diseases associated with the RyR receptors" means disorders and diseases that can be treated and/or prevented by modulating the RyR receptors that regulate calcium channel functioning in cells. "Disorders and diseases associated with the RyR receptors" include, without limitation, cardiac disorders and diseases, skeletal muscular disorders and diseases, cognitive disorders and diseases, malignant hyperthermia, central core disease, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss.

As contemplated herein, the compounds of the invention are capable of treating and preventing disorders and diseases associated with the RyR receptors that regulate calcium channel functioning in cells, by repairing the leak in RyR channels, and enhancing binding of FKBP proteins (e.g., calstabin1) to PKA-phosphorylated RyR. Thus, in one embodiment, the compounds are useful to prevent and treat muscle fatigue that is associated with the RyR receptors that regulate calcium channel functioning in cells.

In one embodiment, the compounds of the invention are effective to treat muscle fatigue that results from pathologies, illnesses, diseases, disorders or conditions that are associated with the RyR receptors that regulate calcium channel functioning in cells. Examples of such disorders and conditions include, but are not limited to, cardiac disease or disorder, defective skeletal muscle function, HIV Infection, AIDS, muscular dystrophy, cancer, malnutrition, exercise-induced muscle fatigue, age-associated muscle fatigue, renal disease, and renal failure.

Examples of cardiac disorders and diseases include, but are not limited to, irregular heartbeat disorders and diseases; exercise-induced irregular heartbeat disorders and diseases; congestive heart failure; chronic obstructive pulmonary disease; and high blood pressure. Examples of irregular heartbeat disorders and diseases and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPTV); and exercise-induced variants thereof.

In one embodiment, the compounds of the invention modulate calcium-ion channels in cells of the subject. In another embodiment, the compounds of the invention decrease the release of calcium into cells of the subject. In another embodiment, the compounds of the invention limit or prevent a decrease in the level of RyR-bound FKBP in the subject. In another embodiment, the compounds of the invention inhibit dissociation of FKBP and RyR in cells of the subject. In another embodiment, the compounds of the invention increase binding between FKBP and RyR in cells of the subject. In another embodiment, the compounds of the invention stabilize the RyR-FKBP complex in cells of a subject. In another embodiment, the compounds of the invention prevent, or treat a leak in a RyR receptor in the subject. In another embodiment, the compounds of the invention modulate the binding of RyR and FKBP in the subject. In another embodiment, the compounds of the invention reduce the open probability of RyR by increasing the affinity of FKBP for PKA-phosphorylated RyR. In another embodiment, the compounds of the invention reduce or inhibit calpain activity so as to treat muscle fatigue. In another embodiment, the compounds of the invention reduce plasma creatine kinase levels so as to treat muscle fatigue.

The methods of the present invention can be practiced in vitro or in vivo. Thus, in one embodiment, the methods of the present invention are practiced in an in vitro system (e.g., in a test tube on isolated cellular components). In another embodiment, the methods of the invention are practiced in vivo, e.g., in cultured cells or tissues, or in subjects.

In another embodiment, the present invention provides use of a compound represented by the structure of formula I, I-a, I-b, I-c, I-d, I-e, I-f, I-g, I-h, I-j, I-k, I-k-1, I-l, I-l-1, I-m, I-m-1, I-n, I-o, I-p, and Formula II in the preparation of a medicament for treating or preventing muscle disorder or disease, for example but not limited to muscle fatigue in a subject.

In another embodiment, muscle fatigue can be caused by increased stress such as in individuals exposed to a continued and prolonged exercise regimen, e.g., soldiers or athletes. Thus in one embodiment, the compounds of the invention are useful for treating muscle fatigue in individuals exposed to stress due to, for example, an intense exercise regimen. Skeletal muscular disorder and diseases include, but are not limited to, stress induced skeletal muscle fatigue, exercise-induced skeletal muscle fatigue, muscular dystrophy, bladder disorders, and incontinence.

Skeletal Muscle Fatigue

Defects in $Ca^{2+}$ release channel; for example increased "leakiness" of the channel can lead to skeletal muscle fatigue. In certain aspects the invention provides that RyCal compounds which treat defects in $Ca^{2+}$ release channel can be used in methods for treating, reducing or preventing muscle disorders, muscle fatigue, including but not limited to exercise-induced muscle fatigue or muscle damage, muscle fatigue or damage associated with a disease condition, for example but not limited to a myopathy, muscular dystrophy and the like. Recent studies suggesting that lactic acid accumulation may not be detrimental have raised questions about the molecular basis underlying skeletal muscle fatigue. Among hypotheses a role for defective regulation of calcium has been proposed.

The invention provides data showing altered function of the major calcium release channel in skeletal muscle sarcoplasmic reticulum (SR), the type 1 ryanodine receptor (RyR1), is required for excitation-contraction coupling (ECC), during chronic exercise. During chronic exercise the RyR1 channel is PKA hyperphosphorylated at Ser2844 (Ser2843 in human). The PKA hyperphosphorylation is associated with depletion of the phosphodiesterase PDE4D3 from the RyR1 complex. Furthermore, PKA hyperphosphorylation contribute to depletion of the RyR1 stabilizing subunit calstabin1 (FKBP12) from the channel macromolecular complex resulting in "leaky" channels (increased open probability under conditions when normal channels are not active). The degree of PKA phosphorylation, and depletion of calstabin1 and PDE4D3 are correlated with the intensity and duration of exercise and progressive fatigue. Mice with skeletal muscle-specific calstabin1 deficiency and PDE4D deficient mice both exhibited significantly impaired exercise capacity. A small molecule, S107, that specifically causes rebinding of calstabin1 to the RyR1 channel improved exercise capacity and force generation of isolated muscle during a 21 day exercise protocol. S107 treated muscle fibers exhibited reduced fatigue, as determined by measurement of intracellular calcium during repeated tetanic contractions. Furthermore, S107 treated chronically exercised mice exhibited reduced levels of plasma creatine kinase, and calcium-dependent neutral protease calpain activity in muscle homogenates. This demonstrates the existence of a mechanism of muscle fatigue, during chronic or high-intensity exercise, where SR calcium leak due calstabin1 depleted RyR1 channels leads to defective calcium signaling and skeletal muscle damage. In one aspect, the invention provides use of RyCal compounds which target molecular mechanisms of muscle fatigue, muscle conditions and disorders, and provide treatments treatment thereof.

Calcium release channel stabilizing drugs prevent muscle fatigue by preventing ryanodine receptor calcium leak during sustained or strenuous exercise. Repeated and strenuous activity of skeletal muscle may cause 1) weakness with intense use (also referred to as fatigue), 2) feeling of sore and weak muscles (referred to as perception), and 3) different degrees of muscle degeneration (referred to as dystrophic remodeling). A dominant theory of muscle fatigue has been that accumulation of intracellular lactic acid resulting in intracellular acidosis directly inhibits force production by the myofibrillar proteins (Hill et al., 1929). Indeed, at lower than physiologic temperatures (20° C.), acidotic changes of intracellular pH were found to accelerate fatigability of skeletal muscles (Hill at al., 1929). However, more recent studies have challenged the significance of acidosis for muscle fatigue by showing that repeated short tetanic contractions which induce fatigue do not result in significant intracellular pH changes under more physiologic conditions at 37° C. (Westerblad at al., 1997) where acidosis does not significantly effect force production. These findings are consistent with lactic acid which is produced during fatiguing contractions being extruded at a substantial rate by lactate transporters. However, during very intense athletic training lactic acid resulting from anaerobic breakdown of glycogen remains an important limiting factor. Importantly, intracellular acidosis was found to preserve muscle excitability and relaxation of the myofilaments during sustained increases of intracellular $Ca^{2+}$ during repeated or sustained tetanic contractions, and thus protects from muscle fatigue (Pedersen at al. 2004).

Given that changes in intracellular pH may not represent a major fatigue mechanism, it is likely that alterations in EC coupling contribute to fatigue. Intracellular $Ca^{2+}$ release via RyR1 channels initiates muscle contraction. Now classic physiologic experiments suggested in 1963, that reversible alterations in contractile activation may play an important role in muscle fatigue (Eberstein et al., 1963). During progressive development of fatigue resulting from repeated tetanic contractions, elevations in intracellular $Ca^{2+}$ concentrations decline which explains reduced force production (Allen et al., 2001). However, caffeine and other compounds, which maximally activate RyR1 channels and cause sudden SR $Ca^{2+}$ release, can briefly normalize tetanic $Ca^{2+}$ concentrations (Allen at al., 2001). Thus alterations of RyR1-dependent SR $Ca^{2+}$ release mechanisms are likely to be involved in fatigue development.

Measurements of SR $Ca^{2+}$ load have demonstrated a decreased pool of releasable $Ca^{2+}$ during skeletal muscle fatigue, which may be one of the causes of reduced SR $Ca^{2+}$ release during fatigue. (Cooke at al. 1985). Another theory involves increased intracellular inorganic phosphate concentrations ($[P_i]_i$) precipitating $Ca^{2+}$ in the SR storage organelle (Allen, 2001; Cooke, 1985). However, $[P_i]_i$ increases occur during the early phase of fatigue resulting from rapid ATP breakdown whereas the decline of tetanic $[Ca^{2+}]_i$ occurs late in fatigue (phase iii). Moreover, after repeated, stretched contractions resting $[Ca^{2+}]_i$ was found elevated while stimulated, tetanic $[Ca^{2+}]_i$ decreased (Warren et al. 1993; Balnave et al. 1995). The increased resting $[Ca^{2+}]_i$ may initiate chronic impairment of EC coupling for example by activating proteases that can damage the SR $Ca^{2+}$ release channel (Lamb et al., 1995; Chin et al., 1996; Bruton et al., 1996).

Fatigue from chronically sustained exercise may be caused by SR $Ca^{2+}$ leak resulting from defective closure of the RyR1 channel and partial depletion of the SR $Ca^{2+}$ store contributing to diminished force production and increased resting $[Ca^{2+}]_i$ interfering with muscle relaxation and when sustained causing muscle degeneration. Recent data shows that an evolutionary conserved stress pathway, the fight-or-flight response, specifically controls RyR1 $Ca^{2+}$ release in skeletal muscle (Gaburjakova et al., 2001; Marx et al., 2001) and that abnormal, chronic activation of this stress pathway causes SR $Ca^{2+}$ leak contributing to muscle fatigue (Reiken et al., 2003).

RyR1/calcium release channels become PKA hyperphosphorylated and depleted of the stabilizing protein calstabin1 during exercise. RyCal compounds of the invention increase the binding affinity of calstabin1 to PKA hyperphosphorylated RyR1. These compounds are called "calcium channel stabilizers" or "RyCals" and are in a class of 1,4-benzothiazepines and related structures. In a non-limiting example, treatment with a RyCal compound improves exercise performance of mice running on a treadmill. Furthermore, there is evidence that a calcium leak via PKA hyperphosphorylated RyR1 channels causes muscle damage due to activation of calcium-dependent proteases and RyCals prevent the calcium leak and inhibit muscle damage during chronic exercise. In certain embodiments, RyCal compound can be used to treat, prevent or improve muscle fatigue in chronic diseases including but not limited to heart failure, AIDS, cancer, renal failure, chronic obstructive pulmonary disease, hypertension, asthma, hyperthyroidism, chronic muscle fatigue. In other embodiments, RyCal compound can be used to treat or improve muscular dystrophies. In other embodiments, treatment with RyCal compound can prevent or reduce muscle fatigue which can improve exercise performance in individuals who are exposed to sustained chronic stress and/or physical exercise. In other embodiments, treatment with RyCals can prevent or reduce muscle fatigue which can improve exercise performance in individuals who are exposed to strenuous physical exercise.

Skeletal muscles become weaker with intense use also referred to as fatigue. Moreover, repeated stretch-dependent contractures can result in additional muscle damage and degeneration. Although fatigue is recognized as an important mechanism of limited peak performance and task failure during stress, the mechanisms that promote fatigue or muscle fiber damage are incompletely characterized. Moreover, defining molecular fatigue mechanisms may enable targeted interventions that could help prevent fatigue and muscle tissue damage (Wehrens, 2005). A key physiologic mechanism that controls skeletal muscle performance is intracellular calcium ($Ca^{2+}$) release from specialized $Ca^{2+}$ stores (the sarcoplasmic reticulum, SR) via ryanodine receptor (RyR1) $Ca^{2+}$ release channels. In skeletal muscle, plasma membrane depolarization activates voltage-gated L-type $Ca^{2+}$ channels (LTCCs; $Ca_V1.1$) which in turn activate RyR1s on the SR mediated by direct contact between both ion channels.

Opening of RyR1 channels results in bulk SR $Ca^{2+}$ release which activates the myofilaments and muscle contraction. Also, disease forms associated with sustained activation of the sympathetic nervous system and increased plasma catecholamine levels cause maladaptive activation of intracellular stress pathways resulting in destabilization of the RyR1 channel closed state and intracellular $Ca^{2+}$ leak (Reiken et al. 2003; Brillantes et al. 1994). SR $Ca^{2+}$ leak via RyR1 channels was found to deplete intracellular SR calcium stores, to increase compensatory energy consumption, and to result in significant acceleration of muscle fatigue. The stress-induced muscle defect limits peak performance and contributes to pathologic forms of muscle fatigue that permanently reduce performance. Also, destabilization of the RyR1 closed state involves depletion of the stabilizing calstabin1 (FKBP12) channel subunit (Reiken et al. 2003; Brillantes et al. 1994). Experiments demonstrate that increasing the binding affinity of calstabin to RyR rescues channel function (Wehrens, 2003).

Skeletal muscle contraction is activated by SR $Ca^{2+}$ release via the type 1 skeletal ryanodine receptor (RyR1). Depolarization of the T-tubule membrane activates the dihydropyridine receptor voltage sensor (Cav1.1) which in turn activates RyR1 channels via a direct protein-protein interaction causing the release of SR $Ca^{2+}$ stores. $Ca^{2+}$ binds to troponin C allowing actin-myosin cross-bridging to occur and sarcomere shortening. $Ca^{2+}$ release channels comprise macromolecular complexes consisting of a homotetramer of 560 kDa RyR1 subunits that form scaffolds for proteins that regulate channel function including: protein kinase A and the phosphodiesterase PDE4D3, both of which are targeted to the channel via the anchoring protein mAKAP, PP1 (targeted via spinophilin), and calstabin1 (FKBP12) (Jayaraman, Brillantes et al. 1992; Brillantes, Ondrias et al. 1994; Marx, Reiken et al. 2000; Marx, Reiken et al. 2001).

A defect in ECC that resulted in a reduction in the amplitude of SR $Ca^{2+}$ release would impair contraction and force generation. Eberstein and Sandow proposed impaired SR $Ca^{2+}$ release as a likely contributor to muscle fatigue (Eberstein and Sandow 1963). Reductions in the amplitude of SR $Ca^{2+}$ release evoked during fatiguing stimulation have been reported (Allen, Lee et al. 1989; Westerblad and Allen 1991; Allen and Westerblad 2001). In addition, it has been shown that $Ca^{2+}$ stores decline during intense and repeated contractions (Kabbara & Allen, 1999), and that the time course of recovery from fatigue parallels the time course over which prolonged depression of SR $Ca^{2+}$ release is observed (Westerblad, Bruton et al. 2000). Furthermore, reduction of free SR $Ca^{2+}$, due to inorganic calcium phosphate salt precipitation during fatigue, has been proposed (Allen and Westerblad 2001).

Evidence of defective SR $Ca^{2+}$ release in fatigued muscle prompted examination of the role of RyR1 mediated SR $Ca^{2+}$ release in skeletal muscle fatigue. The binding of calstabin1 (FKBP12) to RyR1 stabilizes the closed state of the channel and facilitates coupled gating between neighboring channels (Brillantes, Ondrias et al. 1994; Marx, Ondrias et al. 1998). Pharmacologic depletion of calstabin1 from RyR1 (with rapamycin or FK506 both of which bind to calstabin1 and dissociate it from the RyR1 macromolecular complex) promotes subconductance states and, in intact skeletal muscle, can cause a rapid loss of depolarization-induced contraction (Lamb and Stephenson 1996). Mutation of RyR1 resulting in the loss of calstabin1 binding causes impaired ECC with reduced maximal voltage-gated SR $Ca^{2+}$ release without affecting the SR $Ca^{2+}$ store content (Avila, Lee et al. 2003). Genetic deletion of FKBP12 (calstabin1) induced no gross histological or developmental defect in skeletal muscle, though severe developmental cardiac defects were observed which precluded detailed assessment of skeletal muscle function (Shou, Aghdasi et al. 1998). Whereas skeletal muscle-specific knock-out of FKBP12 (calstabin1) resulted in reduced voltage-gated SR $Ca^{2+}$ release and increased L-type channel currents in isolated myotubes (Tang, Ingalls et al. 2004). In extensor digitalis longus (EDL), but not soleus or diaphragm, reduced maximal tetanic force and a rightward shift in force-frequency relationships were observed (Tang, Ingalls et al. 2004). These data indicated that calstabin1 modulates the gain of ECC in skeletal muscle.

The binding of calstabin1 to RyR1 is regulated by PKA phosphorylation at RyR1-S2843 (position S2844 in the mouse RyR1 sequence) (Reiken, Lacampagne et al. 2003). Phosphorylation at RyR1-S2843 increases the mean open probability of RyR1 in the lipid bilayer (Reiken, Lacampagne et al. 2003). RyR1-S2843A mutant channels could not be PKA phosphorylated and did not show the same PKA-dependent increase in open probability. An RyR1-S2843D mutation mimicked PKA phosphorylation with an increased open probability and destabilized open and closed states (Reiken, Lacampagne et al. 2003). The role of PKA phosphorylation of RyR1 is still under investigation as other groups have found little or no effect on channel function (Stange, Xu et al. 2003). Other post-translational modifications of RyR1 which might modulate calstabin1 binding to RyR1 have been suggested, including oxidation, and glutathionylation of the up to 50 free (reduced) thiols on each RyR monomer.

SR $Ca^{2+}$ leak has been documented as aberrant calcium sparks in myofibers following intense exercise and in a model of muscular dystrophy (Wang, Weisleder et al. 2005), possibly due to defective RyR1 function. Chronic activation of the sympathetic nervous system (SNS) during heart failure is associated with early skeletal muscle fatigue and PKA hyperphosphorylation of RyR1 at Ser2844 (meaning that on average 3-4 of the four PKA sites in each homotetrameric channel are PKA phosphorylated in heart failure skeletal muscle), calstabin1 depletion from the RyR1 complex, and a gain-of-function channel defect (Reiken, Lacampagne et al. 2003). RyR1 dysfunction in skeletal muscle leads to altered local subcellular $Ca^{2+}$ release events (Ward, Reiken et al. 2003).

Modifications in the RyR1 complex could alter and are likely to limit peak muscle performance, increase muscle fatigue, and contribute to muscle damage during prolonged or high intensity exercise. In certain aspects the invention provides use of a mouse model of chronic, high-intensity, forced exercise to assess the role of the RyR1 channel in skeletal muscle fatigue. As described herein, the RyR1 channel macromolecular complex undergoes remodeling during exercise such that it is progressively PKA hyperphosphorylated, and depleted of PDE4D3 and calstabin1. Functionally, this remodeling is associated with "leaky" channels (increased open probability) and activation of the calcium-activated protease calpain, and leakage of creatine kinase (CPK) into the plasma, which is consistent with muscle damage. These changes are further associated with decreased force production in isolated muscles and impaired exercise capacity and are exacerbated in mice with PDE4D deficiency or muscle specific calstabin1 deficiency. Preventing the RyR1 channel leak with a calcium channel stabilizer S107, which enhances binding of calstabin1 to RyR1, inhibits calpain activation, CPK leak and improves exercise performance. Therefore, remodeling of the RyR1 channel complex that causes leaky channels, activation of the calcium-activated protease calpain, and leakage of creatine kinase (CPK) into the plasma, is a mechanism involved in muscle fatigue during chronic or high intensity exercise.

Confocal imaging studies of intracellular $Ca^{2+}$ release ($Ca^{2+}$ sparks) in muscle cells after mild and strenuous treadmill exercise, showing that abnormal $Ca^{2+}$ spark activity is induced by fatiguing exercise (Wang et al. 2005). Moreover, myofibers with abnormal $Ca^{2+}$ spark activity resulting form strenuous exercise show histological signs of degeneration from toxic $Ca^{2+}$ effects also known as 'dystrophic remodeling' (Wang et al. 2005). It is likely that sustained exercise over weeks and months results in RyR1 dysfunction, intracellular $Ca^{2+}$ leak, depressed muscle performance, and dystrophic muscle remodeling. Furthermore, 1,4-benzothiazepine based drugs enhance peak muscle performance and prevent dystrophic remodeling by fixing stress-induced intracellular $Ca^{2+}$ leak.

Animal models can establish, in vivo and at the level of isolated skeletal muscle cell, and single RyR1 channel, that defects in RyR1 function cause muscle fatigue and dystrophic remodeling. Use of these animal models of fatigue and the characterized muscle, cells, and channel techniques allows tests of therapeutic approaches based on fixing the leak in RyR1 which will result in improved skeletal muscle performance, decreased muscle fatigue, and reduced dystrophic remodeling during chronic forms of exercise.

Muscular Dystrophy

Myotonic dystrophy type 1 (DM1), the most common muscular dystrophy in adults (1 in 7,400 live births), is a multisystemic disorder caused by a CTG trinucleotide repeat expansion in the 3' untranslated region of the myotonic dystrophy protein kinase (DMPK) gene which causes progressive muscle weakness, inherited muscle hyperexitability (myotonia), cardiac conduction defect, cataract, and insulin resistance (Bachinski L L, Udd B, Meola G, et al. Confirmation of the type 2 myotonic dystrophy (CCTG)n expansion mutation in patients with proximal myotonic myopathy/proximal myotonic dystrophy of different European origins: a single shared haplotype indicates an ancestral founder effect. *Am J Hum Genet*. October 2003; 73(4):835-848; Hamshere M G, Harley H, Harper P, et al. Myotonic dystrophy: the correlation of (CTG) repeat length in leucocytes with age at onset is significant only for patients with small expansions. *J Med Genet*. January 1999; 36(1):59-61; Liguori C L, Ricker K, Moseley M L, et al. Myotonic dystrophy type 2 caused by a CCTG expansion in intron 1 of ZNF9. *Science*. Aug. 3, 2001; 293(5531):864-867). The mutant DMPK messenger RNA (mRNA) containing an expanded CUG repeat is retained in the nucleus and protein levels are reduced (Mankodi A, Logigian E, Callahan L, et al. Myotonic dystrophy in transgenic mice expressing an expanded CUG repeat. *Science*. Sep. 8, 2000; 289(5485):1769-1773). The RNA repeat expansion changes the chromatin structure, silences the expression of the flanking SIX5 gene which codes for a transcription factors, and disrupts regulation of gene expression during development and exercise (Ebralidze A, Wang Y, Petkova V, et al. RNA leaching of transcription factors disrupts transcription in myotonic dystrophy. *Science*. Jan. 16, 2004; 303(5656):383-387).

The cause of the most severe symptoms including muscle weakness and progressive muscle wasting appear to be caused by elevated intracellular $Ca^{2+}$ concentrations and subsequent myofiber degeneration in DM1 (Jacobs A E, Benders A A, Oosterhof A, et al. The calcium homeostasis and the membrane potential of cultured muscle cells from patients with myotonic dystrophy. *Biochim Biophys Acta*. Nov. 14, 1990; 1096(1):14-19). Moreover, a recent study has linked disturbed $Ca^{2+}$ cycling in DM1 to aberrant splicing of RyR1 and SR $Ca^{2+}$ ATPase (SERCA1) mRNAs (Kimura T, Nakamori M, Lueck J D, et al. Altered mRNA Splicing of the Skeletal Muscle Ryanodine Receptor and Sarcoplasmic/Endoplasmic Reticulum Ca2+-ATPase in Myotonic Dystrophy Type 1. *Hum Mol Genet*. Jun. 22, 2005). A muscle-specific genetic mouse model $HSA^{LR}$ of DM1 exists in which expanded CUG repeat expression results in a DM-like phenotype (Mankodi A, Logigian E, Callahan L, et al. Myotonic dystrophy in transgenic mice expressing an expanded CUG repeat. *Science*. Sep. 8, 2000; 289(5485):1769-1773). $HSA^{LR}$ have a myotonic phenotype in the absence of muscle fiber necrosis and the short-versus long-repeat expressing mouse lines show relatively less or more histopathological signs of muscle regeneration and repair, respectively (Mankodi A, Logigian E, Callahan L, et al. Myotonic dystrophy in transgenic mice expressing an expanded CUG repeat. *Science*. Sep. 8, 2000; 289(5485):1769-1773). Since $HSA^{LR}$ mice with short- or long repeat expression show no signs of muscle weakness and since RyR1 alterations have been linked to DM1, the $HSA^{LR}$ mice provide a model to study the effects of exercise and activation of the sympathetic nervous system in these mice. After characterizing RyR1 channel composition, phosphorylation status, and function, the $HSA^{LR}$ mice can be challenge with sustained exercise tests and treated with RyCal compounds. Since the mechanism by which transcripts with expanded CUG repeats cause myotonia and muscle degeneration in DM1 is not known, this would provide 1) study of a genetic animal model of severe fatigue, 2) elucidation of the key molecular mechanism of DM1, and 3) developing a therapeutic rationale for the most common muscular dystrophy in adults.

Stress Pathways and Muscle Fatigue

Sustained activation of intracellular stress pathways such as occurring during strenuous physical exercise, for example but not limited to combat, can result in reduced muscle performance and tissue damage. A major determinant of muscle damage may occur due to toxicity of continuously high catecholamine levels resulting in intracellular $Ca^{2+}$ leak. This concept is supported by: 1) physiologic (non-combat) exercise or stress was reported to induce muscle weakness, cramps, and tissue atrophy in susceptible individuals (stress-induced rhabdomyolysis) (Wappler et al., 2001); 2) strenuous but not mild treadmill exercise induces a significantly elevated Ca$^{2+}$ spark frequency in muscle cells indicating intracellular Ca$^{2+}$ leak (Wang et al., 2005); 3) excess catecholamine levels were found in malignant hyperthermia (MH) and central core disease (CCD) contributing to uncontrolled intracellular Ca$^{2+}$ release (Monnier et al. 2000; MacLennan et al. 1995); 4) a majority of MH/CCD were linked to RyR1 missense mutations (Loke et al., 2003); 5) a hyperadrenergic state as occurring in heart failure causes RyR1 hyperphosphorylation, Ca$^{2+}$ leak, and skeletal muscle fatigue (Reiken et al. 2003); and 6) excess plasma catecholamine levels by activating β-adrenergic receptors, intracellular cAMP synthesis and protein kinase A phosphorylation results in muscle damage (Goldspink et al., 2004; Tan et al. 2003). Stress-dependent muscle damage and dysfunction occurs at the interface between intracellular catecholamine effectors (protein kinase A, PKA) and intracellular Ca$^{2+}$ release. Skeletal ryanodine receptor (RyR1) Ca$^{2+}$ release channels constitute intracellular scaffolds that integrate PKA-mediated stress signaling and regulation of intracellular Ca$^{2+}$ release and therefore determine the gain of EC coupling and muscle function. Importantly, chronically increased PKA phosphorylation of RyR1 occurring from a chronic hyperadrenergic state in vivo depletes the stabilizing calstabin1 subunits resulting in SR Ca$^{2+}$ leak and muscle fatigue. Moreover, these observations extend to an in vivo animal model of fatigue. Therefore, sustained activation of the sympathetic nervous system during continued muscle performance contributes to increased fatigue development and dystrophic skeletal muscle damage. Since skeletal RyR1 Ca$^{2+}$ release channel is PKA hyperphosphorylated and depleted of the stabilizing calstabin1 subunit after 21 days of intense exercise, wherein similar alterations result in intracellular Ca$^{2+}$ leak in animals with heart failure, it is likely that chronic (>1 week) forms of exercise result in adverse intracellular Ca$^{2+}$ leak from defective RyR1 channels.

In one aspect, the invention establishes molecular mechanisms of muscle fatigue occurring from chronically sustained muscle performance. In another aspect the invention provides methods for treating or preventing detrimental intracellular Ca$^{2+}$ leak and muscle damage by administering novel 1,4-benzothiazepine derivatives. The skeletal ryanodine receptor (RyR1) channel is comprised of 4 RyR1 subunits and associated proteins that bind to the cytoplasmic domain of the channel forming a macromolecular signaling complex. Certain aspects of the invention examine mechanisms by which allosteric modulators regulate RyR1 function. Two specific forms of allosteric modulation are examined: 1) regulation of the channel by cAMP-dependent protein kinase A (PKA) that potently activates channel gating; 2) depletion of the stabilizing subunit calstabin1 from the RyR1 channel during chronically increased PKA phosphorylation resulting from chronic activation of the sympathetic nervous system by strenuous, sustained exercise.

Dysregulation of RyR1 by PKA during sustained exercise causes intracellular Ca$^{2+}$ leak and may be a mechanism of increased muscle fatigue and dystrophic remodeling. In certain aspects, the invention determines the effects of fatiguing exercise on 1) RyR1 PKA phosphorylation; 2) RyR1 channel function examined using RyR1 channels reconstituted into planar lipid bilayers; 3) Calstabin1 binding to RyR1; 4) intracellular Ca$^{2+}$ sparks in isolated myofibers; 5) isolated skeletal muscle function; 6) mitochondrial integrity, 7) in vivo exercise performance, 8) skeletal muscle histology, fiber type composition and oxidative capacity, 9) creatine kinase (CK) plasma levels, 10) RyR1 PKA phosphorylation and calstabin1 depletion in leukocytes. Calstabin1 depletion during chronically sustained exercise and PKA hyperphosphorylation causes RyR1 hyperactivity, intracellular Ca$^{2+}$ leak, depletion of SR Ca$^{2+}$ stores, accelerated fatigue and dystrophic muscle remodeling.

In certain embodiments, treatment with any RyCal compound normalizes RyR dysfunction and intracellular Ca$^{2+}$ leak. RyR1, which are protein kinase A (PKA) hyperphosphorylated and "leaky" in heart failure models and during strenuous exercise, can rebind calstabin1 after RyCal compound treatment, which normalizes single channel and improves muscle performance in heart failure. It is likely that RyCals in vivo and in cells treated with RyCals prevent intracellular Ca$^{2+}$ leak and normalize RyR1 channel function during sustained exercise.

By preventing RyR1 Ca$^{2+}$ leak, RyCal compounds improves skeletal muscle fatigue and dystrophic remodeling during strenuous exercise as occurs in combat. By using two animal models of muscle fatigue (swimming and running on a treadmill) in mice and rats, certain aspects of the invention show that treatment with RyCal compounds prevents depletion of calstabin1 from RyR1, which decreases muscle fatigue, improves performance, and inhibits dystrophic muscle remodeling.

Certain aspects of the invention identify molecular mechanisms of muscle fatigue in myotonic dystrophy (DM1). In certain embodiments, by preventing RyR1 Ca$^{2+}$ leak, RyCal compounds improve skeletal muscle fatigue times and dystrophic remodeling in mouse models of myotonic dystrophy.

Other aspects of the invention characterize molecular fatigue mechanisms in genetic mouse models. In certain embodiments, calstabin1 and PDE4D3 knockout mice can be used to further explore molecular fatigue mechanisms and dysregulation during sustained exercise states that contribute to intracellular Ca$^{2+}$ leak. In other aspects, the compounds of the invention reduce calpain activity. In other aspects, the compounds of the invention reduce plasma creatine kinase activity.

Other aspects of the invention, characterize mechanisms that destabilize the closed state of intracellular calcium (Ca$^{2+}$) release channels during chronic activation of the sympathetic nervous system as occurs during sustained exercise and/or in combat. There are two allosteric modulators of skeletal ryanodine receptors (RyR1s), one is PKA and the other one is a stabilizing protein subunit of the channel (calstabin1) (Wehrens et al., 2004). Other aspects of the invention disclose therapeutic and preventive measures wherein a drug molecule that rebinds calstabin1 may prevent skeletal muscle fatigue by normalizing the skeletal (RyR1) ryanodine receptor gating. Protein kinase A (PKA) hyperphosphorylation of RyR1 during chronic activation of the sympathetic nervous system was shown to result in SR Ca$^{2+}$ leak as a cause of fatigue (Reiken et al., 2003) which was reversed by JTV-519 (Wehrens et al., 2005). In certain aspects, the invention provides, thorough characterization of the effects of strenuous exercise on RyR1 Ca$^{2+}$ leak, in vivo and ex vivo muscle performance and energetic metabolism, methods for the use of RyCal compounds to overcome muscle fatigue and to prevent muscle damage and/or fatigue during strenuous, and/or sustained exercise, and muscle damage and/or fatigue associated with defective skeletal muscle function, or any disease condition.

Certain aspects of the invention characterize mechanisms that destabilize the closed state of intracellular calcium (Ca$^{2+}$) release channels which is a prerequisite for muscle relaxation to occur and prevents damage of myofibers from uncontrolled intracellular SR Ca$^{2+}$ leak. Chronic activation of the sympathetic nervous system during forced and sustained exercise caused RyR1 PKA hyperphosphorylation, calstabin1 depletion, and a defective channel closed state are consistent with SR $Ca^{2+}$ leak. Since stress and physical performance in combat are considered significantly more severe compared to the animal use protocols, it can be extrapolated that muscle fatigue and dystrophic degeneration from RyR1 $Ca^{2+}$ leak represents a more severe phenotype in warfighters. The focus is on two allosteric modulators of skeletal ryanodine receptors (RyR1s), one PKA as a key stress pathway and the other one a stabilizing protein subunit of the channel (calstabin1).

Certain aspects of the invention address potential therapeutic and preventive measures in that a drug molecule rebinding calstabin1 may prevent skeletal muscle fatigue by normalizing the skeletal (RyR1) ryanodine receptor channel gating. Protein kinase A (PKA) hyperphosphorylation of RyR1 during chronic activation of the sympathetic nervous system was shown to result in SR $Ca^{2+}$ leak as a cause of fatigue (Wehrens X H, Lehnart S E, Reiken S, et al. Enhancing calstabin binding to ryanodine receptors improves cardiac and skeletal muscle function in heart failure. *Proc Natl Acad Sci USA*. Jul. 5, 2005; 102(27):9607-9612; Ward C W, Reiken S, Marks A R, et al. Defects in ryanodine receptor calcium release in skeletal muscle from post-myocardial infarct rats. *Faseb J*. August 2003; 17(11):1517-1519). Certain aspects of the invention are directed to thorough characterization of the effects of strenuous exercise on RyR1 $Ca^{2+}$ leak, in vivo and ex vivo muscle performance and energetic metabolism, and the use of RyCal compounds to improve muscle fatigue times, to increase exercise capacity, and to prevent muscle damage during and/or after strenuous, sustained exercise.

Life quality and prognosis in heart failure patients is decreased due to skeletal muscle dysfunction (e.g., shortness of breath due to diaphragmatic weakness, and exercise intolerance due to limb skeletal muscle fatigue) (Harrington et al. 1997). Recent studies have identified dysregulation of intracellular $Ca^{2+}$ release from the SR as a pathogenic mechanism underlying skeletal muscle dysfunction in heart failure (Reiken S, Lacampagne A, Zhou H, et al. PKA phosphorylation activates the calcium release channel (ryanodine receptor) in skeletal muscle: defective regulation in heart failure. *J Cell Biol*. Mar. 17, 2003; 160(6):919-928; Ward, 2003; Perreault C L, Gonzalez-Serratos H, Litwin S E, et al. Alterations in contractility and intracellular Ca2+ transients in isolated bundles of skeletal muscle fibers from rats with chronic heart failure. *Circ Res*. August 1993; 73(2):405-412). Heart failure in animals with myocardial infarcts causes significantly accelerated fatigue which is intrinsic to skeletal muscle as measured by the time for the tetanic force to fall below 50% of the maximal contraction (Reiken, 2003).

Skeletal RyR1 are PKA Hyperphosphorylated and Depleted of Calstabin1

Previous studies have suggested that skeletal muscle RyR1 channels are PKA hyperphosphorylated and depleted of calstabin1 in a pacing-induced canine model of heart failure and a rat post-myocardial infarct model (Reiken et al., 2003; Ward et al., 2003). Furthermore, in a mouse model of post-myocardial infarction heart failure, RyR1 in soleus muscle is PKA-hyperphosphorylated. In certain embodiments, treatment with a RyCal compound, allows rebinding of calstabin1 to RyR1 despite intense chronic exercise.

Beta-adrenergic stimulation increases the gain of the EC coupling when enhanced muscle performance is required during exercise or stress (fight-or-flight response). Binding of catecholamines to β-adrenoceptors activates a G-protein coupled intracellular signaling cascade, which leads to increased intracellular cAMP concentrations and activation of protein kinase A (PKA). PKA is targeted to RyR1 via mAKAP forming a signaling complex with the skeletal $Ca^{2+}$ release channel (Reiken et al. 2003). RyR1 phosphorylation by PKA increases the channel open probability and SR $Ca^{2+}$ release (Reiken et al., 2003; Wehrens et al., 2004).

Data from skeletal myofibers have confirmed intracellular $Ca^{2+}$ leak from enhanced RyR1 activity after strenuous exercise consistent with an increased maximal rate of SR $Ca^{2+}$ release. PKA-hyperphosphorylation of RyR1 results in depletion of calstabin1 (FKBP12) from the channel complex due to a reduced binding affinity for calstabin1. Chronic depletion of calstabin1 from the RyR1 channel complex relieves an intrinsic inhibition of the channel and induces uncontrolled intracellular $Ca^{2+}$ leak and reduced fatigue resistance during a sustained hyperadrenergic state. Skeletal muscle fatigue is increased in heart failure patients and in animal models of heart failure (Reiken et al., 2003; Harrington et al., 1997; Perreault et al., 1993; Lunde et al. 2001; Lunde et al. 1998). In both patients and animals with heart failure the skeletal RyR1 channel isoform was found PKA hyperphosphorylated and depleted of the stabilizing calstabin1 subunits (Reiken et al., 2003; Wehrens et al., 2004). Increased fatigue and RyR1 hyperphosphorylation are associated with an increased $Ca^{2+}$ spark frequency and a decreased $Ca^{2+}$ spark amplitude in skeletal myofibers in heart failure animals consistent with intracellular $Ca^{2+}$ leak and decreased SR $Ca^{2+}$ concentrations (Reiken et al., 2003). Therefore, most likely increased muscle fatigue results from a chronic hyperadrenergic state causing an intracellular $Ca^{2+}$ leak via defective RyR1 channels (Reiken et al., 2003).

However, it is important to conceptualize that the role of external $Ca^{2+}$ ions in mammalian skeletal muscle contraction is not completely understood. The LTCC and RyR isoforms in skeletal and cardiac muscles are different, with skeletal muscle expressing the LTCC $\alpha 1_S$ subunit (Tanabe et al., 1988) and RyR1 (Marks et al., 1989), and cardiac muscle expressing the LTCC $\alpha 1_C$ subunit (Mikami et al., 1989) and RyR2 (Nakai et al., 1990). RyR1 in skeletal muscle does not depend on $Ca^{2+}$ influx via LTCC $\alpha 1_S$ to activate SR $Ca^{2+}$ release as evidenced by continuous EC coupling in skeletal muscle cells when external $Ca^{2+}$ is removed or when $Ca^{2+}$ channel blockers are present (Armstrong et al., 1972; Dulhunty et al., 1988; Gonzalez-Serratos et al., 1982). Later experimental findings support RyR1 activation by physical coupling with LTCC $\alpha 1_S$ (Rios et al., 1987; Tanabe et al., 1990). RyR1 $Ca^{2+}$ leak likely increases the cellular energy demands by compensatory SR $Ca^{2+}$ ATPase uptake consuming more ATP which may contribute to earlier skeletal muscle fatigue. From direct oxygen measurements on the surface of contracting muscle preparations, it is estimated that total ATP consumption by SR $Ca^{2+}$ ATPases is significantly elevated in heart failure (Meyer et al., 1998) likely resulting from intracellular $Ca^{2+}$ leak. In agreement with decreased SR $Ca^{2+}$ concentrations due to RyR1 $Ca^{2+}$ leak, muscle-specific calstabin1 knockout increases LTCC $Ca^{2+}$ influx and reduces maximal voltage-gated intracellular $Ca^{2+}$ release (Tang et al., 2004).

Recent studies have demonstrated defective function of RyR1 channels in skeletal muscle during heart failure, which were analogous to those found in RyR2 channels in failing myocardium: PKA hyperphosphorylation of RyR1 and depletion of calstabin1 (Marx et al., 2000; Reiken et al., 2003; Wehrens et al., 2005). These findings suggest that defects in RyR1 function alter intracellular $Ca^{2+}$ handling, thereby contributing to early fatigue in skeletal muscles. Depletion of calstabin1 from the RyR1 macromolecular complex may also uncouple channels from one another and allow stochastic as opposed to coupled gating (Marx et al., 1998), thus providing an attractive hypothesis for explaining the altered $Ca^{2+}$ spark behaviour in skeletal muscle with reduced fatigue resistance (Ward et al., 2003). Thus, alterations in RyR1 could play a significant role in the skeletal muscle specific force decrements and reduced exercise-tolerance seen in models of increased muscle fatigue.

Methods

Aerobic exercise can be defined as a form of physical exercise that increases the heart rate and enhances oxygen intake to improve performance. Examples of aerobic exercise are running, cycling, and swimming. In certain embodiments, mice were challenged by aerobic exercise (forced swimming) for 90 mins twice daily. The animals were accustomed to swimming in preliminary training sessions: day −3 twice 30 mins, day −2 twice 45 mins, day −1 twice 60 mins, day 0 and following twice 90 mins. Mice were then exercised for 1, 7, or 21 additional, consecutive days for 90 mins twice daily. Between swimming sessions separated by a 4 hour rest period the mice are kept warm and given food and water. An adjustable-current water pool was used to exercise mice by swimming. An acrylic pool (90 cm long×45 cm wide×45 cm deep) was filled with water to a depth of 25 cm. A current in the pool was generated with a pump. The current speed during the swimming session was at a constant speed of 1 l/min flow rate. The water temperature was maintained at 34° C. with an electric heater. Age- and weight-matched mice are used to exclude differences in buoyancy from body fat.

Using forced swimming as an efficient protocol to increase skeletal muscle aerobic capacity in mice (Evangelista et al., 2003), the composition and phosphorylation status of the skeletal RyR1 channel complex was investigated. Unexpectedly, after 3 weeks of 90 mins swimming twice daily, C57B16 wild-type mice showed significantly increased RyR2 phosphorylation by PKA while CaMKII phosphorylation was not changed. RyR1 protein expression was stable, however, RyR1 channels were depleted of the stabilizing subunit calstabin1 (FKBP12). RyR1 hyperphosphorylation and calstabin1 depletion are consistent with leaky RyR1 channels that cause intracellular $Ca^{2+}$ leak.

To investigate the influence of the duration of sustained exercise on the RyR1 $Ca^{2+}$ release channel defect, mice were exposed to swimming for 1, 7, or 21 days followed by immediate sacrifice. Longer exposure to sustained exercise shows a significant increase of RyR1 PKA hyperphosphorylation beginning at 7 days and saturating at 21 days.

Moreover, a mouse model of muscular dystrophy which is known to result in intracellular $Ca^{2+}$ leak and dystrophic muscle changes was investigated. Surprisingly, soleus muscles of the dystrophin-deficient mdx mouse show calstabin1 depletion in the absence of increased RyR1-Ser2844 phosphorylation. These results identify RyR1-Ser2844 PKA hyperphosphorylation as a specific event in exercise-induced RyR1 dysfunction.

Additionally, the histological changes in the fast-twitch muscles of mice exposed to 3 weeks of exercise by swimming were characterized. Cross-sections of the mouse M. extensor digitorum longus (EDL) showed histological changes consistent with myofiber degeneration from intracellular $Ca^{2+}$ overload from defective RyR1 channel. Therefore sustained exercise for 90 mins twice daily triggers a distrophic phenotype in EDL muscles of normal C57B16 mice.

Up-regulation of intracellular SR $Ca^{2+}$ release by cAMP-dependent signaling pathways augments the gain of excitation-contraction coupling during peak muscle performance. (Reiken, 2003) Therefore transient PKA phosphorylation of skeletal RyR1 $Ca^{2+}$ release channels represents a key mechanism of the fight-or-flight response. Studies have established that dysregulation of RyR1 $Ca^{2+}$ release channels occurs during strenuous fatiguing exercise. Mice which underwent rigorous exercise for 3 weeks showed significantly increased levels of RyR1 PKA phosphorylation, increased RyR1 channel activity, and dystrophic histological changes. Chronic RyR1 hyperphosphorylation results in depletion of the stabilizing calstabin1, functional channel defects, suggesting intracellular $Ca^{2+}$ leak. At the level of the muscle cell, this model was recently confirmed by a report that increased $Ca^{2+}$ spark frequency after fatiguing exercise in mouse skeletal muscle (Wang et al., 2005). Moreover, it was shown that intracellular $Ca^{2+}$ leak from chronic exercise acts as dystrophic signal in mammalian skeletal muscle (Wang, 2005). This confirms previous observations in cardiac muscle, where hormonal and structural changes contribute to intracellular $Ca^{2+}$ leak causing defective excitation-contraction coupling (Gomez, 1997). From these studies (Wehrens et al., 2005; Reiken et al., 2003) and the $Ca^{2+}$ spark data in fatiguing muscle (Wang et al., 2005) it is likely that intracellular $Ca^{2+}$ leak represents a key pathology that accelerates muscle fatigue and causes dystrophic remodeling of muscles. Accordingly, extended investigation of fatigue models at the in vivo, isolated muscle, muscle cell, mitochondria, and single RyR1 channel level will characterize detrimental effects during peak performance on muscle fatigue and dystrophic remodeling.

1,4-benzothiazepine derivatives prevent muscle dysfunction from intracellular $Ca^{2+}$ leak under conditions of sustained sympathetic nervous system activation occurring from heart failure (Wehrens et al., 2005). In certain aspects, the invention provides RyCal compounds and their use to enhance skeletal muscle performance and to reduce muscle dysfunction during sustained stress as occurs under combat conditions. Defects in the RyR1 $Ca^{2+}$ release channel due to dysregulation by PKA allow rationalizing of a therapeutic concept: intracellular SR $Ca^{2+}$ leak and muscle dysfunction can be prevented by a drug that increases binding of the stabilizing calstabin1 subunit to the RyR1 channel complex and thereby inhibits SR $Ca^{2+}$ leak and dystrophic muscle remodeling from sustained stress or exercise. Applying a drug to prevent SR $Ca^{2+}$ leak can therefore enhance a variety of important physiologic skills which are prone to stress-induced dysfunction. In certain aspects, the invention provides that enhanced binding of calstabin1 to RyR1 by RyCal compounds prevents muscle fatigue. Using animal models of physiologic (swimming and running on a treadmill) and/or pharmacologic activation β-adrenergic receptor agonists) of the sympathetic nervous system combined with different degrees of exercise exposure, it can be tested whether RyCal compounds improve skeletal muscle function and prevent dystrophic muscle degeneration. This may lead to a pharmacologic approach based on allosteric modulation of RyR1 that can result in improved human performance during sustained stress and prevent adverse tissue damage thereby shortening recovery times. In other aspects, the invention provides pharmacologic approaches based on allosteric modulation of RyR1 that can result in improved human performance during sustained stress and prevent adverse tissue damage and shorten recovery times.

RyR1 PKA phosphorylation: quantification of skeletal RyR1 channel phosphorylation by protein kinase A (PKA) following sustained exercise for 2 days, 1 week, and 3 weeks using two independent techniques (RyR1 PKA phospho-epitope detection by specific antibody; incorporation of radiolabeled phosphate by backphosphorylation essay).

RyR1 CaMKII phosphorylation: quantification of skeletal RyR1 channel phosphorylation by $Ca^{2+}$-calmodulin protein kinase II (CaMKII) following sustained exercise for 2 days, 1 week, and 3 weeks using RyR1 CaMKII phospho-epitope detection by specific antibody essay developed in our laboratory. This will allow characterizing specific defects resulting from chronic PKA phosphorylation and/or secondary activation of CaMKII signaling by intracellular $Ca^{2+}$ leak mechanisms.

Calstabin1 depletion in the RyR1 complex: quantification of depletion of the channel stabilizing subunit calstabin1 (FKBP12) from the RyR1 channel complex by immunoprecipitation techniques following sustained exercise for 2 days, 1 week, and 3 weeks. Calstabin1 depletion occurs from Ser2844 phosphorylation by PKA.

RyR1 functional defects—in vivo development of "leaky" RyR1 channels: electrophysiologic characterization of RyR1 single-channel activity and open probability following sustained exercise for 2 days, 1 week, and 3 weeks. This allows for a comprehensive and sensitive assessment of SR $Ca^{2+}$ release channel defects and leak mechanisms that are known to contribute to muscle fatigue. Moreover, these data will allow developing a rationale for preventive treatment of RyR1 $Ca^{2+}$ leak using a small lead RyCal compounds.

Improvement of in vivo fatigue from sustained exercise: quantification of in vivo fatigue using two independent exercise performance tests: swimming and running on a treadmill. The treadmill test will be combined with electrocardiogram telemetry in a subgroup of animals to allow for objective correlation of increased heart rates during exercise with fatigue symptoms. Moreover, plasma and muscle catecholamine levels will be determined to verify sustained activation of the sympathetic nervous system. Three weeks of maximal fatiguing swimming exercise induces progressive RyR1 dysfunction and dystrophic skeletal muscle changes during a low flow rate of 1 l/min (baseline condition which prevents mice from floating passively). To objectively quantify fatigue times during swimming exercise, video tracking system can be used (San Diego Instruments Incorporated) which automatically tracks and digitizes spatio-temporal movements of 8 mice. Improvement of fatigue will be assessed by time to fatigue (defined as significant increase in 2D distance or activity over time).

Improvement of maximal exercise capacity: To determine maximal endurance exercise capacity (i.e., time to exhaustion), the maximum swim times are measured at a flow rate of 7 l/min in repeated measurements three times a week. To reduce the inherent variation in swimming capacity, mice whose mean maximum swim times vary by more than 40% than the average swim time will be excluded. A mouse is qualified as fatigued when it fails to rise to the water surface to breathe and will be rescued at this point. To verify the systemic exhaustion after swimming, plasma lactate and pH will be determined in heparinized arterial blood samples. To objectively quantify fatigue times during forced swimming exercise, we will use a video tracking system (San Diego Instruments Incorporated) which automatically tracks and digitizes spatio-temporal movements of 8 mice in a 2D plane.

Isolated skeletal muscle function: ex vivo characterization of intrinsic muscle resistance to fatigue stimulation or single-twitch contraction protocols following sustained exercise with placebo or a RyCal compound treatment for 2 days, 1 week, and 3 weeks. Two different forms of isolated skeletal muscles will be tested: extensor digitorum longus for a fast-twitch muscle and soleus muscle for a slow-twitch muscle. This test can determine the effect of RyCal compounds on skeletal muscle under fatiguing exercise, or disease conditions. Skeletal muscle contraction and relaxation is critically dependent on intracellular $Ca^{2+}$ metabolism and RyR1 function and therefore a highly sensitive test.

Intracellular $Ca^{2+}$ leak and SR $Ca^{2+}$ content in isolated skeletal myofibers: assessment of isolated skeletal muscle myofibers loaded with fluo-4 $Ca^{2+}$ indicators for resting SR $Ca^{2+}$ leak using intracellular $Ca^{2+}$ sparks. SR $Ca^{2+}$ content will be assessed by caffeine pulse protocols which result in complete release of the free SR $Ca^{2+}$ pool. Previous studies have documented calcium leak resulting from a chronic hyperadrenergic state in myofibers of rats with heart failure (Reiken 2003; Ward 2003; Gomez 2001; Cheng 1996).

Changes in mitochondrial integrity from SR $Ca^{2+}$ leak: mitochondria in mouse skeletal muscle take up $Ca^{2+}$ which under conditions of strong physiologic muscle stimulation result in continuously elevated mitochondrial $Ca^{2+}$ levels which stimulates mitochondrial metabolism (Rudolf et al., 2004). However, myotubes from dystrophic mdx mice showed significantly elevated $Ca^{2+}$ uptake. (Robert V, Massimino M L, Tosello V, et al. Alteration in calcium handling at the subcellular level in mdx myotubes. *J Biol Chem*. Feb. 16, 2001; 276(7):4647-4651.) Cytosolic $Ca^{2+}$ overload is a highly toxic event that represents a common final pathway of cell death. Mitochondria are key players in cell death, and the spatial proximity of RyR1 $Ca^{2+}$ release and mitochondrial $Ca^{2+}$ uptake suggest, that SR $Ca^{2+}$ leak during strenuous exercise can cause mitochondrial $Ca^{2+}$ overload which impacts on mitochondrial structure and function and may trigger cell death. Caspase-12 is localized in the SR, is regulated by $Ca^{2+}$, and participates in the SR stress-induced apoptosis pathway (Yoneda et al., 2001). In certain aspects the invention characterizes the effects of fatiguing exercise on mitochondrial membrane potential by rhodamine 123 uptake, mitochondrial swelling indicating mitochondrial permeability transition by 520 nm spectrophotometry and light scatter, the amount of intra-mitochondrial $Ca^{2+}$ by organelle incubation with $^{45}Ca^{2+}$ followed by radioactivity quantification with a liquid scintillation counter, measurement of cytochrome c from release mitochondria coactivating caspases, and staining of muscle preparations for TUNEL-positive cell nuclei. The in vivo effects of RyCal compounds treatment on mitochondrial integrity and function will be assessed.

Activation of intracellular proteases fragments RyR1: A direct link exists between the cytosolic $Ca^{2+}$ elevations and the proteolysis of intracellular targets through the activation of $Ca^{2+}$-dependent proteases, including calpains and caspases. Calpain activation is part of the apoptosis machinery. Increased activation of the ubiquitous calpains has been found in the mouse model of Duchenne muscular dystrophy (DMD), but null mutations of muscle specific calpain causes limb girdle muscular dystrophy 2A (LGMD2A) (Tidball et al., 2000). These findings indicate that dysregulation of calpain activity contributes to progression of muscle disease by disrupting normal regulatory mechanisms and by a generalized, nonspecific increase of proteolytic capacity. RyR1 and other components of the $Ca^{2+}$ cycling machinery are targets of and cleaved by caspases and calpains (Johnson et al., 2004; Shevchenko at al., 1998). We will therefore investigate if $Ca^{2+}$ dependent protease and/or caspase activation result in RyR1 cleavage following strenuous exercise and if JTV-519 by inhibiting SR $Ca^{2+}$ leak can prevent activation of unspecific proteolysis.

Histologic changes of skeletal muscle from strenuous, fatiguing exercise: Dystrophic changes from sustained exercise may result in muscle fiber necrosis and progressive muscle wasting and weakness. Histological analysis of skeletal muscles will include analysis for eosinophilic hypercontracted muscle fibers, necrotic fibers, ongoing muscle regeneration, and the proliferation of fibroblasts within muscle tissue since the replacement of muscle tissue by connective tissue (fibrosis) is a major cause of permanent muscle weakness. Accordingly, RyCal compounds can be tested for inhibition of these changes. Conventional histology techniques will allow to assess variability in fiber size, split fibers, and centralized nuclei.

Fiber typing by histochemistry in skeletal muscles: Historically, the most widely used classification of fiber types is based on the mATPase (myofibrillar adenosine triphosphatase) activity by histochemistry which distinguishes between type I (low activity) and type II (high activity) fibers (Brooke et al., 1970). By characterizing the pH lability of the mATPase, type II fibers were further subdivided into IIA and IIB fibers. Additional fiber type characterization with physiologic, histochemical, and ultrastructural methods has revealed: type I, intermediate slow-twitch oxidative; type IIA, red fast-twitch oxidative-glycolytic; and type IIB, white fast-twitch glycolytic fibers. Quantitative histochemistry can be used to determine mATPase, succinate dehydrogenase, and α-glycerophosphate dehydrogenase and cross-sectional areas in MHC-based fiber type changes in oxidative and glycolytic capacities resulting from sustained exercise and/or RyCal compound treatment. To determine myofiber ATPase activity, a protocol using 10 μm thick frozen sections which are preincubated for 5 mins under acidic or 12 mins under alkaline conditions can be used. Succinate dehydrogenase staining will allow characterizing activity and distinction between muscle fibers. Changes in oxidative muscle fiber types and improvement after treatment for myotonia have been reported in mice previously (Reininghaus et al., 1988).

Fiber typing by immunocytochemistry in skeletal muscles: To quantitate changes in myonuclear number and location and to distinguish from nuclei of interstitial cells, morphometry by fluorescence microscopy using stains for nuclei (DAPI) and basement membrane (anti-laminin) will be applied. This technique will be particularly important to precisely determine cross-sectional area and number of nuclei in muscle fibers. Moreover, the technique allows for combined immunocytochemistry with the following affinity-purified antibodies: C-terminal RyR2-5029, phospho-epitope-specific RyR1-p2844 (Wehrens et al., 2004), calstabin1 (FKBP12) (Jayaraman et al., 1992), isoform-specific myosin heavy chain (MHC) antibodies (Rivero et al. 1999), and α-actinin (Ruehr et al., 2003) using a previously established protocol with 10 μm thick cryostat sections of EDL or soleus muscles (Moschella et al., 1995). This approach will allow us to classify myofibers and phenotypic changes according to MHC content, metabolic activity, fiber size, RyR1 PKA phosphorylation, and calstabin1 binding occurring from sustained exercise and/or RyCal compound treatment. Further, the fiber type and immunocytochemistry data will be correlated to isolated skeletal muscle function, general histologic data, histochemistry, RyR1 single-channel function, and mitochondria data. Using immunohistochemical staining, fiber type-specific improvement of calstabin1 binding to RyR1 and RyR1 PKA phosphorylation can be determined in the presence or absence, or after RyCal compound treatment in α-actinin positive compartments (Z-disk), and for increased calpain expression in the myofibrillar area (Z disks; compartment containing RyR1 channels) of muscle fibers.

Skeletal muscle oxidative capacity: Muscle oxidative activity correlates with skeletal muscle adoption to aerobic exercise. As a general test, fast- and slow-twitch skeletal muscle oxidative enzyme activity will be assessed by spectrophotometric assessment of the citric acid cycle and citrate synthase activity in muscle homogenates. Activity as determined as the complex from coenzyme A and oxaloacetate is expected to be increased as reported by a group using a similar protocol (Evangelista et al., 2003). This test will be used to confirm changes in oxidative capacity seen by histochemistry.

Improvement of creatine kinase (CK) plasma levels: Creatine kinase (CK) and lactate dehydrogenase (LDH) plasma concentrations (Santos et al., 2004; Thompson et al., 2004), can be determined as indicators or muscle damage and inflammation after exhaustive exercise and to determine effect due to RyCal compound treatment.

RyR1 composition and function in white blood cells: RyR1 in immune cells functions as a $Ca^{2+}$ release channel during B- or T-cell receptor-stimulated activation (Sei et al., 2002; Kraev et al., 2003). For functional analysis, peripheral white blood cells are isolated from mouse blood samples by centrifugation. Leukocytes ($10^6$/ml) are loaded with 1 μm acetoxymethyl ester of fluo-3 (Molecular Probes, Eugene, Oreg.) by incubation for 30 mins at 25° C. and caffeine sensitivity of intracellular $Ca^{2+}$ release is tested. Composition and PKA phosphorylation of the RyR1 channel complex will be characterized. Investigating RyR1 in white blood cells will allow monitoring temporal changes during sustained exercise and RyCal compound treatment in vivo.

Genetically Modified Mice

The RyR1 macromolecular signaling complex plays a key role in modulating activation of the channel and excitation-contraction coupling by the sympathetic nervous system. In the RyR1 complex mAKAP targets PKA and the phosphodiesterase PDE4D3 to the channel and the phosphatase PP1 is targeted to the channel by the targeting protein spinophilin. This signaling module controls PKA phosphorylation of RyR2 at Ser2843 as part of the "fight-or-flight" stress response. During normal exercise 2-3 of the four Ser2843 PKA phosphorylation sites in each tetrameric RyR1 channel are transiently PKA phosphorylated resulting in increased activity of the RyR1 channel.

Activation of the RyR1 due to PKA phosphorylation occurs because PKA phosphorylation decreases the binding affinity of the stabilizing protein calstabin1 (FKBP12) for the channel resulting in increased sensitivity of the channel to $Ca^{2+}$-dependent activation. PDE4D3 in the RyR1 macromolecular signaling complex plays a protective role against PKA hyperphosphorylation and forms a negative feedback loop during PKA activation. The phosphodiesterases in the RyR1 complex by rapidly degrading local cAMP and thereby terminating channel activation by PKA. Mice that are deficient in PDE4D3 or calstabin1 in the RyR1 complex will be tested for accelerated muscle fatigue. Thus, both calstabin1 and PDE4D3 in the RyR2 complex can be thought of as being "protective" against muscle dysfunction during excessive exercise or stress. Thus additional components of the RyR1 macromolecular complex are protective against fatigue as these molecules could potentially be novel therapeutic targets and/or identify adverse pharmaceutical agents for preventing fatigue during intense stress in warfighters.

The muscle-specific genetic mouse model $HSA^{LR}$ of myotonic dystrophy type 1 (DM1) has a DM-like phenotype. Importantly, the $HSA^{LR}$ myotonic phenotype includes variable degrees of histopathological signs of muscle degeneration and repair, which correspond to the expression of more toxic, long or less, toxic short repeat variants. In addition to wild-type mice, susceptibility to muscle fatigue will be investigated using swimming and treadmill running protocols. In a subgroup of mice, implantable telemetry devices will be implanted two weeks before the mice are subjected to an exercise-stress protocol as described. Upon completion of the experiment, mice will be sacrificed and muscles will be flash-frozen in liquid nitrogen or further processed for histological assays. Specific muscle types are carefully dissected under stereoscope vision and flash frozen in liquid nitrogen or examined by histology and immunohistochemistry. In all tissue samples, RyR1 PKA phosphorylation, levels of the components of the RyR2 macromolecular complex including calstabin1, PKA, RII, mAKAP, PP1, spinophilin, PDE4D3, CaMKII, and single channel properties will be examined. The following properties are determined: $Ca^{2+}$ sensitivity of activation and inhibition, $Mg^{2+}$ inhibition, and changes from in vivo RyCal treatment. At conclusion of each single channel experiment ryanodine will be applied to the channel to confirm RyR identity. The $HSA^{LR}$ mouse will allow to test beneficial effects of RyCal compounds in an extreme model of genetic muscle fatigue and dystrophy.

Susceptibility to muscle fatigue can be investigated using swimming and treadmill running protocols. Implantable telemetry devices can be implanted two weeks before the mice are subjected to an exercise-stress protocol. Upon completion of the experiment, mice are sacrificed and muscles are flash-frozen in liquid nitrogen. Upon completion of each experiment, muscles can be dissected and will also be examined by histology and Western blotting. In all tissue samples, RyR1 PKA phosphorylation, levels of the components of the RyR2 macromolecular complex including calstabin1, PKA, RII, mAKAP, PP1, spinophilin, PDE4D3, CaMKII, and single channel properties can be examined. The following properties can be determined: $Ca^{2+}$ sensitivity of activation and inhibition, $Mg^{2+}$ inhibition, response to PKA phosphorylation. At conclusion of each single channel experiment ryanodine is applied to the channel to confirm RyR identity.

RyCal Compounds Prevent Muscle Fatigue and Muscle Degeneration

In certain aspects, the invention provides that RyCal compounds can restore normal function to hyperphosphorylated RyR1. Furthermore, use of PDE4D knockout and FKBP12 haploinsufficient mice allows determination whether RyCal compound prevent muscle fatigue.

The foregoing discussion established two animal models (mouse and rat) of muscle dysfunction and fatiguing, which result from sustained forms of exercise. The models can provide important clues if chronic activation of the sympathetic nervous system resulting from sustained exercise and stress cause a critical defect in the RyR1 $Ca^{2+}$ release channel. Previous experiments in a heart failure model that results in chronic sympathetic hyperactivity have established a critical defect in RyR1 contributing to accelerated muscle fatigue. RyCal compounds have beneficial effects to inhibit muscle fatigue during sustained exercise capacity, and isolated slow- and fast-twitch skeletal muscle function in the investigated fatigue models. Catecholamine-induced muscle fatigue has been established in rat and mouse hearts failure models earlier and therefore we will be able to apply similar techniques to test for muscle fatigue following sustained animal exercise protocols.

Maintenance of muscle performance during sustained activation of the sympathetic nervous system, for example but not limited to combat, requires a maximal rate of intracellular SR $Ca^{2+}$ cycling. Chronic maximal stress results in permanent activation of the sympathetic nervous system potentially causing RyR1 hyperphosphorylation and intracellular $Ca^{2+}$ leak. In skeletal muscles, intracellular $Ca^{2+}$ leak gradually causes a myopathy characterized by significantly reduced duration and maximal power of peak performance as well as accelerated fatigue by additional ATP consumption of SR $Ca^{2+}$ ATPase pumps that compensate for uncontrolled SR $Ca^{2+}$ leak. SR $Ca^{2+}$ leak is unique since it is a direct cause of muscle fatigue intrinsic to myofibers which is not reversible in the acute setting. A drug like any RyCal compound which fixes the SR $Ca^{2+}$ leak by binding calstabin1 to the channel and stabilizing the closed state even during stress therefore helps to prevent accelerated fatigue development and promotes longer performance despite sustained stress (Wehrens, 2005). The pharmacotherapy is unique since it targets a central fatigue mechanism and potentially prevents toxic effects of intracellular $Ca^{2+}$ leak. Moreover the molecular mechanism of this pharmacotherapy is unique, since it treats a specific defect contributing to muscle fatigue and since the mechanism of RyCal action is stabilization of normal RyR1 channel closure by increasing the calstabin1 binding affinity, which is distinct from historical approaches that block ion channel function.

More recently, SR $Ca^{2+}$ leak was documented in myofibers following intense exercise and in a model of muscular dystrophy, (Wang et al., 2005), possibly due to defective skeletal ryanodine receptors (RyR1 s). Also, chronic activation of the sympathetic nervous system (SNS) in the context of heart failure promotes intrinsic skeletal muscle (SM) fatigue due to depletion of the phosphodiesterease PDE4D3 from the RyR1 complex, RyR1 PKA hyperphosphorylation at Serine 2844, calstabin1 depletion from the RyR1 complex, and a gain-of-function channel defect (Reiken et al., 2003). RyR1 dysfunction in the skeletal muscle leads to altered local subcellular $Ca^{2+}$ release events and impaired global calcium transients (Ward et al., 2003). In the context of chronic exercise, there is evidence indicating that changes in the RyR1 macromolecular complex, namely depletion of PDE4D3 from the RyR1 complex, RyR1 PKA hyperphosphorylation at Serine 2844, and calstabin1 depletion from the RyR1 complex are related in a time-dependent and activity-dependent manner with repeated intense exercise in a mouse model. These biochemical changes in the RyR1 macromolecular complex regulation and function are stable following prolonged exercise and recover slowly over days to weeks. Thus RyR1 $Ca^{2+}$ leak limits peak muscle performance and mediates muscle damage during prolonged, stressful exercise.

Molecular Mechanisms of Muscle Fatigue

The hypotheses that muscle fatigue is due to lactic acid accumulation in the cytoplasm and potassium ion accumulation in T-tubules have largely been set aside and attention has shifted to the study of metabolic and mitochondrial regulation and signaling pathways during chronic exercise (Lin, Wu et al. 2002; Wu, Kanatous et al. 2002; Wang, Zhang et al. 2004). These alternative explanations, while important, are unlikely to directly address the underlying abnormalities in ECC observed in fatigued muscle (Berchtold, Brinkmeier et al. 2000). Described herein is the regulation of the skeletal calcium release channel, RyR1, during chronic or high intensity exercise. The remodeling of the RyR1 macromolecular complex during chronic exercise, consisting of PKA hyperphosphorylation at Ser2844, PDE4D3 depletion, and calstabin1 depletion, likely plays a role in determining muscle fatigue during chronic exercise.

Exercise promotes numerous positive effects on an organism, from improvement in cardiovascular performance to increased glucose uptake and normalization of fuel metabolism (Goodyear and Kahn 1998; Pollock, Franklin et al. 2000). In heart failure, light exercise training has been shown to improve skeletal muscle strength and reduce fatigue, perhaps through adaptation to more aerobic muscle properties (Minotti, Johnson et al. 1990; Lunde, Sjaastad et al. 2001; Meyer 2006). On the other hand, high intensity exercise, such as that performed by a marathon runner or a long distance cyclist results in significant muscle damage and can impair task performance for days or weeks after a single event (O'Reilly, Warhol et al. 1987; Balnave and Thompson 1993; Komulainen and Vihko 1994).

Described herein is also a mouse model of intense physiological exercise to examine the changes in RyR1 function and ECC experienced by elite athletes, soldiers, or others under intense stressful activity. By combining daily swimming with level treadmill running assays, a physiological exercise regimen was constructed that did not exclusively involve isometric or eccentric contraction of the hind limb. While this resulted in less dramatic evidence of exercise-induced muscle damage than pure eccentric contractions, the data presented are more readily generalized.

Biochemical changes were identified in the RyR1 macromolecular complex consistent with leaky calcium release channels. Single channel bilayer data confirmed a leaky-phenotype of the RyR1 channels from chronically exercised hind limb muscle, with elevated open probabilities in the chronically exercised group at resting calcium levels compared to sedentary controls. In two mouse genetic models replicating aspects of the biochemical changes in the RyR1 complex, namely muscle-specific deficiency of calstabin1 (cal1-/-) and deficiency of PDE4D3 (PDE4D-/-), exercise defects were identified. The role of calstabin1 depletion was assessed in another way by pharmacologically rebinding the stabilizing subunit to RyR1 with the $Ca^{2+}$ channel stabilizer S107. Calstabin1 rebinding to RyR1, induced by S107 resulted in improved exercise capacity, as measured by treadmill failure times, over the same 21 day time course that depleted calstabin1 in the vehicle treated mice. The lack of an effect of S107 on cal1-/- mice provides evidence that the molecular mechanism of S107 is indeed through calstabin1 rebinding to RyR1.

Figure 48:
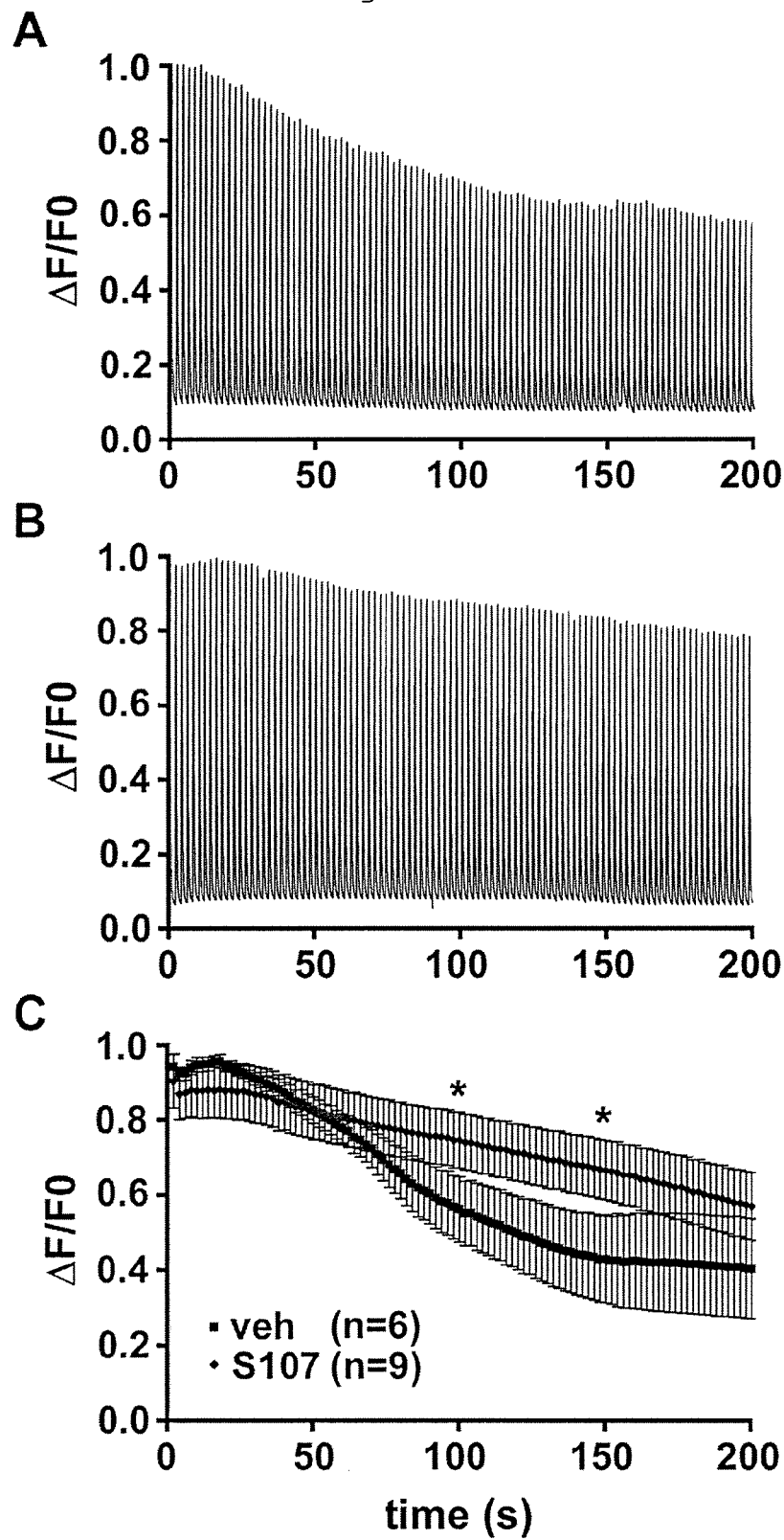
FIG. 48 shows that chronic S107 treatment reduces fatigability of isolated FDB fibers. A) Representative trace from a vehicle treated FDB fiber of fluo-4 fluorescence ($\Delta F/F0$) normalized to the peak during repeated 300 ms long, 120 Hz field-stimulated tetani at a train rate of 0.5. Hz. Isolated cells were continuously perfused with a HEPES buffered Tyrodes solution at room temperature. B) Representative tetanic trace from an S107 treated FDB fiber. C) Mean peak tetanic calcium, as measured by fluo-4 fluorescence ($\Delta F/F0$) normalized to the peak during fatiguing stimulation (n=11 vehicle, n=13 S107). *, $p<0.02$ unpaired t-test.

In vitro fatigue protocols on intact isolated muscles suffer from the limitation that force declines are largely limited by hypoxia (Zhang, Bruton et al. 2006). Therefore, single FDB muscle fibers were isolated from sedentary and chronically exercised mice with and without S107 for assessment of the decline in tetanic $Ca^{2+}$ during fatigue. Exercised fibers with calstabin rebound were relatively protected against fatigue (FIG. 48). The effect of S107 did not appear to be due to a shift in the fiber kinetics to slower calcium cycling.

S107 corrected the leak in RyR1 from chronically exercised mice as measured in a lipid bilayer at low resting $Ca^{2+}$ levels. $Ca^{2+}$ leak resulting from the overactive skeletal ryanodine receptors was not directly visualized in isolated muscle fibers, as calcium sparks were infrequent under all conditions tested, which is consistent with most reports that sparks in skeletal muscle are rare except under certain highly pathological conditions such as hypoosmotic shock or muscular dystrophy (Isaeva, Shkryl et al. 2005; Rios 2005; Wang, Weisleder et al. 2005).

Numerous hypotheses present themselves for how alterations in RyR1 $Ca^{2+}$ leak could result in muscle damage. These data do not identify one muscle damage pathway solely responsible for the physiological effects seen, however, they implicate a role for calpain activation during chronic, and/or high intensity exercise. Several groups have demonstrated that calpain activation is a major mechanism for exercise-induced muscle damage (Belcastro 1993; Spencer and Mellgren 2002). As described herein, calpain activation in isolated EDL muscle was elevated following chronic exercise, but reduced by treatment with S107, suggesting that correction of the leaky RyR1 may protect against calpain activation (FIG. 50). With a potential contribution of other $Ca^{2+}$-dependent pathways such as caspases, calmodulin, or calmodulin-dependent kinases to the damage induced by leaky ryanodine receptors, the present data suggest a mechanism by which local elevation of cytosolic $Ca^{2+}$ could lead to damage. The hypothesis that ryanodine receptor-induced leak can cause muscle damage was further supported by evidence of reduced muscle damage, as measured by serum creatine kinase, in the S107 treated mice (FIG. 50). The data described herein shows that changes in the RyR1 macromolecular complex produces a leaky phenotype during chronic, high intensity exercise which impairs exercise performance.

Neuropathies

In one aspect, the present invention is directed to compositions and methods for the treatment and prevention of neuropathies. The term "neuropathy" as used herein refers to conditions characterized by damage to the nerves, including, but not limited to, damage caused by infections, inflammatory processes, exposure to toxins, treatment with drugs, nutritional deficiency, trauma, pressure on a nerve, neuronal death, neuronal degeneration, and heritable conditions. Although the term "neuropathy" is most frequently used to refer to conditions characterized damage to the peripheral nerves, i.e. "peripheral neuropathies", as used herein, the term "neuropathy" includes both peripheral neuropathies and neuropathies affecting nerves of the central nervous system, i.e. "central neuropathies."

There are various sub-classifications of neuropathies. For example, neuropathies may be classified as either peripheral or central, as either acute or chronic, or as either demyelinating or axonal. Neuropathies may also be classified according to the number of nerves that they affect. A neuropathy may involve damage to only a single nerve or nerve group (referred to as mononeuropathies) or may affect multiple nerves (polyneuropathies).

Peripheral neuropathies may be caused by hereditable disorders, systemic or metabolic disorders, dietary deficiencies, exposure to toxic substances, treatment with drugs, infection, inflammatory response, autoimmune diseases, and multiple other factors. Also, many peripheral neuropathies are of unknown etiology.

Examples of hereditable peripheral neuropathies include, but are not limited to, Charcot-Marie-Tooth disease (CMT) and Friedreich's ataxia.

Examples of peripheral neuropathies caused by systemic or metabolic disorders include, but are not limited to diabetic neuropathy.

Examples of peripheral neuropathies caused by dietary deficiencies include, but are not limited to neuropathy caused by vitamin B-12 deficiency, and neuropathy caused by thiamine deficiency.

Examples of peripheral neuropathies caused by exposure to toxic substances include, but are not limited to neuropathy caused by excessive alcohol use ("alcoholic neuropathy"), neuropathy caused by memia (such as in kidney failure patients), neuropathy caused by arsenic, neuropathy caused by nitrous oxide, neuropathy caused by industrial agents especially solvents, neuropathy caused by heavy metal exposure (such as lead, arsenic, mercury, and the like).

Examples of peripheral neuropathies caused by infectious agents and/or inflammatory or autoimmune processes include, but are not limited to, neuropathies caused by GullainBarre syndrome, polyarteritis nodosa, sarcoidosis, systemic lupus erythematosus, rheumatoid arthritis, sjogren syndrome, HIV infection, syphhilis infection, herpes infection, hepatitis infection, colorado tick fever infection, diptheria infection, leprosy, Lyme disease, and amyloidosis.

Examples of peripheral neuropathies caused by drugs include, but are not limited to neuropathy caused by amiodarone, hydralazine, perhexyline, chemotherapeutic drugs, vincristine, cisplatin, metronidazole (Flagyl), nitrofurantoin, thalidomide, INH (isoniazid), Dapsone, anticonvulsants, Phenyloin, Disulfuram, zidovudine, retrovir, AZT, didanosine (Videx), stavudine (Zerit), zalcitabine (Hivid), ritonavir (Norvir), amprenavir (Agenerase), lovastatin (Mevacor), indapamid (Lozol), gemfibrozil (Lopid).

Other miscellaneous causes or peripheral neuropathy include, but are not limited to ischemia, prolonged exposure to cold temperature, prolonged pressure on, or compression of a nerve, and trauma.

Peripheral neuropathies are characterized by damage to the either the sensory, motor, or autonomic peripheral nerves. The symptoms and effects of peripheral neuropathies depend on the types of nerves affected. Damage to such nerves can result in one or more of pain (neuropathic pain), loss of sensation, and loss of muscular control, abnormal blood pressure, abnormal heart function, digestion problems, and the like.

Damage to sensory fibers may result in changes in sensation, burning sensations, nerve pain (neuralgia, neuropathic pain), tingling, numbness, inability to determine joint position, and incoordination. Damage to the motor fibers may affect muscle control and can cause weakness, cramps, loss of muscle bulk, and loss of dexterity, paralysis, muscle atrophy, Muscle twitching (fasciculation), difficulty breathing or swallowing, falling. The autonomic nerves control involuntary and semi-voluntary functions, such as control of the internal organs, control of breathing, and blood pressure. Damage to autonomic nerves may cause, inability to regulate blood pressure, respiratory problems, problems of the digestive system (including nausea, vomiting, abdominal bloating, early satiety, diarrhea, constipation, unintentional weight loss), problems with the genitourinary system, (such as urinary incontinence, other bladder-function disorders, and male impotence.

Examples of specific nerves that may be affected in peripheral neuropathies include, but are not limited to, the axillary nerve, the brachial plexus, the peroneal nerve, the distal median nerve, the facial nerves palsy, the femoral nerves, the radial nerves, the sciatic nerve, the tibial nerves, and the ulnar nerves.

Examples of central neuropathies include, but are not limited to, vestibular neuropathies, optic neuropathies, optic nerve neuropathies, and retinal neuropathies. Other types of central neuropathy are known to those of skill in the art, and are encompassed by the present invention.

Seizures

The term "seizure" as used herein includes epileptic seizures and non-epileptic seizure. Epileptic seizures result from, temporary abnormal electrical activity in the brain. They can manifest as an alterations tonic or chronic movements, convulsions, sudden and involuntary contraction of a group of muscles, involuntary changes in body movement or function, numbness, alterations in mental state, alterations in sensation, alterations in awareness, changes in behavior, temporary loss of memory, visual disturbances, and various other symptoms. Symptoms experienced by a person during a seizure depend on where in the brain the disturbance in electrical activity occurs.

There are various different types of seizures, all of which are within the scope of the present invention. For example, seizures may be epileptic or non-epileptic, as described below. Seizures may also be classified according to whether the source of the seizure within the brain is localized (partial or focal onset seizures) or distributed (generalized seizures).

Partial seizures are further divided on the extent to which consciousness is affected. If consciousness is unaffected the seizure is referred to as a simple partial seizure. If consciousness is affected, the seizure is referred to as a complex partial seizure. A partial seizure may also spread within the brain—a process known as secondary generalization.

Generalized seizures are divided according to the effect on the body but all involve loss of consciousness. These include absence, myoclonic, clonic, tonic, tonic-clonic, and atonic seizures. In the past, seizures have also been classified as "petit mal", "grand mal", "Jacksonian", "psychomotor", and "temporal-lobe" seizures.

Epilepsy is a chronic neurological condition characterized by recurrent unprovoked seizures. These seizures involve abnormal, rhythmic discharges of cortical neurons. Epilepsy may be symptomatic or idiopathic. Symptomatic epilepsies are caused by structural or metabolic abnormality in the brain, which may be the result of factors such as genetic disorders (such as tuberous sclerosis or ring chromosome 20 syndrome), stroke, head injury, bacterial or viral encephalitis, alcohol use. There are several syndromes that associated with epilepsy, including, but not limited to, infantile spasms (West syndrome), benign childhood epilepsy with centro-temporal spikes (or benign rolandic epilepsy), benign childhood epilepsy with occipital paroxysms, juvenile myoclonic epilepsy (JME), temporal lobe epilepsy, frontal lobe epilepsy, Lennox-Gastaut syndrome, occipital lobe epilepsy, and fetal alcohol spectrum disorder (FASD). Idiopathic seizures are those for which no specific cause has been identified.

Certain triggers or environmental factors or can lead to an increased likelihood of seizures in subjects with epilepsy. Examples of such triggers include, but are not limited to, sleep, the transition between sleep and wakefulness, tiredness, illness, constipation, menstruation, stress, and alcohol consumption. It should also be noted that, even in epileptic subjects, seizures may be triggered by some of the same specific events that cause "provoked" seizures in non-epileptic subjects.

Non-epileptic seizures appear outwardly similar to epileptic seizures but do not involve abnormal, rhythmic discharges of cortical neurons. Non-epileptic seizures are typically provoked by either physiological or psychological conditions. Seizures caused by psychological conditions are referred to as "psychogenic" non-epileptic seizures.

Causes of non-epileptic or "provoked" seizures include, but are not limited to, head injury, intoxication with drugs, drug toxicity (for example aminophylline or local anaesthetic toxicity, drugs that lower the seizure threshold (such as tricyclic antidepressants), infection (such as encephalitis or meningitis), fever leading to febrile convulsions, metabolic disturbances such as hypoglycaemia or hypoxia, withdrawal from drugs (such as anticonvulsants, sedatives, alcohol, barbiturates, and benzodiazepines), brain tumors, other brain lesions, eclampsia during pregnancy, photosensitivity, flashing or flickering lights and electroconvulsive therapy (ECT). It should be noted that the above stimuli may also trigger epileptic seizures.

Cognitive Disorders

In another aspect, the present invention is directed to the treatment and prevention of cognitive disorders, and also to methods and compositions for improvement of cognitive function more generally, even in the absence of a specific cognitive disorder. For example, improvement of cognitive function to combat the normal cognitive decline associated with aging, or to enhance cognitive function for other reasons, is encompassed by the present invention.

The terms "cognitive function" and "cognitive process" as used herein, include the mental processes of attention, learning and memory, perception, language skills, problem solving skills, and other type of cognitive function known to those of skill in the art. The terms "cognitive disorder," "cognitive disease," and "cognitive condition," as used herein, refer to situations in which processes are disrupted or abnormal. The term "cognitive disorder," as used herein encompasses all of the cognitive disorders described below and also all other cognitive disorders known to those of skill in the art. Types of cognitive disorders that are within the scope of the invention include, but are not limited to, dementias, delirium, amnesias, post-traumatic stress disorder and stress-induced cognitive dysfunction.

The term "dementia" as used herein refers to decline in cognitive function due to damage or disease in the brain or central nervous system beyond that which might be expected from normal aging. Dementias typically affect cognitive functions such as learning, memory, attention, language skills, and problem solving skills. Types and causes of dementia include, but are not limited to, chronic diseases such as cancer, Alzheimer's disease, vascular dementia (also known as multi-infarct dementia), Binswanger's disease, dementia with Lewy bodies (DLB), alcohol-induced persisting dementia, frontotemporal lobar degenerations (FTLD), Pick's disease, frontotemporal dementia (or frontal variant FTLD), semantic dementia (or temporal variant FTLD), progressive non-fluent aphasia, Creutzfeldt-Jakob disease, Huntington's disease, Parkinson's disease, and AIDS dementia complex.

Other types of cognitive disorders that may be treated with the methods and compositions of the present invention include the various attention disorders. Attention Deficit/Hyperactivity Disorder (ADHD; ADH is also referred to as Attention-deficit syndrome (ADS)) is a neurological disorder initially appearing in childhood which manifests itself with symptoms such as hyperactivity, forgetfulness, poor impulse control, and distractibility. In neurological terms, ADHD is currently considered to be a persistent and chronic syndrome for which no medical cure is available. ADHD is believed to affect between 3-5% of the United States population, including both children and adults. ADHD is sometimes referred to as ADD when only inattentiveness and distractibility are problematic. ADHD can be classified into three subtypes: predominantly inattentive (sometimes referred to as ADD), predominantly hyperactive-impulsive, and combined. Those presenting impairing symptoms of ADHD who do not fully fit the criteria for any of the three subtypes can be diagnosed with "ADHD Not Otherwise Specified." The symptoms of ADHD are given the name "Hyperkinetic disorders". When a conduct disorder is present, the condition is referred to as "Hyperkinetic conduct disorder". All of the above conditions are within the scope of the present invention.

In one embodiment, the cognitive disorder is not Alzheimer's Disease. In another embodiment, the cognitive disorder is not memory loss. In another embodiment, the cognitive disorder is not age-dependent memory loss.

Prevention and Treatment

In one embodiment, the present invention provides compositions and methods that are useful for treating and/or preventing conditions affecting the nervous system, such as neuropathies, seizures and cognitive disorders.

In certain embodiments, the compositions and methods of the present invention may be used preventively in subjects who are not yet suffering from neuropathies, seizures or cognitive disorders, but whom exhibit one or more "risk factors" or are otherwise predisposed to the development of neuropathies, seizures or cognitive disorders.

Subjects

In preferred embodiments, the compositions described herein are administered therapeutically or prophylactically to subjects who are suffering from, or at risk of developing a disease, disorder or condition affecting the nervous system, such as a neuropathy, seizures or a cognitive disorder. Such a subject may be any animal. For example, in one embodiment, the subject is a mammal. Examples of mammals that may be treated using the methods and compositions of the invention include, but are not limited to, primates, rodents, ovine species, bovine species, porcine species, equine species, feline species and canine species. In preferred embodiments the subjects are human.

In preferred embodiments, the methods and compositions of the invention may be used to treat or prevent a disease, disorder or condition affecting the nervous system, such as a neuropathy, seizures or a cognitive disorder, in a subject having a mutation in a ryanodine receptor gene, such as a mutation that results in defective functioning of the ryanodine receptor, such as an increased open probability or "leakiness" of the ryanodine receptor. In other embodiments, the "subjects" of the present invention may also be in vitro or in vivo systems, including, without limitation, isolated or cultured cells or tissues, in vitro assay systems.

Throughout the specifications, groups and substituent's thereof may be chosen to provide stable moieties and compounds.

The present invention provides compounds that are capable of treating and preventing disorders and diseases associated with the RyR receptors that regulate calcium channel functioning in cells. More particularly, the present invention provides compounds that are capable of treating or preventing a leak in RyR channels. "Disorders and diseases associated with the RyR receptors" means disorders and diseases that can be treated and/or prevented by modulating the RyR receptors that regulate calcium channel functioning in cells. "Disorders and diseases associated with the RyR receptors" include, without limitation, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss.

Compounds

In one embodiment, the present invention provides a method which comprises administering compounds of Formula I:

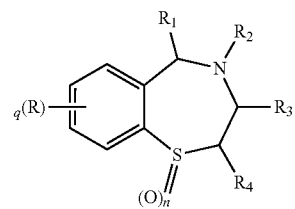

wherein, n is 0, 1, or 2;

q is 0, 1, 2, 3, or 4;

each R is independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, —O-acyl, alkyl, alkoxyl, alkylamino, alkylarylamino, alkylthio, cycloalkyl, alkylaryl, aryl, heteroaryl, heterocyclyl, heterocyclylalkyl, alkenyl, alkynyl, (hetero-)arylthio, and (hetero-)arylamino; wherein each acyl, —O-acyl, alkyl, alkoxyl, alkylamino, alkylarylamino, alkylthio, cycloalkyl, alkylaryl, aryl, heteroaryl, heterocyclyl, heterocyclylalkyl, alkenyl, alkynyl, (hetero-)arylthio, and (hetero-)arylamino may be optionally substituted;

R$_1$ is selected from the group consisting of H, oxo, alkyl, alkenyl, aryl, alkylaryl, cycloalkyl, heteroaryl, and heterocyclyl; wherein each alkyl, alkenyl, aryl, alkylaryl, cycloalkyl, heteroaryl, and heterocyclyl may be optionally substituted;

R$_2$ is selected from the group consisting of H, —C(=O)R$_5$, —C(=S)R$_6$, —SO$_2$R$_7$, —P(=O)R$_8$R$_9$, —(CH$_2$)$_m$—R$_{10}$, alkyl, aryl, alkylaryl, heteroaryl, cycloalkyl, cycloalkylalkyl, and heterocyclyl; wherein each alkyl, aryl, alkylaryl, heteroaryl, cycloalkyl, cycloalkylalkyl, and heterocyclyl may be optionally substituted;

R$_3$ is selected from the group consisting of H, —CO$_2$Y, —C(=O)NHY, acyl, —O-acyl, alkyl, alkenyl, aryl, alkylaryl, cycloalkyl, heteroaryl, and heterocyclyl; wherein each acyl, alkyl, alkenyl, aryl, alkylaryl, cycloalkyl, heteroaryl, and heterocyclyl may be optionally substituted; and wherein Y is selected from the group consisting of H, alkyl, aryl, alkylaryl, cycloalkyl, heteroaryl, and heterocyclyl, and wherein each alkyl, aryl, alkylaryl, cycloalkyl, heteroaryl, and heterocyclyl may be optionally substituted;

R$_4$ is selected from the group consisting of H, alkyl, alkenyl, aryl, alkylaryl, cycloalkyl, heteroaryl, and heterocyclyl; wherein each alkyl, alkenyl, aryl, alkylaryl, cycloalkyl, heteroaryl, and heterocyclyl may be optionally substituted;

R$_5$ is selected from the group consisting of —NR$_{15}$R$_{16}$, —(CH$_2$)$_t$NR$_{15}$R$_{16}$, —NHNR$_{15}$R$_{16}$, —NHOH, —OR$_{15}$, —C(=O)NHNR$_{15}$R$_{16}$, —CO$_2$R$_{15}$, —C(=O)NR$_{15}$R$_{16}$, —CH$_2$X, acyl, alkyl, alkenyl, aryl, alkylaryl, cycloalkyl, cycloalkylalkyl, heteroaryl, heterocyclyl, and heterocyclylalkyl; wherein each acyl, alkyl, alkenyl, aryl, alkylaryl, cycloalkyl, cycloalkylalkyl, heteroaryl, heterocyclyl, and heterocyclylalkyl may be optionally substituted, and wherein t is 1, 2, 3, 4, 5, or 6;

R$_6$ is selected from the group consisting of —OR$_{15}$, —NHNR$_{15}$R$_{16}$, —NHOH, —NR$_{15}$R$_{16}$, —CH$_2$X, acyl, alkenyl, alkyl, aryl, alkylaryl, cycloalkyl, cycloalkylalkyl, heteroaryl, heterocyclyl, and heterocyclylalkyl; wherein each acyl, alkenyl, alkyl, aryl, alkylaryl, cycloalkyl, cycloalkylalkyl, heteroaryl, heterocyclyl, and heterocyclylalkyl may be optionally substituted;

R$_7$ is selected from the group consisting of —OR$_{15}$, —NR$_{15}$R$_{16}$, —NHNR$_{15}$R$_{16}$, —NHOH, —CH$_2$X, alkyl, alkenyl, alkynyl, aryl, alkylaryl, cycloalkyl, cycloalkylalkyl, heteroaryl, heterocyclyl, and heterocyclylalkyl; wherein each alkyl, alkenyl, alkynyl, aryl, alkylaryl, cycloalkyl, cycloalkylalkyl, heteroaryl, heterocyclyl, and heterocyclylalkyl may be optionally substituted;

R$_8$ and R$_9$ independently are selected from the group consisting of OH, acyl, alkenyl, alkoxyl, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted;

R$_{10}$ is selected from the group consisting of —NR$_{15}$R$_{16}$, OH, —SO$_2$R$_{11}$, —NHSO$_2$R$_{11}$, C(=O)(R$_{12}$), NHC=O(R$_{12}$), —OC=O(R$_{12}$), and —P(=O)R$_{13}$R$_{14}$;

R$_{11}$, R$_{12}$, R$_{13}$, and R$_{14}$ independently are selected from the group consisting of H, OH, NH$_2$, —NHNH$_2$, —NHOH, acyl, alkenyl, alkoxyl, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted;

X is selected from the group consisting of halogen, —CN, —CO$_2$R$_{15}$, —C(=O)NR$_{15}$R$_{16}$, —NR$_{15}$R$_{16}$, —OR$_{15}$, —SO$_2$R$_7$, and —P(=O)R$_8$R$_9$; and R$_{15}$ and R$_{16}$ independently are selected from the group consisting of H, acyl, alkenyl, alkoxyl, OH, NH$_2$, alkyl, alkylamino, aryl, alkylaryl, cycloalkyl, cycloalkylalkyl, heteroaryl, heterocyclyl, and heterocyclylalkyl; wherein each acyl, alkenyl, alkoxyl, alkyl, alkylamino, aryl, alkylaryl, cycloalkyl, cycloalkylalkyl, heteroaryl, heterocyclyl, and heterocyclylalkyl may be optionally substituted; and optionally R$_{15}$ and R$_{16}$ together with the N to which they are bonded may form a heterocycle which may be substituted;

the nitrogen in the benzothiazepine ring may optionally be a quaternary nitrogen; and enantiomers, diastereomers, tautomers, pharmaceutically acceptable salts, hydrates, solvates, complexes, and prodrugs thereof;

provided that when q is 0 and n is 0, then R$_2$ is not H, Me, Et, —C(=O)NH$_2$, —C(=O)NHPh, —C(=S)NH-nButyl, —C(=O)NHC(=O)CH$_2$Cl, —C(=O)H, —C(=O)Me, —C(=O)Et, —C(=O)CH=CH$_2$, —S(=O)$_2$Me, —S(=O)$_2$Et, —C(=O)OC(CH$_3$)$_3$, or 9-β-D-ribofuranosyl-9H-purin-6-yl or —C(=O)Ph;

further provided that when q is 0 and n is 1 or 2, then R$_2$ is not H, —C(=O)Me, —C(=O)Et, —S(=O)$_2$Me, —S(=O)$_2$Et or, —C(=O)OC(CH$_3$)$_3$;

further provided that when q is 1, and R is Me, Cl, CN or F at the 6 position of the benzothiazepine ring, or Br at position 7 of the benzothiazepine ring, then R$_2$ is not H, Me, —C(=O)H, —C(=O)Me, —C(=O)Et, —C(=O)Ph, —S(=O)$_2$Me, or —S(=O)$_2$Et;

further provided that when q is 1, n is 0, and R is OH, C$_1$-C$_3$ alkoxyl at the 7 position of the benzothiazepine ring, then R$_2$ is not H, —C(=O)CH=CH$_2$, —C(=O)CH$_2$Br, —(CH$_2$)$_3$-4-benzylpiperidine,

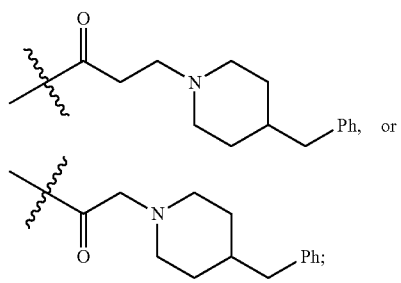

further provided that when q is 0, n is 0 or 2, R$_1$ is H or oxo, R$_3$ is H or Me and R$_4$ is H, then R$_2$ is not —C=ONHPh, —C=ONHCOCH$_2$Cl, —C=ONH$_2$, —C=ONH(n-Bu), —C=S(NHPh), —C=S(NHCOCH$_2$Cl), —C=S(NH$_2$), —C=SNH(n-Bu), —CH$_2$CH$_2$N(Me)$_2$, —CH$_2$CH$_2$NH$_2$ or —C=OCHCl$_2$;

further provided that when q is 2, each R is methoxy at positions 7 and 8 of the benzothiazepine ring, R$_3$ and R$_4$ are each H and n is 0 or 2, then $R_1$ is not methyl, —$CH_2Ph$ or 3,4-dimethoxybenzyl, and $R_2$ is not —C(=O)Me;

further provided that when q is 0, $R_1$, $R_2$ and $R_4$ are each H, then $R_3$ is not H or $CH_3$;

further provided that when q is 0, $R_2$ is H, —$CH_2C$(=O)$OCH_3$, —$CH_2C$(=O)$NH_2$, —C(=O)—$C_6H_4$—Cl, —$CH_2$—$C_6H_4$—Cl, —$(CH_2)_3$-morpholino, —$(CH_2)_3$-4-methylpiperazino, —$(CH_2)_2$—C(=O)$OCH_3$, 2,2',3,3'-tetrahydro-4(5H)-1,4 benzothiazepine, or —$CH_2$-Ph, $R_3$ and $R_4$ are either H or $CH_3$ but not both $CH_3$, then $R_1$ is not oxo;

further provided that when q is 2, each R is methoxy at positions 7 and 8 or 7 and 9 of the benzothiazepine ring, $R_1$, $R_2$ and $R_4$ are each H and n is 0, then $R_3$ is not H;

further provided that when q is 0, $R_1$, $R_3$ and $R_4$ are each H and n is 0, then $R_2$ is not methyl, benzotriazolylmethyl, 4-methoxybenzyl, Ph—C≡C—$CH_2$—, 4-chlorobenzyl, ethyl, pentyl, —$CH_2P$(O)(O$CH_2CH_3$)$_2$, Ph-CO—$CH_2CH_2$—, C(=O)CH=$CH_2$ and C(=O)$CH_2Br$; and further provided that when q is 1, R is $CH_3$ at position 9 of the benzothiazepine ring, $R_1$, $R_3$ and $R_4$ are each H and n is 0, then $R_2$ is not methyl, benzotriazolylmethyl, pentyl, —$CH_2P$(O)(O$CH_2CH_3$)$_2$ or 4-methoxybenzyl.

In one embodiment, the present invention provides compounds of Formula I, as described above, with the proviso that said compound is not S24 or S68.

In one embodiment, the present invention provides compounds of Formula I-a:

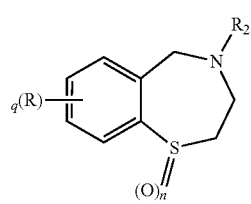

(I-a)

wherein:
n is 0, 1, or 2;
q is 0, 1, 2, 3, or 4;
each R is independently selected from the group consisting of H, halogen, —OH, —$NH_2$, —$NO_2$, —CN, —$CF_3$, —$OCF_3$, —$N_3$, —$SO_3H$, —S(=O)$_2$alkyl, —S(=O)alkyl, —OS(=O)$_2CF_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; wherein each acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino may be substituted or unsubstituted;

$R_2$ is selected from the group consisting of H, —C=O($R_5$), —C=S($R_6$), —$SO_2R_7$, —P(=O)$R_8R_9$, —$(CH_2)_m$—$R_{10}$, alkyl, aryl, heteroaryl, cycloalkyl, cycloalkylalkyl, and heterocyclyl; wherein each alkyl, aryl, heteroaryl, cycloalkyl, cycloalkylalkyl, and heterocyclyl may be substituted or unsubstituted;

$R_5$ is selected from the group consisting of —$NR_{15}R_{16}$, —$NHNR_{15}R_{16}$, —NHOH, —$OR_{15}$, —C(=O)$NHNR_{15}R_{16}$, —$CO_2R_{15}$, —C(=O)$NR_{15}R_{16}$, —$CH_2X$, acyl, alkyl, alkenyl, alkynyl, aryl, cycloalkyl, cycloalkylalkyl, heterocyclyl, and heterocyclylalkyl; wherein each acyl, alkyl, alkenyl, alkynyl, aryl, cycloalkyl, cycloalkylalkyl, heterocyclyl, and heterocyclylalkyl may be substituted or unsubstituted;

$R_6$ is selected from the group consisting of —$OR_{15}$, —$NHNR_{15}R_{16}$, —NHOH, —$NR_{15}R_{16}$, —$CH_2X$, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted or unsubstituted;

$R_7$ is selected from the group consisting of H, —$OR_{15}$, —$NR_{15}R_{16}$, —$NHNR_{15}R_{16}$, —NHOH, —$CH_2X$, alkyl, akenyl, alkynyl, aryl, cycloalkyl, cycloalkylalkyl, heterocyclyl, and heterocyclylalkyl; wherein each alkyl, akenyl, alkynyl, aryl, cycloalkyl, cycloalkylalkyl, heterocyclyl, and heterocyclylalkyl may be substituted or unsubstituted;

$R_8$ and $R_9$ independently are selected from the group consisting of —OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted;

$R_{10}$ is selected from the group consisting of —$NR_{15}R_{16}$, OH, —$SO_2R_{11}$, —$NHSO_2R_{11}$, —C(=O)$R_{12}$, —NH(C=O)$R_{12}$, —O(C=O)$R_{12}$, and —P(=O)$R_{13}R_{14}$;

m is 0, 1, 2, 3, or 4;

$R_{11}$, $R_{12}$, $R_{13}$, and $R_{14}$ independently are selected from the group consisting of H, OH, $NH_2$, —$NHNH_2$, —NHOH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted;

X is selected from the group consisting of halogen, —CN, —$CO_2R_{15}$, —C(=O)$NR_{15}R_{16}$, —$NR_{15}R_{16}$, —$OR_{15}$, —$SO_2R_7$, and —P(=O)$R_8R_9$; and $R_{15}$ and $R_{16}$ independently are selected from the group consisting of H, acyl, alkenyl, alkoxyl, OH, $NH_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally $R_{15}$ and $R_{16}$ together with the N to which they are bonded may form a heterocycle which may be substituted or unsubstituted; the nitrogen in the benzothiazepine ring may be optionally a quaternary nitrogen; and enantiomers, diastereomers, tautomers, pharmaceutically acceptable salts, hydrates, solvates, complexes, and prodrugs thereof;

provided that when q is 0 and n is 0, then $R_2$ is not H, Me, Et, —C(=O)$NH_2$, —C(=O)NHPh, —C(=S)NH-nButyl, —C(=O)NHC(=O)$CH_2Cl$, —C(=O)H, —C(=O)Me, —C(=O)Et, —C(=O)CH=$CH_2$, —S(=O)$_2$Me, —S(=O)$_2$Et, —C(=O)OC($CH_3$)$_3$, or 9-β-D-ribofuranosyl-9H-purin-6-yl or —C(=O)Ph; further provided that when q is 0 and n is 1 or 2, then $R_2$ is not H, —C(=O)Me, —C(=O)Et, —S(=O)$_2$Me, —S(=O)$_2$Et or —C(=O)O($CH_3$)$_3$;

further provided that when q is 1, and R is Me, Cl, CN or F at the 6 position of the benzothiazepine ring, or Br at position 7 of the benzothiazepine ring, then $R_2$ is not H, Me, —C(=O)H, —C(=O)Me, —C(=O)Et, —C(=O)Ph, —S(=O)$_2$Me, or —S(=O)$_2$Et;

further provided that when q is 1, n is 0, and R is OH, $C_1$-$C_3$ alkoxyl at the 7 position of the benzothiazepine ring, then $R_2$ is not H, —C(=O)CH=$CH_2$, —C(=O)$CH_2Br$, —$(CH_2)_{3-4}$-benzylpiperidine,

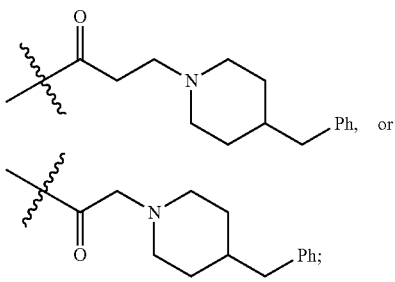

further provided that when q is 0 and n is 0 or 2, then $R_2$ is not —C=ONHPh, —C=ONHCOCH$_2$Cl, —C=ONH$_2$, —C=ONH(n-Bu), —C=S(NHPh), —C=S(NHCOCH$_2$Cl), —C=S(NH$_2$), —C=SNH(n-Bu), —CH$_2$CH$_2$N(Me)$_2$, —CH$_2$CH$_2$NH$_2$ or —C=OCHCl$_2$;

further provided that when q is 2, each R is methoxy at positions 7 and 8 of the benzothiazepine ring, and n is 0 or 2, then $R_2$ is not —C(=O)Me;

further provided that when q is 0, $R_2$ is not H;

further provided that when q is 0, and n is 0, then $R_2$ is not methyl, benzotriazolylmethyl, 4-methoxybenzyl, Ph-C$_4$-chlorobenzyl, ethyl, pentyl, —CH$_2$P(O)(OCH$_2$CH$_3$)$_2$, Ph-CO—CH$_2$CH$_2$—, C(=O)CH=CH$_2$ and C(=O)CH$_2$Br; and further provided that when q is 1, R is CH$_3$ at position 9 of the benzothiazepine ring, and n is 0, then $R_2$ is not methyl, benzotriazolylmethyl, pentyl, —CH$_2$P(O)(OCH$_2$CH$_3$)$_2$ or 4-methoxybenzyl.

In certain embodiments, the present invention provides compounds of formula I-a, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-a, wherein $R_2$ is selected from the group consisting of —C=O(R$_5$), —C=S(R$_6$), —SO$_2$R$_7$, —P(=O)R$_8$R$_9$, and —(CH$_2$)$_m$—R$_{10}$.

In yet another embodiment, the present invention provides compounds of formula I-b:

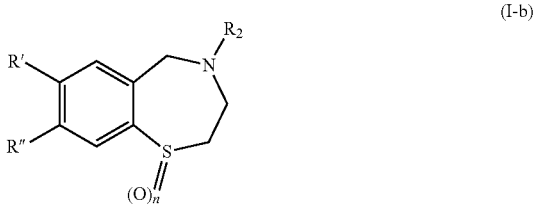

(I-b)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O) alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_2$ and n are as defined in compounds of formula I-a above;

and enantiomers, diastereomers, tautomers, pharmaceutically acceptable salts, hydrates, solvates, complexes and prodrugs thereof.

In certain embodiments, the present invention provides compounds of formula I-b, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R' is H or OMe, and R" is H.

In other embodiments, the present invention provides compounds of formula I-b, wherein $R_2$ is selected from the group consisting of —C=O(R$_5$), —C=S(R$_6$), —SO$_2$R$_7$, —P(=O)R$_8$R$_9$, and —(CH$_2$)$_m$—R$_{10}$.

In yet another embodiment, the present invention provides compounds formula of I-c:

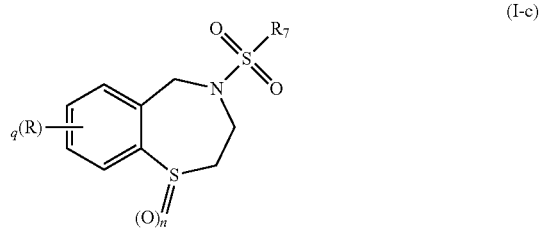

(I-c)

wherein each R, $R_7$, q, and n is as defined in compounds of formula I-a above; and enantiomers, diastereomers, tautomers, pharmaceutically acceptable salts, hydrates, solvates, complexes and prodrugs thereof.

In certain embodiments, the present invention provides compounds of formula I-c, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-c, wherein $R_7$ is selected from the group consisting of —OH, —NR$_{15}$R$_{16}$, alkyl, alkenyl, aryl, cycloalkyl, cycloalkylalkyl, heterocyclyl, and heterocyclylalkyl; wherein each alkyl, akenyl, aryl, cycloalkyl, cycloalkylalkyl, heterocyclyl, and heterocyclylalkyl may be substituted or unsubstituted.

In a further embodiment, the present invention provides compounds of formula of I-d:

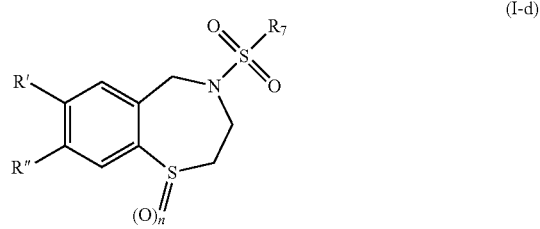

(I-d)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O) alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_7$ and n are as defined in compounds of formula I-a above; and enantiomers, diastereomers, tautomers, pharmaceutically acceptable salts, hydrates, solvates, complexes and prodrugs thereof.

In certain embodiments, the present invention provides compounds of formula wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R' is H or OMe, and R" is H.

In other embodiments, the present invention provides compounds of formula I-d, wherein $R_7$ is selected from the group consisting of —OH, —NR$_{15}$R$_{16}$, alkyl, alkenyl, aryl, cycloalkyl, cycloalkylalkyl, heterocyclyl, and heterocyclylalkyl; wherein each alkyl, akenyl, aryl, cycloalkyl, cycloalkylalkyl, heterocyclyl, and heterocyclylalkyl may be substituted or unsubstituted.

In one embodiment, the present invention provides compounds of formula of I-e:

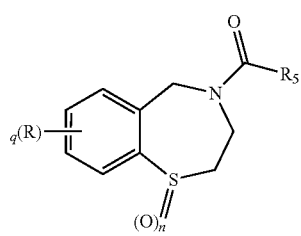

(I-e)

wherein each R, $R_5$, q and n is as defined compounds of formula I-a above; and enantiomers, diastereomers, tautomers, pharmaceutically acceptable salts, hydrates, solvates, complexes and prodrugs thereof.

In certain embodiments, the present invention provides compounds of formula I-e, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1, or 2.

In other embodiments, the present invention provides compounds of formula I-e, wherein $R_5$ is selected from the group consisting of —NR$_{15}$R$_{16}$, —NHOH, —OR$_{15}$, —CH$_2$X, alkyl, alkenyl, aryl, cycloalkyl, cycloalkylalkyl, heterocyclyl, and heterocyclylalkyl; wherein each acyl, alkyl, alkenyl, aryl, cycloalkyl, cycloalkylalkyl, heterocyclyl, and heterocyclylalkyl may be substituted or unsubstituted.

In some embodiments, the present invention provides compounds of formula I-e, wherein $R_5$ is an alkyl substituted by at least one labeling group, such as a fluorescent, a bioluminescent, a chemiluminescent, a colorimetric and a radioactive labeling group. A fluorescent labeling group can be selected from bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, arginine, and variants and derivatives thereof.

In another embodiment, the present invention provides compounds of formula of I-f:

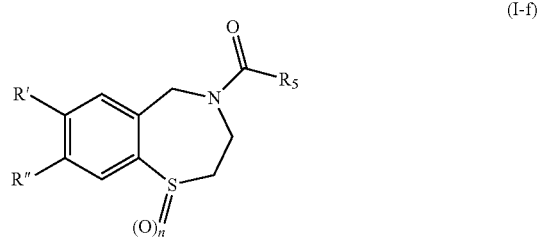

(I-f)

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

$R_5$ and n are as defined in compounds of formula I-a above; and enantiomers, diastereomers, tautomers, pharmaceutically acceptable salts, hydrates, solvates, complexes and prodrugs thereof.

In certain embodiments, the present invention provides compounds of formula I-f, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R' is H or OMe, and R" is H.

In other embodiments, the present invention provides compounds of formula I-f, wherein $R_5$ is selected from the group consisting of —NR$_{15}$R$_{16}$, —NHOH, —OR$_{15}$, —CH$_2$X, alkyl, alkenyl, aryl, cycloalkyl, cycloalkylalkyl, heterocyclyl, and heterocyclylalkyl; wherein each acyl, alkyl, alkenyl, aryl, cycloalkyl, cycloalkylalkyl, heterocyclyl, and heterocyclylalkyl may be substituted or unsubstituted.

In yet another embodiment, the present invention provides compounds of formula of I-g:

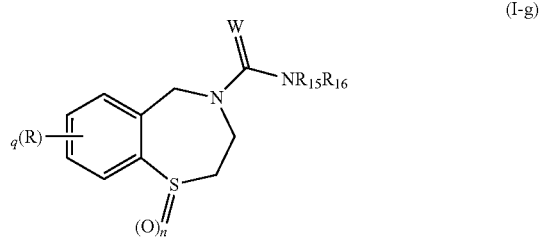

(I-g)

wherein W is S or O; each R, $R_{15}$, $R_{16}$, q, and n is as defined in compounds of formula I-a above; and enantiomers, diastereomers, tautomers, pharmaceutically acceptable salts, hydrates, solvates, complexes and prodrugs thereof.

In certain embodiments, the present invention provides compounds of formula I-g, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-

C₄alkyl, —OS(=O)₂CF₃, Ph, —NHCH₂Ph, —C(=O)Me, —OC(=O)Me, morpholinyl and propenyl; and n is 0, 1, or 2.

In other embodiments, the present invention provides compounds of formula I-g, wherein $R_{15}$ and $R_{16}$ independently are selected from the group consisting of H, OH, NH₂, alkyl, alkylamino, aryl, cycloalkyl, cycloalkylalkyl, heterocyclyl, and heterocyclylalkyl; wherein each alkyl, alkylamino, aryl, cycloalkyl, cycloalkylalkyl, heterocyclyl, and heterocyclylalkyl may be substituted; and optionally $R_{15}$ and $R_{16}$ together with the N to which they are bonded may form a heterocycle which may be substituted.

In some embodiments, the present invention provides compounds of formula I-g, wherein W is O or S.

In yet another embodiment, the present invention provides compounds of formula of I-h:

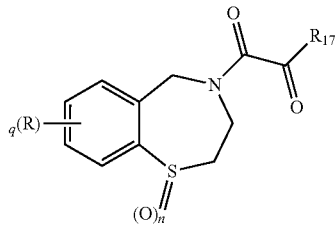

(I-h)

wherein W is S or O;
wherein R' and R" are independently selected from the group consisting of H, halogen, —OH, —NH₂, —NO₂, —CN, —CF₃, —OCF₃, —N₃, —SO₃H, —S(=O)₂alkyl, —S(=O)alkyl, —OS(=O)₂CF₃, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;
$R_{15}$, $R_{16}$ and n are as defined in compounds of formula I-a above;
and enantiomers, diastereomers, tautomers, pharmaceutically acceptable salts, hydrates, solvates, complexes and prodrugs thereof.

In certain embodiments, the present invention provides compounds of formula wherein R' and R" are independently selected from the group consisting of H, halogen, —OH, OMe, —NH₂, —NO₂, —CN, —CF₃, —OCF₃, —N₃, —S(=O)₂C₁-C₄alkyl, —S(=O)C₁-C₄alkyl, —S—C₁-C₄alkyl, —OS(=O)₂CF₃, Ph, —NHCH₂Ph, —C(=O)Me, —OC(=O)Me, morpholinyl and propenyl; and n is 0, 1 or 2. In some cases, R' is H or OMe, and R" is H.

In other embodiments, the present invention provides compounds of formula I-h, wherein $R_{15}$ and $R_{16}$ independently are selected from the group consisting of H, OH, NH₂, alkyl, alkylamino, aryl, cycloalkyl, cycloalkylalkyl, heterocyclyl, and heterocyclylalkyl; wherein each alkyl, alkylamino, aryl, cycloalkyl, cycloalkylalkyl, heterocyclyl, and heterocyclylalkyl may be substituted; and optionally $R_{15}$ and $R_{16}$ together with the N to which they are bonded may form a heterocycle which may be substituted.

In some embodiments, the present invention provides compounds of formula I-g, wherein W is O or S.

In a further embodiment, the present invention provides compounds of formula of I-i:

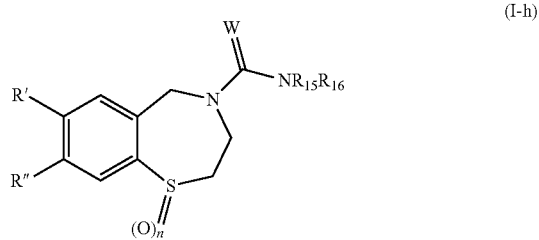

(I-i)

wherein $R_{17}$ is selected from the group consisting of —NR₁₅R₁₆, —NHNR₁₅R₁₆, —NHOH, —OR₁₅, —CH₂X, alkenyl, aryl, cycloalkyl, cycloalkylalkyl, heterocyclyl, and heterocyclylalkyl; wherein each alkenyl, aryl, cycloalkyl, cycloalkylalkyl, heterocyclyl, and heterocyclylalkyl may be substituted or unsubstituted;
each R, q, and n is as defined in compounds of formula I-a above; and enantiomers, diastereomers, tautomers, pharmaceutically acceptable salts, hydrates, solvates, complexes and prodrugs thereof.

In certain embodiments, the present invention provides compounds of formula I-i, wherein each R is independently selected from the group consisting of H, halogen, —OH, OMe, —NH₂, —NO₂, —CN, —CF₃, —OCF₃, —N₃, —S(=O)₂C₁-C₄alkyl, —S(=O)C₁-C₄alkyl, —S—C₁-C₄alkyl, —OS(=O)₂CF₃, Ph, —NHCH₂Ph, —C(=O)Me, —OC(=O)Me, morpholinyl and propenyl; and n is 0, 1, or 2.

In other embodiments, the present invention provides compounds of formula I-i, wherein $R_{17}$ is —NR₁₅R₁₆, and —OR₁₅. In certain other embodiments, $R_{17}$ is —OH, —OMe, —NEt, —NHEt, —NHPh, —NH₂, or —NHCH₂pyridyl.

In one embodiment, the present invention provides compounds of formula of I-j:

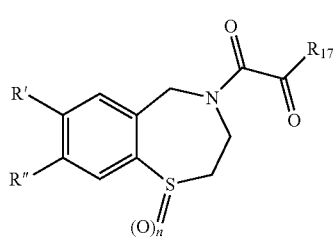

(I-j)

wherein R' and R" are independently selected from the group consisting of H, halogen, —OH, —NH₂, —NO₂, —CN, —CF₃, —OCF₃, —N₃, —SO₃H, —S(=O)₂alkyl, —S(=O)alkyl, —OS(=O)₂CF₃, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;
$R_{17}$ is selected from the group consisting of —NR₁₅R₁₆, —NHOH, —OR₁₅, —CH₂X, alkenyl, aryl, cycloalkyl, cycloalkylalkyl, heterocyclyl, and heterocyclylalkyl; wherein each alkenyl, aryl, cycloalkyl, cycloalkylalkyl, heterocyclyl, and heterocyclylalkyl may be substituted or unsubstituted;
n is as defined in compounds of formula I-a; and enantiomers, diastereomers, tautomers, pharmaceutically acceptable salts, hydrates, solvates, complexes and prodrugs thereof.

In certain embodiments, the present invention provides compounds of formula I-j, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R' is H or OMe, and R" is H.

In other embodiments, the present invention provides compounds of formula I-j, wherein R$_{17}$ is —NR$_{15}$R$_{16}$ or —OR$_{15}$. In certain other embodiments, R$_{17}$ is —OH, —OMe, —NEt, —NHEt, —NHPh, —NH$_2$, or —NHCH$_2$pyridyl.

In another embodiment, the present invention provides compounds of formula I-k or I-k-1:

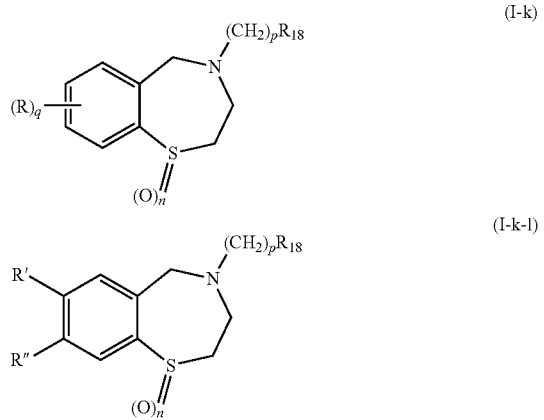

wherein R, R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

R$_{18}$ is selected from the group consisting of —NR$_{15}$R$_{16}$, —C(=O)NR$_{15}$R$_{16}$, —(C=O)OR$_{15}$, —OR$_{15}$, alkyl, aryl, cycloalkyl, heterocyclyl, and at one labeling group; wherein each alkyl, aryl, cycloalkyl, and heterocyclyl may be substituted or unsubstituted;

wherein
q is 0, 1, 2, 3, or 4;
p is 1, 2, 3, 4, 5, 6, 7, 8 9, or 10;
and n is 0, 1, or 2;
and enantiomers, diastereomers, tautomers, pharmaceutically acceptable salts, hydrates, solvates; complexes and prodrugs thereof.

In certain embodiments, the present invention provides compounds of formula I-k, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R is H or is OMe at position 7 of the benzothiazepine ring.

In certain embodiments, the present invention provides compounds of formula I-k-1, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R' is H or OMe, and R" is H.

In other embodiments, the present invention provides compounds of formula I-k or I-k-1, wherein R$_{18}$ is selected from the group consisting of —NR$_{15}$R$_{16}$, —(C=O)OR$_{15}$, —OR$_{15}$, alkyl, aryl, and at one labeling group; and wherein each alkyl and aryl may be substituted or unsubstituted. In some cases, m is 1, and R$_{18}$ is Ph, C(=O)OMe, C(=O)OH, aminoalkyl, NH$_2$, NHOH, or NHCbz. In other cases, m is 0, and R$_{18}$ is C$_1$-C$_4$ alkyl, such as Me, Et, propyl, and butyl. In yet other cases, m is 2, and R$_{18}$ is pyrrolidine, piperidine, piperazine, or morpholine. In some embodiments, m is 3, 4, 5, 5, 7, or 8, and R$_{18}$ is a fluorescent labeling group selected from bodipy, dansyl, fluorescein, rhodamine, Texas red, cyanine dyes, pyrene, coumarins, Cascade Blue™, Pacific Blue, Marina Blue, Oregon Green, 4',6-Diamidino-2-phenylindole (DAPI), indopyra dyes, lucifer yellow, propidium iodide, porphyrins, arginine, and variants and derivatives thereof.

In yet another embodiment, the present invention provides compounds of formula of I-l or I-l-1:

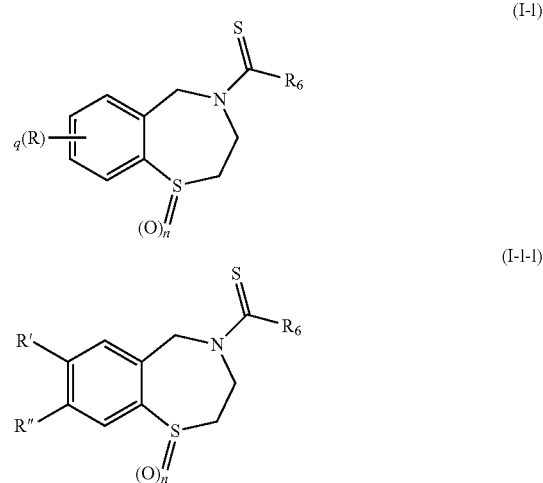

wherein R, R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;

R$_6$ and n and q are as defined in compounds of formula I-a; and enantiomers, diastereomers, tautomers, pharmaceutically acceptable salts, hydrates, solvates, complexes and prodrugs thereof.

In certain embodiments, the present invention provides compounds of formula I-l, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R is H or is OMe at position 7 of the benzothiazepine ring.

In certain embodiments, the present invention provides compounds of formula I-l-1, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R' is H or OMe, and R" is H.

In other embodiments, the present invention provides compounds of formula I-l or I-l-1, wherein R$_6$ is selected from the group consisting of —NR$_{15}$R$_{16}$, —NHNR$_{15}$R$_{16}$, —OR$_{15}$, —NHOH, —CH$_2$X, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted or unsubstituted. In some cases, R$_6$ is —NR$_{15}$R$_{16}$ such as —NHPh, pyrrolidine, piperidine, piperazine, morpholine, and the like. In some other cases, R$_6$ is alkoxyl, such as —O-tBu.

In a further embodiment, the present invention provides compounds of formula I-m or I-m-1:

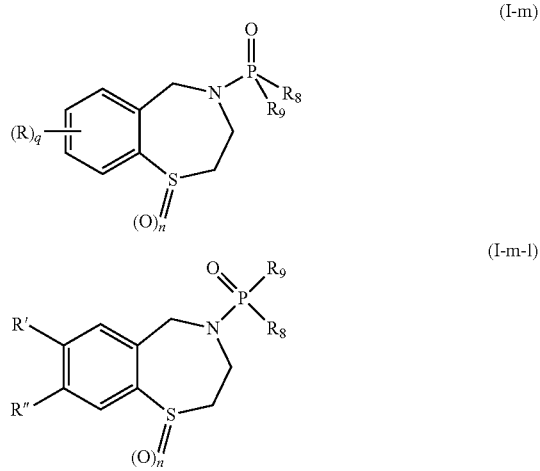

wherein R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O) alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; and wherein each acyl, alkyl, alkoxyl, alkylamino, cycloalkyl, aryl, heterocyclyl, heterocyclylalkyl, alkenyl, alkynyl, (hetero-)aryl, (hetero-)arylthio may be substituted or unsubstituted;
wherein R$_8$, R$_9$ l and n are as defined in compounds of formula I-a above; and enantiomers, diastereomers, tautomers, pharmaceutically acceptable salts, hydrates, solvates, complexes and prodrugs thereof.

In certain embodiments, the present invention provides compounds of formula I-m, wherein each R is independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R is H or is OMe at position 7 of the benzothiazepine ring.

In certain embodiments, the present invention provides compounds of formula I-m-1, wherein R' and R" are independently selected from the group consisting of H, halogen, —OH, OMe, —NH$_2$, —NO$_2$, —CN, —CF$_3$, —OCF$_3$, —N$_3$, —S(=O)$_2$C$_1$-C$_4$alkyl, —S(=O)C$_1$-C$_4$alkyl, —S—C$_1$-C$_4$alkyl, —OS(=O)$_2$CF$_3$, Ph, —NHCH$_2$Ph, —C(=O)Me, —OC(=O)Me, morpholinyl and propenyl; and n is 0, 1 or 2. In some cases, R' is H or OMe, and R" is H.

In other embodiments, the present invention provides compounds of formula I-m or I-m-1, wherein R$_8$ and R$_9$ are independently alkyl, aryl, —OH, alkoxyl, or alkylamino. In some cases, R$_8$ is C$_1$-C$_4$alkyl such as Me, Et, propyl and butyl; and R$_9$ is aryl such as phenyl.

In other embodiments, the present invention provides compounds of formula I-n,

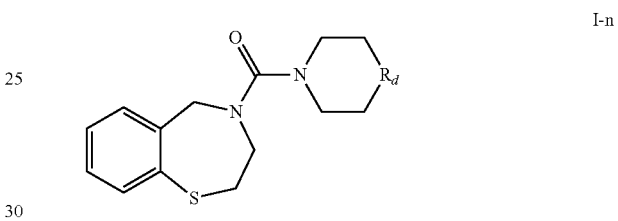

wherein:

R$_d$ is CH$_2$, or NR$_a$; and

R$_a$ is H, alkoxy (for example but not limited to methoxy), —(C$_1$-C$_6$ alkyl)-aryl, wherein the aryl is a bisubstituted phenyl or a benzo[1,3]dioxo-5-yl group, or a Boc group. In one embodiment, R$_a$ is H.

Representative compounds of Formula I-n include without limitation S101, S102, S103, and S114.

In certain other embodiments, the invention provides compounds of Formula I-o:

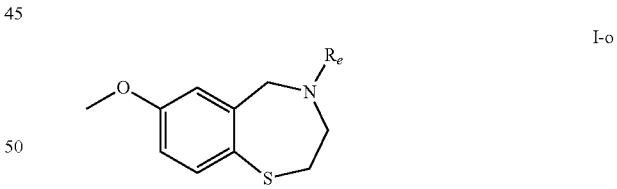

wherein:

R$_e$ is —(C$_1$-C$_6$ alkyl)-phenyl, —(C$_1$-C$_6$ alkyl)-C(O)R$_b$, or substituted or unsubstituted —C$_1$-C$_6$ alkyl; and R$_b$ is —OH or —O—(C$_1$-C$_6$ alkyl), and wherein the phenyl or substituted alkyl is substituted with one or more of halogen, hydroxyl, —C$_1$-C$_6$ alkyl, —O—(C$_1$-C$_6$ alkyl), —NH$_2$, —NH(C$_1$-C$_6$ alkyl), —N(C$_1$-C$_6$ alkyl)$_2$, cyano, or dioxolane.

Representative compounds of Formula I-o include without limitation S107, S110, S111, S120, and S121.

In certain other embodiments, the invention provides compounds of Formula I-p:

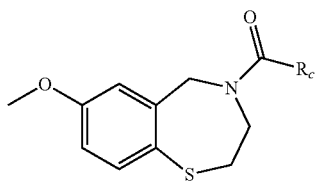

I-p wherein:

$R_c$ is —($C_1$-$C_6$ alkyl)-$NH_2$, —($C_1$-$C_6$ alkyl)-$OR_f$, wherein $R_f$ is H or —C(O)—($C_1$-$C_6$)alkyl, or —($C_1$-$C_6$ alkyl)-$NHR_g$ wherein Rg is carboxybenzyl. Representative compounds of Formula I-n include without limitation S109, S122, and S123.

In non-limiting examples, Formulae I-a, I-b, I-e, I-f, I-g, I-h, I-n are represented by compounds S101, S102, S103. In a non-limiting example, Formulae I-a, I-b, I-e, I-f, I-i, I-j are represented by compound S104. In a non-limiting example, Formulae I-a, I-b, I-o are represented by S107. In a non-limiting example, Formulae I-a, I-b, I-e, I-f are represented by S108. In a non-limiting example, Formulae I-a, I-b, I-e, I-f, I-p are represented by S109. In a non-limiting example, Formulae I-a, I-b, I-k, I-k-1, I-o are represented by S110. In a non-limiting example, Formulae I-a, I-b, I-k, I-k-1 I-o are represented by S111. In a non-limiting example, Formulae I-a, I-b, I-c, I-d are represented by S112. In a non-limiting example, Formulae I-a, I-b are represented by S113. In a non-limiting example, Formulae I-a, I-b, I-e, I-f, I-g, I-h are represented by S114. In a non-limiting example, Formulae I-a, I-b, I-g, I-h, I-l and I-l-1 are represented by S115. In a non-limiting example, Formulae I-a, I-b, I-g, I-h, are represented by S116. In a non-limiting example, Formulae I-a, I-b, I-e, I-f are represented by S117. In a non-limiting example, Formulae I-a, I-b, I-e, I-f are represented by S118. In a non-limiting example, I-a, I-b are represented by S119. In a non-limiting example, Formulae I-a, I-b, I-k, I-k-1, I-o are represented by S120. In a non-limiting example, Formulae I-a, I-b, I-k, I-k-1 I-o, I-p are represented by S121. In a non-limiting example, Formulae I-a, I-b, I-e, I-f, I-p are represented by S122. In a non-limiting example, Formulae I-a, I-b, I-e, I-f, I-p are represented by S123.

The compounds of Formula I, I-a, I-b, I-c, I-d, I-e, I-f, I-g, I-h, I-j, I-k, I-k-1, I-l, I-l-1, I-m, I-m-1, I-n, I-o, and I-p, and Formula II can be used in methods that treat or prevent disorders and diseases associated with the RyR receptors.

Examples of such compounds include, without limitation, S1, S2, S3, S4, S5, S6, S7, S9, S11, S12, S13, S14, S19, S20, S22, S23, S24, S25, S26, S27, S36, S37, S38, S40, S43, S44, S45, S46, S47, S48, S49, S50, S51, S52, S53, S54, S55, S56, S57, S58, S59, S60, S61, S62, S63, S64, S66, S67, S68, S69, S70, S71, S72, S73, S74, S75, S76, S77, S78, S79, S80, S81, S82, S83, S84, S85, S86, S87, S88, S89, S90, S91, S92, S93, S94, S95, S96, S97, S98, S99, S100, S101, S102, S103, S104, S105, S107, S108, S109, S110, S111, S112, S113, S114, S115, S116, S117, S118, S119, S120, S121, S122, and S123, as herein defined. In certain embodiments, the compounds are isolated and substantially pure.

In a certain embodiment of the methods the compound is not S4. In another embodiment, the compound is not S7. In another embodiment, the compound is not S8. In another embodiment, the compound is not S10. In another embodiment, the compound is not S20. In another embodiment, the compound is not S24. In another embodiment, the compound is not S25. In another embodiment, the compound is not S26. In another embodiment, the compound is not S27. In another embodiment, the compound is not S36. In another embodiment, the compound is not JTV-519.

Certain RyCal compounds of the invention have the following structures:

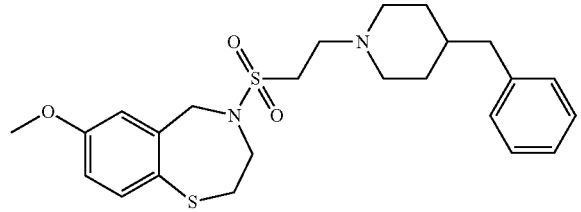

S1

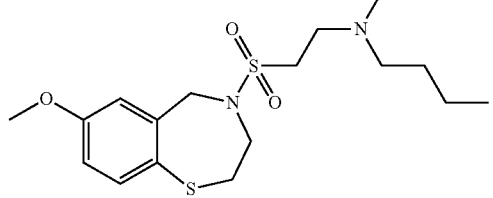

S2

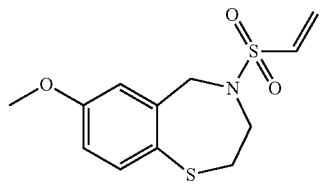

S3

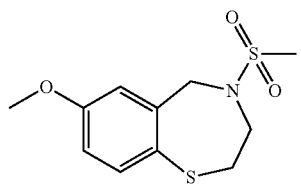

S4

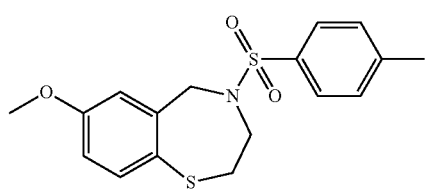

S5

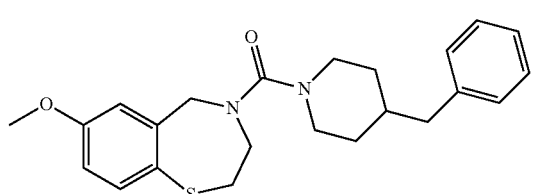

S6

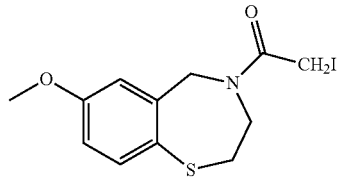

S7

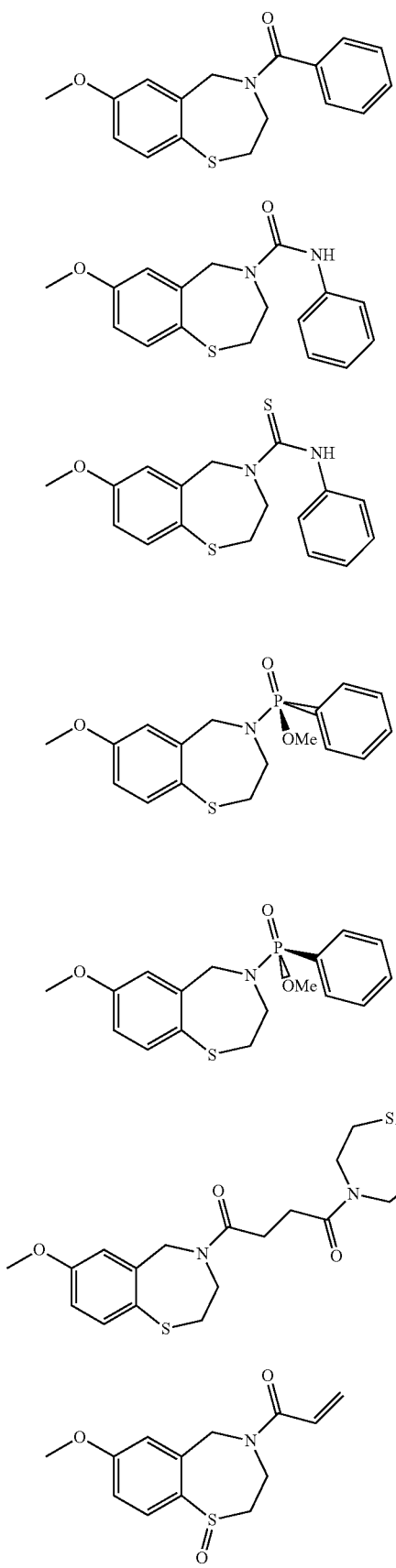
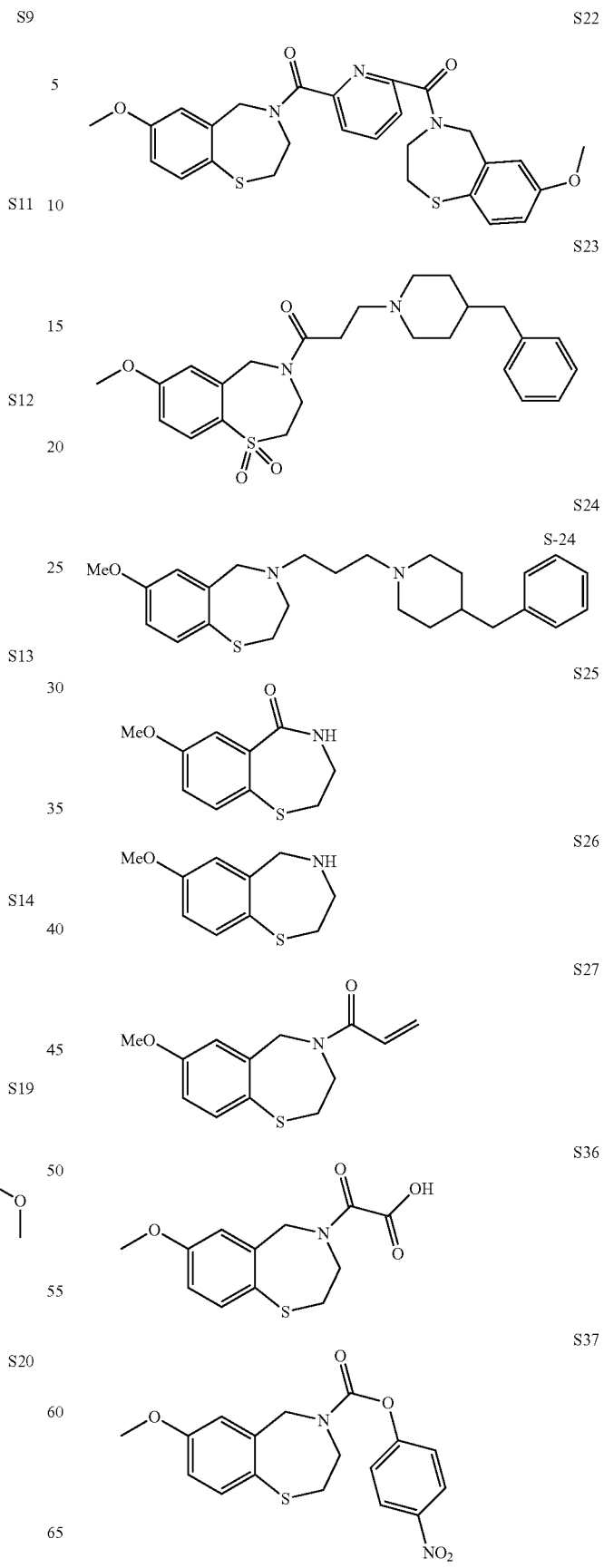

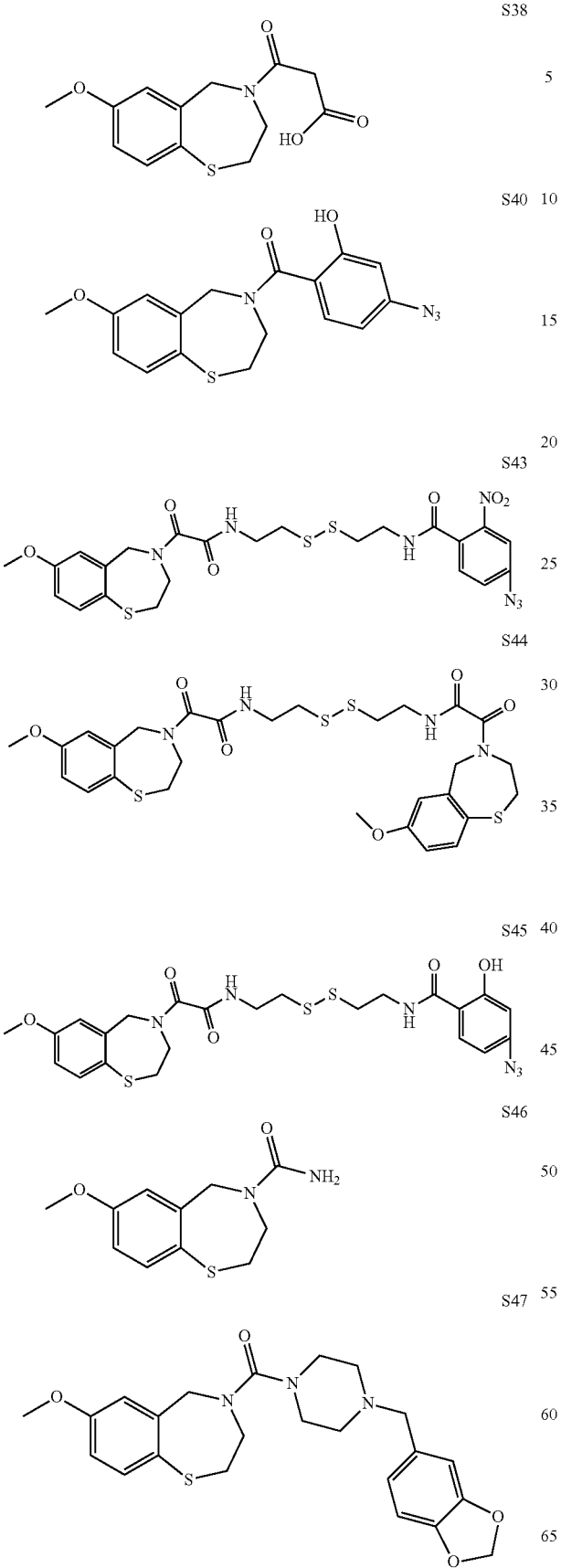

S55
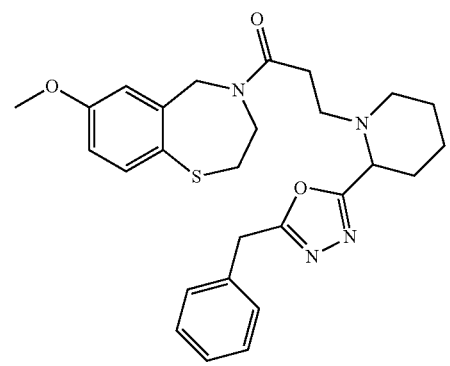
S56
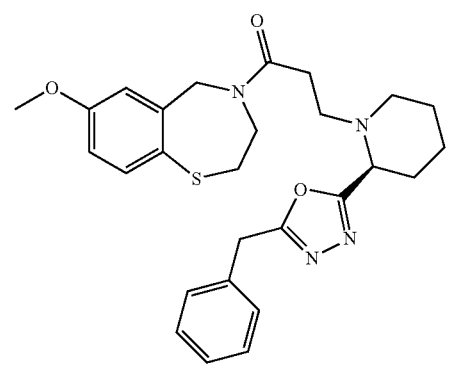
S57
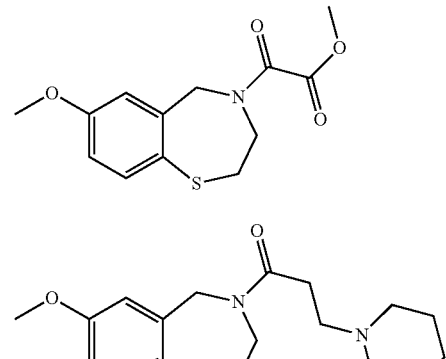
S58
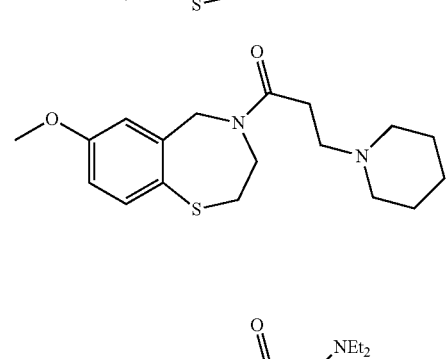
S59
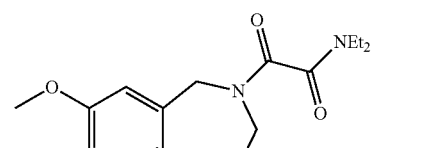
S60
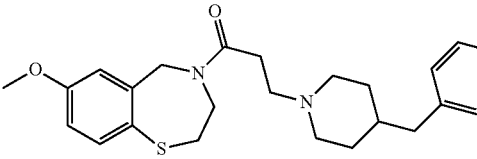
S61
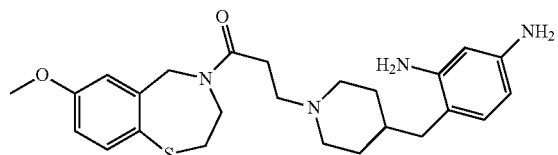
S62
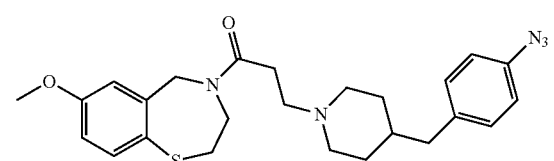
S63
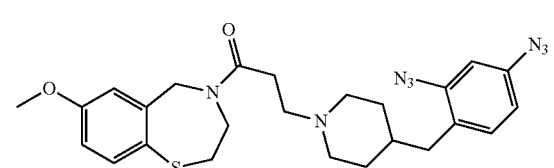
S64
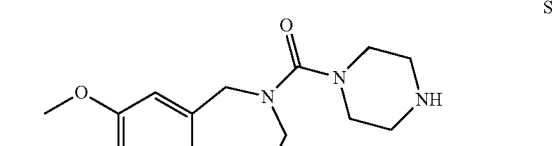
S66
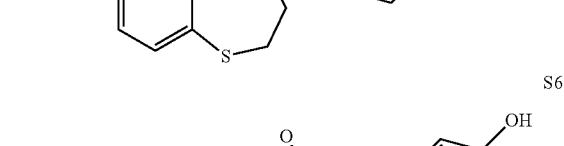
S67
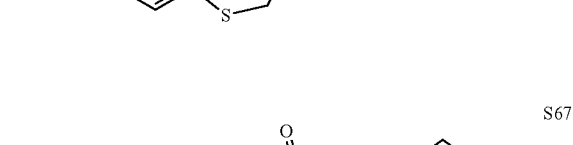
S68
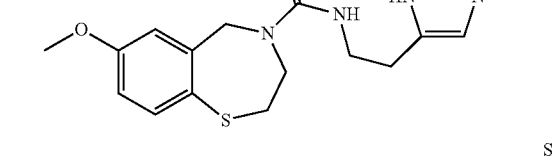
S69
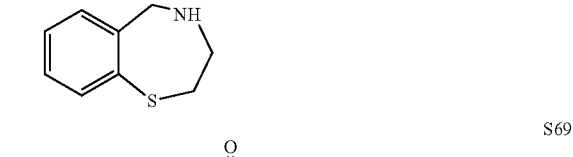

| | |
|---|---|
| S70 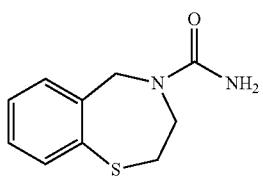 | S78 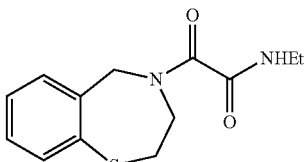 |
| S71 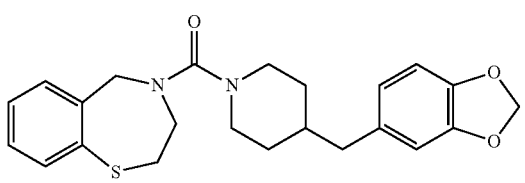 | S79 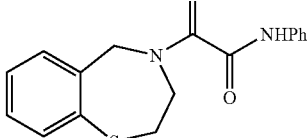 |
| S72 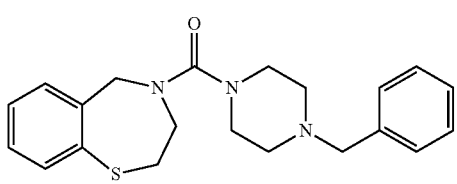 | S80 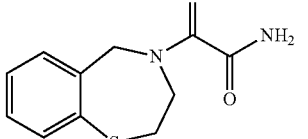 |
| S73 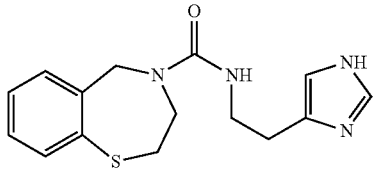 | S81 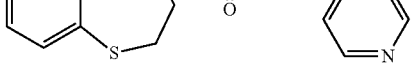 |
| S74 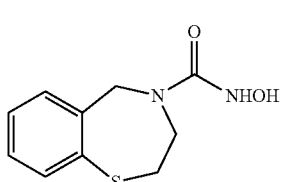 | S82 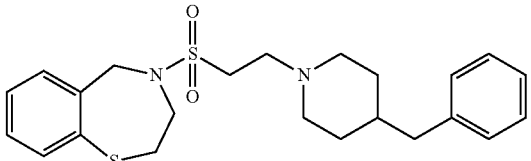 |
| S75 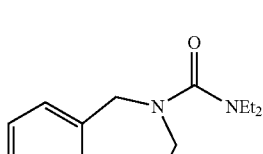 | S83 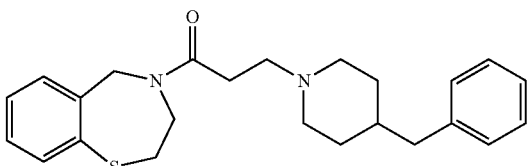 |
| S76 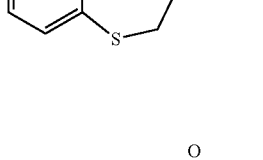 | S84 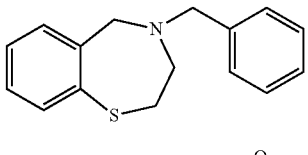 |
| S77 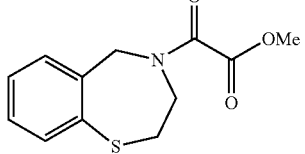 | S85 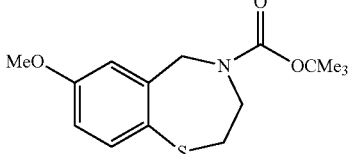 |
| | S86 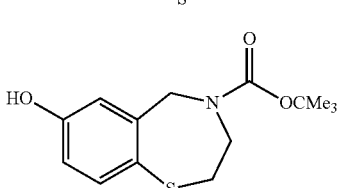 |

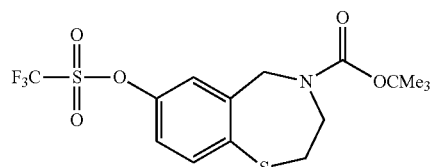 S87
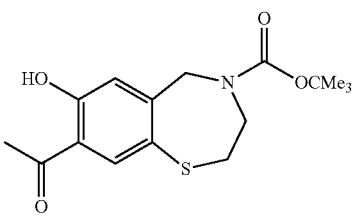 S95
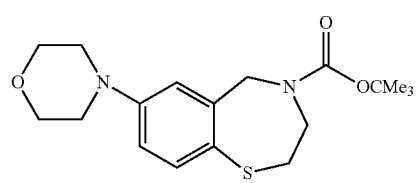 S88
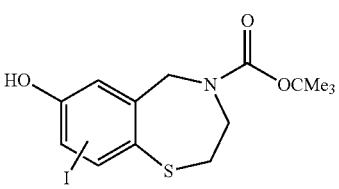 S96
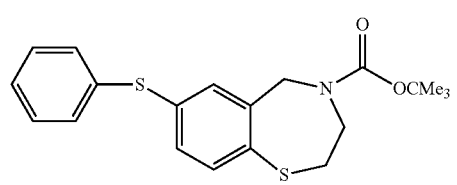 S89
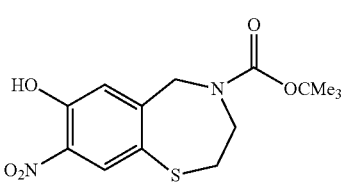 S97
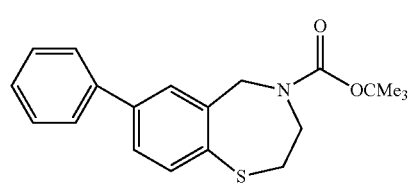 S90
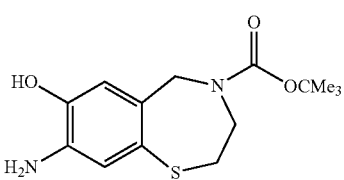 S98
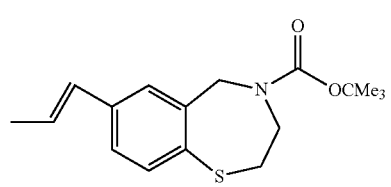 S91
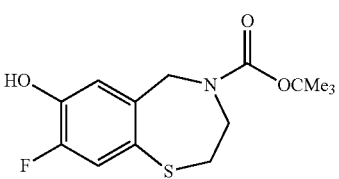 S99
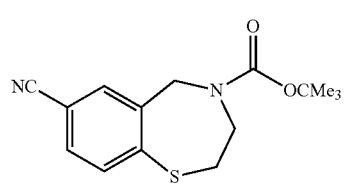 S92
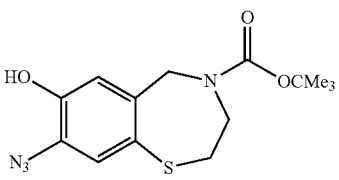 S100
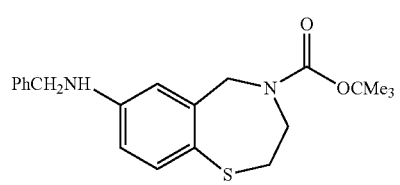 S93
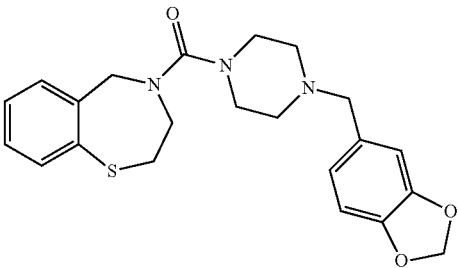 S101
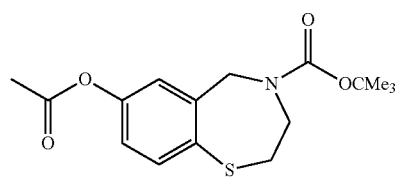 S94
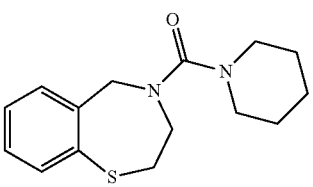 S102

-continued
S103 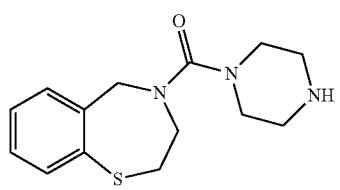
S104 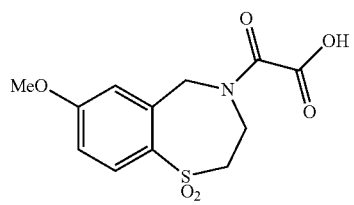
S105 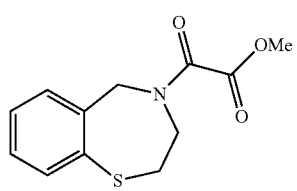
S107 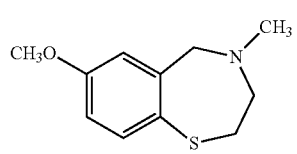
S108 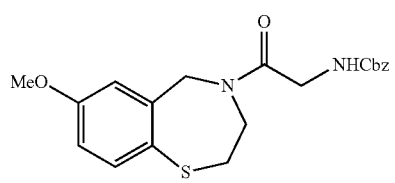
S109 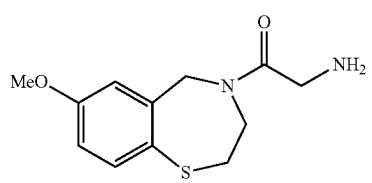
S110 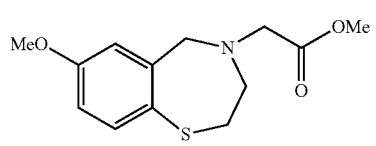
S111 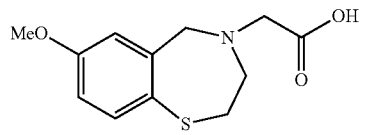
S112 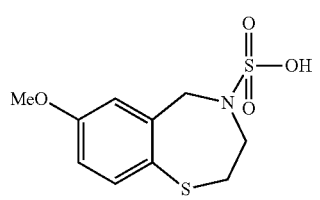
-continued
S113 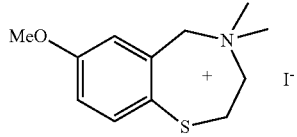
S114 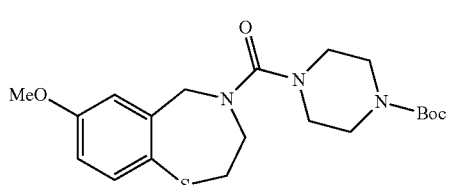
S115 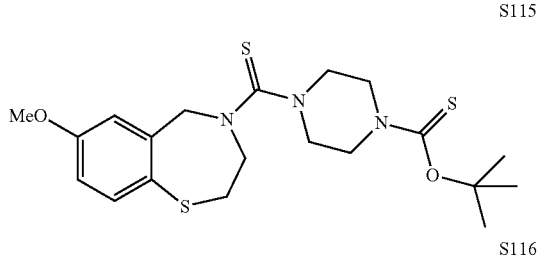
S116 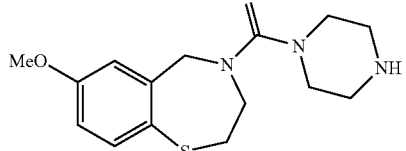
S117 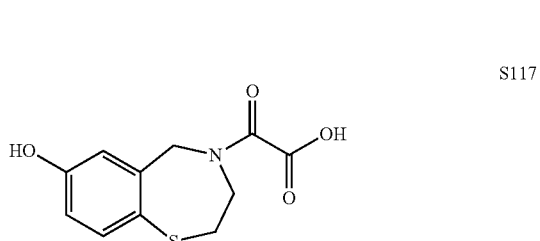
S118 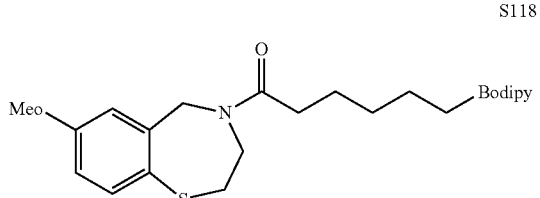
S119 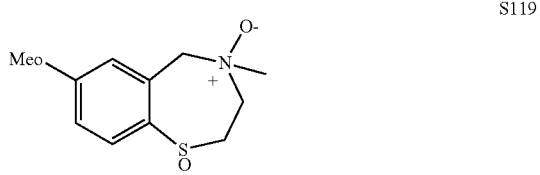
S120 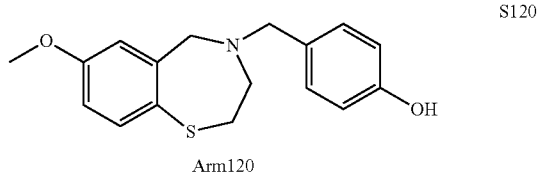
Arm120

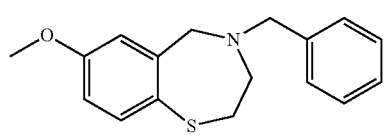

Arm121

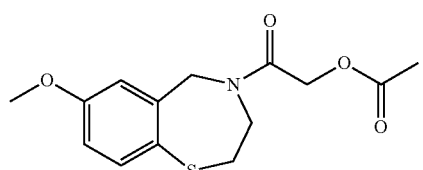

Arm122

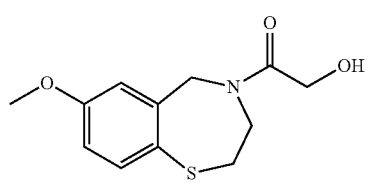

Arm123

In one embodiment of the present invention, for compounds of Formula I, if $R_2$ is C=O($R_5$) or SO$_2$R$_7$, then R is at positions 2, 3, or 5 on the benzene ring (i.e., positions 6, 7 or 9 of the benzothiazepine ring).

In another embodiment of the invention, for compounds of Formula I, if $R_2$ is C=O($R_5$) or SO$_2$R$_7$, then each R is independently selected from the group consisting of H, halogen, —OH, —NH$_2$, —NO$_2$, —CN, —N$_3$, —SO$_3$H, acyl, alkyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —N$_3$, —SH, nitro, oxo, acyl, alkyl, alkoxyl, alkylamino, alkenyl, aryl, (hetero-)cycloalkyl, and (hetero-)cyclyl.

In another embodiment of the invention, for compounds of Formula I, if $R_2$ is C=O($R_5$) or SO$_2$R$_7$, then there are at least two R groups attached to the benzene ring. Furthermore, there are at least two R groups attached to the benzene ring, and both R groups are attached at positions 2, 3, or 5 on the benzene ring. Still furthermore, each R is independently selected from the group consisting of H, halogen, —OH, —NH$_2$, —NO$_2$, —CN, —N$_3$, —SO$_3$H, acyl, alkyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-) arylthio, and (hetero-)arylamino may be substituted with one or more radicals independently selected from the group consisting of halogen, N, O, —S—, —CN, —N$_3$, —SH, nitro, oxo, acyl, alkyl, alkoxyl, alkylamino, alkenyl, aryl, (hetero-)cycloalkyl, and (hetero-)cyclyl.

In another embodiment of the invention, for compounds of Formula I, if $R_2$ is C=O($R_5$), then $R_5$ is selected from the group consisting of —NR$_{16}$, NHNHR$_{16}$, NHOH, —OR$_{15}$, CONH$_2$NHR$_{16}$, CONR$_{16}$, CH$_2$X, acyl, aryl, cycloalkyl, cycloalkylalkyl, heterocyclyl, and heterocyclylalkyl; wherein each acyl, aryl, cycloalkyl, cycloalkylalkyl, heterocyclyl, and heterocyclylalkyl may be substituted with one or more radicals independently selected from the group consisting of halogen, N, O, —S—, —CN, —N$_3$, nitro, oxo, acyl, alkyl, alkoxyl, alkylamino, alkenyl, aryl, (hetero-)cycloalkyl, and (hetero-)cyclyl.

In another embodiment, the present invention provides use of compounds of Formula II:

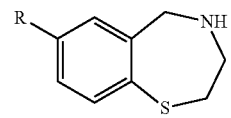

wherein R=OR', SR', N(R')$_2$, alkyl, or halide and R'=alkyl, aryl, or H, and wherein R can be at position 2, 3, 4, or 5 (i.e., positions 6, 7, 8 or 9 of the benzothiazepine ring). Formula II is discussed also in co-pending application Ser. No. 10/680,988, the disclosure of which is incorporated herein in its entirety by reference.

Routes of Activity

The compounds of the invention reduce the open probability of RyR by increasing the affinity of FKBP12 (calstabin1) and FKBP12.6 (calstabin2) for, respectively PKA-phosphorylated RyR1 and PKA-phosphorylated RyR2. Moreover, the compounds of Formula I normalize gating of mutant RyR channels, including CPVT-associated mutant RyR2 channels, by increasing FKBP12 (calstabin1) and FKBP12.6 (calstabin2) binding affinity. Therefore, the compounds of the invention prevent disorders and conditions involving modulation of the RyR receptors, particularly the RyR1 and RyR2 receptors. Examples of such disorders and conditions include, without limitation, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss. The compounds of the invention treat these disorders and conditions by increasing FKBP12 (calstabin1)-RyR1 binding affinity and increasing FKBP12.6 (calstabin2)-RyR2 binding affinity.

In accordance with the foregoing, the present invention provides a method for limiting or preventing a decrease in the level of RyR-bound FKBP (calstabin) in cells of a subject. As used herein, "RyR" includes RyR1, RyR2, and RyR3. Additionally, FKBP includes both FKBP12 (calstabin1) and FKBP12.6 (calstabin2). "RyR-bound FKBP" therefore refers to RyR1-bound FKBP12 (calstabin1), RyR2-bound FKBP12.6 (calstabin2), and RyR3-bound FKBP12 (calstabin1).

As used herein, "RyR" also includes an "RyR protein" and an "RyR analogue." An "RyR analogue" is a functional variant of the RyR protein, having RyR biological activity, that has 60% or greater amino-acid-sequence homology with the RyR protein. The RyR of the present invention are unphosphorylated, phosphorylated (e.g., by PKA), or hyperphosphorylated (e.g., by PKA). As further used herein, the term "RyR biological activity" refers to the activity of a protein or peptide that demonstrates an ability to associate physically with, or bind with, FKBP12 (calstabin1) in the case of RyR1 and RyR3, and FKBP12.6 (calstabin2) in the case of RyR2 (i.e., binding of approximately two fold or, approximately five fold, above the background binding of a negative control), under the conditions of the assays described herein.

As used herein, "FKBP" includes both an "FKBP protein" and an "FKBP analogue," whether it be FKBP12 (calstabin1) or FKBP12.6 (calstabin2). Unless otherwise indicated herein, "protein" shall include a protein, protein domain, polypeptide, or peptide, and any fragment thereof. An "FKBP analogue" is a functional variant of the FKBP protein, having FKBP biological activity, that has 60% or greater amino-acid-sequence homology with the FKBP protein, whether it be FKBP12 (calstabin1) or FKBP12.6 (calstabin2). As further used herein, the term "FKBP biological activity" refers to the activity of a protein or peptide that demonstrates an ability to associate physically with, or bind with, unphosphorylated or non-hyperphosphorylated RyR2 (i.e., binding of approximately two fold, or approximately five fold, above the background binding of a negative control), under the conditions of the assays described herein.

FKBP binds to the RyR channel, one molecule per RyR subunit. Accordingly, as used herein, the term "RyR-bound FKBP" includes a molecule of an FKBP12 (calstabin1) protein that is bound to an RyR1 protein subunit or a tetramer of FKBP12 that is in association with a tetramer of RyR1, a molecule of FKBP12.6 (calstabin2) protein that is bound to an RyR2 protein subunit or a tetramer of FKBP12.6 that is in association with a tetramer of RyR2, and a molecule of an FKBP12 (calstabin1) protein that is bound to an RyR3 protein subunit or a tetramer of FKBP12 that is in association with a tetramer of RyR3. Therefore, "RyR-bound FKBP" refers to "RyR1-bound FKBP12," "RyR2-bound FKBP12.6," and "RyR3-bound FKBP12."

In accordance with the method of the present invention, a "decrease" or "disorder" in the level of RyR-bound FKBP in cells of a subject refers to a detectable decrease, diminution or reduction in the level of RyR-bound FKBP in cells of the subject. Such a decrease is limited or prevented in cells of a subject when the decrease is in any way halted, hindered, impeded, obstructed or reduced by the administration of compounds of the invention, such that the level of RyR-bound FKBP in cells of the subject is higher than it would otherwise be in the absence of the administered compound.

The level of RyR-bound FKBP in a subject is detected by standard assays and techniques, including those readily determined from the known art (e.g., immunological techniques, hybridization analysis, immunoprecipitation, Western-blot analysis, fluorescence imaging techniques and/or radiation detection, etc.), as well as any assays and detection methods disclosed herein. For example, protein is isolated and purified from cells of a subject using standard methods known in the art, including, without limitation, extraction from the cells (e.g., with a detergent that solubilizes the protein) where necessary, followed by affinity purification on a column, chromatography (e.g., FTLC and HPLC), immunoprecipitation (with an antibody), and precipitation (e.g., with isopropanol and a reagent such as Trizol). Isolation and purification of the protein is followed by electrophoresis (e.g., on an SDS-polyacrylamide gel). A decrease in the level of RyR-bound FKBP in a subject, or the limiting or prevention thereof, is determined by comparing the amount of RyR-bound FKBP detected prior to the administration of a compound of the invention (in accordance with methods described below) with the amount detected a suitable time after administration of the compound.

A decrease in the level of RyR-bound FKBP in cells of a subject is limited or prevented, for example, by inhibiting dissociation of FKBP and RyR in cells of the subject; by increasing binding between FKBP and RyR in cells of the subject; or by stabilizing the RyR-FKBP complex in cells of a subject. As used herein, the term "inhibiting dissociation" includes blocking, decreasing, inhibiting, limiting or preventing the physical dissociation or separation of an FKBP subunit from an RyR molecule in cells of the subject, and blocking, decreasing, inhibiting, limiting or preventing the physical dissociation or separation of an RyR molecule from an FKBP subunit in cells of the subject. As further used herein, the term "increasing binding" includes enhancing, increasing, or improving the ability of phosphorylated RyR to associate physically with FKBP (e.g., binding of approximately two fold or, approximately five fold, above the background binding of a negative control) in cells of the subject and enhancing, increasing or improving the ability of FKBP to associate physically with phosphorylated RyR (e.g., binding of approximately two fold, or, approximately five fold, above the background binding of a negative control) in cells of the subject. Additionally, a decrease in the level of RyR-bound FKBP in cells of a subject is limited or prevented by directly decreasing the level of phosphorylated RyR in cells of the subject or by indirectly decreasing the level of phosphorylated RyR in the cells (e.g., by targeting an enzyme (such as PKA) or another endogenous molecule that regulates or modulates the functions or levels of phosphorylated RyR in the cells). In one embodiment, the level of phosphorylated RyR in the cells is decreased by at least 10% in the method of the present invention. In another embodiment, the level of phosphorylated RyR is decreased by at least 20%.

The subject of the present invention are in vitro and in vivo systems, including, without limitation, isolated or cultured cells or tissues, non-cell in vitro assay systems and an animal (e.g., an amphibian, a bird, a fish, a mammal, a marsupial, a human, a domestic animal (such as a cat, dog, monkey, horse, mouse or rat) or a commercial animal (such as a cow or pig)).

The cells of a subject include striated muscle cells. A striated muscle is a muscle in which the repeating units (sarcomeres) of the contractile myofibrils are arranged in registry throughout the cell, resulting in transverse or oblique striations that are observed at the level of a light microscope. Examples of striated muscle cells include, without limitation, voluntary (skeletal) muscle cells and cardiac muscle cells. In one embodiment, the cell used in the method of the present invention is a human cardiac muscle cell. As used herein, the term "cardiac muscle cell" includes cardiac muscle fibers, such as those found in the myocardium of the heart. Cardiac muscle fibers are composed of chains of contiguous heart-muscle cells, or cardiomyocytes, joined end to end at intercalated disks. These disks possess two kinds of cell junctions: expanded desmosomes extending along their transverse portions, and gap junctions, the largest of which lie along their longitudinal portions.

A decrease in the level of RyR-bound FKBP is limited or prevented in cells of a subject by administering the compounds of the invention to the subject; this would also permit contact between cells of the subject and the compounds of the invention. The compounds of the invention are modulators of calcium-ion channels. In addition to regulating $Ca^{2+}$ levels in myocardial cells, the compounds of the invention modulate the $Na^+$ current and the inward-rectifier $K^+$ current in cells, such as guinea pig ventricular cells, and inhibits the delayed-rectifier $K^+$ current in cells, such as guinea pig atrial cells.

Pharmaceutical Composition

The compounds of the invention are formulated into pharmaceutical compositions for administration to human subjects in a biologically compatible form suitable for administration in vivo. According to another aspect, the present invention provides a pharmaceutical composition comprising compounds of the invention in admixture with a pharmaceutically acceptable diluent and/or carrier. The pharmaceutically-acceptable carrier must be "acceptable" in the sense of being compatible with the other ingredients of the composition and not deleterious to the recipient thereof. The pharmaceutically-acceptable carrier employed herein is selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. If necessary, pharmaceutical additives, such as antioxidants, aromatics, colorants, flavor-improving agents, preservatives, and sweeteners, are also added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others.

The pharmaceutical formulations of the present invention are prepared by methods well-known in the pharmaceutical arts. For example, the compounds of the invention are brought into association with a carrier and/or diluent, as a suspension or solution. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

The compounds of the invention are administered to a subject by contacting target cells (e.g., cardiac muscle cells) in vivo in the subject with the compounds. The compounds of the invention are contacted with (e.g., introduced into) cells of the subject using known techniques utilized for the introduction and administration of proteins, nucleic acids and other drugs. Examples of methods for contacting the cells with (i.e., treating the cells with) the compounds of the invention include, without limitation, absorption, electroporation, immersion, injection, introduction, liposome delivery, transfection, transfusion, vectors and other drug-delivery vehicles and methods. When the target cells are localized to a particular portion of a subject, it is desirable to introduce the compounds for the invention directly to the cells, by injection or by some other means (e.g., by introducing the compounds into the blood or another body fluid). The target cells are contained in tissue of a subject and are detected by standard detection methods readily determined from the known art, examples of which include, without limitation, immunological techniques (e.g., immunohistochemical staining), fluorescence imaging techniques, and microscopic techniques.

Additionally, the compounds of the present invention are administered to a human or animal subject by known procedures including, without limitation, oral administration, sublingual or buccal administration, parenteral administration, transdermal administration, via inhalation or intranasally, vaginally, rectally, and intramuscularly. The compounds of the invention are administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous or sublingual injection, or by way of catheter. In one embodiment, the agent is administered to the subject by way of delivery to the subject's muscles including, but not limited to, the subject's cardiac muscles. In an embodiment, the agent is administered to the subject by way of targeted delivery to cardiac muscle cells via a catheter inserted into the subject's heart. In other embodiments, the agent is administered via a subcutaneous pump.

For oral administration, a formulation of the compounds of the invention is presented as capsules, tablets, powders, granules or as a suspension or solution. The formulation has conventional additives, such as lactose, mannitol, corn starch or potato starch. The formulation also is presented with binders, such as crystalline cellulose, cellulose derivatives, acacia, corn starch or gelatins. Additionally, the formulation is presented with disintegrators, such as corn starch, potato starch or sodium carboxymethylcellulose. The formulation also is presented with dibasic calcium phosphate anhydrous or sodium starch glycolate. Finally, the formulation is presented with lubricants, such as talc or magnesium stearate.

For parenteral administration (i.e., administration by injection through a route other than the alimentary canal), the compounds of the invention are combined with a sterile aqueous solution that is isotonic with the blood of the subject. Such a formulation is prepared by dissolving a solid active ingredient in water containing physiologically-compatible substances, such as sodium chloride, glycine and the like, and having a buffered pH compatible with physiological conditions, so as to produce an aqueous solution, then rendering said solution sterile. The formulation is presented in unit or multi-dose containers, such as sealed ampoules or vials. The formulation is delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subject's heart.

For transdermal administration, the compounds of the invention are combined with skin penetration enhancers, such as propylene glycol, polyethylene glycol, isopropanol, ethanol, oleic acid, N-methylpyrrolidone and the like, which increase the permeability of the skin to the compounds of the invention and permit the compounds to penetrate through the skin and into the bloodstream. The compounds of the invention/enhancer composition also are further combined with a polymeric substance, such as ethylcellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the composition is in unit dose form such as a tablet, capsule or single-dose vial. Suitable unit doses, i.e., therapeutically effective amounts, can be determined during clinical trials designed appropriately for each of the conditions for which administration of a chosen compound is indicated and will, of course, vary depending on the desired clinical endpoint. The present invention also provides articles of manufacture for treating and preventing disorders, such as cardiac disorders, in a subject. The articles of manufacture comprise a pharmaceutical composition of one or more of the compounds of the invention as described herein. The articles of manufacture are packaged with indications for various disorders that the pharmaceutical compositions are capable of treating and/or preventing. For example, the articles of manufacture comprise a unit dose of a compound disclosed herein that is capable of treating or preventing a muscular disorder, and an indication that the unit dose is capable of treating or preventing a certain disorder, for example an arrhythmia.

In accordance with a method of the present invention, the compounds of the invention are administered to the subject (or are contacted with cells of the subject) in an amount effective to limit or prevent a decrease in the level of RyR-bound FKBP in the subject, particularly in cells of the subject. This amount is readily determined by the skilled artisan, based upon known procedures, including analysis of titration curves established in vivo and methods and assays disclosed herein. A suitable amount of the compounds of the invention effective to limit or prevent a decrease in the level of RyR-bound FKBP in the subject ranges from about 5 mg/kg/day to about 20 mg/kg/day, and/or is an amount sufficient to achieve plasma levels ranging from about 300 ng/ml to about 1000 ng/ml. In an embodiment, the amount of compounds from the invention ranges from about 10 mg/kg/day to about 20 mg/kg/day. In another embodiment, from about 0.01 mg/kg/day to about 10 mg/kg/day is administered. In another embodiment, from about 0.01 mg/kg/day to about 5 mg/kg/day is administered. In another embodiment, from about 0.05 mg/kg/day to about 5 mg/kg/day is administered. In another, preferred embodiment, from about 0.05 mg/kg/day to about 1 mg/kg/day is administered.

Uses

The present invention provides a new range of therapeutic treatments for patients with various disorders involving modulation of the RyR receptors, particularly skeletal muscular disorders (RyR1), cardiac (RyR2) disorders, and cognitive (RyR3) disorders.

In one embodiment of the present invention, the subject has not yet developed a disorder, such as cardiac disorders (e.g., exercise-induced cardiac arrhythmia). In another embodiment of the present invention, the subject is in need of treatment for a disorder, including a cardiac disorder.

In one embodiment of the present invention, the subject has not yet developed symptoms of muscle fatigue, (e.g., exercise-induced muscle fatigue). In another embodiment of the present invention, the subject is in need of treatment for a disorder associated with muscle fatigue, including skeletal muscular disorders.

Various disorders that the compounds of the invention treat or prevent include, but are not limited to, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's. Disease, forms of memory loss, and age-dependent memory loss. One skilled in the art will recognize still other diseases, including but not limited to muscular and cardiac disorders, that the compounds of the invention are useful to treat, in accordance with the information provided herein.

The amount of compounds of the invention effective to limit or prevent a decrease in the level of RyR2-bound FKBP12.6 in the subject is an amount effective to prevent exercise-induced cardiac arrhythmia in the subject. Cardiac arrhythmia is a disturbance of the electrical activity of the heart that manifests as an abnormality in heart rate or heart rhythm. As used herein, an amount of compounds of the invention "effective to prevent exercise-induced cardiac arrhythmia" includes an amount of compounds of Formula I, I-a, I-b, I-c, I-d, I-e, I-f, I-g, I-h, I-j, I-k, I-k-1, I-l, I-l-1, I-m, I-m-1, I-n, I-o, I-p, and II, effective to prevent the development of the clinical impairment or symptoms of the exercise-induced cardiac arrhythmia (e.g., palpitations, fainting, ventricular fibrillation, ventricular tachycardia and sudden cardiac death). The amount of the compounds effective to prevent exercise-induced cardiac arrhythmia in a subject will vary depending upon the particular factors of each case, including the type of exercise-induced cardiac arrhythmia, the subject's weight, the severity of the subject's condition, and the mode of administration of the compounds. This amount is readily determined by the skilled artisan, based upon known procedures, including clinical trials, and methods disclosed herein. In one embodiment, the amount of the compounds of the invention effective to prevent the exercise-induced cardiac arrhythmia is an amount effective to prevent exercise-induced sudden cardiac death in the subject. In another embodiment, the compounds of the invention prevent exercise-induced cardiac arrhythmia and exercise-induced sudden cardiac death in the subject.

The amount of compounds of the invention effective to limit or prevent a decrease in the level of RyR1-bound FKBP12 in the subject is an amount effective to prevent muscle fatigue in the subject. This amount is readily determined by the skilled artisan, based upon known procedures, including clinical trials, and methods disclosed herein.

Because of its ability to stabilize RyR-bound FKBP and maintain and restore balance in the context of dynamic PKA phosphorylation and dephosphorylation of RyR, the compounds of the invention are also useful in treating a subject who has already experienced clinical symptoms of these various disorders. For example, if the symptoms of the disorder are observed in the subject early enough, the compounds of the invention are effective in limiting or preventing a further decrease in the level of RyR-bound FKBP in the subject.

Additionally, the subject of the present invention is a candidate for exercise-induced cardiac disorders, such as exercise-induced cardiac arrhythmia. Exercise-induced cardiac arrhythmia is a heart condition (e.g., a ventricular fibrillation or ventricular tachycardia, including any that leads to sudden cardiac death) that develops during/after a subject has undergone physical exercise. A "candidate" for an exercise-induced cardiac disorder is a subject who is known to be, or is believed to be, or is suspected of being, at risk for developing a cardiac disorder during/after physical exercise. Examples of candidates for exercise-induced cardiac arrhythmia include, without limitation, an animal/person known to have catecholaminergic polymorphic ventricular tachycardia (CPVT); an animal/person suspected of having CPVT; and an animal/person who is known to be, or is believed to be, or is suspected of being at risk for developing cardiac arrhythmia during/after physical exercise, and who is about to exercise, is currently exercising or has just completed exercise. As discussed above, CPVT is an inherited disorder in individuals with structurally-normal hearts. It is characterized by stress-induced ventricular tachycardia—a lethal arrhythmia that causes sudden cardiac death. In subjects with CPVT, physical exertion and/or stress induce bidirectional and/or polymorphic ventricular tachycardias that lead to sudden cardiac death (SCD) in the absence of detectable structural heart disease. Individuals with CPVT have ventricular arrhythmias when subjected to exercise, but do not develop arrhythmias at rest.

Also, the subject of the present invention can be a candidate for muscle fatigue disorder, including but not limited to any chronic disorder associated with muscle fatigue, or stress or exercise-induced muscle fatigue.

Accordingly, in still another embodiment of the present invention, the subject has been exercising, or is currently exercising, and has developed an exercise-induced disorder. In this case, the amount of the compounds of the invention effective to limit or prevent a decrease in the level of RyR-bound FKBP in the subject is an amount of compound effective to treat the exercise-induced disorder in the subject. As used herein, an amount of compounds of the invention "effective to treat an exercise-induced disorder" includes an amount of compound of the invention effective to alleviate or ameliorate the clinical impairment or symptoms of the exercise-induced disorder characterized by muscle fatigue or an amount of compound of the invention effective to alleviate or ameliorate the clinical impairment or symptoms of the exercise-induced disorder (e.g., in the case of cardiac arrhythmia, palpitations, fainting, ventricular fibrillation, ventricular tachycardia, and sudden cardiac death). The amount of compounds of the invention effective to treat an exercise-induced disorder in a subject will vary depending upon the particular factors of each case, including the type of exercise-induced disorder, the subject's weight, the severity of the subject's condition, and the mode of administration of the compounds of the invention. This amount is readily determined by the skilled artisan, based upon known procedures, including clinical trials, and methods disclosed herein. In an embodiment, the compounds of the invention treat exercise-induced disorders in the subject.

The present invention further provides a method for treating exercise-induced disorders in a subject. The method comprises administering the compounds of the invention to the subject in an amount effective to treat the exercise-induced disorder in the subject. A suitable amount of the compounds of the invention effective to treat, for example, exercise-induced cardiac arrhythmia in the subject ranges from about 5 mg/kg/day to about 20 mg/kg/day, and/or is an amount sufficient to achieve plasma levels ranging from about 300 ng/ml to about 1000 ng/ml. The present invention also provides a method for preventing an exercise-induced disorder in a subject. The method comprises administering the compounds of the invention to the subject in an amount effective to prevent the exercise-induced disorder in the subject. A suitable amount of the compounds of the invention effective to prevent the exercise-induced disorder in the subject ranges from about 5 mg/kg/day to about 20 mg/kg/day, and/or is an amount sufficient to achieve plasma levels ranging from about 300 ng/ml to about 1000 ng/ml. Additionally, the present invention provides a method for preventing exercise-induced disorders in a subject. The method comprises administering the compounds of the invention to the subject in an amount effective to prevent an exercise-induced disorder in the subject. A suitable amount of the compounds of the invention effective to prevent an exercise-induced disorder in the subject ranges from about 5 mg/kg/day to about 20 mg/kg/day, and/or is an amount sufficient to achieve plasma levels ranging from about 300 ng/ml to about 1000 ng/ml.

Additionally, the compounds prevent irregular heartbeat disorders in subjects with heterozygous defects in the FKBP12.6 gene.

The compounds of the invention can be used alone, in combination with each other, or in combination with other agents that have cardiovascular activity including, but not limited to, diuretics, anticoagulants, antiplatelet agents, antiarrhythmics, inotropic agents, chronotropic agents, α and β blockers, angiotensin inhibitors and vasodilators. Further, such combinations of the compounds of the present invention and other cardiovascular agents are administered separately or in conjunction. In addition, the administration of one element of the combination is prior to, concurrent to or subsequent to the administration of other agent(s).

In various embodiments of the above-described methods, the exercise-induced cardiac arrhythmia in the subject is associated with VT. In some embodiments, the VT is CPVT. In other embodiments of these methods, the subject is a candidate for exercise-induced cardiac arrhythmia, including candidates for exercise-induced sudden cardiac death.

In view of the foregoing methods, the present invention also provides use of the compounds of the invention in a method for limiting or preventing a decrease in the level of RyR-bound FKBP in a subject who is a candidate for a disorder. The present invention also provides use of the compounds of the invention in a method for treating or preventing a muscular disorder in a subject. Furthermore, the present invention provides use of the compounds of the invention in a method for treating or preventing exercise-induced muscular disorders in a subject.

Accordingly, the present invention further provides a method for assaying the effects of the compounds of the invention in preventing disorders and diseases associated with the RyR receptors. The method comprises the steps of: (a) obtaining or generating a culture of cells containing RyR; (b) contacting the cells with one or more of the compounds of the invention; (c) exposing the cells to one or more conditions known to increase phosphorylation of RyR in cells; and (d) determining if the one or more compounds of the invention limits or prevents a decrease in the level of RyR-bound FKBP in the cells. As used herein, a cell "containing RyR" is a cell in which RyR, including RyR1, RyR2, and RyR3, or a derivative or homologue thereof, is naturally expressed or naturally occurs. Conditions known to increase phosphorylation of RyR in cells include, without limitation, PKA.

In the method of the present invention, cells are contacted with one or more of the compounds of the invention by any of the standard methods of effecting contact between drugs/agents and cells, including any modes of introduction and administration described herein. The level of RyR-bound FKBP in the cell is measured or detected by known procedures, including any of the methods, molecular procedures and assays known to one of skill in the art or described herein. In one embodiment of the present invention, the one or more compounds of the invention limits or prevents a decrease in the level of RyR-bound FKBP in the cells.

RyR, including RyR1, RyR2, and RyR3, has been implicated in a number of biological events in cells. For example, it has been shown that RyR2 channels play an important role in EC coupling and contractility in cardiac muscle cells. Therefore, it is clear that preventive drugs designed to limit or prevent a decrease in the level of RyR-bound FKBP in cells, particularly RyR2-bound FKPB12.6 in cardiac muscle cells, are useful in the regulation of a number of RyR-associated biological events, including EC coupling and contractility. Thus, the one or more compounds of the invention are evaluated for effect on EC coupling and contractility in cells, particularly cardiac muscle cells, and therefore, usefulness for preventing exercise-induced sudden cardiac death.

Accordingly, the method of the present invention further comprises the steps of contacting one or more compounds of the invention with a culture of cells containing RyR; and determining if the one or more compounds has an effect on an RyR-associated biological event in the cells. As used herein, a "RyR-associated biological event" includes a biochemical or physiological process in which RyR levels or activity have been implicated. As disclosed herein, examples of RyR-associated biological events include, without limitation, EC coupling and contractility in cardiac muscle cells. According to this method of the present invention, the one or more compounds are contacted with one or more cells (such as cardiac muscle cells) in vitro. For example, a culture of the cells is incubated with a preparation containing the one or more compounds of the invention. The compounds' effect on a RyR-associated biological event then is assessed by any biological assays or methods known in the art, including immunoblotting, single-channel recordings and any others disclosed herein.

The present invention is further directed to one or more compounds of the invention, identified by the above-described identification method, as well as a pharmaceutical composition comprising the compound and a pharmaceutically acceptable carrier and/or diluent. The compounds are useful for preventing exercise-induced sudden cardiac death in a subject, and for treating or preventing other RyR-associated conditions. As used herein, a "RyR-associated condition" is a condition, disease, or disorder in which RyR level or activity has been implicated, and includes an RyR-associated biological event. The RyR-associated condition is treated or prevented in the subject by administering to the subject an amount of the compound effective to treat or prevent the RyR-associated condition in the subject. This amount is readily determined by one skilled in the art. In one embodiment, the present invention provides a method for preventing exercise-induced sudden cardiac death in a subject, by administering the one or more compounds of the invention to the subject in an amount effective to prevent the exercise-induced sudden cardiac death in the subject.

The present invention also provides an in vivo method for assaying the effectiveness of the compounds of the invention in preventing disorders and diseases associated with the RyR receptors. The method comprises the steps of: (a) obtaining or generating an animal containing RyR; (b) administering one or more of the compounds of the invention to the animal; (c) exposing the animal to one or more conditions known to increase phosphorylation of RyR in cells; and (d) determining the extent the compound limits or prevents a decrease in the level of RyR-bound FKBP in the animal. The method further comprises the steps of: (e) administering one or more of the compounds of the invention to an animal containing RyR; and (f) determining the extent of the effect of the compound on a RyR-associated biological event in the animal. Also provided is a pharmaceutical composition comprising this compound; and a method for preventing exercise-induced sudden cardiac death in a subject, by administering this compound to the subject in an amount effective to prevent the exercise-induced sudden cardiac death in the subject.

It has been demonstrated that compounds which block PKA activation would be expected to reduce the activation of the RyR channel, resulting in less release of calcium into the cell. Compounds that bind to the RyR channel at the FKBP binding site, but do not come off the channel when the channel is phosphorylated by PKA, would also be expected to decrease the activity of the channel in response to PKA activation or other triggers that activate the RyR channel. Such compounds would also result in less calcium release into the cell.

By way of example, the diagnostic assays screen for the release of calcium into cells via the RyR channel, using calcium-sensitive fluorescent dyes (e.g., Fluo-3, Fura-2, and the like). Cells are loaded with the fluorescent dye of choice, then stimulated with RyR activators to determine the reduction of the calcium-dependent fluorescent signal (Brillantes, et al., Stabilization of calcium release channel (ryanodine receptor) function by FK506-binding protein. *Cell,* 77:513-23, 1994; Gillo, et al., Calcium entry during induced differentiation in murine erythroleukemia cells. *Blood,* 81:783-92, 1993; Jayaraman, et al., Regulation of the inositol 1,4,5-trisphosphate receptor by tyrosine phosphorylation. *Science,* 272:1492-94, 1996). Calcium-dependent fluorescent signals are monitored with a photomultiplier tube, and analyzed with appropriate software. This assay can easily be automated to screen the compounds of the invention using multiwell dishes.

To demonstrate that the compounds of inhibit the PKA-dependent activation of RyR-mediated intracellular calcium release, an assay involves the expression of recombinant RyR channels in a heterologous expression system, such as Sf9, HEK293, or CHO cells. RyR could also be co-expressed with beta-adrenergic receptors. This would permit assessment of the effect of compounds of the invention on RyR activation, in response to addition of beta-adrenergic receptor agonists.

The level of PKA phosphorylation of RyR2 which correlates with the degree of heart failure also is assayed and then used to determine the efficacy of the one or more compounds of the invention to block the PKA phosphorylation of the RyR2 channel. Such an assay is based on the use of antibodies that are specific for the RyR2 protein. For example, the RyR2-channel protein is immunoprecipitated and then back-phosphorylated with PKA and [gamma$^{32}$P]-ATP. The amount of radioactive [$^{32}$P] label that is transferred to the RyR2 protein then is measured using a phosphorimager (Marx, et al., PKA phosphorylation dissociates FKBP12.6 from the calcium release channel (ryanodine receptor): defective regulation in failing hearts. *Cell,* 101:365-76, 2000).

Another assay of the compounds of the invention involves use of a phosphoepitope-specific antibody that detects RyR1 that is PKA phosphorylated on Ser 2843 or RyR2 that is PKA phosphorylated on Ser 2809. Immunoblotting with such an antibody can be used to assess efficacy of these compounds for therapy for heart failure and cardiac arrhythmias. Additionally, RyR2 S2809A and RyR2 S2809D knock-in mice are used to assess efficacy of therapy for heart failure and cardiac arrhythmias. Such mice further provide evidence that PKA hyperphosphorylation of RyR2 is a contributing factor in heart failure and cardiac arrhythmias by showing that the RyR2 S2809A mutation inhibits heart failure and arrhythmias, and that the RyR2 S2809D mutation worsens heart failure and arrhythmias.

Therefore, in a specific embodiment, the present invention provides a method of treating heart failure, atrial fibrillation or exercise-induced cardiac arrhythmia, comprising administering to an animal in need thereof, a therapeutically effective amount of a compound selected from the compounds of the invention.

Intracellular $Ca^{2+}$ leak is proposed as a principal mediator of depressed muscle performance and dystrophic muscle remodeling. Muscular dystrophies are heterogeneous hereditary diseases characterized by weakness and progressive muscle wasting. Of all forms of muscular dystrophies involving the dystrophin-associated protein complex (referred to as dystrophinopathies), Duchenne muscular dystrophy (DMD) is one of the most frequent genetic diseases (X-linked; 1 in 3,500 boys) with death usually occurring before age 30 by respiratory and/or cardiac failure in high numbers of patients. Becker muscular dystrophy (BMD) represents a milder form of the disease associated with a reduction in the amount or expression of a truncated form of the dystrophin protein whereas Duchenne patients have been characterized by complete absence or very low levels of dystrophin. Duchenne and Becker's muscular dystrophy (DMD/BMD) are caused by mutations in the gene encoding the 427-kDa cytoskeletal protein dystrophin. However, with increasing age in BMD cardiac symptoms are more common than in DMD patients and do not correlate with skeletal muscle symptoms. Since genetic screening will not eliminative DMD due to a high incidence of sporadic cases, an effective therapy is highly desirable. DMD/BMD have been consistently associated with disturbed intracellular calcium metabolism. Because alterations of intracellular $Ca^{2+}$ concentrations in DMD myofibers are believed to represent a central pathogenic mechanism, development of a therapeutic intervention that prevents intracellular $Ca^{2+}$ abnormalities as a cause of skeletal muscle degeneration is highly desirable.

It is well established that lack of dystrophin expression is the primary genetic defect in DMD and BMD. However, the key mechanism leading to progressive muscle damage is largely unknown. It has been suggested that elevations of intracellular $Ca^{2+}$ concentrations ($[Ca^{2+}]_i$) under resting conditions directly contributed to toxic muscle cell (myofiber) damage and concurrent activation of $Ca^{2+}$-dependent proteases. Since calpain activity is increased in necrotic muscle fibers of mdx mice and calpain dysfunction contributes to limb-girdle muscular dystrophy, preventing activation of calcium-dependent proteases by inhibiting intracellular $Ca^{2+}$ elevations represents a strategy to prevent muscle wasting in DMD. Significant differences in $[Ca^{2+}]_i$ between normal and dystrophic muscles have been reported in myotubes and animal models including the dystrophin-deficient mdx mouse. Intracellular $Ca^{2+}$ elevations are prevented by administration of a pharmaceutical composition comprising a compound of the invention.

The present invention also provides a method of diagnosis of a disease or disorder in a subject, said method comprising: obtaining a cell or tissue sample from the subject; obtaining DNA from the cell or tissue; comparing the DNA from the cell or tissue with a control DNA encoding RyR to determine whether a mutation is present in the DNA from the cell or tissue, the presence of a mutation indicating a disease or disorder. In one embodiment, the mutation is a RyR2 mutation on chromosome 1q42-q43. In another embodiment, the mutation is one or more CPTV mutations. In another embodiment, the mutation may be a mutation that is present in the DNA encoding RyR2 of a SIDS subject. The diagnostic method is used to detect the presence of a disease or disorder in an adult, a child or a fetus. The disease and disorders include, but are not limited to, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss.

The present invention further provides a method of diagnosis of disorders and diseases in a subject, said method comprising: obtaining cells or tissue sample from the subject; incubating the cells or tissue sample with the compound of the invention under conditions which increase phosphorylation of RyR in cells; determining (a) whether RyR bound to calstabin (i.e. RyR1 bound to calstabin1, RyR2 bound to calstabin2, or RyR3 bound to calstabin1) is increased in the cells or tissue compared to RyR bound to calstabin in control cells or tissues said control cells or tissues lacking mutant RyR calcium channels, or (b) whether a decrease in release of calcium occurs in RyR channels compared to a lack of decrease in release of calcium in the control cells; an increase in RyR-bound calstabin in (a) indicating a disorder or disease in the subject or a decrease in release of calcium in RyR channels in (b) compared to the control cells indicating a cardiac disease or disorder in the subject. The diagnostic method is used to detect the presence of a disease or disorder in an adult, a child or a fetus. The disease and disorders include, but are not limited to, cardiac disorders and diseases, skeletal muscular disorders and diseases, cognitive disorders and diseases, malignant hyperthermia, diabetes, and sudden infant death syndrome. Cardiac disorder and diseases include, but are not limited to, irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof. Skeletal muscular disorder and diseases include, but are not limited to, skeletal muscle fatigue, exercise-induced skeletal muscle fatigue, muscular dystrophy, bladder disorders, and incontinence. Cognitive disorders and diseases include, but are not limited to, Alzheimer's Disease, forms of memory loss, and age-dependent memory loss.

The present invention further provides a method of diagnosis of a cardiac disorder or disease in a subject, said method comprising: obtaining cardiac cells or tissue sample from the subject; incubating the cardiac cells or tissue sample with the compound of the invention, under conditions which increase phosphorylation of RyR2 in cells; determining (a) whether RyR2 bound to calstabin2 is increased in the cells or tissue compared to RyR2 bound to calstabin2 in control cells or tissues said control cells or tissues lacking mutant RyR2 calcium channels, or (b) whether a decrease in release of calcium occurs in RyR2 channels compared to a lack of decrease in release of calcium in the control cells; an increase in RyR2-bound calstabin2 in (a) indicating a disorder or disease in the subject or a decrease in release of calcium in RyR2 channels in (b) compared to the control cells indicating a cardiac disease or disorder in the subject. The provided method is used to diagnose CPTV. The provided method also is used to diagnose sudden infant death syndrome (SIDS). The provided method additionally is used to diagnose cardiac irregular heartbeat disorders and diseases; exercise-induced irregular heartbeat disorders and diseases; sudden cardiac death; exercise-induced sudden cardiac death; congestive heart failure; chronic obstructive pulmonary disease; and high blood pressure. Irregular heartbeat disorders and diseases include and exercise-induced irregular heartbeat disorders and diseases include, but are not limited to, atrial and ventricular arrhythmia; atrial and ventricular fibrillation; atrial and ventricular tachyarrhythmia; atrial and ventricular tachycardia; catecholaminergic polymorphic ventricular tachycardia (CPVT); and exercise-induced variants thereof.

In addition to the above-mentioned therapeutic uses, the compounds of the invention are also useful in diagnostic assays, screening assays and as research tools.

Methods of Synthesis

The present invention provides, in a further aspect, processes for the preparation of a compound of invention, and salts, solvates, hydrates, complexes, and prodrugs thereof, and pharmaceutically acceptable salts of such prodrugs. These processes are disclosed in the applications that are incorporate by reference in the first paragraph of this document, as well as in U.S. Pat. No. 7,704,409 and U.S. application Ser. Nos. 10/680,988 and 12/480,396, the content of each of which is also expressly incorporated herein by reference thereto.

It should be noted that the compounds used as starting materials for, or generated as intermediates in, the synthesis of the compounds of the invention, may themselves have structures encompassed by the formulae of the invention, and/or may themselves be active agents useful in the methods and compositions of the present invention. Such starting materials and intermediates may be useful for, inter alia, treating or preventing various disorders and diseases associated with RyR receptors such as muscular and cardiac disorders, treating or preventing a leak in a RyR2 receptor in a subject, or modulating the binding of RyR and FKBP in a subject. The present invention encompasses any of the starting materials or intermediates disclosed herein that have structures encompassed by Formula I, I-a, I-b, I-c, I-d, I-e, I-f, I-g, I-h, I-j, I-k, I-k-1, I-l, I-l-1, I-m, I-m-1, I-n, I-o, I-p or II, and/or which are useful as active agents in the methods and compositions of the present invention. For example, in one embodiment the compound S68, which is useful as a starting material for the synthesis of compounds S69-S75, may be used for, inter alia, treating or preventing various disorders and diseases associated with RyR receptors, treating or preventing a leak in a RyR2 receptor, or modulating the binding of RyR and FKBP in a subject.

In another embodiment, the compound S26, which is useful in the synthesis of many of the compounds described herein (including S3, S4, S5, S7, S9, S11, S12, S13, S14 and other compounds) may be used for, inter alia, treating or preventing various disorders and diseases associated with RyR receptors, treating or preventing a leak in a RyR2 receptor, or modulating the binding of RyR and FKBP in a subject.

Similarly, in another embodiment, the compound S25 (see U.S. Pat. No. 7,718,644) may also be used for, inter alia, treating or preventing various disorders and diseases associated with RyR receptors, treating or preventing a leak in a RyR2 receptor, or modulating the binding of RyR and FKBP in a subject.

The compounds of the present invention are prepared in different forms, such as salts, hydrates, solvates, complexes, prodrugs or salts of prodrugs and the invention includes all variant forms of the compounds.

The present invention further provides a composition, comprising radio labeled compounds of the invention. Labeling of the compounds of the invention is accomplished using one of a variety of different radioactive labels known in the art. The radioactive label of the present invention is, for example, a radioisotope. The radioisotope is any isotope that emits detectable radiation including, without limitation, $^{35}S$, $^{125}I$, $^{3}H$, or $^{14}C$. Radioactivity emitted by the radioisotope can be detected by techniques well known in the art. For example, gamma emission from the radioisotope is detected using gamma imaging techniques, particularly scintigraphic imaging.

By way of non-limiting example, radio-labeled compounds of the invention are prepared as follows. A compound of the invention is demethylated at the phenyl ring using $BBr_3$. The resulting phenol compound then is re-methylated with a radio-labeled methylating agent (such as $^3H$-dimethyl sulfate) in the presence of a base (such as NaH) to provide $^3H$-labeled compounds.

Using forced swimming as an efficient protocol to increase skeletal muscle aerobic capacity in mice, the composition and phosphorylation status of the skeletal RyR1 channel complex have been investigated. Unexpectedly, after 3 weeks of 90 mins swimming twice daily, C57B16 wild-type mice showed significantly increased RyR1 phosphorylation by PKA while $Ca^{2+}$-calmodulin kinase II (CaMKII) phosphorylation was not changed indicating specificity of the stress pathway RyR1 protein expression was stable, however, RyR1 channels were depleted of the stabilizing subunit calstabin1 (FKBP12). It has been shown that RyR1 hyperphosphorylation and calstabin1 depletion are consistent with leaky RyR1 channels that cause intracellular SR $Ca^{2+}$ leak.

RyR1 channels are PKA hyperphosphorylated and depleted of the stabilizing calstabin1 subunit after 3 weeks of 90 mins swimming twice daily. The immunoprecipitated RyR1 macromolecular channel complex shows increased PKA phosphorylation at Ser-2844 (corresponding to human RyR1-Ser-2843) whereas CaMKII phosphorylation at Ser-2849 (corresponding to human RyR1-Ser-2848) is unchanged. Concomitant with increased RyR1-Ser-2844 PKA hyperphosphorylation, calstabin1 is depleted from the channel complex. Normalization of phosphorylation and calstabin1 content to four subunits of the tetrameric channel complex shows a significant in increase in PKA phosphorylation and depletion of the stabilizing calstabin1 subunit.

The compounds of the present invention are prepared in different forms, such as salts, hydrates, solvates, complexes, pro-drugs or salts of prodrugs and the invention includes all variant forms of the compounds.

The term "compound(s) of the invention" as used herein means a compound of Formula I, I-a, I-b, I-c, I-d, I-e, I-f, I-g, I-h, I-j, I-k, I-k-1, I-l, I-l-1, I-m, I-m-1, I-n, I-o, I-p and II, and salts, hydrates, prodrugs and solvates thereof.

A "pharmaceutical composition" refers to a mixture of one or more of the compounds described herein, or pharmaceutically acceptable salts, hydrates or pro-drugs thereof, with other chemical components, such as physiologically acceptable carriers and excipients. The purpose of a pharmaceutical composition is to facilitate administration of a compound to an organism.

A "prodrug" refers to an agent which is converted into the parent drug in vivo. Pro-drugs are often useful because, in some situations, they are easier to administer than the parent drug. They are bioavailable, for instance, by oral administration whereas the parent drug is not. The prodrug also has improved solubility in pharmaceutical compositions over the parent drug. For example, the compound carries protective groups which are split off by hydrolysis in body fluids, e.g., in the bloodstream, thus releasing active compound or is oxidized or reduced in body fluids to release the compound.

A compound of the present invention also can be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

The compounds of the present invention form hydrates or solvates, which are included in the scope of the claims. When the compounds of the present invention exist as regioisomers, configurational isomers, conformers or diasteroisomeric forms all such forms and various mixtures thereof are included in the scope of Formula I, I-a, I-b, I-c, I-d, I-e, I-f, I-g, I-h, I-j, I-k, I-k-1, I-l, I-l-1, I-m, I-m-1, I-n, I-o, I-p and II. It is possible to isolate individual isomers using known separation and purification methods, if desired. For example, when a compound of the present invention is a racemate, the racemate can be separated into the (S)-compound and (R)-compound by optical resolution. Individual optical isomers and mixtures thereof are included in the scope of Formula I, I-a, I-b, I-c, I-d, I-e, I-f, I-g, I-h, I-j, I-k, I-k-1, I-l, I-l-1, I-m, I-m-1, I-n, I-o, I-p and II.

The terms "animal," "subject" and "patient" as used herein include all members of the animal kingdom including, but not limited to, mammals, animals (e.g., cats, dogs, horses, etc.) and humans.

The present invention further provides a composition, comprising radio labeled compounds of Formula I, I-a, I-b, I-c, I-d, I-e, I-f, I-g, I-h, I-j, I-k, I-k-1, I-l, I-l-1, I-m, I-m-1, I-n, I-o, and I-p. Labeling of the compounds is accomplished using one of a variety of different radioactive labels known in the art. The radioactive label of the present invention is, for example, a radioisotope. The radioisotope is any isotope that emits detectable radiation including, without limitation, $^{35}S$, $^{125}I$, $^{3}H$, or $^{14}C$. Radioactivity emitted by the radioisotope can be detected by techniques well known in the art. For example, gamma emission from the radioisotope is detected using gamma imaging techniques, particularly scintigraphic imaging.

By way of example, radio-labeled compounds of the invention are prepared as follows. A compound of the invention may be demethylated at the phenyl ring using $BBr_3$. The resulting phenol compound then is re-methylated with a radio-labeled methylating agent (such as $^3H$-dimethyl sulfate) in the presence of a base (such as NaH) to provide $^3H$-labeled compounds.

In accordance with the method of the present invention, the decrease in the level of RyR-bound FKBP is limited or prevented in the subject by decreasing the level of phosphorylated RyR in the subject. In one embodiment, the amount of the agent effective to limit or prevent a decrease in the level of RyR2-bound FKBP12.6 in the subject is an amount of the agent effective to treat or prevent heart failure, atrial fibrillation and/or exercise-induced cardiac arrhythmia in the subject. In another embodiment, the amount of the agent effective to limit or prevent a decrease in the level of RyR2-bound FKBP12.6 in the subject is an amount of the agent effective to prevent exercise-induced sudden cardiac death in the subject.

In view of the foregoing, the present invention further provides a method for treating or preventing exercise-induced cardiac arrhythmia in a subject, comprising administering to the subject a 1,4-benzothiazepine compound, as disclosed herein, in an amount effective to treat or prevent exercise-induced cardiac arrhythmia in the subject. Similarly, the present invention provides a method for preventing exercise-induced sudden cardiac death in a subject, comprising administering to the subject a 1,4-benzothiazepine compound, as disclosed herein, in an amount effective to prevent exercise-induced sudden cardiac death in the subject. Additionally, the present invention provides a method for treating or preventing atrial fibrillation or heart failure in a subject, comprising administering to the subject a compound, as disclosed herein, in an amount effective to treat or prevent the atrial fibrillation or heart failure in the subject. In each of these methods, the compound is selected from the group of compounds consisting of compounds of the formula:

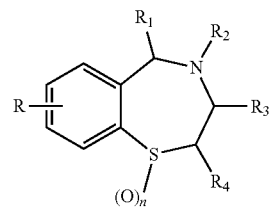

wherein,
n is 0, 1, or 2;
R is located at one or more positions on the benzene ring;
each R is independently selected from the group consisting of H, halogen, —OH, —$NH_2$, —$NO_2$, —CN, —$N_3$, —$SO_3H$, acyl, alkyl, alkoxyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl;
$R_1$ is selected from the group consisting of H, oxo, alkyl, alkenyl, aryl, cycloalkyl, and heterocyclyl;
wherein each alkyl, alkenyl, aryl, cycloalkyl, and heterocyclyl may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl;
$R_2$ is selected from the group consisting of H, —C=O($R_5$), —C=S($R_6$), —$SO_2R_7$, —$POR_8R_9$, —$(CH_2)_m$—$R_{10}$, alkyl, aryl, heteroaryl, cycloalkyl, cycloalkylalkyl, and heterocyclyl; wherein each alkyl, aryl, heteroaryl, cycloalkyl, cycloalkylalkyl, and heterocyclyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;
$R_3$ is selected from the group consisting of H, $CO_2Y$, CONY, acyl, alkyl, alkenyl, aryl, cycloalkyl, and heterocyclyl; wherein each acyl, alkyl, alkenyl, aryl, cycloalkyl, and heterocyclyl may be substituted with one or more radicals independently selected from the group consisting of halogen, N, O, —S—, —CN, —N3, —SH, nitro, oxo, acyl, alkyl, alkoxyl, alkylamino, alkenyl, aryl, (hetero-)cycloalkyl, and (hetero-)cyclyl; and wherein Y is selected from the group consisting of H, alkyl, aryl, cycloalkyl, and heterocyclyl;

$R_4$ is selected from the group consisting of H, alkyl, alkenyl, aryl, cycloalkyl, and heterocyclyl; wherein each alkyl, alkenyl, aryl, cycloalkyl, and heterocyclyl may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl;

$R_5$ is selected from the group consisting of —$NR_{16}$, $NHNHR_{16}$, NHOH, —$OR_{15}$, $CONH_2NHR_{16}$, $CO_2R_{15}$, $CONR_{16}$, $CH_2X$, acyl, alkenyl, aryl, cycloalkyl, cycloalkylalkyl, heterocyclyl, and heterocyclylalkyl;

wherein each acyl, alkenyl, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_6$ is selected from the group consisting of –$OR_{15}$, $NHNR_{16}$, NHOH, —$NR_{16}$, $CH_2X$, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_7$ is selected from the group consisting of —$OR_{15}$, —$NR_{16}$, $NHNHR_{16}$, NHOH, $CH_2X$, alkyl, aryl, cycloalkyl, cycloalkylalkyl, heterocyclyl, and heterocyclylalkyl; wherein each alkyl, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_8$ and $R_9$ independently are selected from the group consisting of OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl;

$R_{10}$ is selected from the group consisting of $NH_2$, OH, —$SO_2R_{11}$, —$NHSO_2R_{11}$, C=$O(R_{12})$, NHC=$O(R_{12})$, —OC=$O(R_{12})$, and —$POR_{13}R_{14}$;

$R_{11}$, $R_{12}$, $R_{13}$, and $R_{14}$ independently are selected from the group consisting of H, OH, $NH_2$, $NHNH_2$, NHOH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted with one or more radicals independently selected from the group consisting of halogen, —N—, —O—, —S—, —CN, —$N_3$, nitro, oxo, acyl, alkenyl, alkoxyl, alkyl, alkylamino, amino, aryl, cycloalkyl, cycloalkylalkyl, heterocyclyl, heterocyclylalkyl, and hydroxyl;

X is selected from the group consisting of halogen, CN, $CO_2R_{15}$, $CONR_{16}$, —$NR_{16}$, —$OR_{15}$, —$SO_2R_7$, and —$POR_8R_9$; and $R_{15}$ and $R_{16}$ independently are selected from the group consisting of H, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted with one or more radicals independently selected from the group consisting of halogen, —N—, —O—, —S—, —CN, —$N_3$, nitro, oxo, acyl, alkenyl, alkoxyl, alkyl, alkylamino, amino, aryl, cycloalkyl, cycloalkylalkyl, heterocyclyl, heterocyclylalkyl, and hydroxyl, and wherein each substituted acyl, alkenyl, alkoxyl, alkyl, alkylamino, aryl, cycloalkyl, cycloalkylalkyl, heterocyclyl, and heterocyclylalkyl radical may itself be substituted with one or more radicals independently selected from the group consisting of halogen, —N—, —O—, —S—, —CN, —$N_3$, nitro, oxo, acyl, alkenyl, alkoxyl, alkyl, alkylamino, amino, aryl, cycloalkyl, cycloalkylalkyl, heterocyclyl, heterocyclylalkyl, and hydroxy;

and salts, hydrates, solvates, complexes, and prodrugs thereof.

In an embodiment of the present invention, if $R_2$ is C=O ($R_5$) or $SO_2R_7$, then R is at positions 2, 3, or 5 on the benzene ring.

In another embodiment of the invention, if $R_2$ is C=$O(R_5)$ or $SO_2R_7$, then each R is independently selected from the group consisting of H, halogen, —OH, —$NH_2$, —$NO_2$, —CN, —$N_3$, —$SO_3H$, acyl, alkyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl.

In another embodiment of the invention, if $R_2$ is C=$O(R_5)$ or $SO_2R_7$, then there are at least two R groups attached to the benzene ring. Furthermore, there are at least two R groups attached to the benzene ring, and both R groups are attached at positions 2, 3, or 5 on the benzene ring. Still further, each R is independently selected from the group consisting of H, halogen, —OH, —$NH_2$, —$NO_2$, —CN, —$N_3$, —$SO_3H$, acyl, alkyl, alkylamino, cycloalkyl, heterocyclyl, heterocyclylalkyl, alkenyl, (hetero-)aryl, (hetero-)arylthio, and (hetero-)arylamino; wherein each acyl, alkyl, alkoxyl, alkylamino, cycloalkyl, heterocyclyl, heterocyclylalkyl, alkenyl, (hetero-)aryl, (hetero-)arylthio, and (hetero-)arylamino may be substituted with one or more radicals independently selected from the group consisting of halogen, N, O, —S—, —CN, —$N_3$, —SH, nitro, oxo, acyl, alkyl, alkoxyl, alkylamino, alkenyl, aryl, (hetero-)cycloalkyl, and (hetero-)cyclyl.

In another embodiment of the invention, if $R_2$ is C=$O(R_5)$, then $R_5$ is selected from the group consisting of —$NR_{16}$, $NHNHR_{16}$, NHOH, —$OR_{15}$, $CONH_2NHR_{16}$, $CONR_{16}$, $CH_2X$, acyl, aryl, cycloalkyl, cycloalkylalkyl, heterocyclyl, and heterocyclylalkyl; wherein each acyl, aryl, cycloalkyl, cycloalkylalkyl, heterocyclyl, and heterocyclylalkyl may be substituted with one or more radicals independently selected from the group consisting of halogen, N, O, —S—, —CN, —$N_3$, nitro, oxo, acyl, alkyl, alkoxyl, alkylamino, alkenyl, aryl, (hetero-)cycloalkyl, and (hetero-)cyclyl.

Efficacy Demonstrations

Figure 1B:
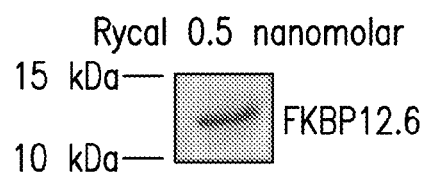
Figure 1C:
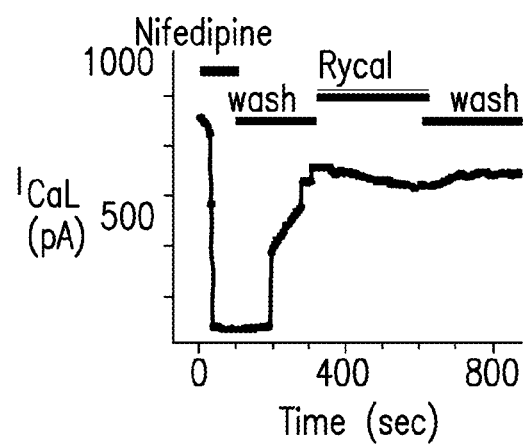
Figure 2A:
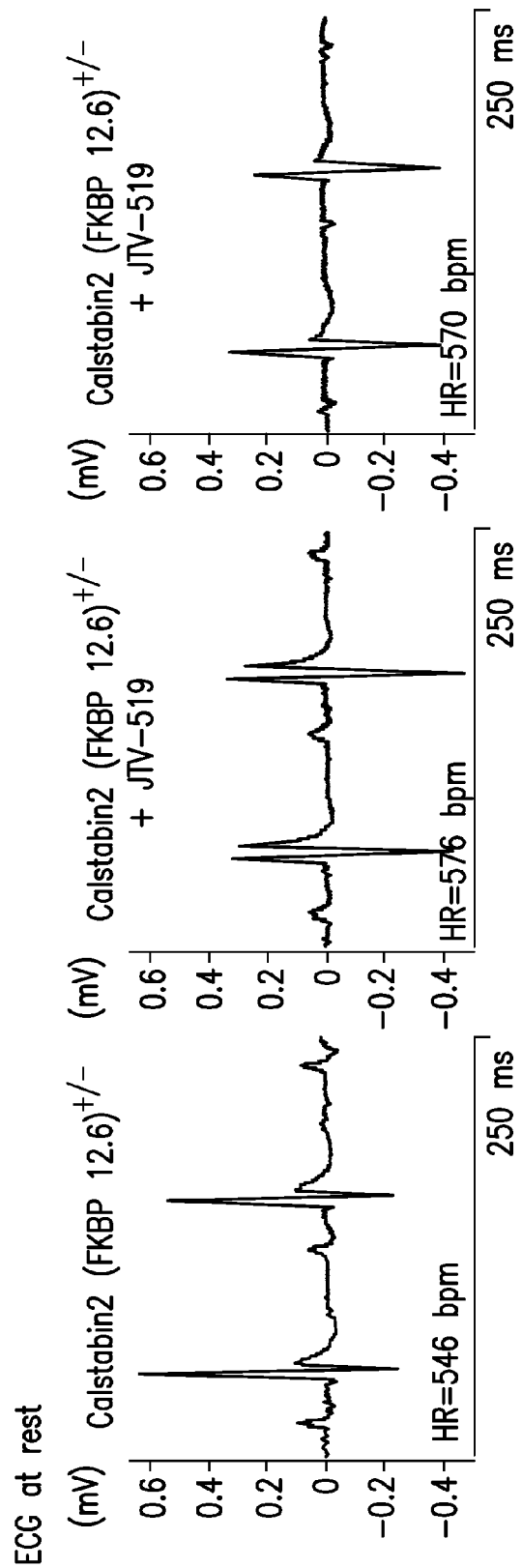
FIG. 2, embodiments A, B, C, and D demonstrate the prevention of exercise-induced ventricular arrhythmias by JTV-519 in haploinsufficient calstabin (FKBP12.6)$^{+/-}$ mice. Embodiment A are representative telemetric electrocardiograms (ECGs) of an untreated calstabin2 (FKBP12.6)$^{+/-}$ mouse (left), a JTV-519-treated calstabin2 (FKBP12.6)$^{+/-}$ mouse (middle), and a calstabin2 (FKBP12.6)$^{-/-}$ mouse (right). Embodiment B are telemetry recordings of a sustained polymorphic ventricular tachycardia (sVT) in (upper) an untreated haploinsufficient calstabin2 (FKBP12.6)$^{+/-}$ mouse and (lower) a JTV-519-treated calstabin2 (FKBP12.6)$^{+/-}$ mouse, each subjected to exercise testing immediately followed by injection with 0.5 mg epinephrine per kilogram of body weight. Embodiment C are graphs showing the numbers of mice with cardiac death (left), sustained VTs (middle), and nonsustained VTs (right) in experimental groups of mice subjected to exercise testing and injection with 0.5 mg/kg epinephrine. Embodiment D provides graphs comparing the dose dependence of pharmacological effects of JTV-519 and S36 in regard to sudden cardiac death (left), sustained VTs (middle), and nonsustained VTs (right).
Figure 2B:
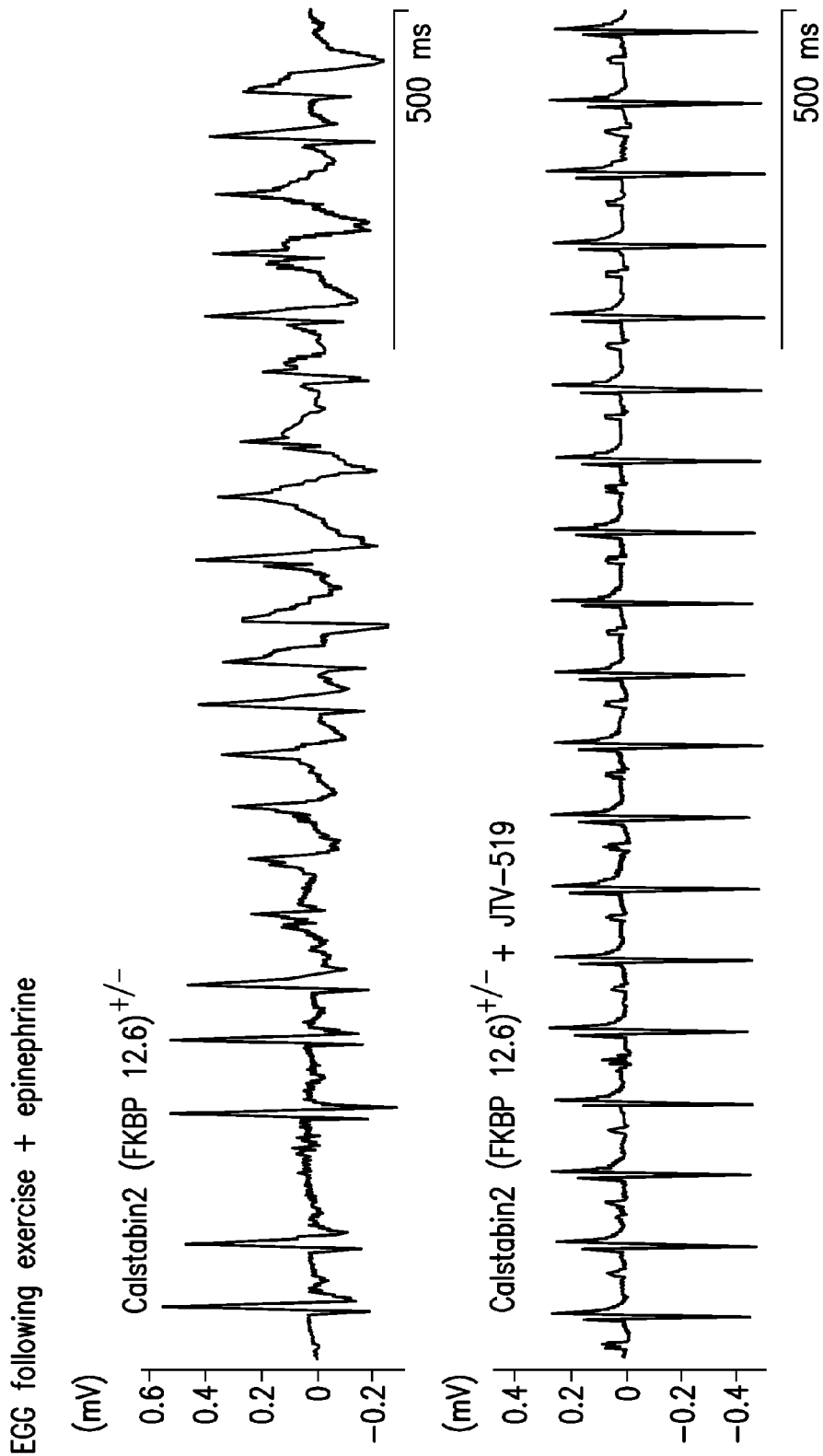
Figure 2C:
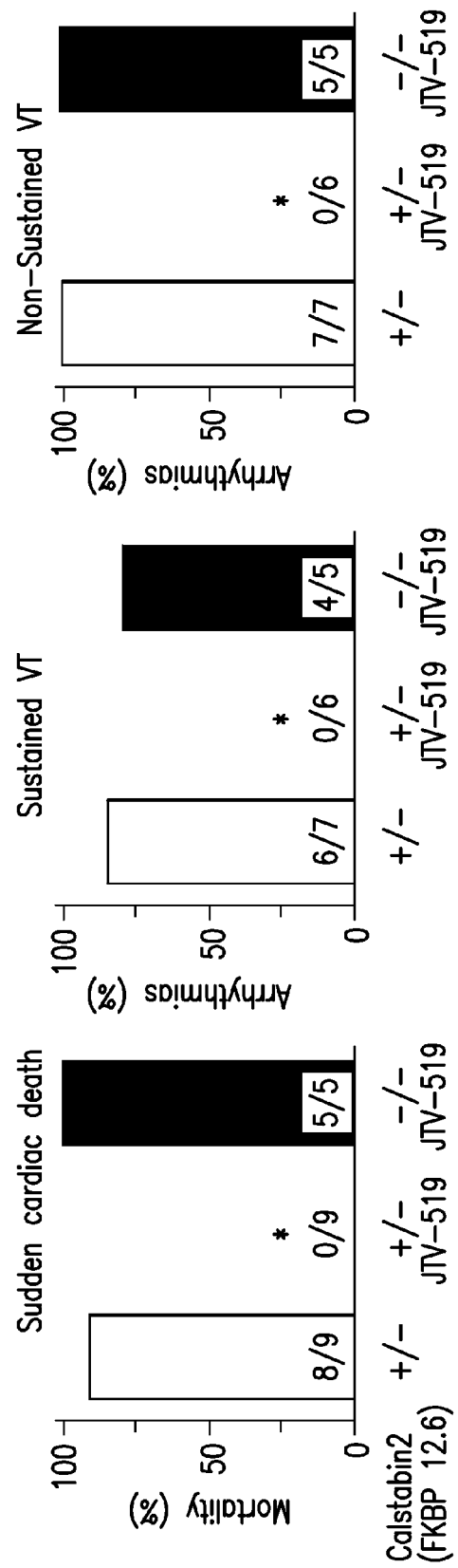
Figure 2D:
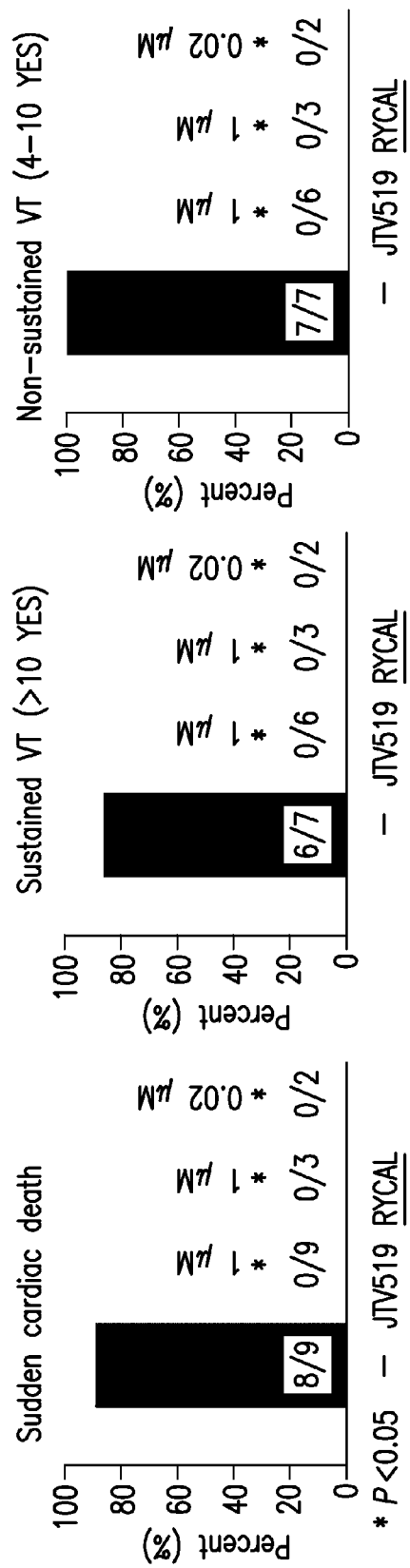

As demonstrated by FIG. 1, embodiments A, B, C, and D, S36 is more potent at increasing the binding of FKBP12.6 and RyR2 than JTV-519 and does not block the L-type Ca2+ channel ($I_{Ca,L}$) or HERG K+ channel ($I_{Kr}$). In embodiment A, PKA phosphorylated RyR2 is generated as follows: cardiac SR membrane preparations (5 μl, 50 μg) are added to a total of 100 μl of kinase buffer (8 mM $MgCl_2$, 10 mM EGTA, 50 mM Tris-PIPES, pH 6.8) containing 100 μM MgATP and 40 units of PKA, and incubated at room temperature. Samples are centrifuged at 95,000 g for 10 min and the pellets are washed three times in 0.2 ml imidazole buffer. The final pellets are pooled and resuspended in imidazole buffer (final concentration≈10 μg/μl). To test for the FKBP12.6 rebinding efficiency of JTV-519, PKA phosphorylated cardiac SR (50 mg) is incubated for 30 minutes at room temperature with the test compounds and 250 nM FKBP12.6 in 10 mM imidizol buffer, pH 7.0. Samples then are centrifuged at 100,000 g for 10 minutes and pellets washed 3 times with imidizol buffer. After washing, proteins are size-fractionated on 15% PAGE. Immunoblots are developed using an anti-FKBP antibody (1:3,000 dilution). The amount of rebinding is quantified using densitometry of Western blots and is compared to the amount of FKBP associated with RyR in non-phosphorylated SR. $EC_{50}$'s for the compounds are determined by generating FKBP binding data using concentrations of compounds ranging from 0.5-1000 nM. In embodiment B, currents through L-type $Ca^{2+}$ channels in isolated mouse cardiomyocytes are recorded using whole-cell patch clamp recording conditions with $Ba^{2+}$ as the charge carrier. The extracellular solution contains (in mM): N-methyl-D-glucamine, 125; $BaCl_2$, 20; CsCl, 5; $MgCl_2$, 1; HEPES, 10; glucose, 5; pH 7.4 (HCl). The intracellular solution contains (in mM): CsCl, 60; $CaCl_2$, 1; EGTA, 11; $MgCl_2$, 1; $K_2ATP$, 5; HEPES, 10; aspartic acid, 50; pH 7.4 (CsOH). Under these conditions, it is expected that the measured current was carried by $Ba^{2+}$ primarily through L-type calcium channels which is referred to as $I_{Ca,L}$. Drugs are applied by a local solution changer and reach the cell membrane within 1 s. The effects of nifedipine and S36 are tested with 20 ms long voltage-clamp steps to +10 or +20 mV (peak of current-voltage relation for each individual cell) from holding potentials of −80 mV or −40 mV. In embodiment C, the voltage-dependence of L-type $Ca^{2+}$ current blocked by JTV-519 (1 μM) and S36 (1 μM) are measured and presented.

As demonstrated by FIG. 2, embodiments A, B, C, and D, S36 prevents exercise-induced sudden cardiac death at lower plasma levels compared with JTV-519. In embodiment A are shown representative ECGs of an untreated FKBP12.6+/− mouse and JTV-519-treated FKBP12.6+/− and FKBP12.6−/− mice. Mice are treated with 0.5 mg JTV-519/per kilogram of body weight per hour for 7 days with an implanted osmotic mini-pump. JTV-519 has no effect on resting heart rate or other ECG parameters such as heart rate (HR). In embodiment B are shown sustained polymorphic ventricular tachycardia recorded by telemetry in an untreated FKBP12.6+/− mouse (upper tracing) subjected to exercise testing, immediately followed by injection with 0.5 mg epinephrine per kilogram of body weight. Representative telemetry ECG recording of a JTV-519-treated FKBP12.6+/− mouse following the same protocol is shown in the bottom tracing. In embodiment C are shown numbers of mice with cardiac death (left), sustained VTs (>10 beats, middle), and nonsustained VTs (3 to 10 arrhythmogenic beats, right) in experimental groups of mice subjected to exercise testing and injection with 0.5 mg/kg epinephrine. In embodiment D, the dose-dependence of pharmacological effects of JTV-519 and S36 is shown. Plasma levels of 1 μM JTV-519 prevent cardiac arrhythmias and sudden cardiac death in FKBP12.6+/− mice. Plasma levels of 1 μM and 0.02 μM S36 also prevent cardiac arrhythmias and sudden cardiac death in FKBP12.6+/− mice.

Figure 3:
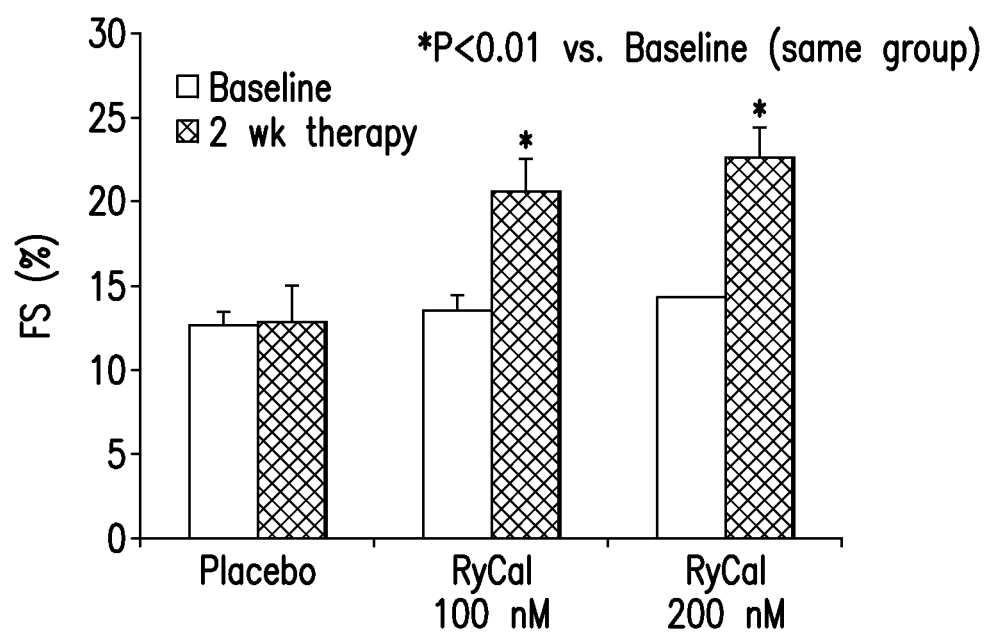
FIG. 3 is a graph showing fractional shortening (FS) of the left ventricle assessed by M-mode echocardiography 2 weeks post-myocardial infarction in mice.

FIG. 3 shows the results of treated mice that are subjected to permanent ligation of the left anterior descending coronary artery resulting in myocardial infarction.

Figure 4:
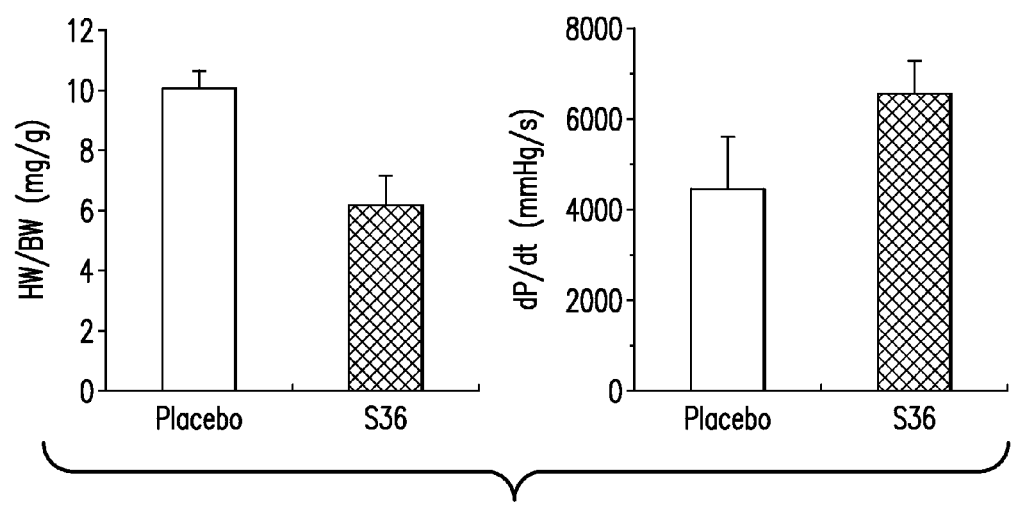
FIG. 4 is a graph showing heart weight to body weight (HW/BW) ratios and pressure-volume loops quantifications (dP/dt) one week post-myocardial infarction of placebo and S36-treated mice. S36 treatment results in a beneficial reduction of the HW/BW ratio and increased velocity of pressure development in S36 as compared to placebo treated mice.

As demonstrated by FIG. 4, S36 improves cardiac function in chronic heart failure post-myocardial infarction. Wild-type mice are subjected to permanent ligation of the left anterior descending coronary artery resulting in myocardial infarction. Seven days following myocardial infartion, mice are treated with S36 (plasma concentration 200 nM) or placebo. Heart weight to body weight (HW/BW) ratios and pressure-volume loops quantifications (dP/dt, slope of the maximum derivative of change in systolic pressure over time) show reverse remodeling and improved cardiac contractility in S36-treated mice compared with placebo.

Figure 5:
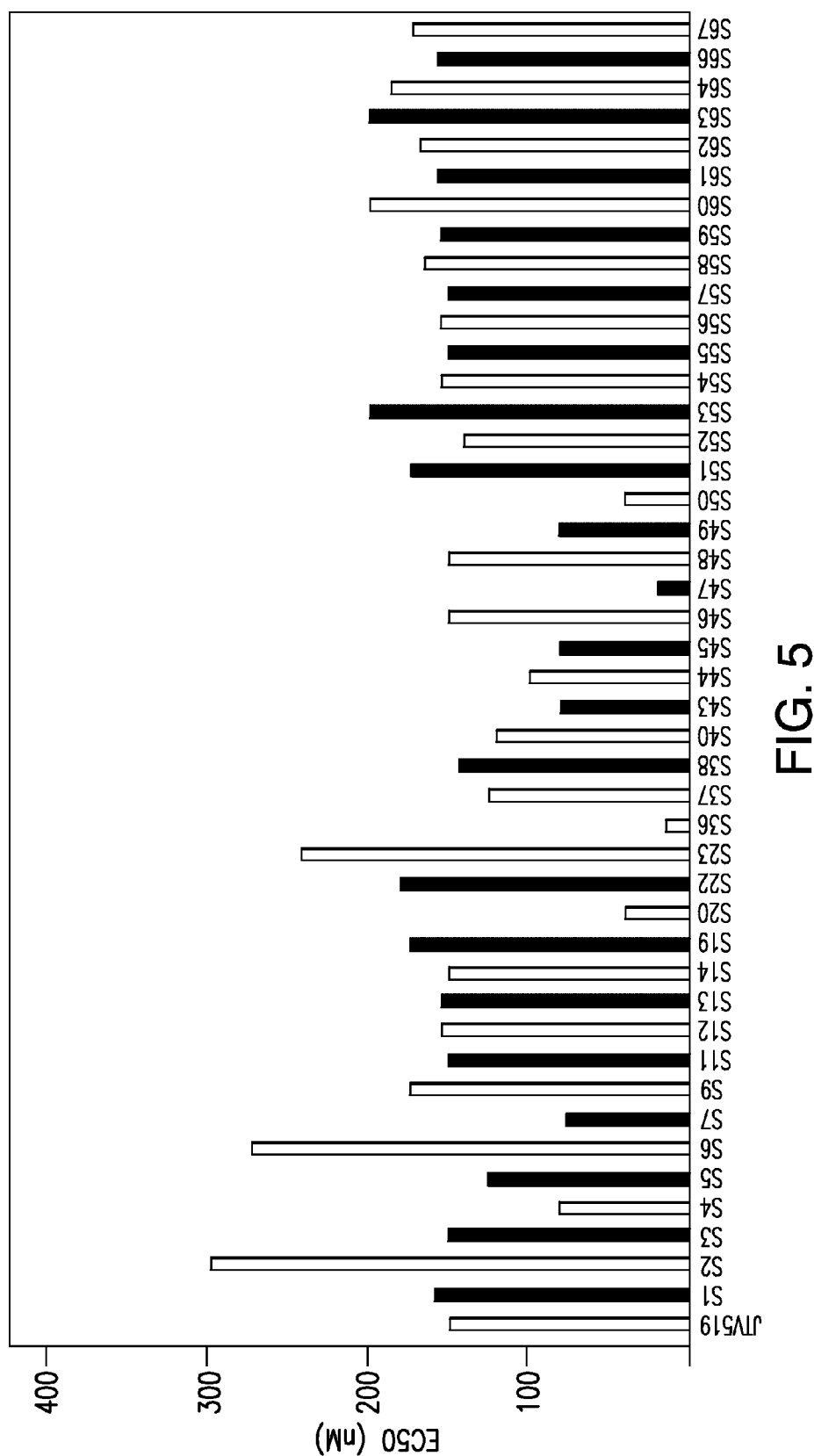
FIG. 5 is a graph summarizing $EC_{50}$ values of JTV-519 and a series of Rycal compounds indicating several compounds with a higher biologic activity as evidenced by significantly lower $EC_{50}$ values compared to JTV-519.

FIG. 5 is a summary graph of EC50 values of JTV-519 and compounds S1-S67 disclosed herein. The FKBP12.6 rebinding assay described above is used to determine the amount of FKBP12.6 binding to PKA-phosphorylated RyR2 at various concentrations (0.5-1000 nM) of the compounds shown. $EC_{50}$ values are calculated using Michaelis-Menten curve fitting.

Figure 6A:
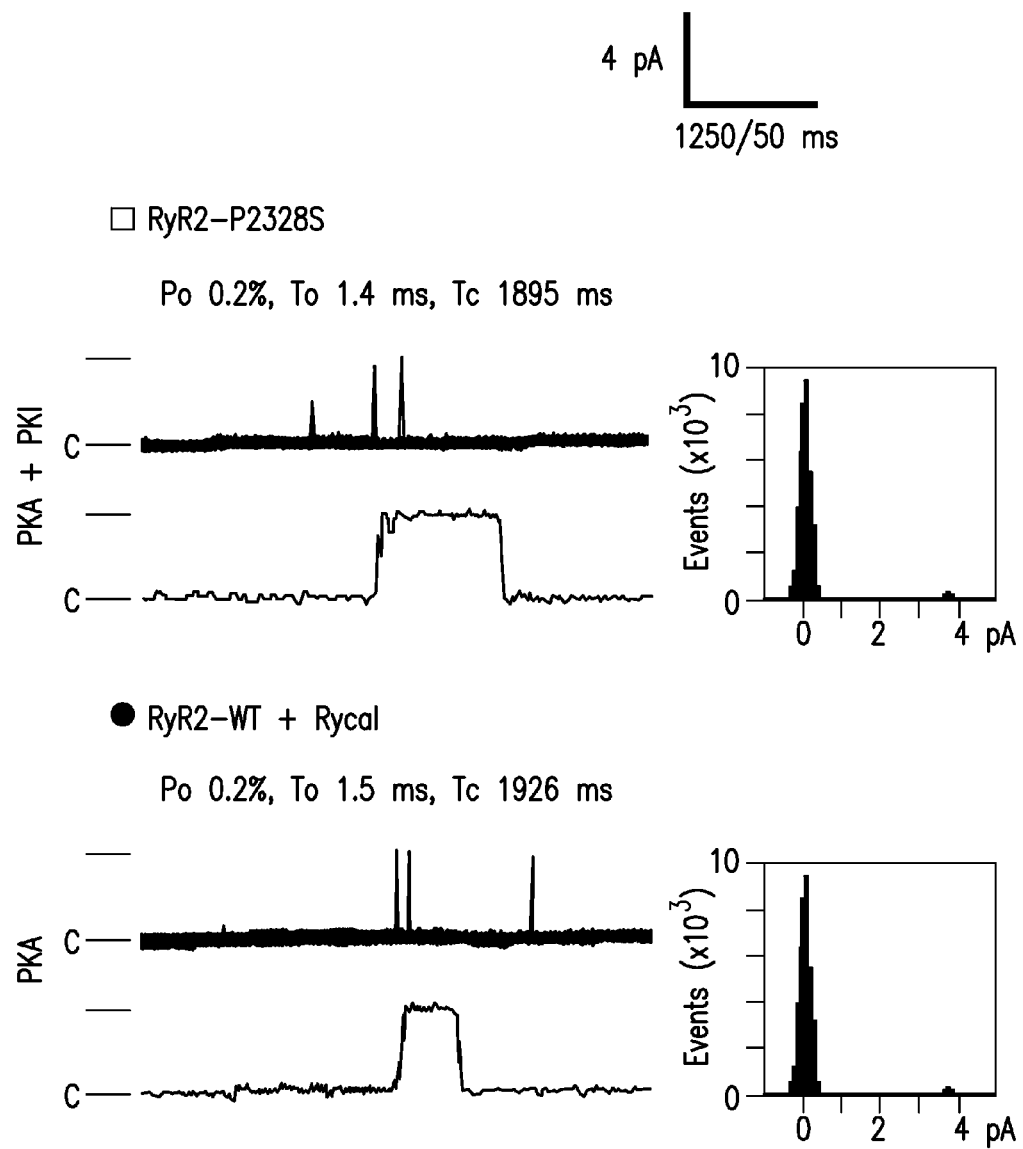
FIG. 6, embodiments A, B, and C are, respectively, (A) single-channel current traces of RyR2-P2328S and RyR2-WT; (B) single-channel current traces of RyR2-P2328S; and (C) immunoblot analysis of calstabin-2 binding of RyR2-P2328S.
Figure 6B:
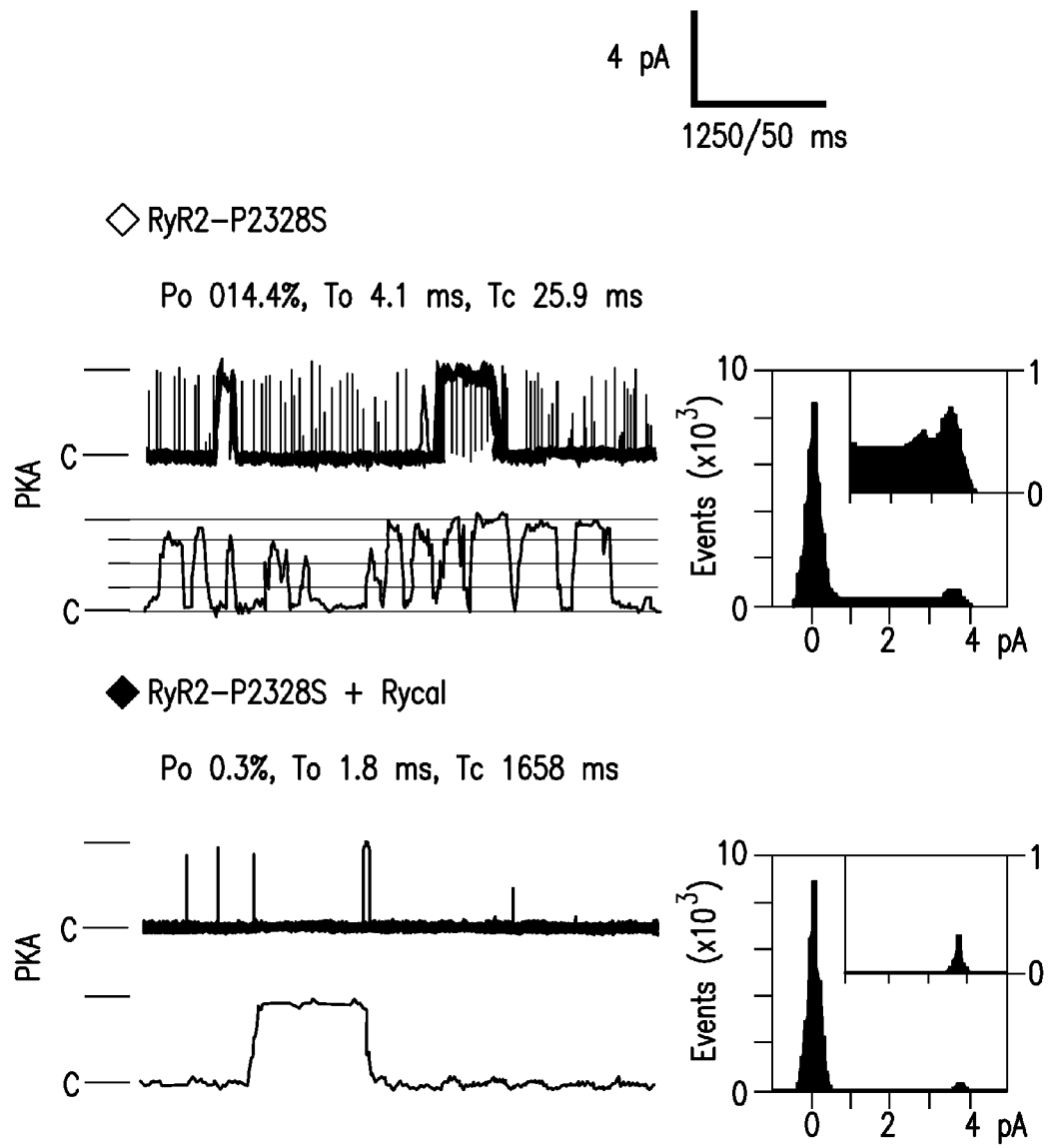
Figure 6C:
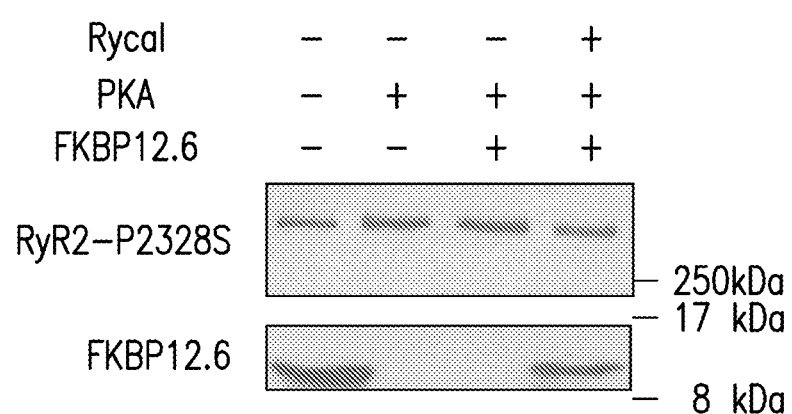

FIG. 6, embodiments A, B, and C, show CPVT-associated RyR2-P2328S channel function and structure. In embodiment A are shown representative single-channel current traces of RyR2-P2328S and RyR2-WT while embodiment B shows RyR2-P2328S. Embodiment C shows immunoblot analysis of calstabin-2 binding of RyR2-P2328S.

Figure 7A:
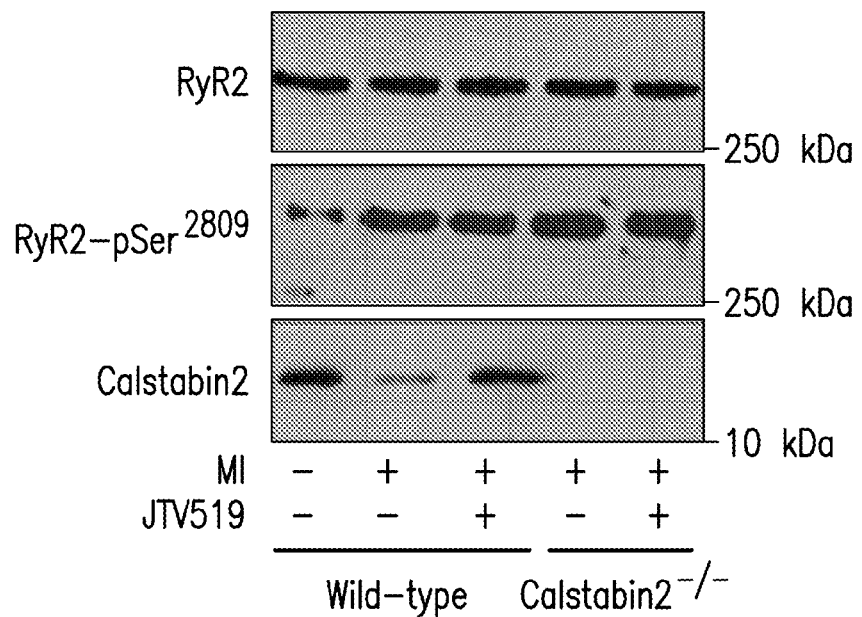
FIG. 7, embodiments A and B, are, respectively, (A) an immunoblot of RyR2 immunoprecipitated with an antibody against RyR2, and immunoblots of RyR2 PKA phosphorylation at Ser-2809 and calstabin2; and (B) a bar graph quantifying the relative amount of PKA phosphorylated RyR2 at Ser-2808 (corresponding to human Ser-2809) bound to RyR2 in wild-type (control) and calstabin2-deficient (FKBP12.6$^{-/-}$) mice.
Figure 7B:
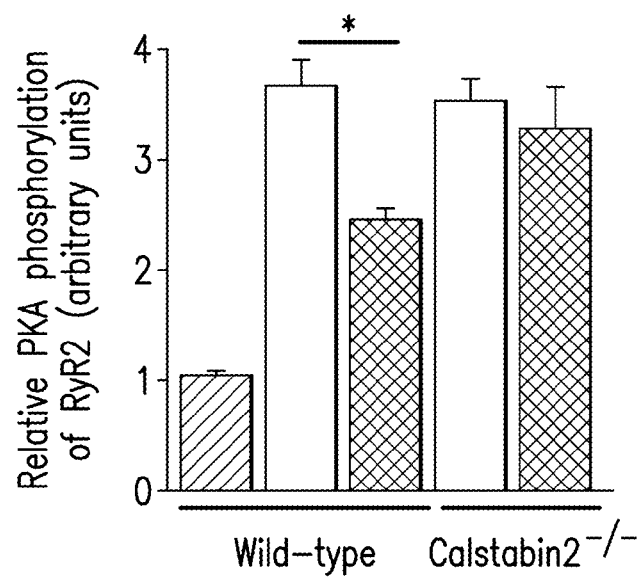

As demonstrated by FIG. 7, embodiments A and B, treatment with JTV-519 reduces PKA phosphorylation of RyR2 in mice with heart failure. Equivalent amounts of RyR2 are immunoprecipitated with an antibody against RyR2 (top blot). Representative immunoblots (embodiment A) and bar graphs (embodiment B) show the amount of PKA phosphorylated RyR2 at Ser-2808 bound to RyR2 in wild-type and calstabin2(FKBP12.6)−/− mice. Treatment with JTV-519 (0.5 mg/kg/h) for 28 days post-myocardial infarction reduces PKA-phosphorylation of RyR2, presumably due to reverse cardiac remodeling, in wildtype but not calstabin-2 (FKBP12.6)−/− mice.

Figure 8A:
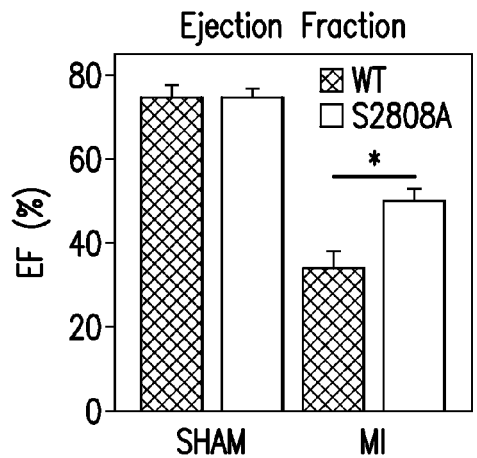
FIG. 8, embodiments A, B, and C, are, respectively, bar graphs of (A) quantitative in vivo M-mode echocardiograms comparing ejection fraction (EF) before and following sham operation or permanent left anterior descending (LAD) coronary artery ligation in wild-type and RyR2-S2808A knockin mice; (B) in vivo pressure-volume loop quantification of maximal pressure change over time (dP/dt) in wild-type and RyR2-S2808A knockin mice after sham operation or permanent left anterior descending coronary artery (LAD) ligation; and (C) quantitative M-mode echocardiographic assessment of end-systolic diameter (ESD) in wildtype and RyR2-S2808A knockin mice after sham operation or permanent left anterior descending coronary artery (LAD) ligation.
Figure 8B:
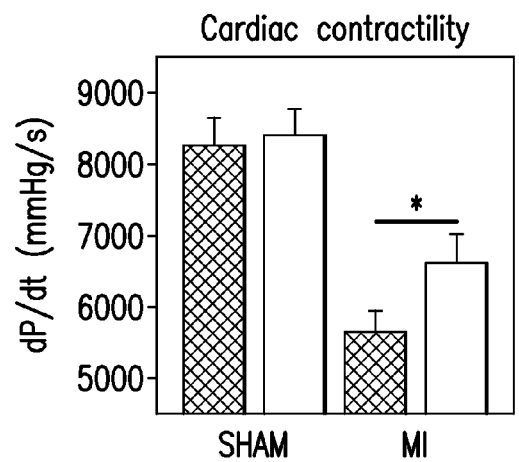
Figure 8C:
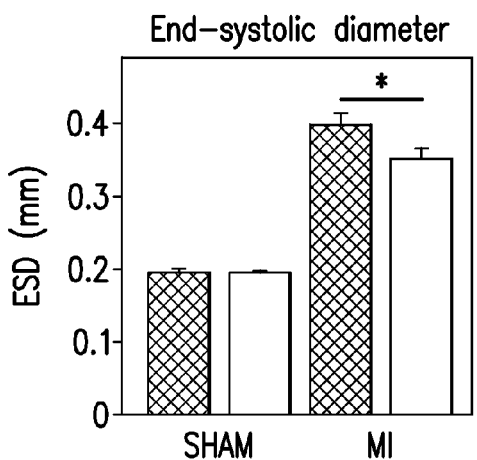

As demonstrated by FIG. 8, embodiments A and B, mice in which cardiac RyR2 cannot be PKA phosphorylated (RyR2-S2808A knockin mice) have improved cardiac function following myocardial infarction. Shown in embodiment A is the quantification of M-mode echocardiograms showing improved ejection fraction in RyR2-S2808A knockin mice compared with wildtype 28 days following permanent coronary artery ligation. Shown in embodiments B and C are pressure-volume loop quantifications showing (embodiment B) improved cardiac contractility and decreased cardiac dilation (embodiment C) in RyR2-S2808A knockin mice compared with wildtype following myocardial infarction.

Figure 9A:
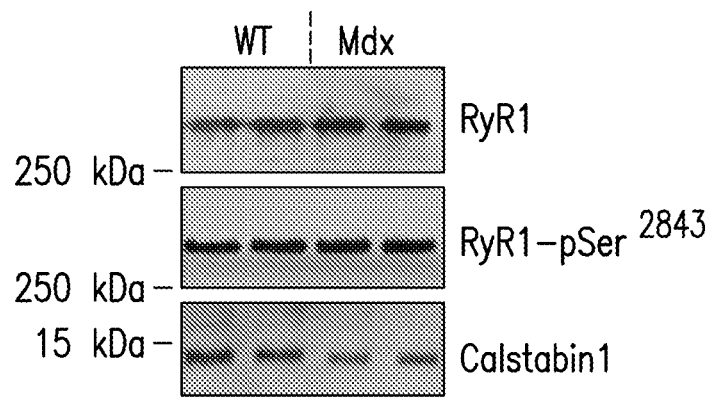
FIG. 9, embodiments A and B, are, respectively, immunoblots of RyR1, RyR1-pSer$^{2843}$, and RyR1-associated calstabin1 in mdx mice and wild-type mice; and bar graphs of the relative amounts of RyR1-pSer$^{2843}$ and calstabin1 in mdx and wild-type mice.
Figure 9B:
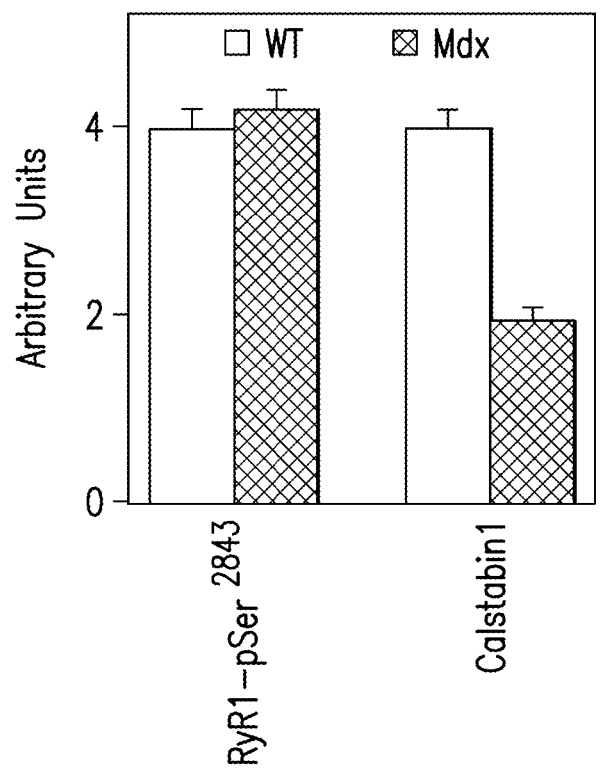

FIG. 9, embodiments A and B, demonstrate that mdx skeletal muscle has normal levels of RyR1 PKA phosphorylation, but depleted levels of calstabin1. The immunoblots in embodiment A show that mdx type mice have depleted levels of calstabin1 compared to a control (wild-type) mouse. The summary bar graphs of embodiment B show that the mdx mouse, nevertheless, has an equivalent level of PKA-phosphorylation. Therefore, it is concluded that calstabin1 depletion is a defect that is consistent with the intracellular $Ca^{2+}$ leak observed in skeletal muscle cells from mdx mice and myofibers from human mutation carriers. Intracellular SR Ca$^{2+}$ leak is likely to contribute to myofiber death and wasting of muscle mass by toxic intracellular Ca$^{2+}$ overload and activation of proteases.

Figure 10A:
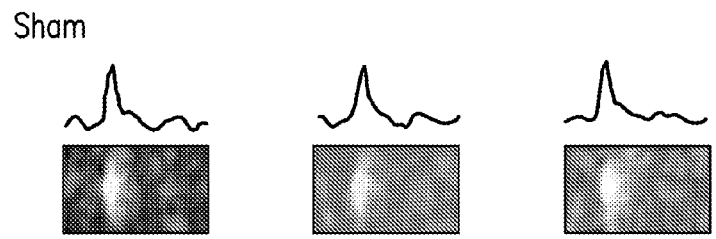
FIG. 10, embodiments A, B, and C, demonstrate that a SR $Ca^{2+}$ leak is detectable in the skeletal muscles of animals with heart failure. Embodiments A and B are fluorescence line scan images of $Ca^{2+}$ sparks in myofibers from, respectively, sham and postmyocardial infarction (PMI) rats. Embodiment C provides bar graphs summarizing the amplitude, rise time, FDHM, and FWHM of the $Ca^{2+}$ sparks for the sham (open symbols) and PMI (closed symbols) rats.
Figure 10B:
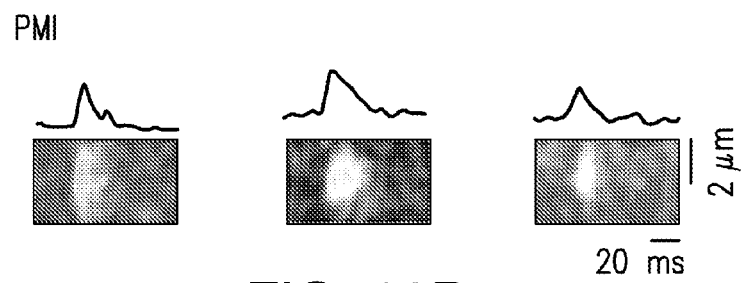
Figure 10C:
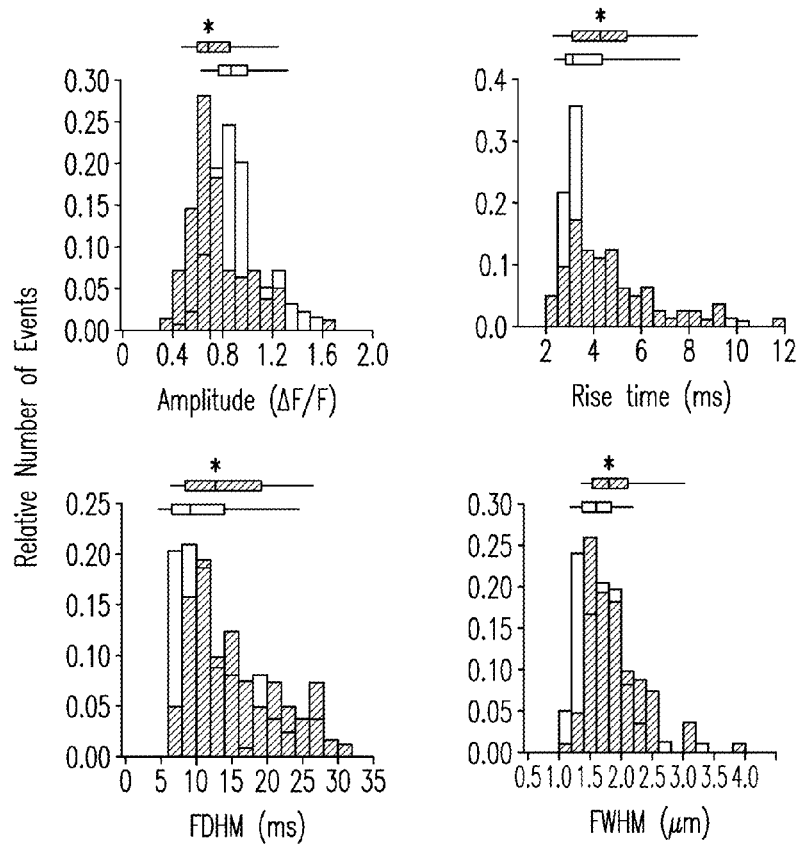
Figure 11A:
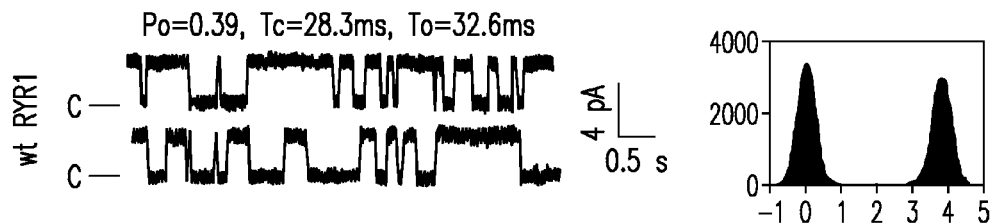
FIG. 11, embodiments A, B, C, and D, demonstrate that PKA phosphorylation of Ser-2843 increases the open probability and gating kinetics of RyR1 channels. Embodiment A provides single channel current traces and corresponding histogram of wild-type RyR1. Embodiment B provides single channel current traces and corresponding histogram of wild-type RyR1 that is PKA phosphorylated. Embodiment C provides single channel current traces and corresponding histogram of RyR1-Ser-2843A. Embodiment D provides single channel current traces and corresponding histogram of RyR1-Ser-2843D.
Figure 11B:
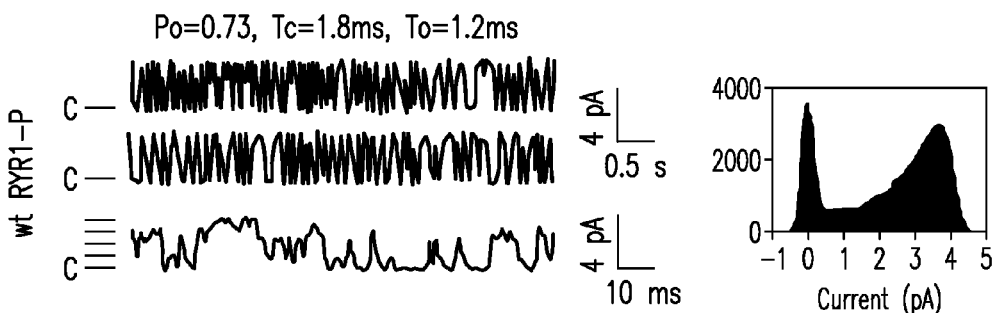
Figure 11C:
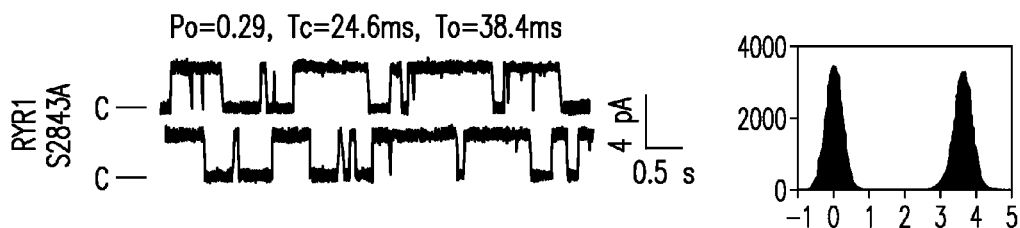
Figure 11D:
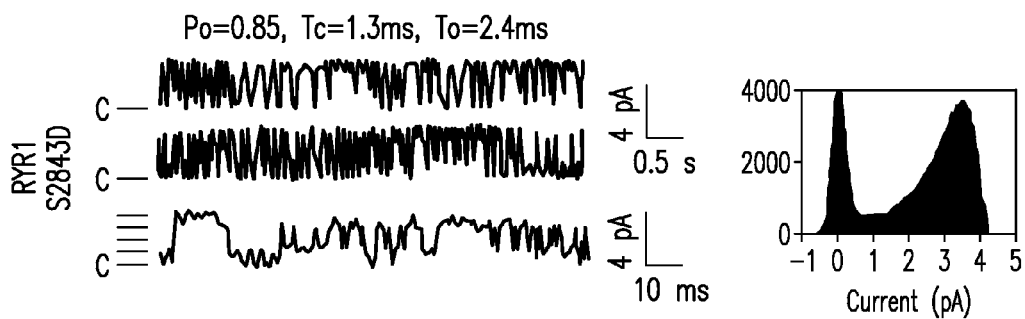

FIG. 10, embodiments A, B, and C, demonstrates that SR Ca$^{2+}$ leak at the subcellular level in skeletal muscles of animals with heart failure is detectable. Life quality and prognosis in heart failure (HF) patients is severely decreased due to skeletal muscle dysfunction (e.g., shortness of breath due to diaphragmatic weakness, and exercise intolerance due to limb skeletal muscle fatigue) in addition to depressed cardiac function. Dysregulation of intracellular SR Ca$^{2+}$ release is a pathogenic mechanism underlying skeletal muscle dysfunction in HF. HF in animals causes significantly accelerates intrinsic skeletal muscle fatigue.

Embodiments A and B of FIG. 10 are $\Delta$F/F fluorescence line scan images of representative examples of Ca$^{2+}$ sparks in myofibers from sham and postmyocardial infarction (PMI) rats and corresponding Ca$^{2+}$ spark time course. Embodiment C shows the relative distribution of the spatio-temporal properties of the Ca$^{2+}$ sparks. Charts indicate 25, 50, 75 percentiles, the horizontal lines indicate the range from 1-99% of the distribution. Sham, open symbols (n=137, three animals); postmyocardial infarction (PMI), gray symbols (n=82, two animals). *, P<0.05. FDHM, full duration at 50% peak amplitude; FWHM, full width at 50% peak amplitude.

FIG. 11, embodiment A, B, C, and D demonstrates that Ser-2843 is the unique PKA phosphorylation site in skeletal RyR1 channels. (A) Representative single channel traces of wild-type RyR1, (B) effect of exogenous PKA phosphorylation of RyR1 (wt RyR1-P), (C) PKA does not affect RyR1-S2843A that contains a non-functional PKA phosphorylation site. Since PKA does not increase RyR1-S2843A activity, Ser-2843 appears to constitute the unique PKA phosphorylation site in RyR1 channels in skeletal muscle. Accordingly, (D) constitutively phosphorylated RyR1-S2843D mimics exogenous PKA phosphorylation shown in (B) confirming that Ser-2843 is the unique PKA phosphorylation site in skeletal RyR1 channels. RyR1 single channel recordings in planar lipid bilayers show activity of the channels at 150 nM [Ca$^{2+}$]$_{cis}$ (cytosolic side) with 1 mM ATP. Recordings were at 0 mV, closed state of the channels as indicated by 'c', and channel openings are upward deflections. All point amplitude histograms are shown on the right. Open probability (P$_o$) and mean closed (Tc) and open (To) dwell times are indicated above each channel tracing.

Figure 12A:
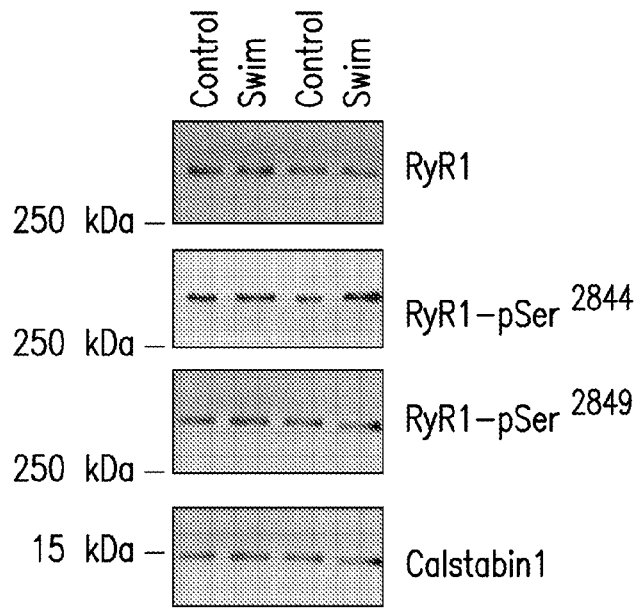
FIG. 12, embodiments A and B, demonstrate the PKA hyperphosphorylation and calstabin 1 deficiency of RyR1 channels after sustained exercise. Embodiment A are immunoblots of RyR1, RyR1-pSer$^{2844}$, RyR1-pSer$^{2849}$, and calstabin1 for control and swim mice following an exercise regime. Embodiment B is a bar graph summarizing the relative amounts of the indicated compounds following the exercise regime.
Figure 12B:
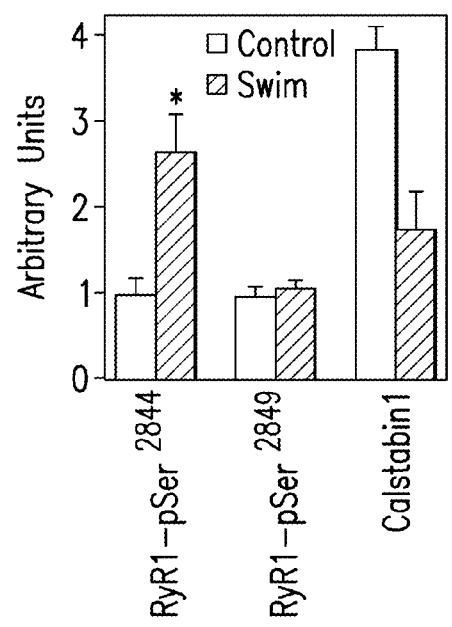

FIG. 12, embodiments A and B, demonstrates the depletion of stabilizing calstabin1 and PKA hyperphosphorylation of RyR1 channels from sustained exercise. Aerobic exercise can be defined as a form of physical exercise that increases the heart rate and enhances oxygen intake to improve performance. Examples of aerobic exercise are running, cycling, and swimming. During the study of FIG. 12, mice were challenged by aerobic exercise (forced swimming) for 90 mins twice daily. The animals were accustomed to swimming in preliminary training sessions: day –3 twice 30 mins, day –2 twice 45 mins, day –1 twice 60 mins, day 0 and following twice 90 mins. Mice were then exercised for 1, 7, or 21 additional, consecutive days for 90 mins twice daily. Between swimming sessions separated by a 4 hour rest period the mice are kept warm and given food and water. An adjustable-current water pool was used to exercise mice by swimming. An acrylic pool (90 cm long×45 cm wide×45 cm deep) filled with water to a depth of 25 cm was used. A current in the pool was generated with a pump. The current speed during the swimming session was at a constant speed of 1 l/min flow rate. The water temperature was maintained at 34° C. with an electric heater. Age- and weight-matched mice were used to exclude differences in buoyancy from body fat.

Using forced swimming as an efficient protocol to increase skeletal muscle aerobic capacity in mice, the composition and phosphorylation status of the skeletal RyR1 channel complex have been investigated. Unexpectedly, after 3 weeks of 90 mins swimming twice daily, C57B16 wild-type mice showed significantly increased RyR1 phosphorylation by PKA while Ca$^{2+}$-calmodulin kinase II (CaMKII) phosphorylation was not changed indicating specificity of the stress pathway RyR1 protein expression was stable, however, RyR1 channels were depleted of the stabilizing subunit calstabin1 (FKBP12). It has been shown that RyR1 hyperphosphorylation and calstabin1 depletion are consistent with leaky RyR1 channels that cause intracellular SR Ca$^{2+}$ leak.

RyR1 channels are PKA hyperphosphorylated and depleted of the stabilizing calstabin1 subunit after 3 weeks of 90 mins swimming twice daily. As seen in Embodiment A, the immunoprecipitated RyR1 macromolecular channel complex shows increased PKA phosphorylation at Ser-2844 (corresponding to human RyR1-Ser-2843) whereas CaMKII phosphorylation at Ser-2849 (corresponding to human RyR1-Ser-2848) is unchanged. Concomitant with increased RyR1-Ser-2844 PKA hyperphosphorylation, calstabin1 is depleted from the channel complex. As seen in embodiment B, normalization of phosphorylation and calstabin1 content to four subunits of the tetrameric channel complex shows a significant in increase in PKA phosphorylation and depletion of the stabilizing calstabin1 subunit. Control, non-exercised mice; swim, mice exercised 90 mins twice daily for 3 weeks (preliminary data). P<0.05.

Figure 13A:
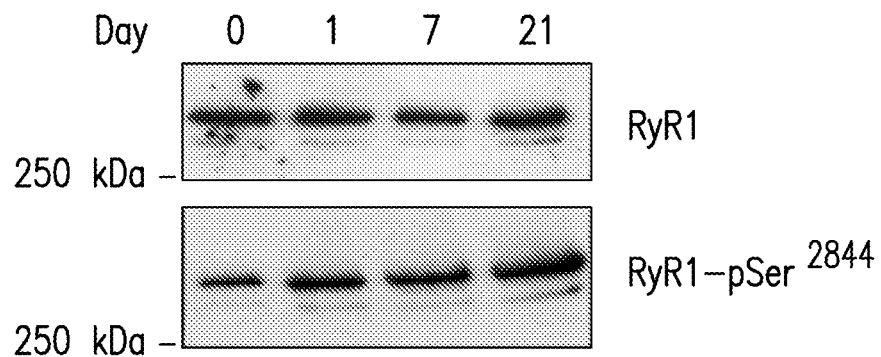
FIG. 13, embodiments A and B, demonstrate that RyR1 PKA phosphorylation increases after exposure to increasing durations of sustained exercise. Embodiment A provides immunoblots of RyR1 and RyR1-pSer$^{2844}$ following increasing durations of sustained exercise. Embodiment B is a graph showing the relative PKA phosphorylation of RyR1 for varying durations of exercise.
Figure 13B:
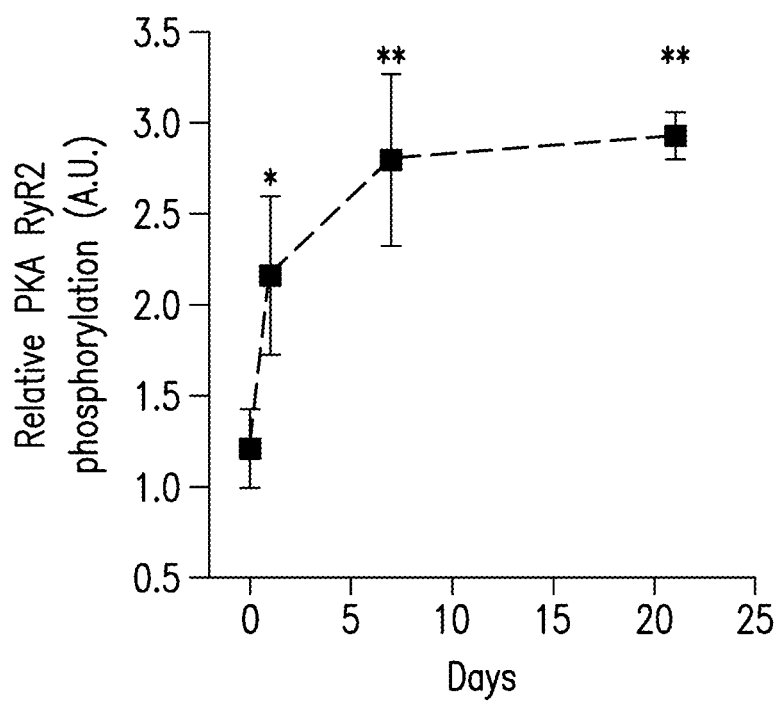

FIG. 13, embodiments A and B, demonstrate that PKA phosphorylation increases for increasing durations of sustained exercise. To investigate the influence of the duration of sustained exercise on the RyR1 Ca$^{2+}$ release channel defect, mice were exposed to swimming for 1, 7, or 21 days followed by immediate sacrifice. Longer exposure to sustained exercise results in a significant increase of RyR1 PKA hyperphosphorylation beginning at 7 days and saturating at 21 days.

In FIG. 13, embodiment A, the immunoprecipitated RyR1 channel complex shows significantly and above physiologic levels increased PKA phosphorylation at Ser-2844 (corresponding to human RyR1-Ser-2843) after 7 days of swimming exercise. In FIG. 13, embodiment B, normalization of RyR2-Ser-2844 phosphorylation within the tetrameric channel complex documents a significant increase in PKA phosphorylation. *, P<0.05; **, P<0.005.

In summary, the data of FIG. 13 shows that sustained exercise results in significantly increased RyR1 phosphorylation by protein kinase A (PKA) which contributes to depletion of the stabilizing calstabin1 subunit from the channel complex as the cause of a gain-of-function defect.

Figure 14A:
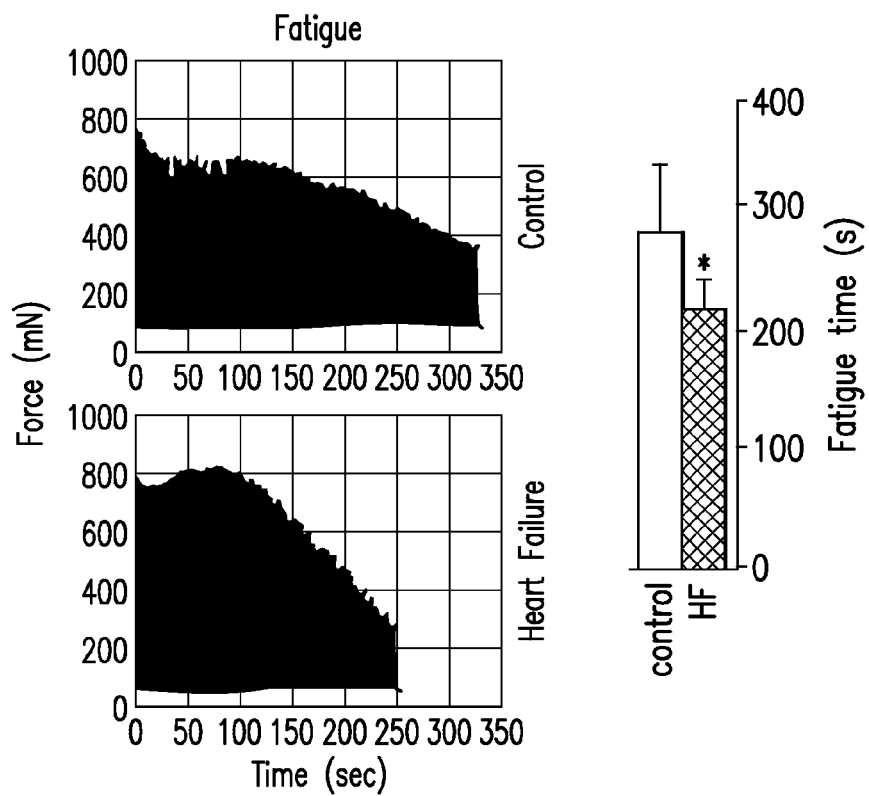
FIG. 14, embodiments A, B, and C, demonstrate that RyR1 PKA phosphorylation increases with muscle fatigue. Embodiments A and B are, respectively, fatigue time tracings and a bar graph showing mean fatigue times for rat soleus muscle of heart failure and control subjects. Embodiment C is a graph of PKA phosphorylation versus fatigue time.
Figure 14B:
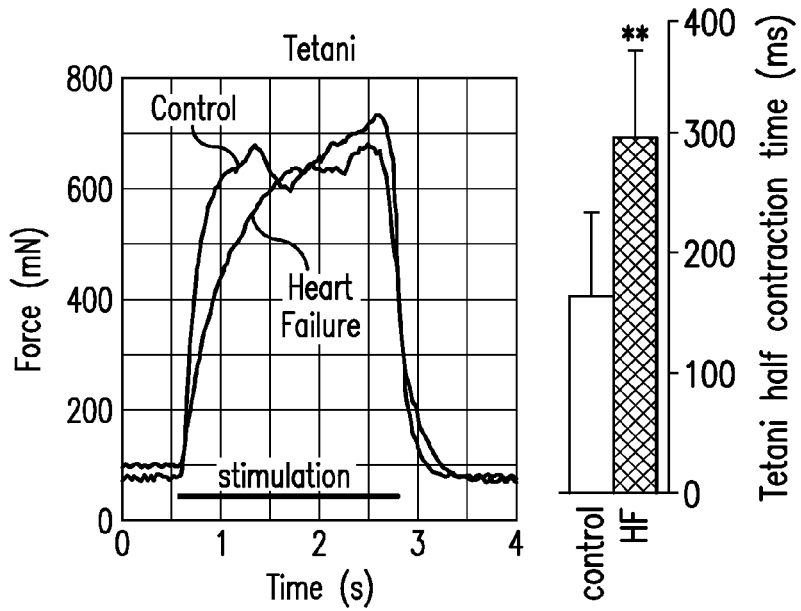
Figure 14C:
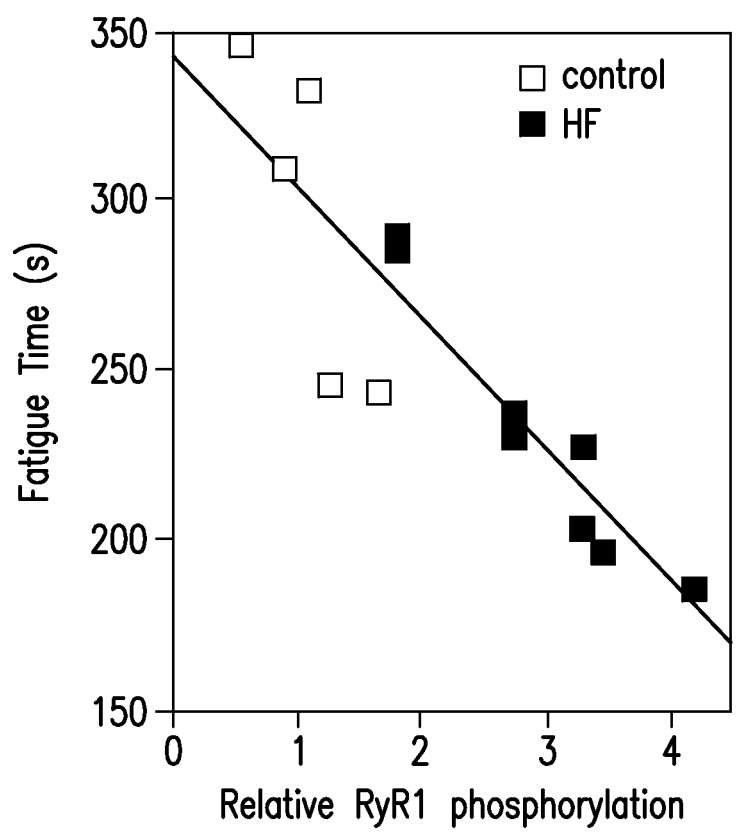

FIG. 14 provides data showing that showing that chronically increased sympathetic stimulation of skeletal muscles, results in RyR1-dependent intracellular Ca$^{2+}$ leak and significantly increased muscle fatigue. As shown in FIG. 14 for mice and rats with heart failure from myocardial infarction, chronic RyR1 PKA hyperphosphorylation results in increased muscle fatigue.

In embodiment A, it can be seen that heart failure skeletal muscle fatigues earlier than control. Rat soleus muscle (n=5 control, n=8 HF) was mounted in a tissue bath to assess contractile function. Representative fatigue time tracing is shown for control and HF skeletal muscles. Bar graph shows mean (±S.D.) time to 40% fatigue. *, P<0.05. In embodiment B, it can be seen that heart failure skeletal muscle achieved maximal tetanic force more slowly than control skeletal muscles. Tetanic force was induced by high-frequency field stimulation. Bar graph shows tetanic 50% contraction time. **, P<0.01. Embodiment C demonstrates the correlation between time to fatigue and RyR1 PKA phosphorylation (r=0.88) in rat skeletal muscle from sham and heart failure animals. Muscle function and RyR1 PKA phosphorylation were assessed using contralateral soleus muscles from each animal.

In summary, FIG. 14 provides data showing that sustained exercise causes RyR1 PKA hyperphosphorylation and calstabin1 depletion, and FIG. 14 shows that the identical defect occurs in disease forms with increased sympathetic activity causing intracellular SR $Ca^{2+}$ leak and significantly accelerated skeletal muscle fatigue.

Figure 15:
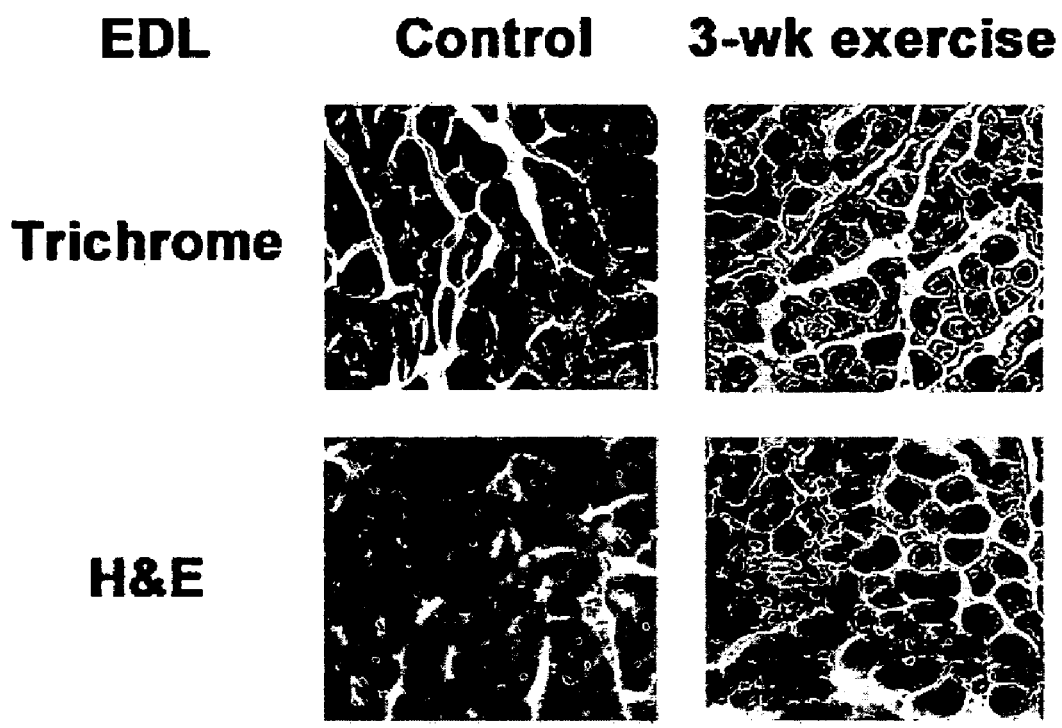
FIG. 15 are trichrome and hematoxylin-eosin stains of cross-sections of the mouse M. extensor digitorum longus, and demonstrates myofiber degeneration consistent with dystrophic remodeling following sustained exercise.

An additional problem during sustained exercise and stress is skeletal muscle degeneration further contributing to decreased skeletal muscle performance. To assess structural changes during sustained exercise, histologic changes in the fast-twitch muscles of mice exposed to 3 weeks of exercise by swimming have been characterized. Results are shown in FIG. 15. Cross-sections of the mouse M. extensor digitorum longus (EDL) showed histologic changes consistent with myofiber degeneration from intracellular $Ca^{2+}$ overload from defective RyR1 channels. Therefore sustained exercise for 90 mins twice daily triggers a dystrophic phenotype in EDL muscles of normal C57Bl6 mice.

Trichrome stain shows packed myofibers of similar cross-sectional dimension in non-exercised control (WT) mice (left). Three weeks swimming results in myofiber degeneration and interstitial collagen deposits with irregular fiber sizes. Hematoxylin-eosin (H&E) stain indicates nuclear changes and myofiber death. These changes are consistent with dystrophic remodeling.

The rapid delayed rectifier potassium channel (I(Kr)) is important for repolarization of the cardiac action potential. HERG is the pore-forming subunit of the I(Kr) channel. Suppression of I(Kr) function, for example as a side-effect of a drug or the result of a mutation in hERG, can lead to long-QT (LQT) syndrome, which is associated with increased risk of life-threatening arrhythmias. The compounds of the present invention exhibit a lower level of hERG blocking activity than JTV-519, as demonstrated in FIGS. 16-35. Thus, the compounds of the present invention are expected to be less toxic and/or exhibit fewer side effects than JTV-519.

FIGS. 16 to 19 illustrate the effect of the compound ARM036 (also referred to as S36) and ARM036-Na (a sodium salt of ARM036) on hERG currents.

Figure 16:
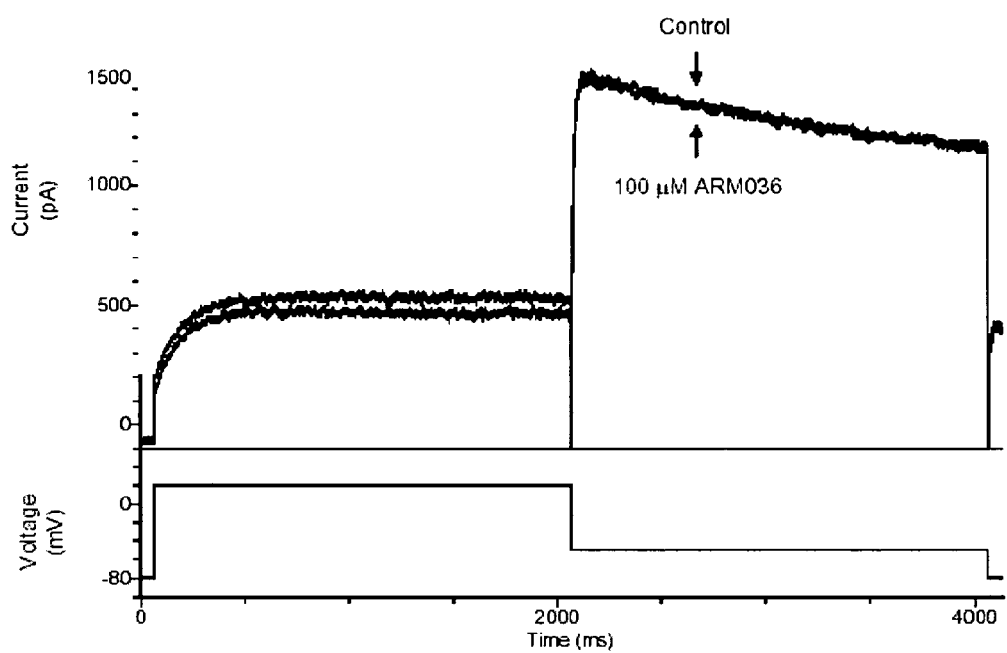
FIG. 16 shows a sample hERG current trace before (control) and after application of ARM036 at 100 μM. Also shown is the voltage pulse protocol used to evoke the hERG currents.

FIG. 16 shows a typical hERG voltage-clamp current recording before (control) and after application of ARM036 at 100 µM. The voltage pulse protocol used to activate the hERG currents is illustrated below the current trace. It can be seen that, following activation by the conditioning prepulse (to +20 mV), partial repolarization (−50 mV test pulse) of the membrane evoked a large, slowly decaying outward tail current. Application of ARM036 minimally reduced the outward tail current in a concentration- and time-dependent manner.

Figure 17:
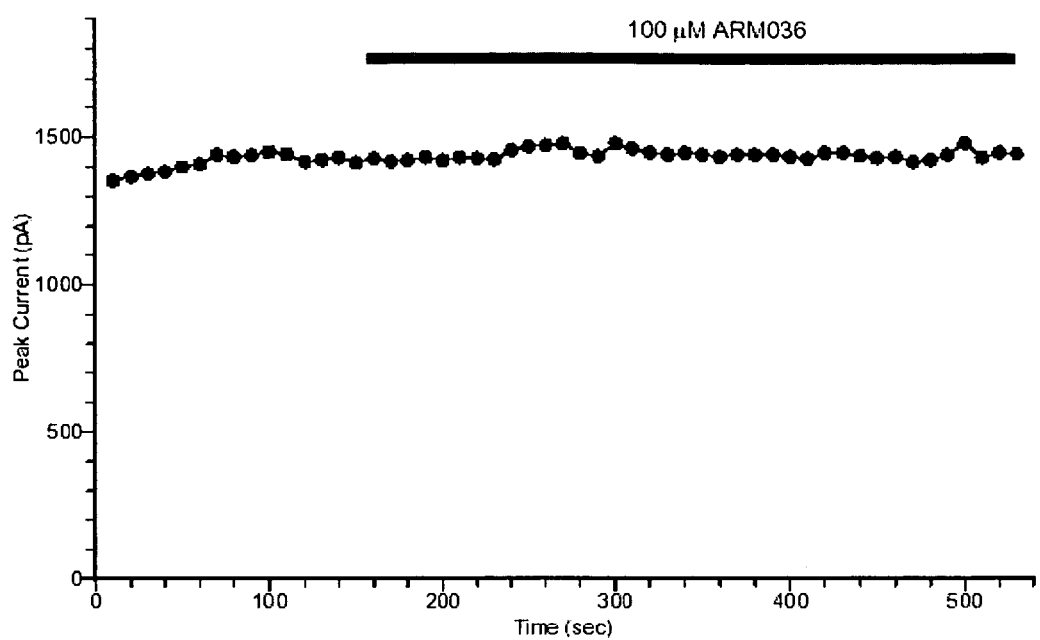
FIG. 17 shows a typical time course of the effect of ARM036 on hERG current amplitude. Application of 10 μM ARM036 is indicated by the horizontal bar.

FIG. 17 shows a typical time course of the effect of ARM036 at 100 mM on the amplitude of the hERG channel current.

Figure 18:
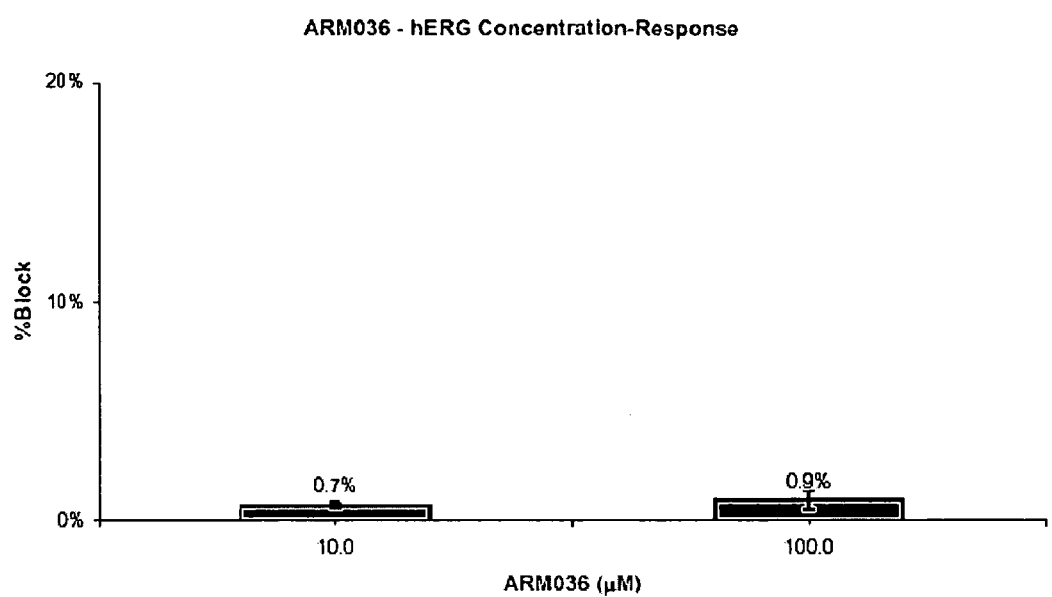
FIGS. 18 to 34 are concentration-response graphs showing the percent inhibition of hERG current after application of various concentrations of ARM036, ARM036-Na, ARM047, ARM048, ARM050, ARM057, ARM064, ARM074, ARM075, ARM076, ARM077, ARM101, ARM102, ARM103, ARM104, ARM106 and ARM107, respectively.

FIG. 18 is a graph showing the concentration-dependence of the effect of ARM036 on the hERG current. Table 1 provides the numerical data that is illustrated graphically in FIG. 18. Because the highest concentration of ARM036 tested resulted in less than 50% current inhibition, it was not possible to determine an $IC_{50}$ value for ARM036.

TABLE 1

| Concentration (µM) | Mean | SD | SEM | N |
|---|---|---|---|---|
| 10 | 0.7% | 0.3% | 0.2% | 3 |
| 100 | 0.9% | 0.7% | 0.4% | 3 |

Figure 19:
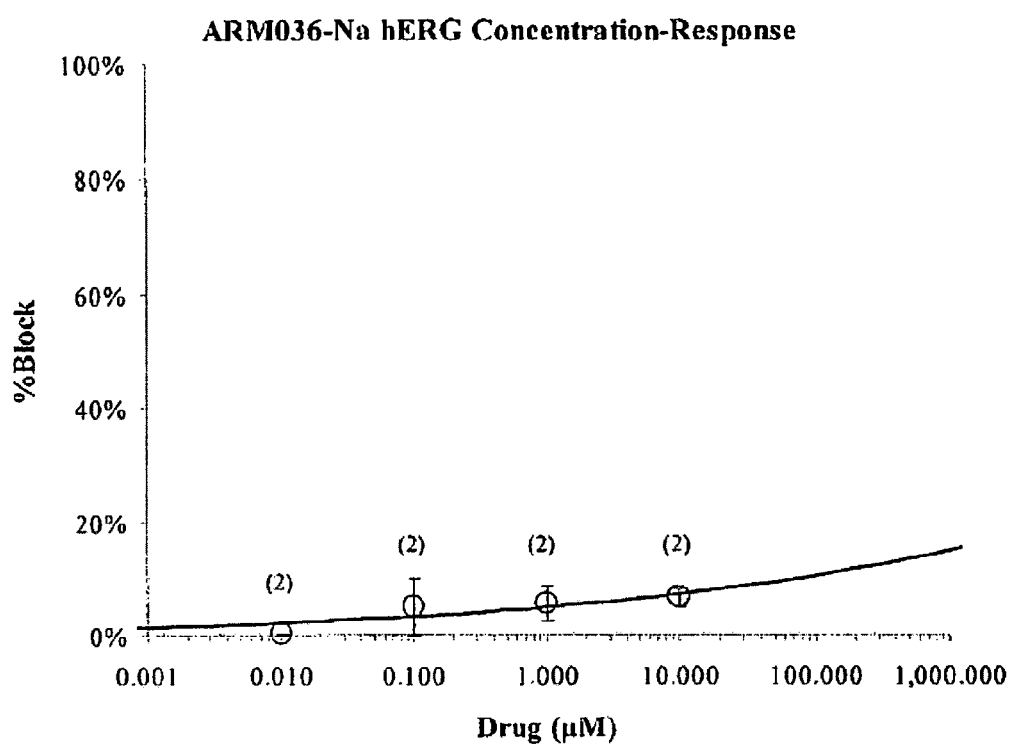

FIG. 19 is a graph showing the concentration-dependence of the effect of ARM036-Na on the hERG current. Table 2 provides the numerical data that is illustrated graphically in FIG. 18. Because the highest concentration of ARM036-Na tested resulted in less than 50% current inhibition, it was not possible to determine an $IC_{50}$ value for ARM036-NA.

TABLE 2

| Test Article ID | $IC_{50}$ (µM) | Conc. (µM) | Mean % hERG Inhibition | % Standard Deviation | % Standard Error | n | Individual Data (% Inhibition) |
|---|---|---|---|---|---|---|---|
| ARM036-Na | ND | 0.01 | 0.2% | 0.2% | 0.2% | 2 | 0.0% 0.3% |
|  |  | 0.1 | 5.0% | 7.1% | 5.0% | 2 | 10.0% 0.0% |
|  |  | 1 | 5.5% | 4.4% | 3.1% | 2 | 2.4% 8.6% |
|  |  | 10 | 6.7% | 2.2% | 1.6% | 2 | 5.1% 8.2% |

Figure 20:
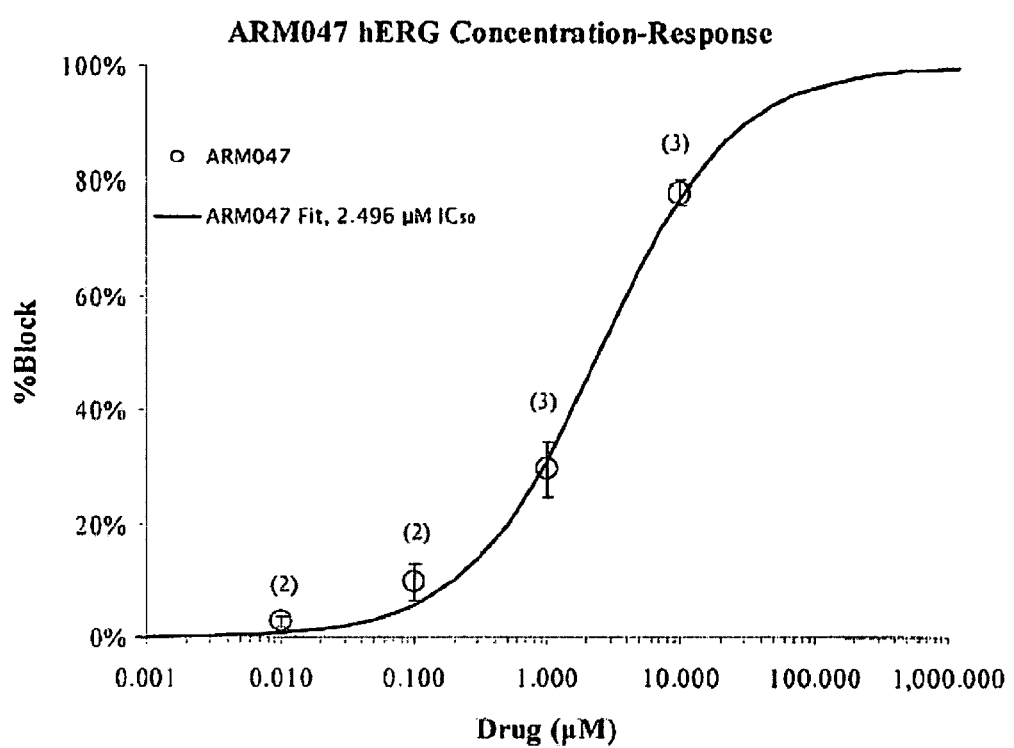

FIG. 20 is a graph showing the concentration-dependence of the effect of ARM047 on the hERG current. Table 3 provides the numerical data that is illustrated graphically in FIG. 20. The $IC_{50}$ value for ARM047 block of the hERG current was 2.496 µM.

TABLE 3

| Test Article ID | $IC_{50}$ (µM) | Conc. (µM) | Mean % hERG Inhibition | % Standard Deviation | % Standard Error | n | Individual Data (% Inhibition) |
|---|---|---|---|---|---|---|---|
| ARM047 | 2.496 | 0.01 | 2.7% | 1.4% | 1.0% | 2 | 1.7% 3.7% |

TABLE 3-continued

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| | | 0.1 | 9.7% | 4.5% | 3.2% | 2 | 6.5% |
| | | | | | | | 12.9% |
| | | 1 | 29.6% | 8.6% | 5.0% | 3 | 30.8% |
| | | | | | | | 20.4% |
| | | | | | | | 37.5% |
| | | 10 | 78.0% | 3.6% | 2.1% | 3 | 82.1% |
| | | | | | | | 75.9% |
| | | | | | | | 75.9% |

Figure 21:
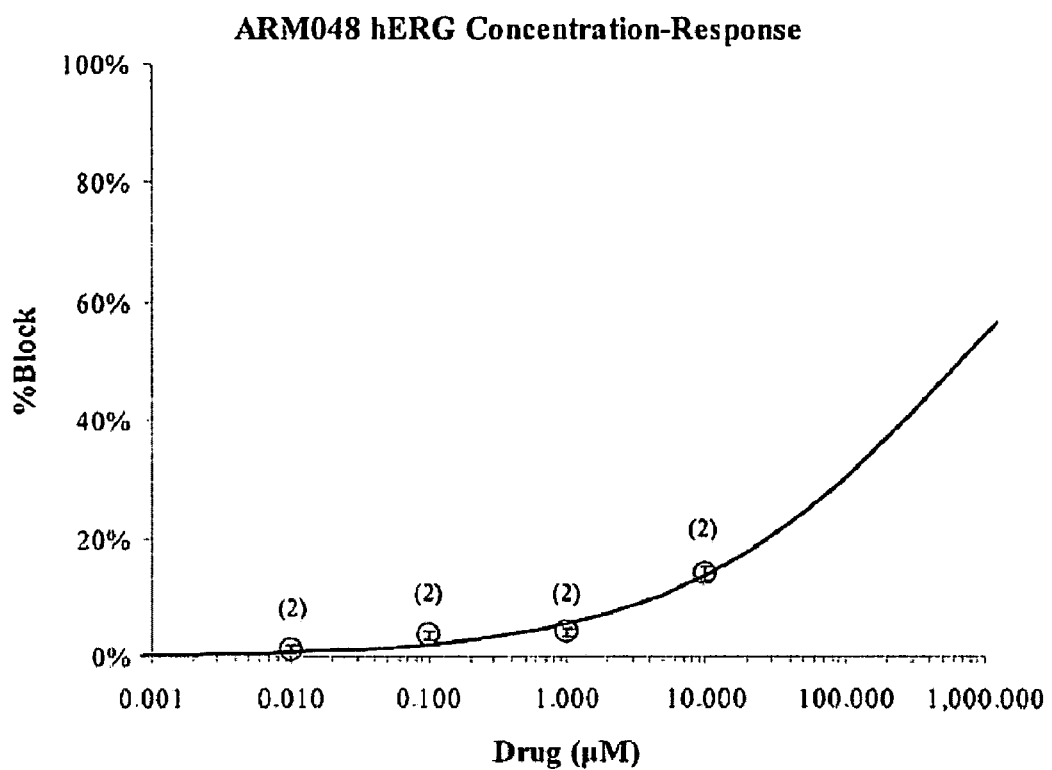

FIG. 21 is a graph showing the concentration-dependence of the effect of ARM048 on the hERG current. Table 4 provides the numerical data that is illustrated graphically in FIG. 21. Because the highest concentration of ARM048 tested resulted in less than 50% current inhibition, it was not possible to determine an IC$_{50}$ value for ARM048.

TABLE 4

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM048 | ND | 0.01 | 1.3% | 1.1% | 0.8% | 2 | 0.5% |
| | | | | | | | 2.0% |
| | | 0.1 | 3.6% | 0.9% | 0.6% | 2 | 4.2% |
| | | | | | | | 2.9% |
| | | 1 | 4.1% | 0.8% | 0.6% | 2 | 4.7% |
| | | | | | | | 3.5% |
| | | 10 | 14.0% | 1.7% | 1.2% | 2 | 15.2% |
| | | | | | | | 12.8% |

Figure 22:
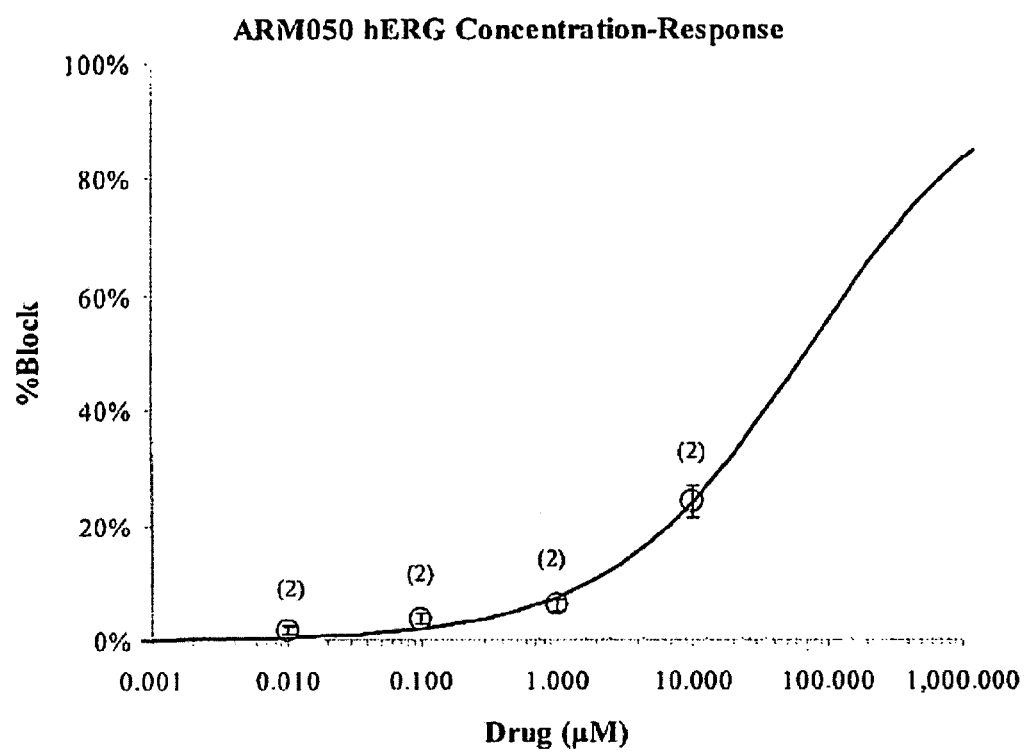

FIG. 22 is a graph showing the concentration-dependence of the effect of ARM050 on the hERG current. Table 5 provides the numerical data that is illustrated graphically in FIG. 22. Because the highest concentration of ARM050 tested resulted in less than 50% current inhibition, it was not possible to determine an IC$_{50}$ value for ARM050.

TABLE 5

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM050 | ND | 0.01 | 1.8% | 0.9% | 0.7% | 2 | 1.1% |
| | | | | | | | 2.4% |
| | | 0.1 | 3.7% | 1.4% | 1.0% | 2 | 2.7% |
| | | | | | | | 4.7% |
| | | 1 | 6.1% | 1.4% | 1.0% | 2 | 7.1% |
| | | | | | | | 5.1% |
| | | 10 | 24.2% | 4.0% | 2.9% | 2 | 27.0% |
| | | | | | | | 21.3% |

Figure 23:
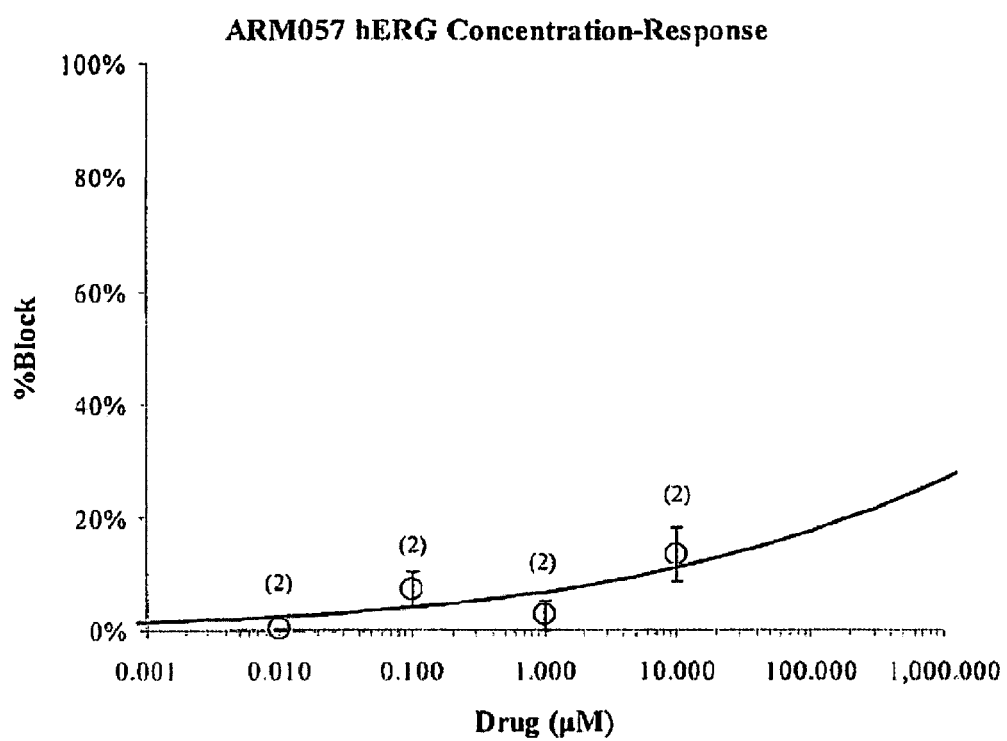

FIG. 23 is a graph showing the concentration-dependence of the effect of ARM057 on the hERG current. Table 6 provides the numerical data that is illustrated graphically in FIG. 23. Because the highest concentration of ARM057 tested resulted in less than 50% current inhibition, it was not possible to determine an IC$_{50}$ value for ARM057.

TABLE 6

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM057* | ND | 0.01 | 0.2% | 0.2% | 0.2% | 2 | 0.3% 0.0% |
|  |  | 0.1 | 7.3% | 4.5% | 3.2% | 2 | 4.1% 10.4% |
|  |  | 1 | 2.7% | 3.7% | 2.6% | 2 | 5.3% 0.1% |
|  |  | 10 | 13.6% | 6.7% | 4.8% | 2 | 18.3% 8.8% |

Figure 24:
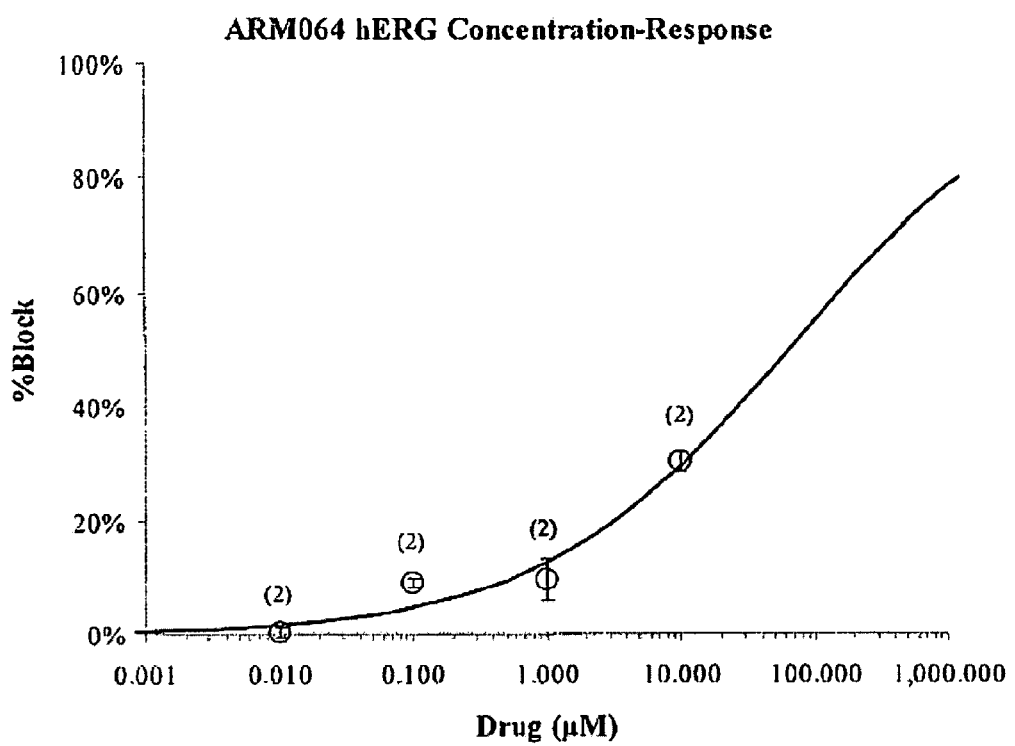

FIG. 24 is a graph showing the concentration-dependence of the effect of ARM064 on the hERG current. Table 7 provides the numerical data that is illustrated graphically in FIG. 24. Because the highest concentration of ARM064 tested resulted in less than 50% current inhibition, it was not possible to determine an IC$_{50}$ value for ARM064.

TABLE 7

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM064 | ND | 0.01 | 0.2% | 1.1% | 0.8% | 2 | −0.6% 1.0% |
|  |  | 0.1 | 9.0% | 1.3% | 0.9% | 2 | 9.9% 8.1% |
|  |  | 1 | 9.6% | 5.1% | 3.6% | 2 | 13.2% 6.0% |
|  |  | 10 | 30.3% | 2.5% | 1.7% | 2 | 32.0% 28.5% |

Figure 25:
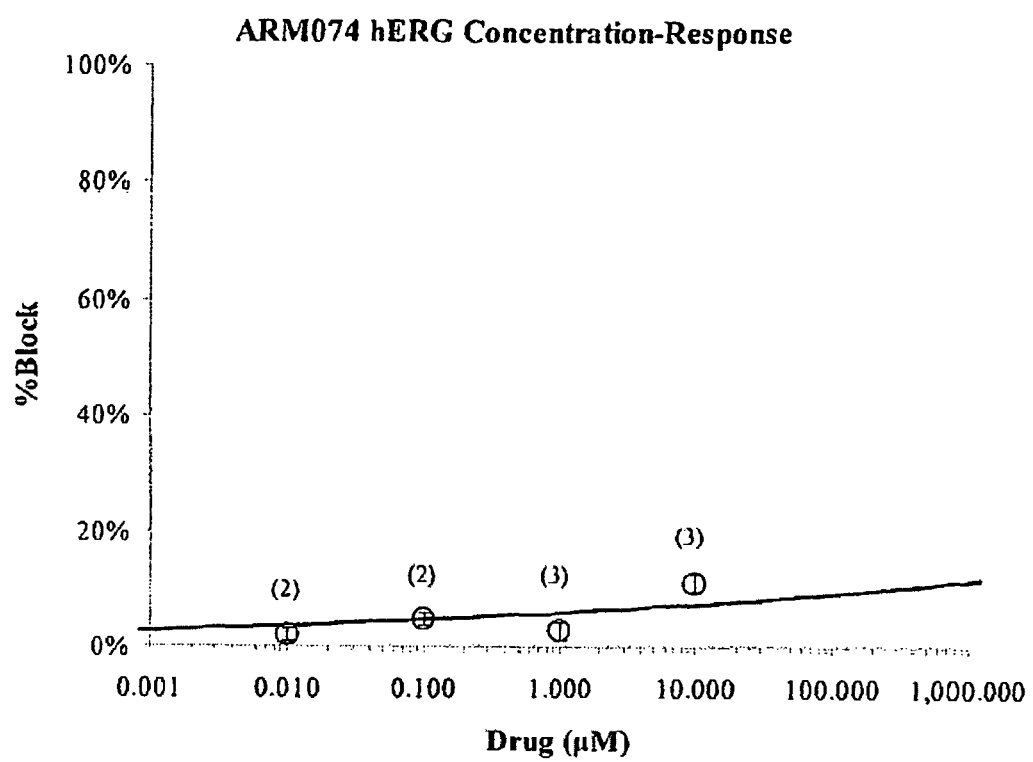

FIG. 25 is a graph showing the concentration-dependence of the effect of ARM074 on the hERG current. Table 8 provides the numerical data that is illustrated graphically in FIG. 25. Because the highest concentration of ARM050 tested resulted in less than 50% current inhibition, it was not possible to determine an IC$_{50}$ value for ARM074.

TABLE 8

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM074 | ND | 0.01 | 1.9% | 1.6% | 1.1% | 2 | 0.8% 3.0% |
|  |  | 0.1 | 4.8% | 1.6% | 1.1% | 2 | 5.9% 3.7% |
|  |  | 1 | 1.3% | 1.6% | 1.1% | 2 | 0.2% 2.4% 5.6% |
|  |  | 10 | 9.5% | 0.2% | 0.2% | 2 | 9.3% 9.6% 14.0% |

Figure 26:
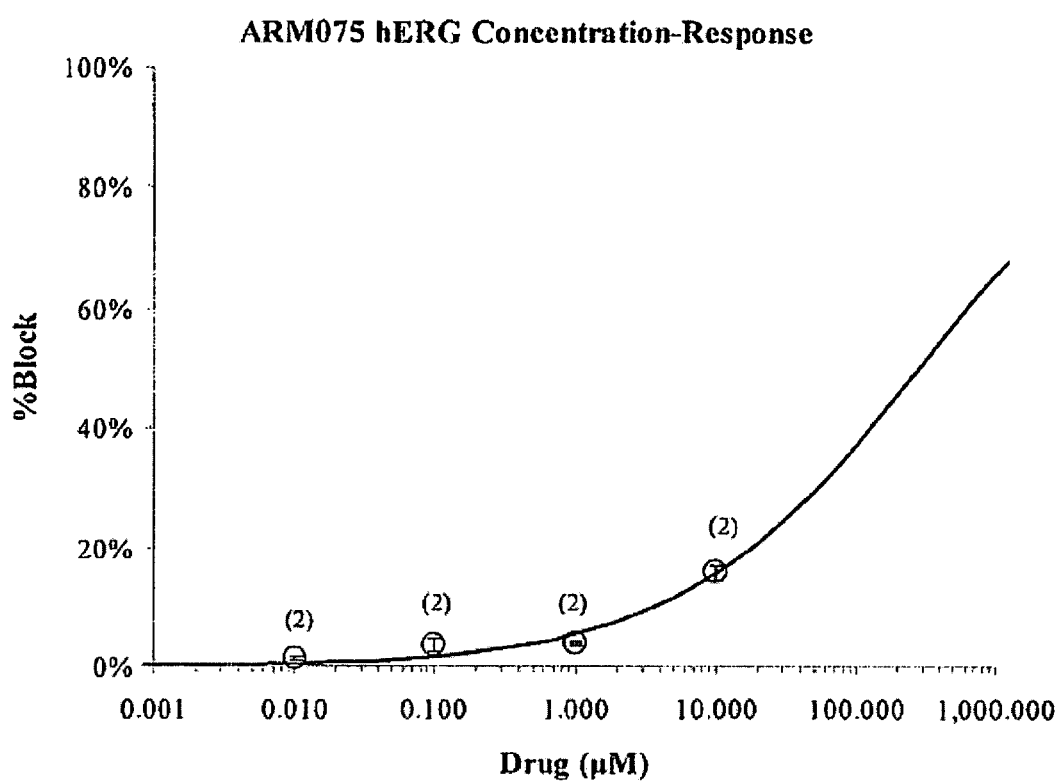

FIG. 26 is a graph showing the concentration-dependence of the effect of ARM075 on the hERG current. Table 9 provides the numerical data that is illustrated graphically in FIG. 26. Because the highest concentration of ARM075 tested resulted in less than 50% current inhibition, it was not possible to determine an IC$_{50}$ value for ARM075.

TABLE 9

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM075 | ND | 0.01 | 1.4% | 0.4% | 0.3% | 2 | 1.7% 1.1% |
| | | 0.1 | 3.7% | 1.6% | 1.1% | 2 | 2.6% 4.8% |
| | | 1 | 3.9% | 0.3% | 0.2% | 2 | 3.7% 4.1% |
| | | 10 | 16.0% | 1.8% | 1.3% | 2 | 14.7% 17.2% |

Figure 27:
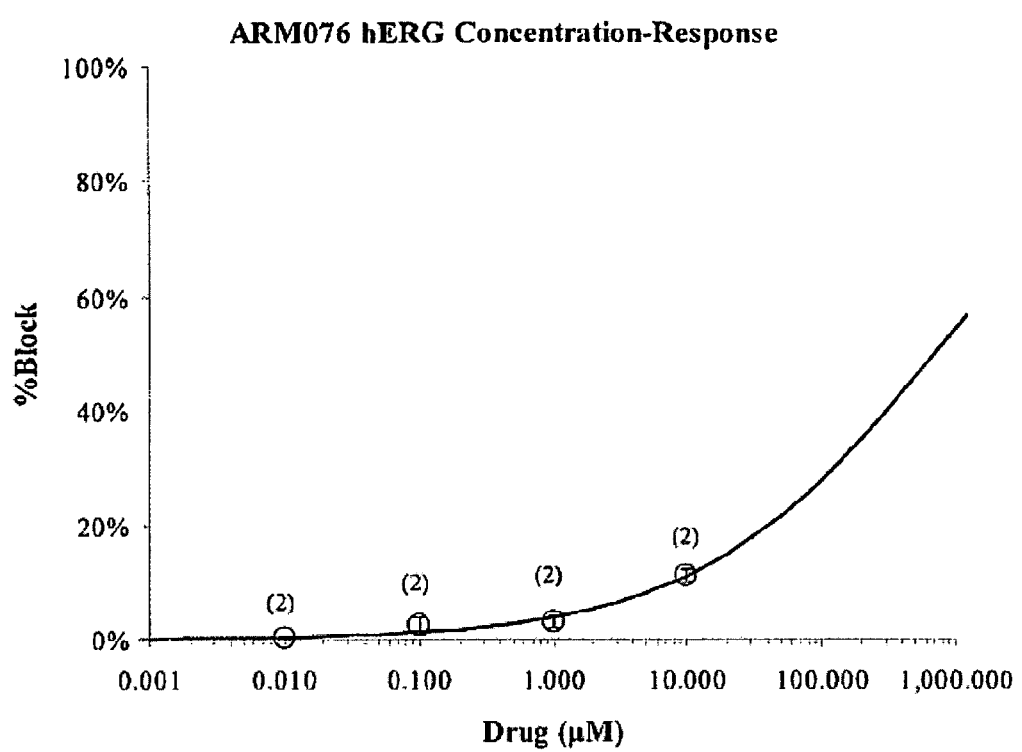

FIG. 27 is a graph showing the concentration-dependence of the effect of ARM076 on the hERG current. Table 10 provides the numerical data that is illustrated graphically in FIG. 27. Because the highest concentration of ARM076 tested resulted in less than 50% current inhibition, it was not possible to determine an IC$_{50}$ value for ARM076.

TABLE 10

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM076 | ND | 0.01 | 0.4% | 0.5% | 0.4% | 2 | 0.0% 0.7% |
| | | 0.1 | 2.5% | 2.2% | 1.6% | 2 | 4.0% 0.9% |
| | | 1 | 3.1% | 1.5% | 1.1% | 2 | 2.0% 4.1% |
| | | 10 | 11.2% | 1.6% | 1.2% | 2 | 10.0% 12.3% |

Figure 28:
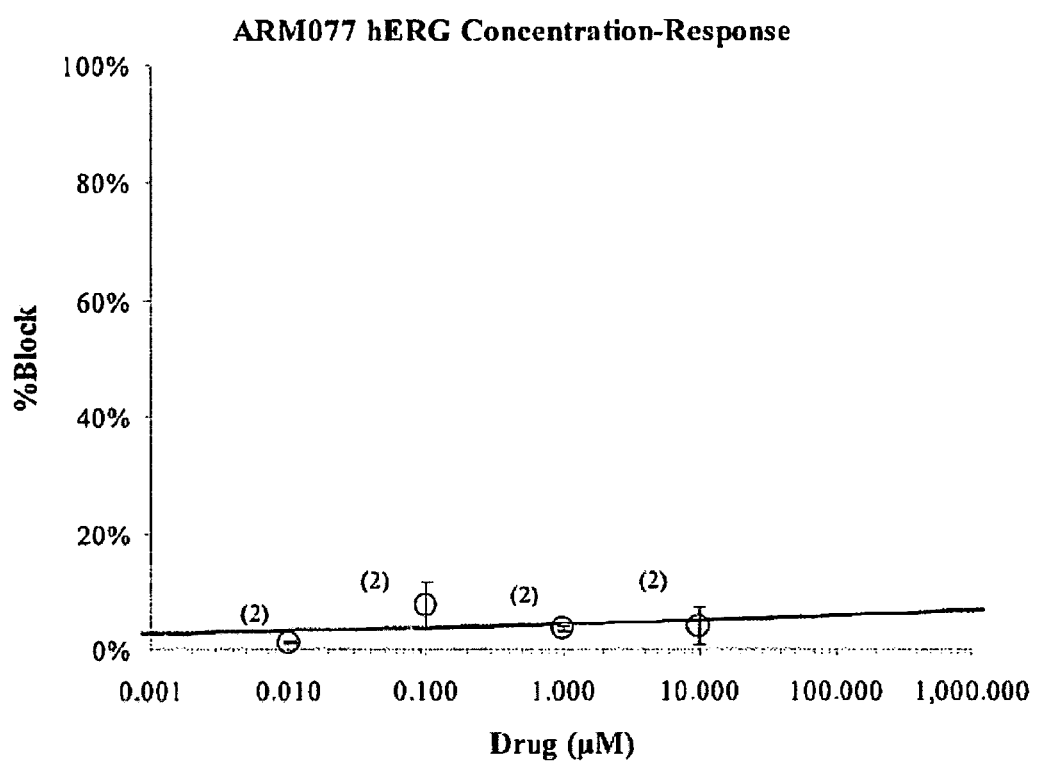

FIG. 28 is a graph showing the concentration-dependence of the effect of ARM077 on the hERG current. Table 11 provides the numerical data that is illustrated graphically in FIG. 28. Because the highest concentration of ARM077 tested resulted in less than 50% current inhibition, it was not possible to determine an IC$_{50}$ value for ARM077.

TABLE 11

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM077 | ND | 0.01 | 1.3% | 0.2% | 0.2% | 2 | 1.4% 1.1% |
| | | 0.1 | 7.5% | 5.5% | 3.9% | 2 | 11.4% 3.6% |
| | | 1 | 3.6% | 0.6% | 0.4% | 2 | 3.1% 4.0% |
| | | 10 | 4.1% | 4.5% | 3.2% | 2 | 0.9% 7.2% |

Figure 29:
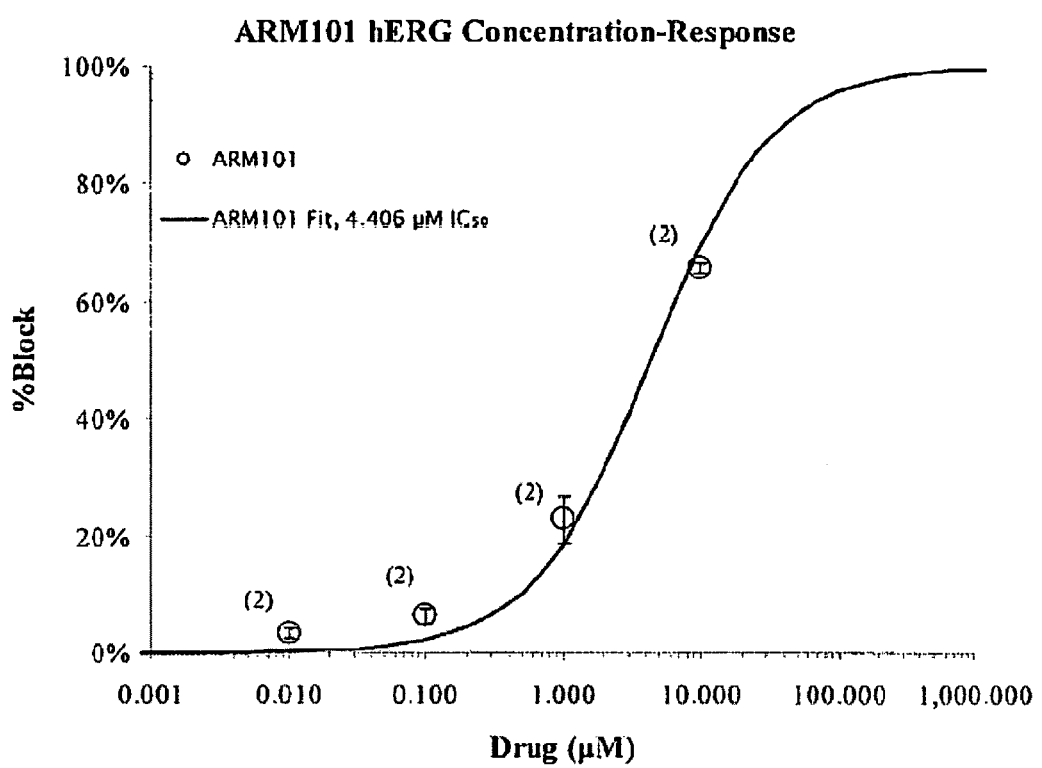

FIG. 29 is a graph showing the concentration-dependence of the effect of ARM101 on the hERG current. Table 12 provides the numerical data that is illustrated graphically in FIG. 29. Because the highest concentration of ARM101 tested resulted in less than 50% current inhibition, it was not possible to determine an IC$_{50}$ value for ARM101.

TABLE 12

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM101 | 4.406 | 0.01 | 3.4% | 1.3% | 0.9% | 2 | 4.3% 2.5% |
| | | 0.1 | 6.4% | 1.8% | 1.3% | 2 | 5.1% 7.6% |
| | | 1 | 23.0% | 5.7% | 4.1% | 2 | 18.9% 27.0% |
| | | 10 | 65.8% | 1.3% | 0.9% | 2 | 66.7% 64.9% |

Figure 30:
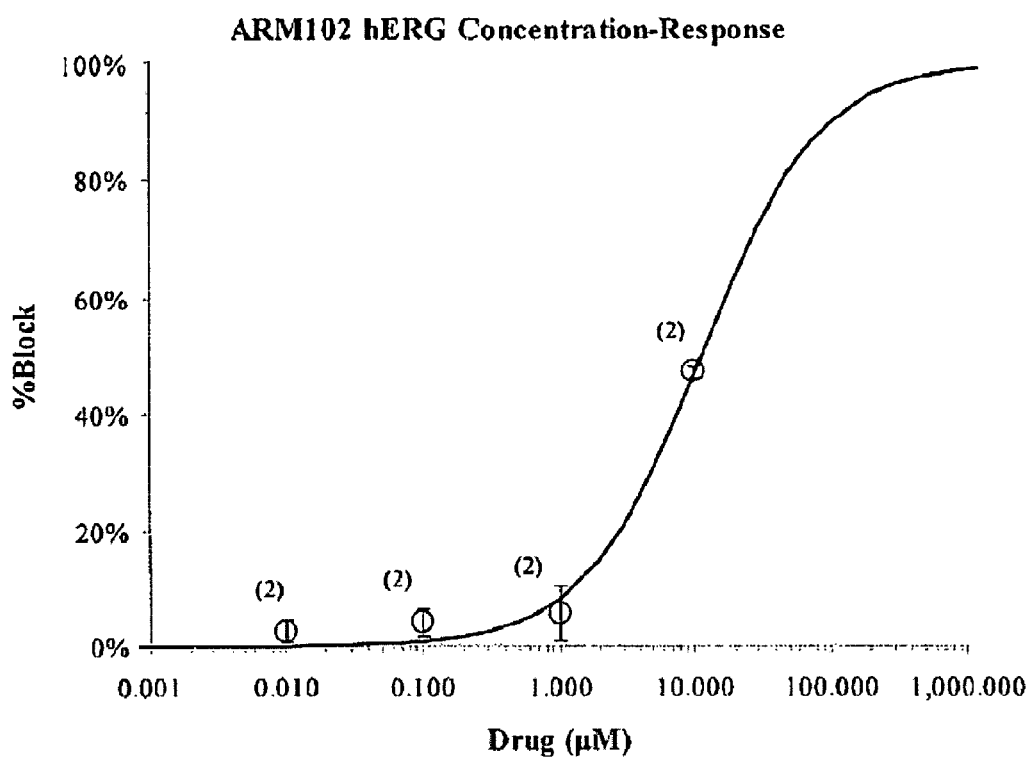

FIG. 30 is a graph showing the concentration-dependence of the effect of ARM102 on the hERG current. Table 13 provides the numerical data that is illustrated graphically in FIG. 30. Because the highest concentration of ARM102 tested resulted in less than 50% current inhibition, it was not possible to determine an IC$_{50}$ value for ARM102.

TABLE 13

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM102* | ND | 0.01 | 2.5% | 2.8% | 2.0% | 2 | 0.5% 4.4% |
| | | 0.1 | 4.2% | 3.3% | 2.4% | 2 | 1.8% 6.5% |
| | | 1 | 5.7% | 6.9% | 4.9% | 2 | 0.8% 10.5% |
| | | 10 | 47.3% | 1.5% | 1.1% | 2 | 46.2% 48.3% |

Figure 31:
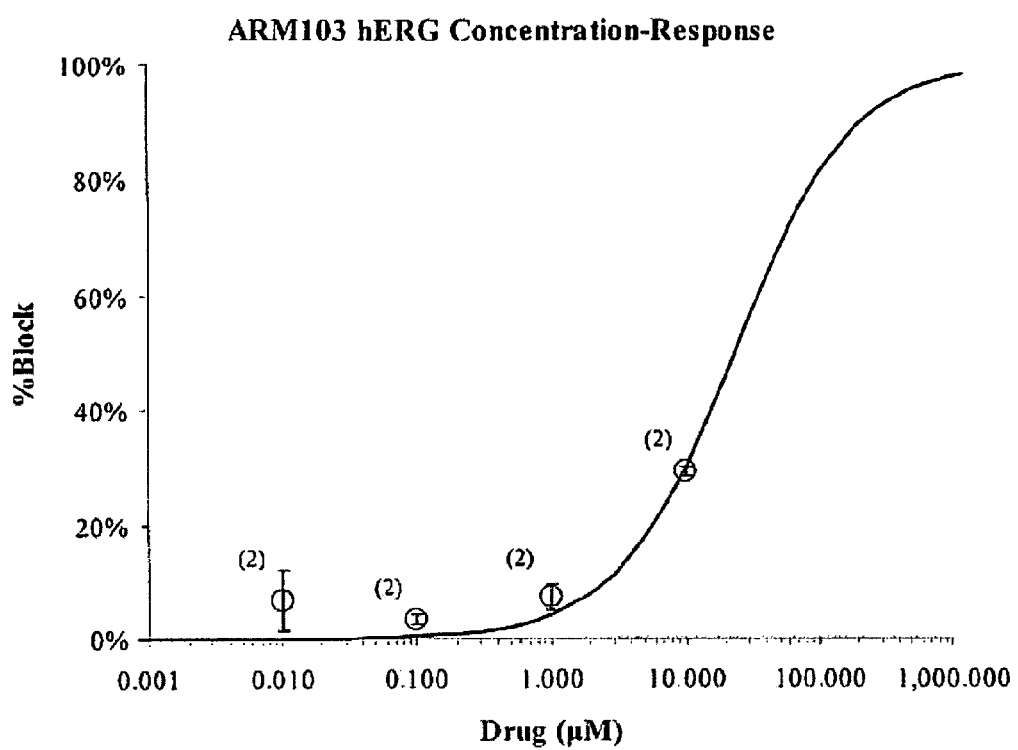

FIG. 31 is a graph showing the concentration-dependence of the effect of ARM103 on the hERG current. Table 14 provides the numerical data that is illustrated graphically in FIG. 31. Because the highest concentration of ARM103 tested resulted in less than 50% current inhibition, it was not possible to determine an IC$_{50}$ value for ARM103.

TABLE 14

| Test Article ID | IC$_{50}$ (µM) | Conc. (µM) | Mean % hERG Inhibition | % Standard Deviation | % Standard Error | n | Individual Data (% Inhibition) |
|---|---|---|---|---|---|---|---|
| ARM103* | ND | 0.01 | 6.8% | 7.5% | 5.3% | 2 | 12.1% 1.5% |
| | | 0.1 | 3.3% | 1.3% | 0.9% | 2 | 4.2% 2.4% |
| | | 1 | 7.3% | 3.3% | 2.3% | 2 | 5.0% 9.6% |
| | | 10 | 29.2% | 1.1% | 0.8% | 2 | 28.4% 29.9% |

Figure 32:
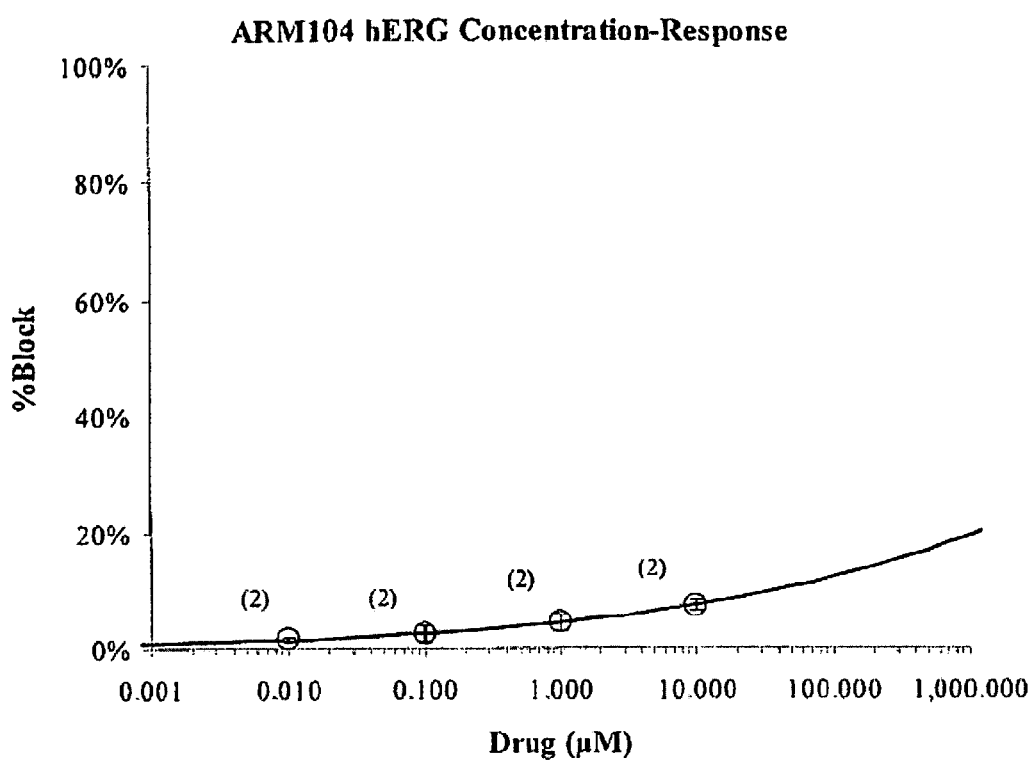

FIG. 32 is a graph showing the concentration-dependence of the effect of ARM104 on the hERG current. Table 15 provides the numerical data that is illustrated graphically in FIG. 32. Because the highest concentration of ARM104 tested resulted in less than 50% current inhibition, it was not possible to determine an IC$_{50}$ value for ARM104.

TABLE 15

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM104 | ND | 0.01 | 1.6% | 0.5% | 0.4% | 2 | 1.2% 1.9% |
| | | 0.1 | 2.5% | 2.0% | 1.4% | 2 | 1.1% 3.9% |
| | | 1 | 4.6% | 2.1% | 1.5% | 2 | 3.1% 6.0% |
| | | 10 | 7.4% | 1.3% | 0.9% | 2 | 8.3% 6.5% |

Figure 33:
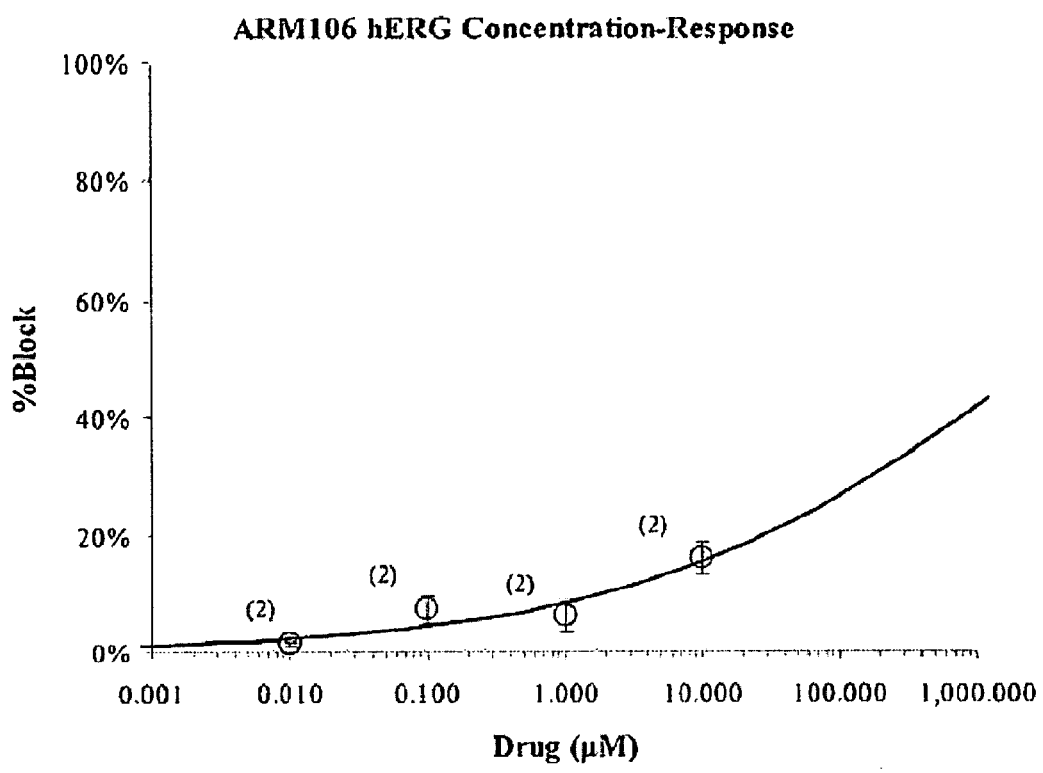

FIG. 33 is a graph showing the concentration-dependence of the effect of ARM106 on the hERG current. Table 16 provides the numerical data that is illustrated graphically in FIG. 33. Because the highest concentration of ARM106 tested resulted in less than 50% current inhibition, it was not possible to determine an IC$_{50}$ value for ARM106.

TABLE 16

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM106 | ND | 0.01 | 1.3% | 0.6% | 0.4% | 2 | 0.9% 1.7% |
| | | 0.1 | 7.2% | 3.5% | 2.5% | 2 | 9.6% 4.7% |
| | | 1 | 6.1% | 3.7% | 2.7% | 2 | 8.7% 3.4% |
| | | 10 | 15.9% | 4.0% | 2.8% | 2 | 18.7% 13.1% |

Figure 34:
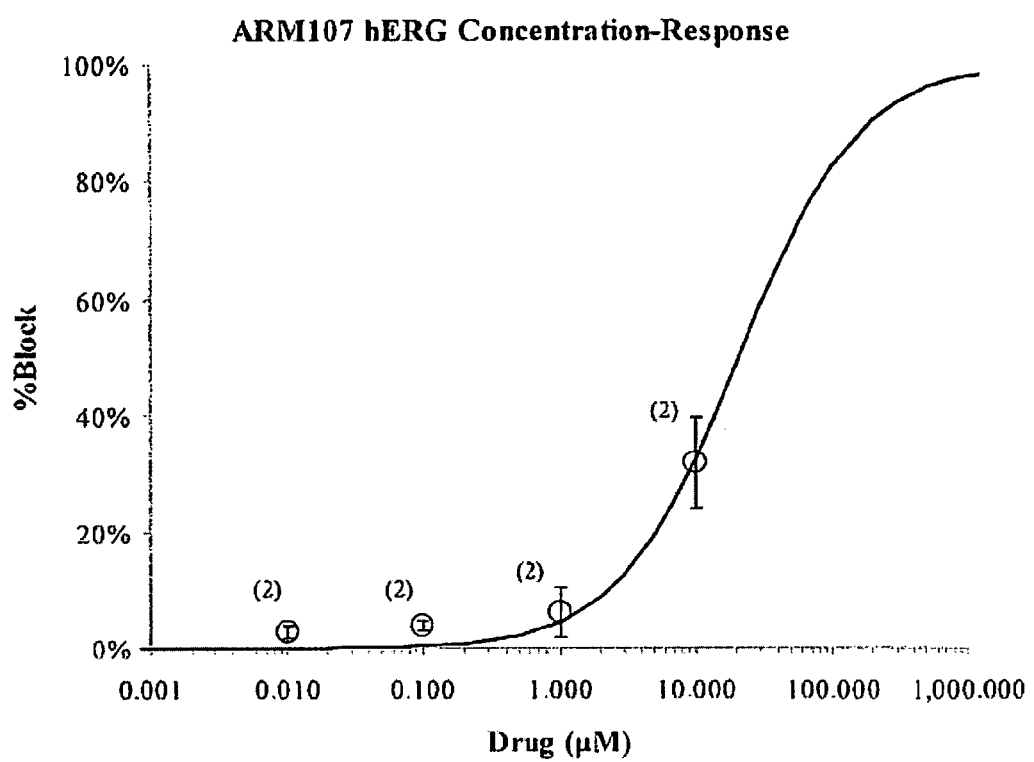
Figure 35:
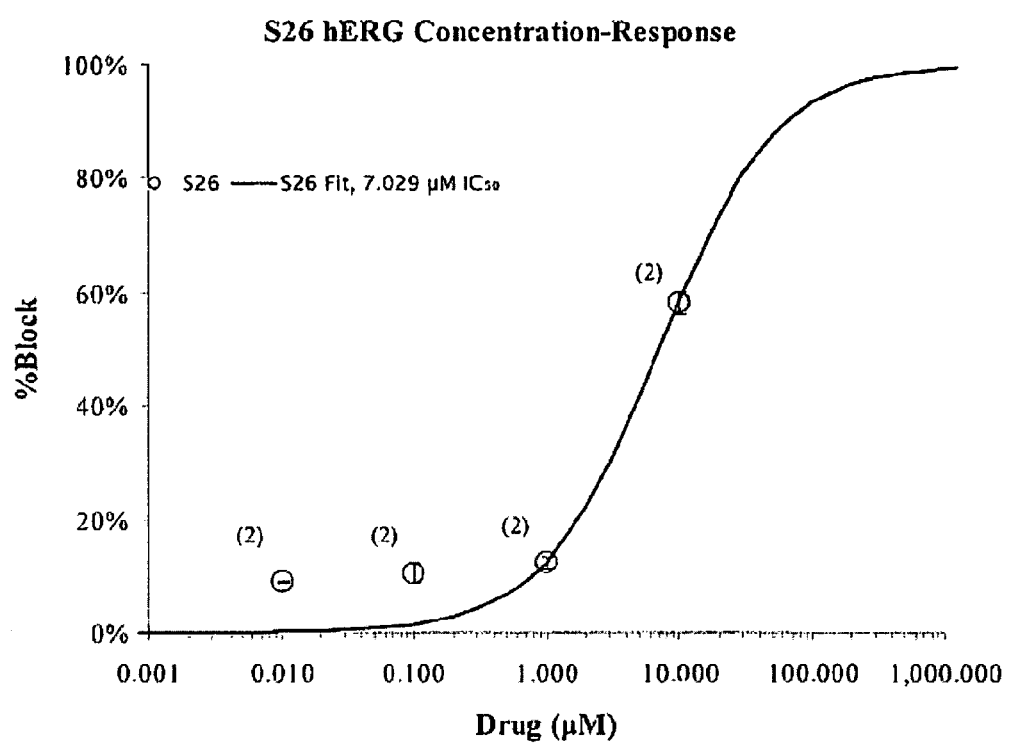
FIGS. 35A and B are concentration-response graphs showing the percent inhibition of hERG current after application of S26 (A) or JTV-519 ("ARM00X") (B) at various concentrations.
Figure 35:
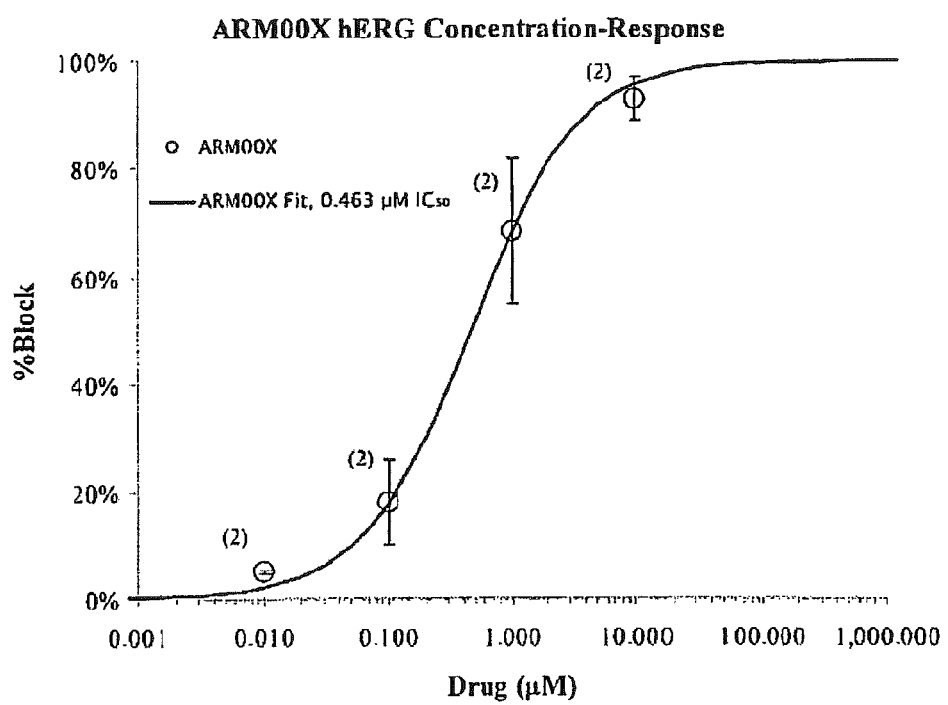
Figure 37A:
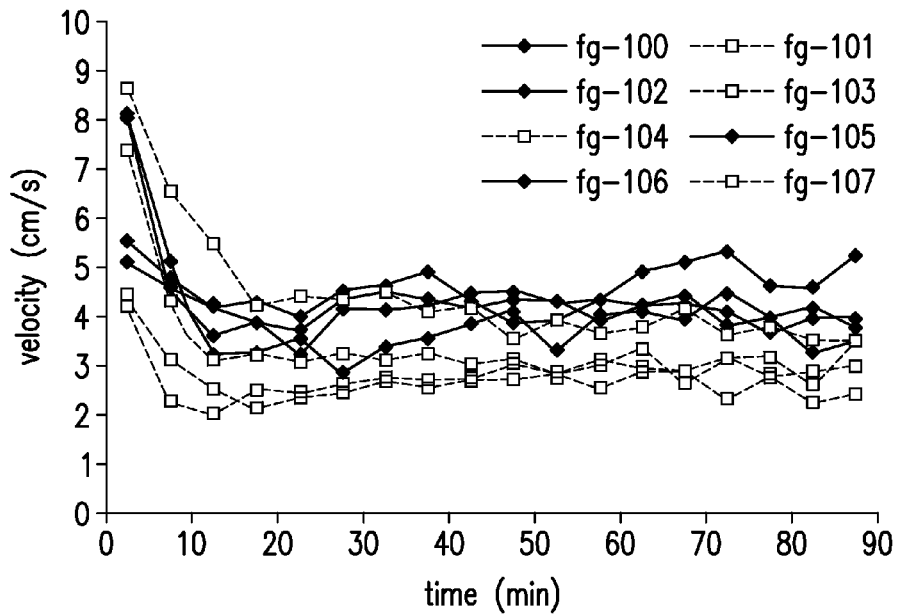
FIG. 37 shows that there is no substantial difference between the different treatment groups after 7 days of exercise. Embodiments A and B show results of swimming exercise for PBS and S36 treated mice. Individual mouse velocities over five minute time intervals are shown in Embodiment A and mean velocities of each treatment group are shown in FIG. 37B (n=3 PBS, n=4 S36). Embodiments C-F show results of a treadmill running exercise on day 7. As described, mice were run on the treadmill on an exercise protocol of increasing intensity, shown on the left marked velocity (m/min) in grey. Embodiment C shows individual traces reflecting the number of visits to the shocking area at the rear of the treadmill over each three minute interval. Task failure can be clearly appreciated from the rapid rise in visits to the shocking area as the mice fail. Embodiment D shows the number of shocks delivered to each mouse in each three minute interval, on an inverted axis, plotted as points with a three point moving average interpolation for each mouse. Embodiment E depicts quantification of total distance run in meters before failure for PBS and S36 treatment groups (n=3 PBS, n=4 S36), and Embodiment F depicts quantification of fatigue times, defined as time to task failure, for PBS and S36 treatment groups. (n=3 PBS, n=4 S36). No significant difference is observed between the different treatment groups.
Figure 37B:
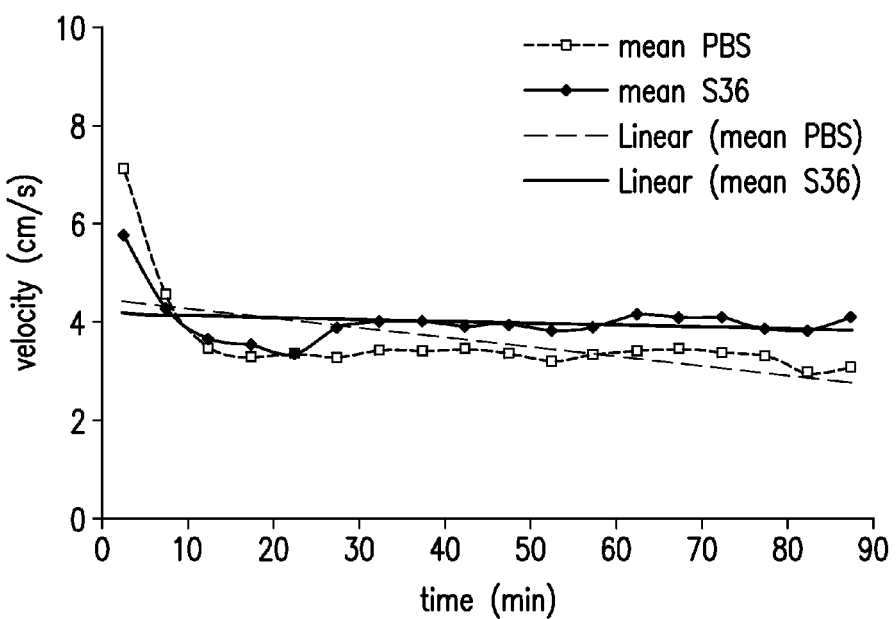
Figure 37C:
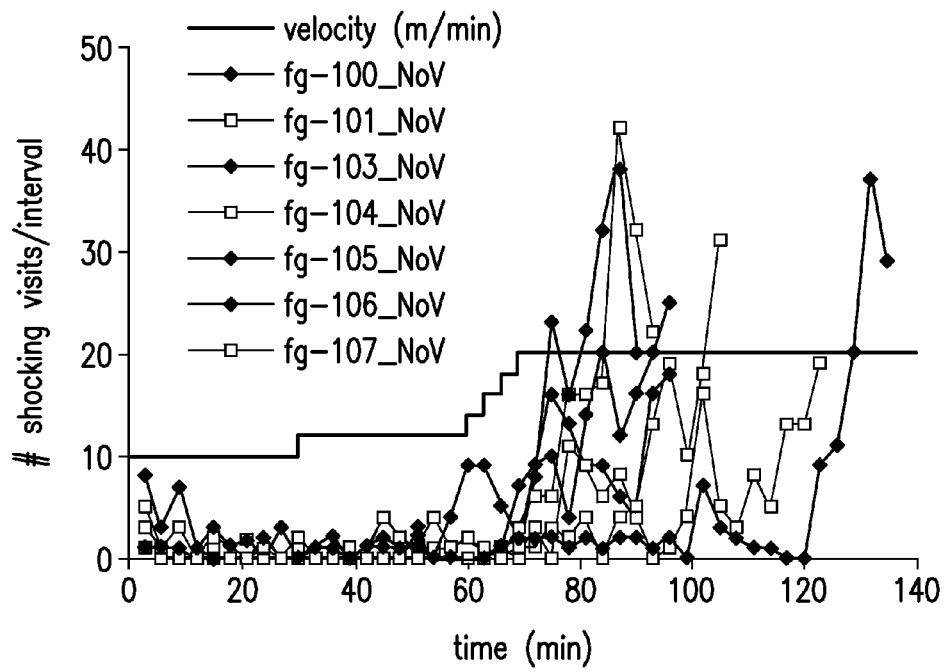
Figure 37D:
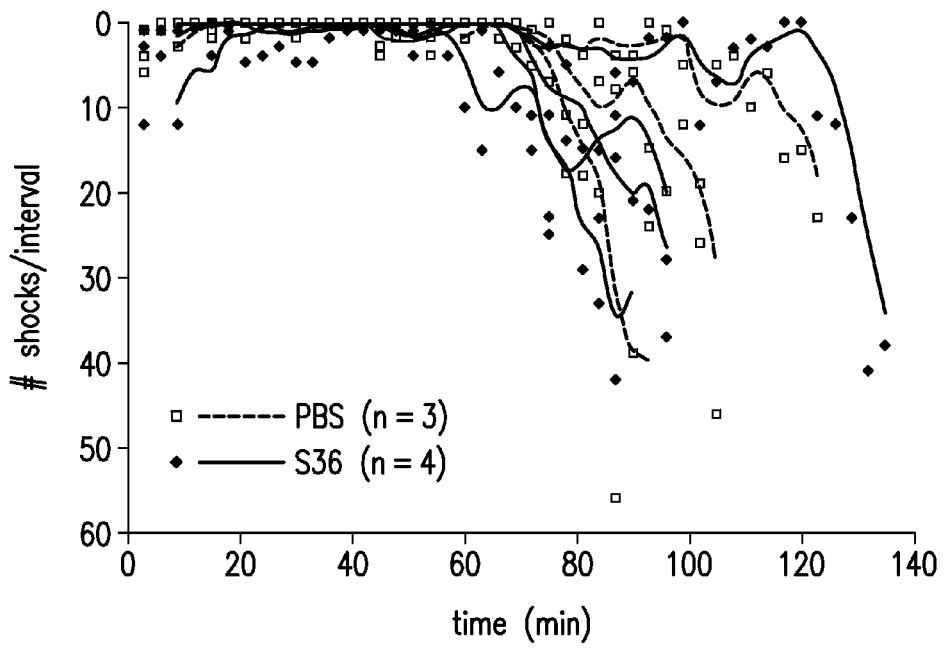
Figure 37E:
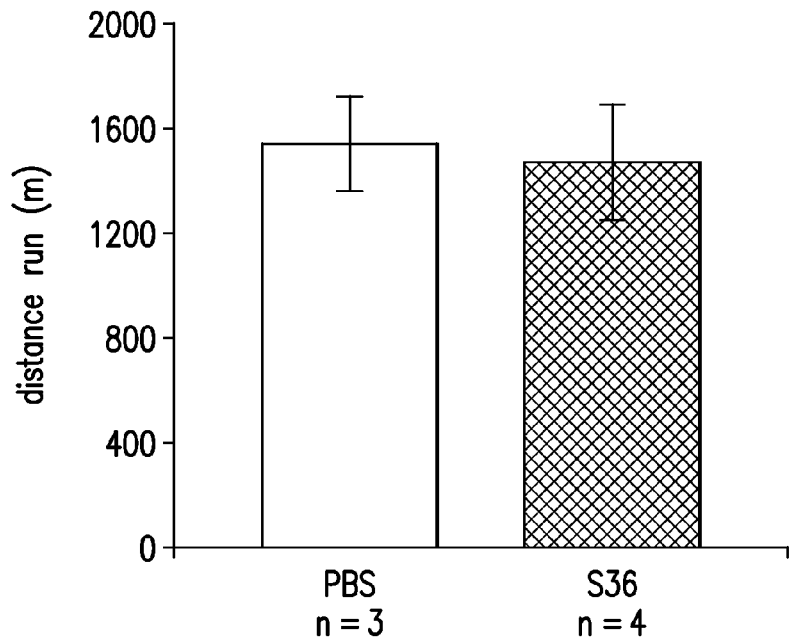
Figure 37F:
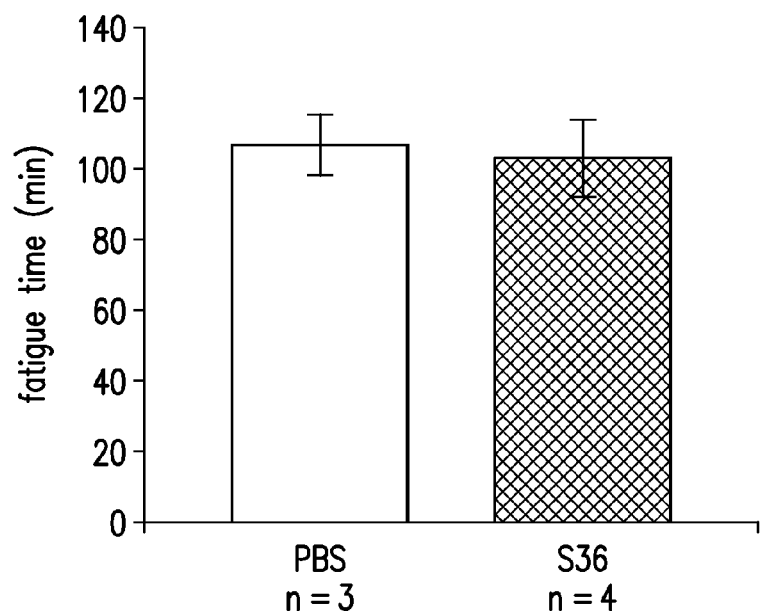
Figure 38A:
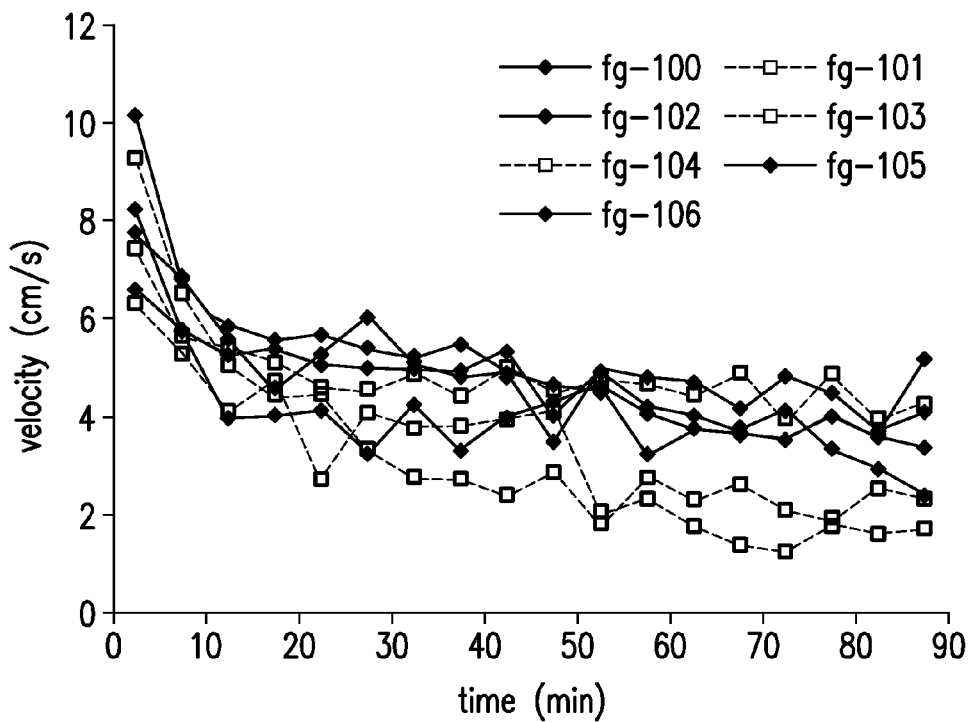
FIG. 38 shows that after 14 days of swimming, there is no significant difference in the swimming velocities of the different treatment groups. Embodiment A shows individual mouse velocities, and Embodiment B shows mean velocities for each treatment group. n=3 PBS, n=4 S36. Treadmill running on day fourteen demonstrates a trend toward improved performance in S36 treated mice. An increasing intensity exercise protocol was used, shown on the left marked velocity (m/min) in grey. Embodiment C shows individual traces reflecting the number of visits to the shocking area at the rear of the treadmill over each three minute interval. Embodiment D shows the number of shocks delivered to each mouse in each three minute interval, on an inverted axis, plotted as points with a three point moving average interpolation for each mouse. Embodiment E depicts quantification of total distance run in meters before failure for PBS and S36 treatment groups. (n=3 PBS, n=4 S36), and Embodiment F depicts quantification of fatigue times, defined as time to task failure, for PBS and S36 treatment groups. (n=3 PBS, n=4 S36).
Figure 38B:
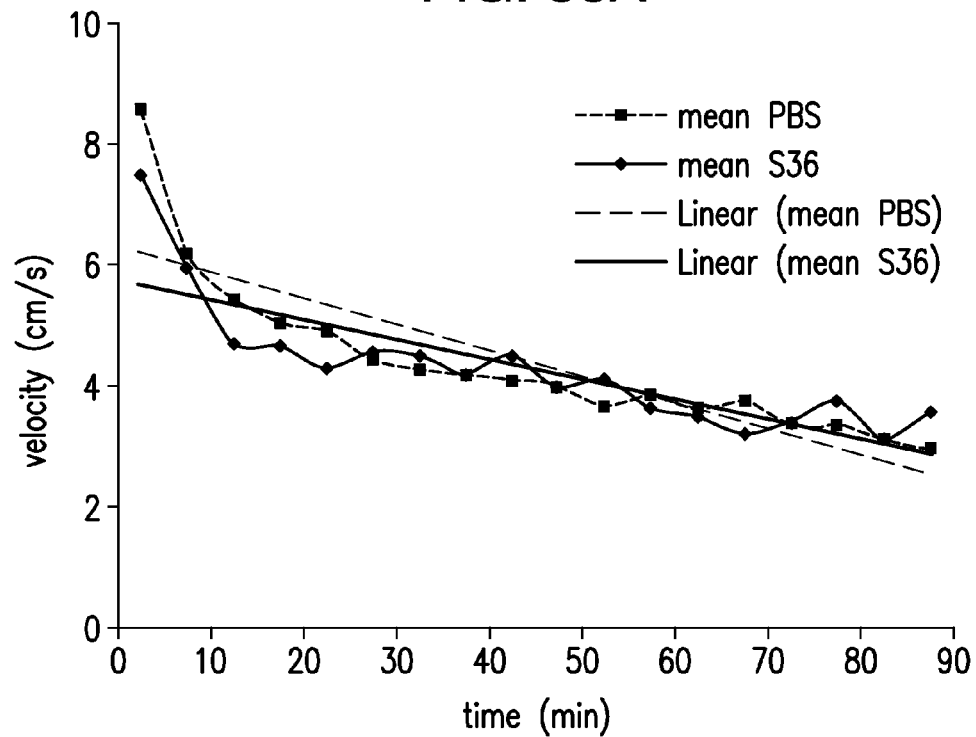
Figure 38C:
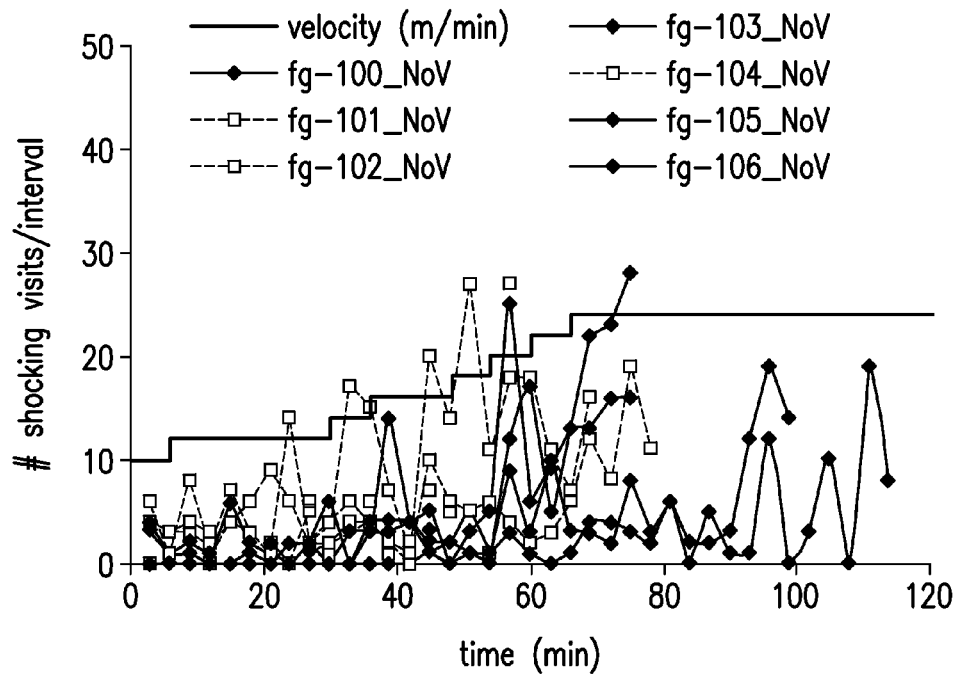
Figure 38D:
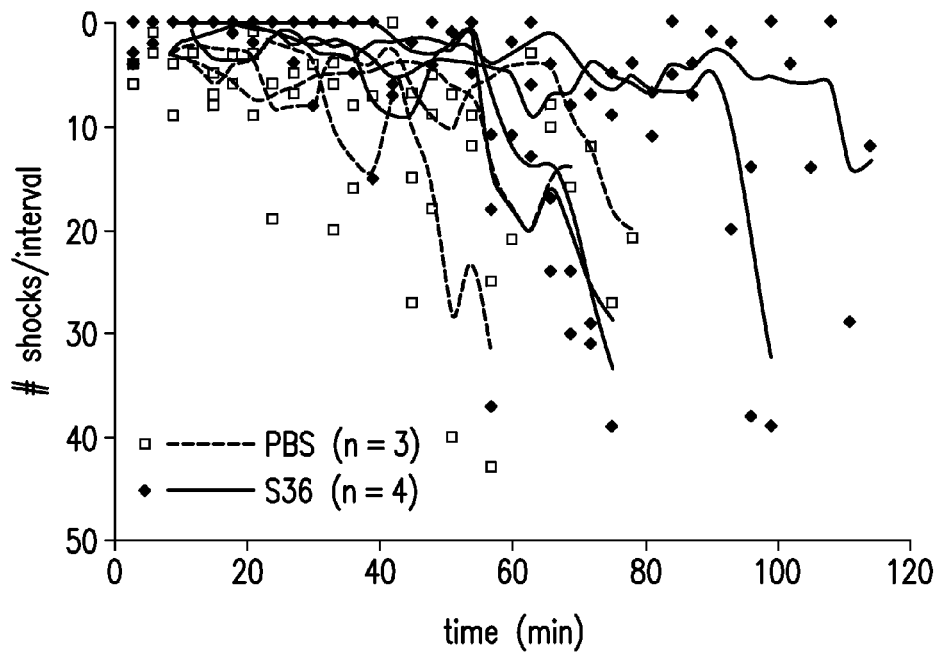
Figure 38E:
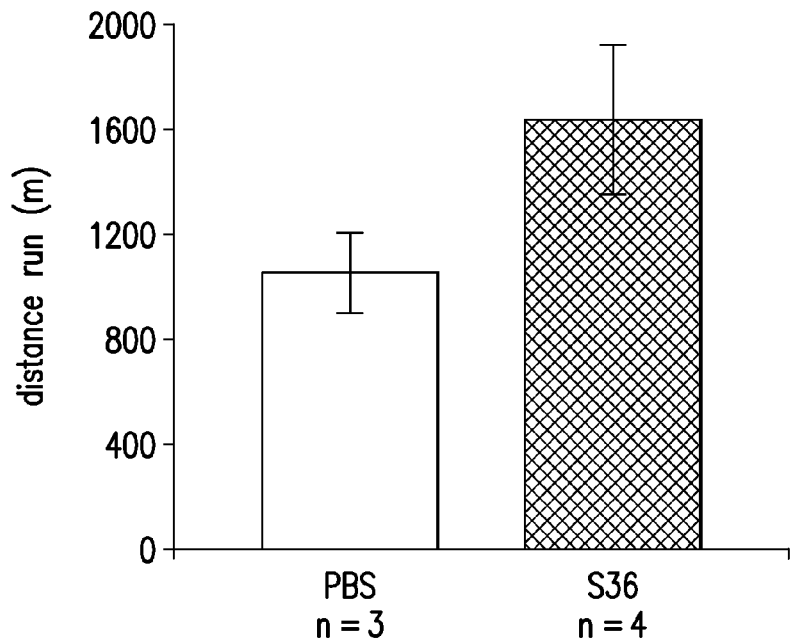
Figure 38F:
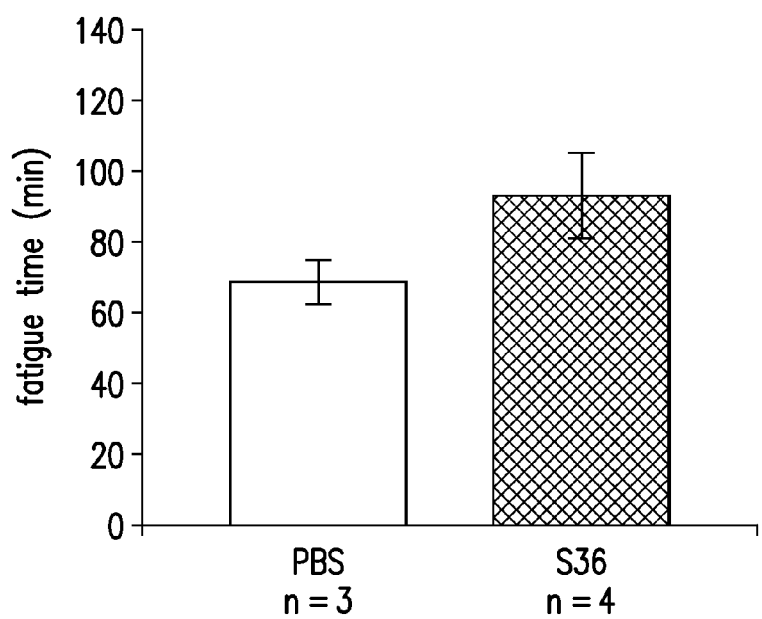
Figure 39A:
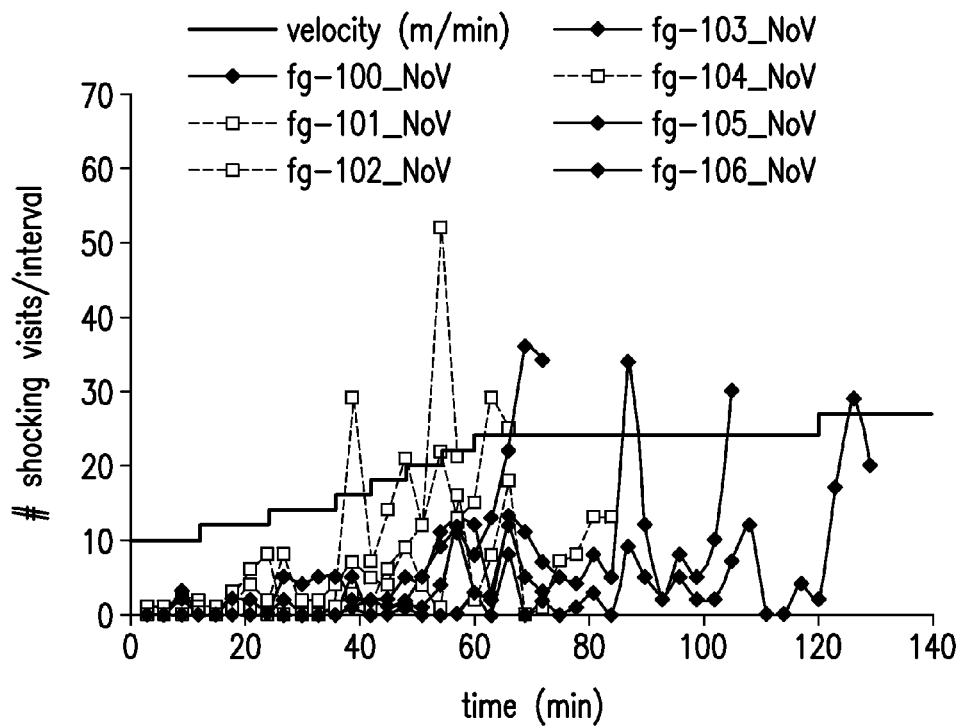
FIG. 39 embodiments A, B, C and D show analysis of data on day 16 of exercise regimen. Embodiments (A) and (B) shows results of treadmill running on day sixteen that replicates the trend toward improved performance in S36 treated mice. An increasing intensity exercise protocol was used, shown on the left marked velocity (m/min) in black. Embodiment A shows individual traces, which reflect the number of visits to the shocking area at the rear of the treadmill over each three-minute interval. Embodiment B shows the number of shocks delivered to each mouse in each three minute interval, on an inverted axis, plotted as points with a three point moving average interpolation for each mouse. Embodiment (C) shows quantification of total distance run in meters before failure for PBS and S36 treatment groups. (n=3 PBS, n=4 S36) Embodiment (D) shows quantification of fatigue times, defined as time to task failure, for PBS and S36 treatment groups. (n=3 PBS, n=4 S36).
Figure 39B:
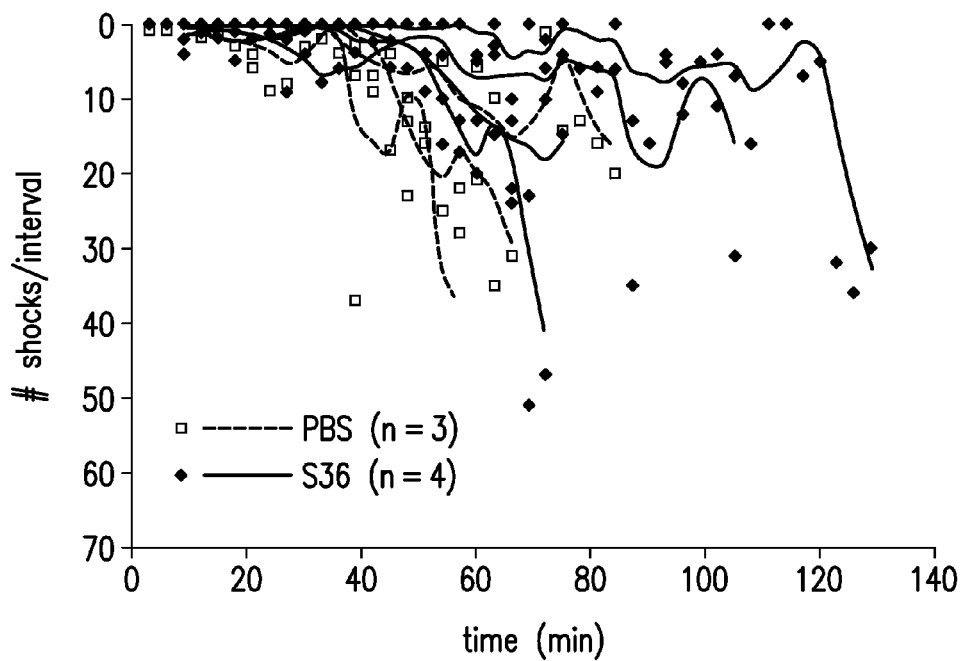
Figure 39C:
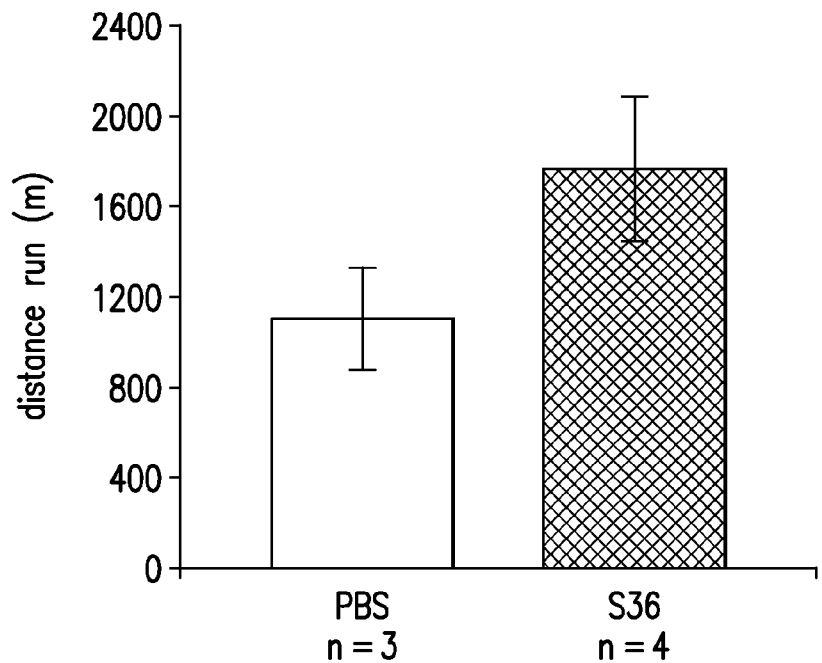
Figure 39D:
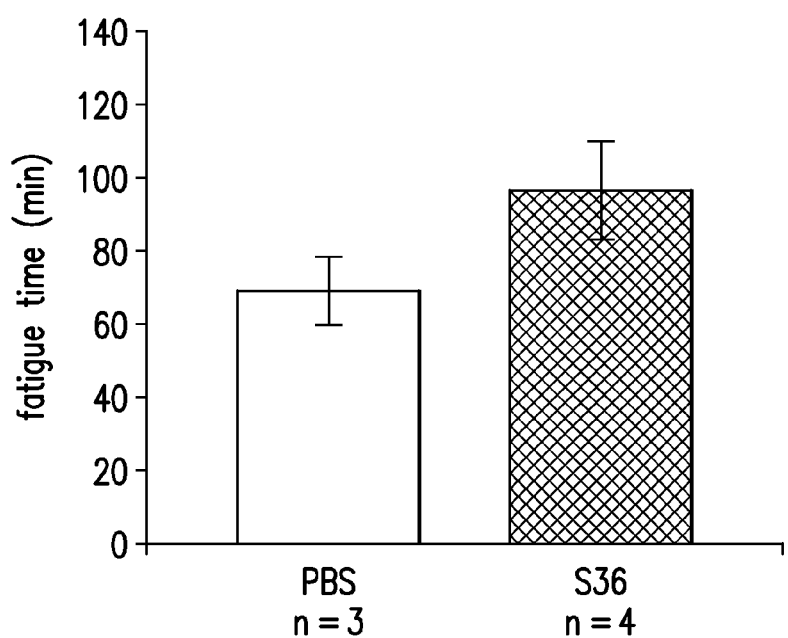
Figure 40:
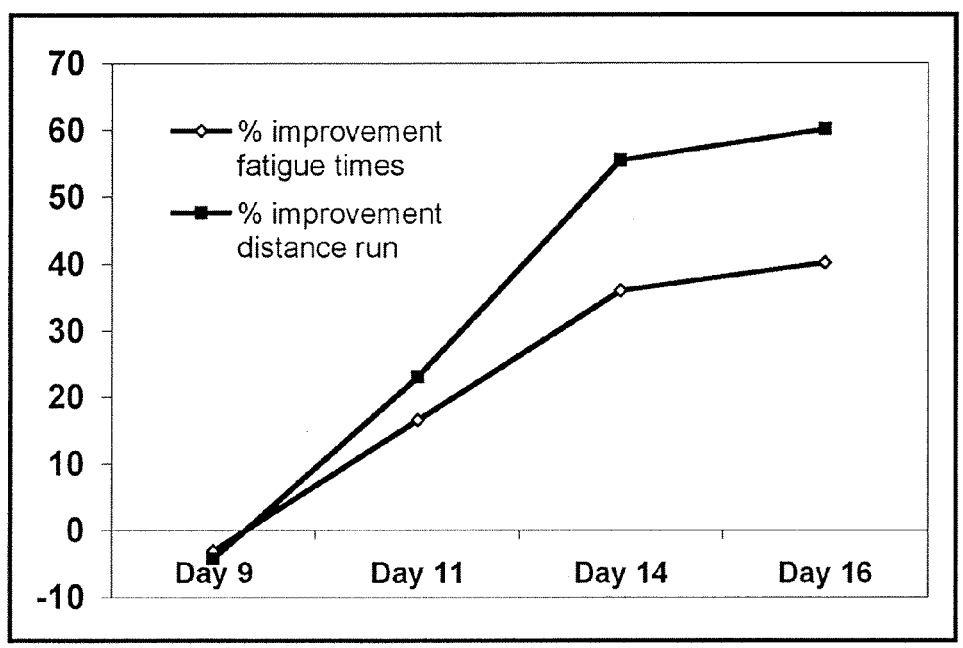
FIG. 40 shows percent improvements in fatigue times and distance run of S36 treated mice compared to PBS vehicle treated mice under the same conditions at each day, as measured by the treadmill assay.
Figure 41:
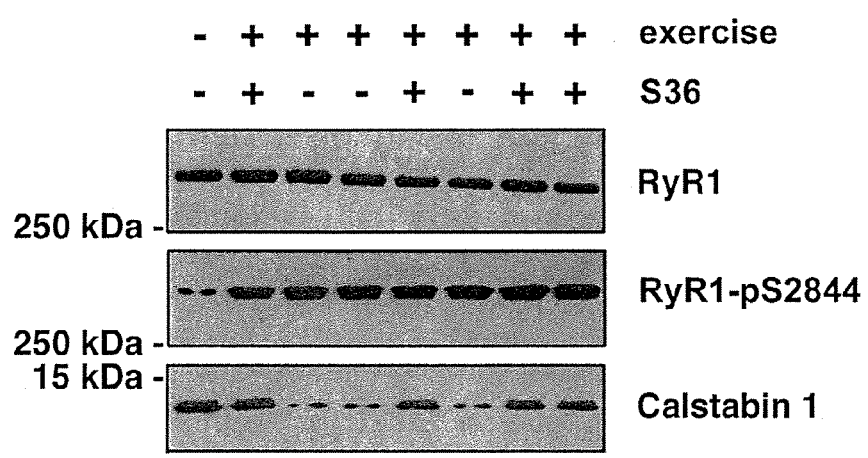
FIG. 41 shows that in vivo treatment with S36 (ARM036) allows RyR1 to rebind calstabin1 despite intense chronic exercise. RyR1 was immunoprecipitated from soleus muscle homogenates of mice following 21 days of exercise with or without simultaneous subcutaneous mini-osmotic pump treatment with S36 and then western blotted back for RyR1, phospho-epitope specific RyR1-pS2844, and calstabin1 bound to the RyR1 macromolecular complex.

FIG. 34 is a graph showing the concentration-dependence of the effect of ARM107 on the hERG current. Table 17 provides the numerical data that is illustrated graphically in FIG. 34. Because the highest concentration of ARM107 tested resulted in less than 50% current inhibition, it was not possible to determine an IC$_{50}$ value for ARM107.

TABLE 17

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM107 | ND | 0.01 | 2.9% | 1.6% | 1.2% | 2 | 1.7% 4.0% |
| | | 0.1 | 4.0% | 1.2% | 0.9% | 2 | 3.1% 4.8% |
| | | 1 | 6.2% | 5.9% | 4.2% | 2 | 2.0% 10.4% |
| | | 10 | 32.1% | 11.1% | 7.9% | 2 | 24.2% 39.9% |

FIG. 35A is a graph showing the concentration-dependence of the effect of S26 on the hERG current. Table 18 provides the numerical data that is illustrated graphically in FIG. 35A. The IC$_{50}$ value for S26 was 7.029 μM.

TABLE 18

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| S26 | 7.029 | 0.01 | 8.9% | 0.3% | 0.2% | 2 | 9.1% |
|  |  |  |  |  |  |  | 8.7% |
|  |  | 0.1 | 10.5% | 2.6% | 1.9% | 2 | 12.3% |
|  |  |  |  |  |  |  | 8.6% |
|  |  | 1 | 12.3% | 1.3% | 1.0% | 2 | 11.3% |
|  |  |  |  |  |  |  | 13.2% |
|  |  | 10 | 58.3% | 2.6% | 1.8% | 2 | 56.4% |
|  |  |  |  |  |  |  | 60.1% |

FIG. 35B is a graph showing the concentration-dependence of the effect of JTV-519 (referred to in the figure as "ARM00X") on the hERG current. Table 19 provides the numerical data that is illustrated graphically in FIG. 35B. The IC$_{50}$ value for JTV-519 was 0.463 μM.

TABLE 19

| Test Article ID | IC$_{50}$ (μM) | Conc. (μM) | Mean % hERG Inhibition | % Standard Deviation | % Standard Error | n | Individual Data (% Inhibition) |
|---|---|---|---|---|---|---|---|
| ARM0XX | 0.463 | 0.01 | 5.0% | 0.3% | 0.2% | 2 | 5.2% |
|  |  |  |  |  |  |  | 4.8% |
|  |  | 0.1 | 18.1% | 11.4% | 8.1% | 2 | 10.0% |
|  |  |  |  |  |  |  | 26.1% |
|  |  | 1 | 68.4% | 19.1% | 13.5% | 2 | 81.9% |
|  |  |  |  |  |  |  | 54.9% |
|  |  | 10 | 92.8% | 5.8% | 4.1% | 2 | 96.9% |
|  |  |  |  |  |  |  | 88.7% |

The antiarrhythmic drug E-4031, a known blocker of hERG currents, was used as a positive control. E-4031 blocked the hERG current with an IC$_{50}$ of 0.5 μM (n=6).

In summary, the compounds of the present invention exhibit reduced hERG blocking activity as compared to JTV-519. Thus, the compounds of the invention are expected to be less toxic and/or exhibit fewer side effects than JTV-519.

Table 20 below provides EC$_{50}$ values for compounds S1-S107. These EC$_{50}$ data were obtained using the FKBP12.6 rebinding assay described above to determine the amount of FKBP12.6 binding to PKA-phosphorylated RyR2 at various concentrations (0.5-1000 nM) of the compounds shown in Table 20. The EC$_{50}$ values are calculated using Michaelis-Menten curve fitting.

TABLE 20

| Compound No. | EC50 (nM) |
|---|---|
| 1 | 150 |
| 2 | 211 |
| 3 |  |
| 4 | 102 |
| 5 | 208 |
| 6 | 252 |
| 7 | 55 |
| 9 | 205 |
| 11 | 181 |
| 12 | 197 |
| 13 | 174 |
| 14 | 182 |
| 19 | 265 |
| 20 |  |
| 22 | 355 |
| 23 | 268 |
| 25 | 40 |
| 26 | 40 |

TABLE 20-continued

| Compound No. | EC50 (nM) |
|---|---|
| 27 | ca. 50 |
| 36 | 15 |
| 37 |  |
| 38 | 44 |
| 40 | 100 |
| 43 | 80 |
| 44 | 121 |
| 45 | 80 |
| 46 | 150 |
| 47 | 20 |
| 48 | 100 |
| 49 | 81 |
| 50 | 40 |
| 51 | 175 |
| 52 | 143 |
| 53 | 200 |
| 54 | 77 |
| 55 | 111 |
| 56 | 95 |
| 57 | 73 |
| 58 | 55 |
| 59 | 102 |
| 60 | 68 |
| 61 | 95 |
| 62 | 45 |
| 63 | 52 |
| 64 | 44 |
| 66 | 110 |
| 67 | 89 |
| 68 | ca. 100 |
| 74 | 220 |
| 75 | 150 |
| 76 | 25 |
| 77 | 60 |
| 101 | 105 |
| 102 | 135 |

TABLE 20-continued

| Compound No. | EC50 (nM) |
| --- | --- |
| 104 | 111 |
| 107 | 190 |

High-Throughput Screening Method

In addition to the compounds disclosed herein, other compounds can be discovered that are capable of modulating calcium ion channel activity, in particular those channels related to the RyR series of calcium ion channels. Provided herein is a highly-efficient assay for high-throughput screening of other compounds that are capable of modulating calcium ion channel activity.

By way of example, and as shown in Example 5 below, a highly-efficient assay for high-throughput screening for small molecules is developed by immobilizing FKBP, either FKBP12 or FKBP12.6 (e.g., wild-type FKBP12.6 or a fusion protein, such as GST-FKBP12.6) onto a 96-well plate coated with glutathione, using standard procedures. PKA-phosphorylated ryanodine receptor (RyR), specifically RyR1 or RyR3 in the case of FKBP12 and RyR2 in the case of FKBP12.6, is loaded onto the FKBP-coated plate, and incubated with compounds at various concentrations (10-100 nM) for 30 min. Thereafter, the plate is washed to remove the unbound RyR, and then incubated with anti-RyR antibody (e.g., for 30 min). The plate is washed again to remove unbound anti-RyR antibody, and then treated with florescent-labeled secondary antibody. The plate is read by an automatic fluorescent plate reader for binding activity.

Alternatively, RyR is PKA-phosphorylated in the presence of $^{32}$P-ATP. Radioactive PKA-phosphorylated RyR is loaded onto an FKBP-coated, 96-well plate, in the presence of JTV-519 analogues and other compounds at various concentrations (10-100 nM) for 30 min. The plate is washed to remove the unbound radiolabeled RyR, and then read by an automatic plate reader. PKA-phosphorylated RyR also is coated to the plate, and incubated with $^{32}$S-labeled FKBP in the presence of the compounds.

The present invention is described in the following Examples, which are set forth to aid in the understanding of the invention and should not be construed to limit in any way the scope of the invention as defined in the claims which follow thereafter.

EXAMPLES

Example 1

RyR2PKA Phosphorylation and FKBP12.6 Binding

Cardiac SR membranes are prepared, as previously described (Marx, et al., PKA phosphorylation dissociates FKBP12.6 from the calcium release channel (ryanodine receptor): defective regulation in failing hearts. *Cell*, 101: 365-76, 2000; Kaftan, et al., Effects of rapamycin on ryanodine receptor/Ca$^{(2+)}$-release channels from cardiac muscle. *Circ. Res.*, 78:990-97, 1996). $^{35}$S-labelled FKBP12.6 was generated using the TNT™ Quick Coupled Transcription/Translation system from Promega (Madison, Wis.). [$^{3}$H] ryanodine binding is used to quantify RyR2 levels. 100 μg of microsomes are diluted in 100 μl of 10-mM imidazole buffer (pH 6.8), incubated with 250-nM (final concentration) [$^{35}$S]-FKBP12.6 at 37° C. for 60 min, then quenched with 500 μl of ice-cold imidazole buffer. Samples are centrifuged at 100,000 g for 10 min and washed three times in imidazole buffer. The amount of bound [$^{35}$S]-FKBP12.6 is determined by liquid scintillation counting of the pellet.

Example 2

Immunoblots

Immunoblotting of microsomes (50 μg) is performed as described, with anti-FKBP12/12.6 (1:1,000), anti-RyR-5029 (1:3,000) (Jayaraman, et al., FK506 binding protein associated with the calcium release channel (ryanodine receptor). *J. Biol. Chem.*, 267:9474-77, 1992), or anti-phosphoRyR2-P2809 (1:5,000) for 1 h at room temperature (Reiken, et al., Beta-blockers restore calcium release channel function and improve cardiac muscle performance in human heart failure. *Circulation*, 107:2459-66, 2003). The P2809-phospho-epitope-specific anti-RyR2 antibody is an affinity-purified polyclonal rabbit antibody, custom-made by Zymed Laboratories (San Francisco, Calif.) using the peptide, CRTRRI-(pS)-QTSQ, which corresponds to RyR2PKA-phosphorylated at Ser$^{2809}$. After incubation with HRP-labeled anti-rabbit IgG (1:5,000 dilution; Transduction Laboratories, Lexington, Ky.), the blots are developed using ECL (Amersham Pharmacia, Piscataway, N.J.).

Example 3

Single-Channel Recordings

Single-channel recordings of native RyR2 from mouse hearts, or recombinant RyR2, are acquired under voltage-clamp conditions at 0 mV, as previously described (Marx, et al., PKA phosphorylation dissociates FKBP12.6 from the calcium release channel (ryanodine receptor): defective regulation in failing hearts. *Cell*, 101:365-76, 2000). Symmetric solutions used for channel recordings are: trans compartment—HEPES, 250 mmol/L; Ba(OH)$_2$, 53 mmol/L (in some experiments, Ba(OH)$_2$ is replaced by Ca(OH)$_2$); pH 7.35; and cis compartment—HEPES, 250 mmol/L; Tris-base, 125 mmol/L; EGTA, 1.0 mmol/L; and CaCl$_2$, 0.5 mmol/L; pH 7.35. Unless otherwise indicated, single-channels recordings are made in the presence of 150-nM [Ca$^{2+}$] and 1.0-mM [Mg$^{2+}$] in the cis compartment. Ryanodine (5 mM) is applied to the cis compartment to confirm identity of all channels. Data is analyzed from digitized current recordings using Fetchan software (Axon Instruments, Union City, Calif.). All data is expressed as mean±SE. The unpaired Student's t-testis used for statistical comparison of mean values between experiments. A value of $p<0.05$ is considered statistically significant.

Example 4

High-Throughput Screening Method

Assays for screening biologically-active small molecules have been developed. These assays are based on rebinding of FKBP12 protein to RyR.

A highly-efficient assay for high-throughput screening for small molecules is developed by immobilization of FKBP12.6 (GST-fusion protein) onto a 96-well plate coated with glutathione. PKA-phosphorylated ryanodine receptor type 2 (RyR2) is loaded onto the FKBP12.6-coated plate, and incubated with JTV-519 analogues at various concentrations (10-100 nM) for 30 min. Thereafter, the plate is washed to remove the unbound RyR2, and then incubated with anti-RyR2 antibody for 30 min. The plate is again washed to remove unbound anti-RyR2 antibody, and then treated with florescent-labeled secondary antibody. The plate is read by an automatic fluorescent plate reader for binding activity.

In an alternative assay, RyR2 is PKA-phosphorylated in the presence of 32P-ATP. Radioactive PKA-phosphorylated RyR2 is loaded onto an FKBP12.6-coated, 96-well plate, in the presence of JTV-519 analogues at various concentrations (10-100 nM) for 30 min. The plate is washed to remove the unbound radiolabeled RyR2, and then read by an automatic plate reader.

Example 5

Effect of ARM036 Compounds on hERG Currents

The effects of the compounds of the invention on hERG currents were studied using cultured human embryonic kidney 293 (HEK 293) cells which had been stably tranfected with hERG cDNA. HEK 293 cells do not express endogenous hERG. HEK293 cells were transfected with a plasmid containing the hERG cDNA and a neomycin resistance gene. Stable transfectants were selected by culturing the cells in the presence of G418. The selection pressure was maintained by continued culture in the presence of G418. Cells were cultures in Dulbecco's Modified Eagle Medium/Nutreint Mizture F-12 (D-MEM/F-12) supplemented with 10% fetal bovin serum, 199 U/ml penicillin G sodium, 10 µg/mL streptomycin sulfate and 500 µg/mL G418. Cells for use in electrophysiology were cultured in 35 mm dishes.

Electrophysiological recordings (using the whole-cell patch clamp method) were performed at room temperature (18° C.-24° C.). Each cell acted as its own control. The effect of ARM0036 was evaluated at two concentrations: 10 and 100 µM. Each concentration was tested in at least three cells (n≥3). 90 nM Cisapride (commercially available from TOCRIS Bioscience) was used as a positive control for hERG blockade. For recording, cells were transferred to the recording chamber and superfused with vehicle control solution. The patch pipette solution for whole cell recording contained 130 mM potassium aspartate, 5 mM MgCl$_2$, 5 mM EGTA, 4 mM ATP and 10 mM HEPES. The pH was adjusted to 7.2 with KOH. The pipette solution was prepared in batches, aliquoted, and stored frozen. A fresh aliquot was thawed and used each day. Patch pipettes were made from glass capillary tubing using a P-97 micropipette puller (Sutter Instruments, Novato, Calif.). A commercial patch clamp amplifier was used for whole cell recordings. Before digitization, current records were low-pass filtered at one-fifth of the sampling frequency.

Onset and steady state block of hERG current was measured using a pulse pattern with fixed amplitudes (conditioning prepulse: +20 mV for 2 seconds; test pulse: -50 mV for 2 seconds) repeated at 10 second intervals, from a holding potential of -80 mV. Peak tail current was measured during the 2 second step to -50 mV. A steady state was maintained for at least 30 seconds before applying the test compound or the positive control. Peak tail current was monitored until a new steady state was achieved. Test compound concentrations were applied cumulatively in ascending order without washout between applications.

Data acquisition and analysis was performed using the suite of pCLAMP (Vre. 8.2) programs (Axon Instruments, Union City, Calif.). Steady state was defined by the limiting constant rate of change with time (linear time dependence). The steady state before and after application of the test or control compounds was used to calculate the percentage of current inhibited at each concentration. Concentration-response data were fit to an equation of the form:

$$\% \text{ Block} = \{1 - 1/[\text{Test}]/\text{IC}_{50})^{NJ}\} \times 100$$

where [Test] is the concentration of the test compound, IC$_{50}$ (inhibitory concentration 50) is the concentration of the test compound producing half-maximal inhibition, N is the Hill coefficient, and % Block is the percentage of hERG current inhibited at each concentration of the test compound. Nonlinear squares fits were solved with the Solver add-in for Excel 2000 (Microsoft, Redmond, Wash.). For some compounds it was not possible to determine the IC$_{50}$ because the highest concentration of the test compound used did not block the hERG channel by 50% or more.

Example 6

Effect of Various Compounds on hERG Currents

Multiple compounds of the invention were tested for their effects on hERG currents. The compounds tested were: ARM036-Na, ARM047, ARM048, ARM050, ARM057, ARM064, ARM074, ARM075, ARM076, ARM077, ARM101, ARM102, ARM103, ARM104, ARM106, ARM107 and ARM26. By way of comparison, the effect of JTV-519 (referred to in the figures as "ARM00X") on hERG currents was also tested. Electrophysiological recordings were made using the PatchXpress 7000 A (Molecular Devices) automatic parallel patch clamp system. Each compound was tested at 0.01, 0.1, 1 and 10 mM, with each concentration tested in 2 cells (n>2). The duration of exposure to each test concentration was 5 minutes. Other aspects of the experimental protocols were essentially similar to those described in Example 5. For some compounds it was not possible to determine the IC$_{50}$ because the highest concentration of the test compound used did not block the hERG channel by 50% or more.

Example 7

Effect of S36

The RyCal compounds referred to as S36, S107 were synthesized as described herein.

FIGS. 36-41 show some aspects of the molecular mechanisms which lead to muscle fatigue and the effect of S36 on muscle fatigue.

Drug Delivery: Eight-week-old, wild-type, weight-matched, C57BL/6J littermate mice were randomized to either S36 or vehicle treatment. On day -2, osmotic infusion pumps (Alzet Model 2004, 200 µl total volume, 0.25 µl/hr delivery, Durect, Cupertino, Calif.) filled with either 200 ul of PBS or 200 µl of S36 (10 µg/ul diluted in PBS) were implanted subcutaneously on the dorsal surface of the mice by a horizontal incision just behind the neck. Mice were allowed to recover for three days prior to the initiation of exercise. Standard food and water were provided ad libitum.

Exercise Protocols: Beginning on day 1, mice were exercised for three weeks by swimming 5 days/week and by running on a treadmill an additional 1 day/week.

Swimming Model: The daily swimming protocol consisted of swimming sessions twice-daily separated by one-hour rest periods. After an initial conditioning regimen lasting 5 days during which the swimming sessions were increased in 10 minute increments from 40 minutes each to 80 minutes each, the swimming sessions thereafter lasted 90 minutes each. A 30 cm wide by 30 cm long opaque acrylic tank was filled with tap water to a depth of at least 20 cm. Water was circulated and warmed to 32-34 degrees C. using a separate reservoir with heating element, thermostat, and pump. Compressed room air was bubbled from Tygon tubing with small needle holes placed at the bottom of the tank to agitate the water surface. 4 mice, matched pair-wise with respect to treatment group, swam at any one time in the tank. Littermates who did not exercise were reserved as negative controls.

In order to track the swimming activity of each individually identified mouse, a video tracking system was used (San Diego Instruments, San Diego, Calif.), which includes Sony CCD video recorder, DVD/Hard Drive, frame grabber card, and custom SMART 2.0 software with Social Behavior package capable of tracking up to 8 mice simultaneously under ideal conditions.) Mice were anesthetized by using 1.5% isoflurane in $O_2$, and small, 0.75 cm, Velcro coins were sutured with 5-0 nylon suture to the scalp of each mouse. Plastic 1 cm colored dots, glued to the hook side of the Velcro, could be securely attached to the mouse and used for multiple subject tracking under appropriate lighting conditions. Each resultant mouse track in x,y, and time was analyzed and mean velocities, and distance swam over 2, 5, and 10 minute intervals was obtained.

Treadmill running: A Columbus Instruments (Columbus, Ohio) treadmill (Model: Exer-6M Treadmill with Treadmill Shock Detection Unit) with 6 lanes was used to run the mice. Mice were placed in their respective lanes at the lowest speed (7 meters/min) with the shocking apparatus turned off and allowed to adjust to the surroundings for 6 minutes. The forward half of the treadmill was covered with aluminum foil to block out light. A desk lamp illuminated the shocking area at the rear of the treadmill. After the adjustment period, the electric current was turned on, and the number of shocks delivered during the next two three minute intervals (training period) were recorded. The shock counter was then reset, the speed was increased to 10 m/min, and visits to the shocking area and shocks delivered to each mouse were recorded at three-minute intervals until the end of the experiment. At regular intervals, the speed of the treadmill was ramped up from the initial 10 m/min to as high as 36 m/min. The speed was increased no more than 2 m/min every 6 minutes. Consistent treadmill speed increases were used for all mice on a given day, but the protocol increased in difficulty over the course of the 21 day experiment. Task failure was defined when a mouse could not continue running to avoid the shocking area and gave up or when the mouse had received 200 cumulative shocks. In nearly all cases, these two times were very close to identical.

Muscle Isolation: Following the $21^{st}$ and $22^{nd}$ day of exercise, mice were swum a final time on a staggered schedule. Following 90 minutes of swimming, each mouse was immediately sacrificed by carbon dioxide inhalation and cervical dislocation. Blood was removed by intracardiac aspiration, spun down, and plasma was eluted and frozen in liquid nitrogen. Both extensor digitorum longus (EDL) muscles were exposed, moistened with Tyrode's solution, and 4-0 silk sutures were tied to the proximal and distal tendons and the muscles were dissected free. The muscles were perfused with Tyrode's solution containing 2.0 mM $CaCl_2$, bubbled with 100% $O_2$, warmed to 35 C, and hung on isometric force transducers (F-30, Harvard Apparatus, Cambridge, Mass.). After equilibration for 10 minutes at a resting tension of 1 cN and a brief potentiation protocol, force-frequency relationships were measured, with 60 second delays between 800 ms stimulations at 40-150 Hz. Fatigue was produced with a protocol of 50 Hz tetani (each 600 ms long) every 2 seconds for 120 seconds. DMC v4.1.6 (Aurora Scientific, Canada) was used to stimulate and record muscle responses, and DMA v3.2 (Aurora Scientific, Canada) was used to analyze the resultant data.

Following stimulation, muscle length was determined at the resting tension, and muscle dry weight was recorded. One EDL muscle was frozen in isopentane (−80° C.) for histology and the other was frozen in liquid $N_2$ for biochemistry.

In addition, both soleus muscles were dissected and likewise one was frozen in isopentane for histology and one was frozen in liquid $N_2$ for biochemical analysis. The vastus lateralis, heart, and diaphragm were also dissected from each animal and frozen in liquid $N_2$ for biochemical analysis.

Biochemistry: RyR channels were immunoprecipitated from skeletal muscle homogenates with anti-RyR antibody in 0.5 ml of buffer (50 mM Tris HCl buffer, pH 7.4 0.9% NaCl 5.0 mM NaF 1.0 mM $Na_3VO_4$ 0.5% Triton X-100+protease inhibitors) for 1 hour at 4° C. The samples were incubated with protein A Sepharose beads (Amersham Pharmacia) at 4° C. for 1 h, after which the beads were washed three times with buffer. Proteins were separated on SDS PAGE gels (6% for RyR2 and 15% for calstabin2) and transferred onto nitrocellulose membranes overnight (SemiDry transfer blot, Bio-Rad). After incubation with 5% nonfat milk to prevent nonspecific antibody binding and a wash in Tris-buffered saline with 0.1% Tween-20, membranes were incubated for 1-2 h at room temperature with primary antibodies anti-calstabin (1:1,000), anti-RyR (5029; 1:5,000), or anti-phospho-RyR2-pSer2809 (1:5,000), which detects PKA-phosphorylated mouse RyR1-pSer2844 and RyR2-pSer2808. After three washes, membranes were incubated with horseradish peroxidase-labeled anti-rabbit IgG (1:5,000, Transduction Laboratories, Lexington, Ky.), and developed with an enhanced chemiluminescent detection system (Amersham Pharmacia). Band densities were quantified by using QUANTITY ONE software (Bio-Rad).

Example 8

Effect of S107

FIGS. 42-55 show molecular mechanisms of muscle fatigue and the effect of S107.

Drug Delivery Eight-week-old, weight-matched, C57BL/6J littermate mice were randomized to dosing with either S107 or vehicle ($H_2O$). On day −3 of each trial, osmotic pumps (Alzet Model 2004, 200 ul total volume, 0.25 ul/hr delivery, Durect, Cupertino, Calif.) filled with either 200 ul of PBS or 200 ul of S107 (10 ug/ul diluted in $H_2O$) were implanted subcutaneously on the dorsal surface of each mouse by a horizontal incision on the neck. Mice were allowed to recover for three days prior to the initiation of exercise. Standard food and water were provided ad libitum through the experiment.

Chronic Exercise Model: The daily swimming protocol consisted of twice-daily swimming sessions separated by a one-hour rest period. After an initial conditioning regimen lasting 5 days during which the swimming sessions were increased in 10 minute increments from 40 minutes each to 80 minutes each, the swimming sessions thereafter lasted 90 minutes each. A 30 cm wide by 30 cm long opaque acrylic tank was filled with tap water to a depth of at least 20 cm. Water was circulated and warmed to 32-34° C. using a separate reservoir with heating element, thermostat, and pump. 8 mice, balanced pair-wise with respect to genotype and/or treatment group, swam at any one time in the tank. Littermates who did not exercise were reserved as sedentary controls.

In order to confirm that uniform exercise conditions were achieved, pilot experiments were performed in which the motion of each individually identified mouse was tracked with a video tracking system (San Diego Instruments, San Diego, Calif.). Individual recorded tracks over the full 90 minutes of each swim were analyzed for distance swam, mean velocities over time, etc. using the SMART 2.0 software with Social Behavior package (San Diego Instruments). No significant differences in the degree of exercise were noted.

Treadmill performance: A Columbus Instruments (Columbus, Ohio) treadmill (Model: Exer-6M Treadmill with Treadmill Shock Detection Unit) with 6 lanes was used to run the mice. Mice were placed in their respective lanes with the shocking apparatus turned off and allowed to adjust to the surroundings for 10 minutes. The forward half of the treadmill was covered with aluminum foil to block out light and a desk lamp illuminated the shocking area at the rear of the treadmill. After the adjustment period, the treadmill was set to 10 meters/min, and the mice were trained to run with gentle prodding for 6 minutes. The electric current was then turned on, and the number of shocks delivered during the next two three minute intervals (training period) were recorded. The shock counter was then reset and visits to the shocking area and shocks delivered to each mouse were recorded at three-minute intervals until the end of the experiment. At regular intervals, the speed of the treadmill was ramped up from the initial 10 m/min to 24 m/min. The speed was increased no more than 2 m/min every 6 minutes. Task failure was defined when a mouse could not continue running despite gentle prodding.

Intact muscle preparation: Immediately following a forced exercise session, each mouse was sacrificed by carbon dioxide inhalation and cervical dislocation. Blood was removed by intracardiac aspiration, spun down, and plasma was eluted and frozen in liquid nitrogen. 4-0 silk sutures were tied to the proximal and distal tendons of intact EDL and soleus muscles and the muscles were dissected free and placed in a modified Ringer's solution (140 mM NaCl, 5 mM KCl, 2.0 mM $CaCl_2$, 2 mM $MgCl_2$, 10 mM HEPES, 10 mM glucose, pH 7.4) bubbled with 100% $O_2$. Muscles were hung vertically in 50 mL Radnoti jacketed glass chambers with one tendon attached with 4-0 silk suture to an isometric force transducer (F30, Harvard Apparatus, Cambridge, Mass.) and the other tendon attached by suture to a stationary arm with built in platinum stimulating plate electrodes. After perfusion with 35C Ringer's and equilibration for 10 minutes at a resting tension of 1 cN and a brief potentiation protocol, force-frequency relationships were measured, with 60 second delays between 800 ms stimulations at 40-150 Hz. DMCv4.1.6 (Aurora Scientific, Canada) was used to stimulate and record muscle responses, and DMA v3.2 (Aurora Scientific, Canada) was used to analyze the resultant data. Following stimulation, muscle length was determined at resting tension, and muscle dry weight was recorded.

Confocal microscopy: Single flexor digitorum brevis (FDB) fibers were enzymatically dissociated by standard methods (Reiken, Lacampagne et al. 2003). Briefly, the muscle was dissected from the paw, placed in a modified Ringer's solution, and stripped of all fascia. Type 1 collagenase-(2 mg/ml, Sigma) in Ringer's solution was prepared fresh, and the muscle was digested for 2 hours at 37° C. in a incubator shaking at 125 rpm. The muscle was placed in fresh Ringer's and gently triturated. Single fibers were collected and allowed to attach to glass coverslips coated in laminin (Sigma L-2020). The cells were loaded with 2 µM fluo-4-AM ester (Invitrogen) for 20 minutes, placed on the Zeiss Live 5 microscope stage and superfused for 15 minutes with Ringer's. The fibers were paced at 1 Hz for 10 minutes prior to imaging baseline fiber properties. Linescan images were continuously acquired at 1 ms scan rate during a tetanic sequence consisting of 300 ms stimulation at 100 Hz with a 2 Hz train rate. Images were analyzed in ImageJ, and an F/F0 ratio was calculated for each fiber.

Human Exercise Protocol: Three weeks prior to test sessions, subjects reported to the Human Performance Laboratory at Appalachian State University for baseline measurements of cardiorespiratory fitness and body composition. On three consecutive test session days, subjects ate a standardized breakfast (7-8:00 am) and lunch (completed by 12:30 pm), and then reported to the ASU Human Performance Laboratory at 2:00 pm. Subjects exercised on exercise bikes at 70% $VO_{2max}$ from 3:00-6:00 pm. Test sessions days were Monday, Tuesday, and Wednesday afternoons. Oxygen consumption and other metabolic parameters were measured using a metabolic cart (with a mouthpiece and noseclip) every 30 minutes, and blood lactate and glucose (via finger stick) every 60 minutes to verify that subjects were adhering to the prescribed exercise workloads. Subjects ingested 0.5-1.0 liters water every hour of exercise while avoiding all forms of ingested energy (e.g., bars, drinks). Resting control subjects sat in the laboratory during the exercise test sessions. Blood, urine, and saliva samples were collected 15-30 minutes before exercise/sitting, and then within 5-10 minutes post-exercise on each of the 3 test sessions. Muscle biopsy samples were obtained 15-30 minutes before exercise/sitting, and then within 5-10 minutes post-exercise using a needle biopsy procedure on Days 1 and 3. Four samples were taken (two from each thigh), about 2 inches apart. Biopsies were snap frozen in liquid nitrogen and stored at −80° C.

Single channel recording and data acquisition: SR vesicles from skeletal muscle of sedentary mice and mice chronically exercised and treated either with vehicle or S107 were prepared as described previously (Reiken, Lacampagne et al. 2003). RyR1 channels were reconstituted by spontaneous fusion of microsomes into the planar lipid bilayer (a mixture of phosphatidylethanolamine and phosphatidylserine in a 3:1 ratio, Avanti Polar Lipids). Planar lipid bilayers were formed across a 200 µm aperture in a polysulfonate cup (Warner Instruments, Inc.), which separated two bathing solutions (1 mM EGTA, 250/125 mM HEPES/Tris, 50 mM KCl, 0.5 mM $CaCl_2$, pH 7.35 as cis solution and 53 mM $Ba(OH)_2$, 50 mM KCl, 250 mM HEPES, pH 7.35 as trans solution). After incorporation, RyR1 channel activity was recorded continuously for at least 10 minutes. The concentration of free $Ca^{2+}$ in the cis chamber was calculated with WinMaxC program (version 2.50) (Bers, Patton et al. 1994). Single channel currents were recorded at 0 mV using the Axopatch 200A patch-clamp amplifier (Axon Instruments, USA) in gap-free mode, filtered at 1 kHz, and digitized at 10 kHz. Data acquisition was performed using Digidata 1322A and Axoscope 9 software (Axon Instruments, USA). The recordings were analyzed using Clampfit 10.1 (Molecular Devices, USA) and Origin software (ver. 6.0, Microcal Software, Inc., USA).

Analysis of Ryanodine Receptor Complex: 10 mg muscle samples were isotonically lysed. The ryanodine receptor (RyR1) was immunoprecipitated by incubating 250 µg of homogenate with anti-RyR antibody (2 µl 5029 Ab) in 0.5 ml of a modified RIPA buffer (50 mM Tris-HCl pH 7.4, 0.9% NaCl, 5.0 mM NaF, 1.0 mM $Na_3VO_4$, 0.5% Triton-X100, and protease inhibitors) for 1 hr at 4° C. The samples were incubated with protein A Sepharose beads (Amersham Pharmacia) at 4° C. for 1 h, after which the beads were washed three times with buffer. Proteins were separated on SDS-PAGE gels (4-20% gradient) and transferred onto nitrocellulose membranes overnight (SemiDry transfer blot, Bio-Rad). After incubation with blocking solution (LICOR Biosciences, Lincoln Nebr.) to prevent non-specific antibody binding and a wash in Tris-buffered saline with 0.1% Tween-20, membranes were incubated for 1-2 h at room temperature with primary antibodies anti-calstabin (1:2500 in blocking buffer), anti-RyR (5029, 1:5,000), or anti-phospho-RyR2-pSer2809 (1:5000), which detects PKA-phosphorylated mouse RyR1-pSer2844 and RyR2-pSer2808, anti-PDE4D3 (1:1000). After three washes, membranes were incubated with infrared labeled secondary antibodies (1:10,000 dilution, LICOR Biosystems). Band densities were quantified using the Odyssey Infrared Imaging System (LICOR Biosciences).

Figure 42B:
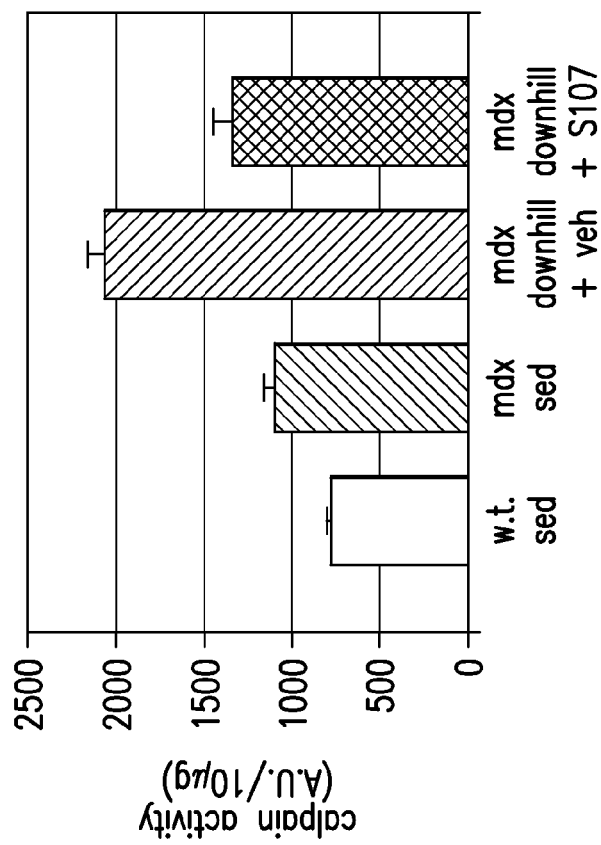
FIG. 42 provides data illustrating that the RyCal compound S107 reduces calpain activity in the mdx mouse muscular dystrophy model during exercise, and indicates that RyCals are useful for treating muscle related diseases, such as muscular dystrophies.
Figure 42A:
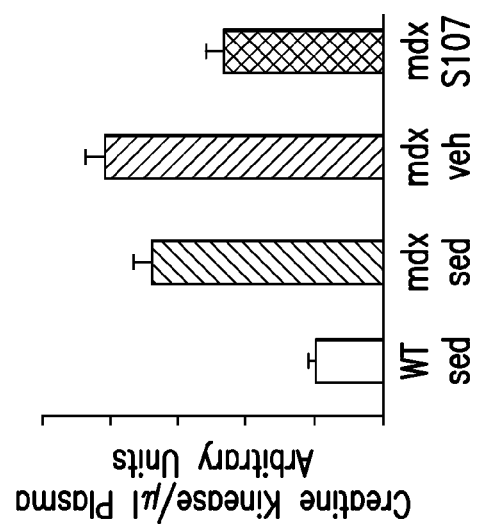

Calpain and Creatine Kinase Assays: Tissue calpain activities were measured using a calpain activity assay kit (Calbiochem, San Diego, Calif.) (FIG. 42B). This assay is based on the degradation of the fluorescent peptide substrate Suc-LLVY-AMC (Calbiochem). Muscle homogenates were diluted to a final concentration of 600 µg/ml and the calpain activity in the homogenate was determined as per manufactures instructions. Plasma creatine kinase (CK) activity was assayed using the regent kit from Pointe Scientific, Inc. (Canton, Mich.) (FIG. 42A). Plasma samples (duplicates, 5 µl each) were added to 200 µl of CK reagent and the change in absorbance at 340 nM was recorded over 4 minutes using a plate reader. The average absorbance change per minute was used to determine the CPK levels as per manufacturer's instructions.

Statistics: Data are presented as mean±SEM. Independent t-test with a significance level of 0.05 was employed to test differences between cal1−/− and WT, PDE4D−/− and WT, and Ex+veh and Ex+S107, except as noted below. The distributions of treadmill failure data were found in several cases to be asymmetric. As such, Wilcoxon rank sum tests were used for all such data comparisons.

High intensity exercise induces RyR1 PKA hyperphosphorylation, and depletion of calstabin1 and PDE4D3 from the channel complex: Exercise models in the mouse have been grouped into two categories: 1) voluntary exercise including running wheels; and 2) involuntary exercise, including swimming or forced treadmill runs to exhaustion. In order to achieve high intensity exercise, a twice daily swimming protocol was adapted to achieve uniform exercise in mice over days to weeks. This mouse exercise protocol was not designed to be either explicitly eccentric or isometric in character, but rather a physiologic mix of eccentric and isometric exercise. Following forced exercise, RyR1 was immunoprecipitated out of whole muscle homogenates from hind limb muscles, and the RyR1 channel complex was size-fractionated on SDS-PAGE and immunoblotted for channel complex components. High-intensity exercise in the mouse resulted in progressive phosphorylation of RyR1 at the PKA site Ser2844 (RyR1-pS2844) that saturated by 14 days of twice daily swimming (90 min sessions, e.g. FIG. 43A).

Figure 43A:
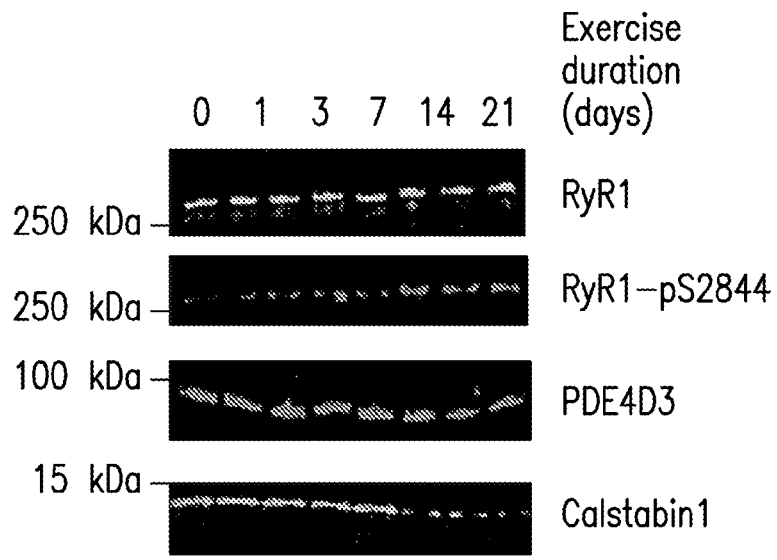
FIG. 43 shows that the RyR1 Macromolecular Complex Undergoes Substantial Remodeling Following Exercise. A) Composition of the RyR1 complex in extensor digitorum longus (EDL) muscle following an exercise protocol (consisting of twice daily swimming) lasting the indicated number of days by immunoprecipitation of RyR1 and immunoblot for RyR, RyR1-pS2844, and PDE4D3 and calstabin1 bound to the receptor. B) Densitometric quantification of A, where each value is relative to the total RyR1 immunoprecipitated. C) Composition of the RyR1 complex in EDL muscle following low intensity and high intensity exercise for 5 days. D) Densitometric quantification of C. In all cases, the product of a single RyR1 immunoprecipitation was separated on a 4-20% gradient polyacrylamide gel, transferred, and probed for both total RyR1 and one or more of the modifications noted. The blots shown are representative of three independent experiments.
Figure 43B:
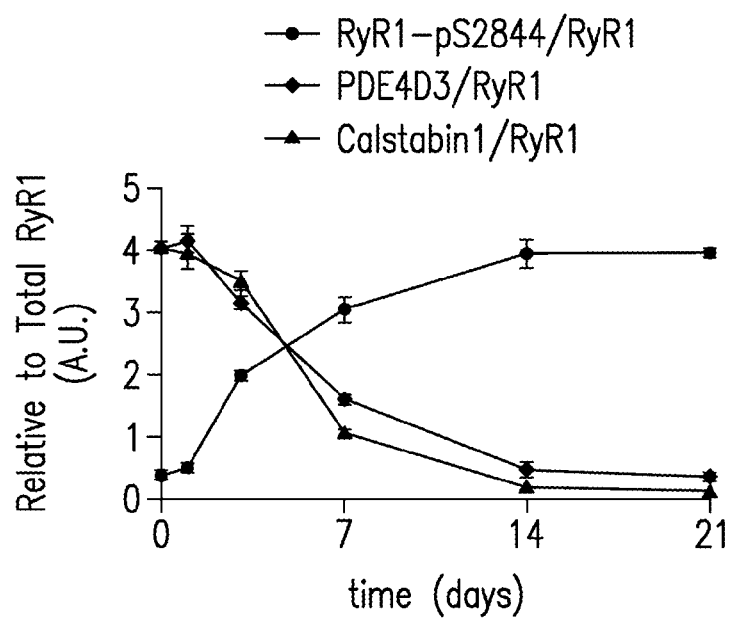
Figure 43C:
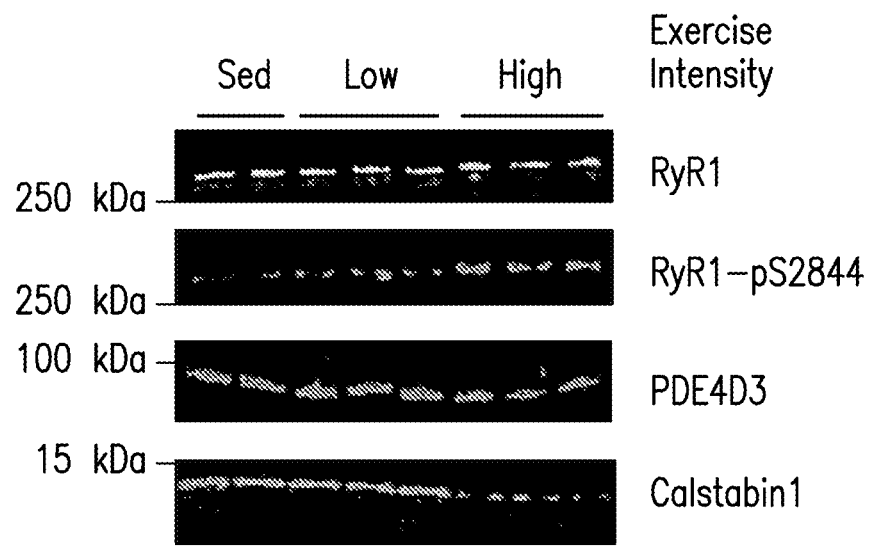
Figure 43D:
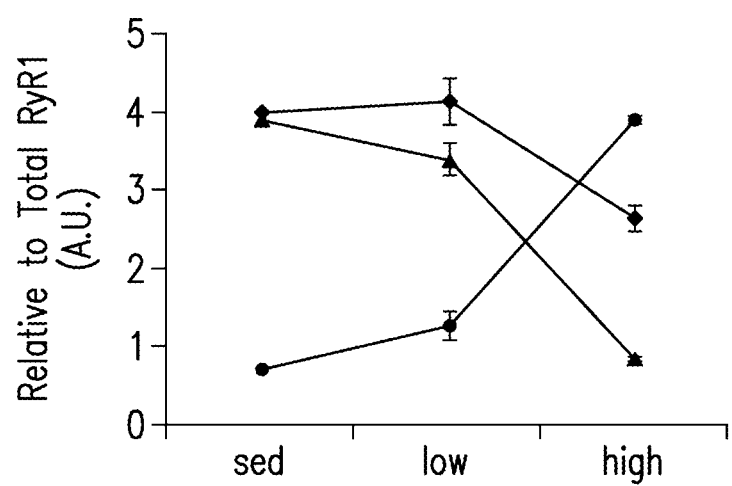
Figure 45:
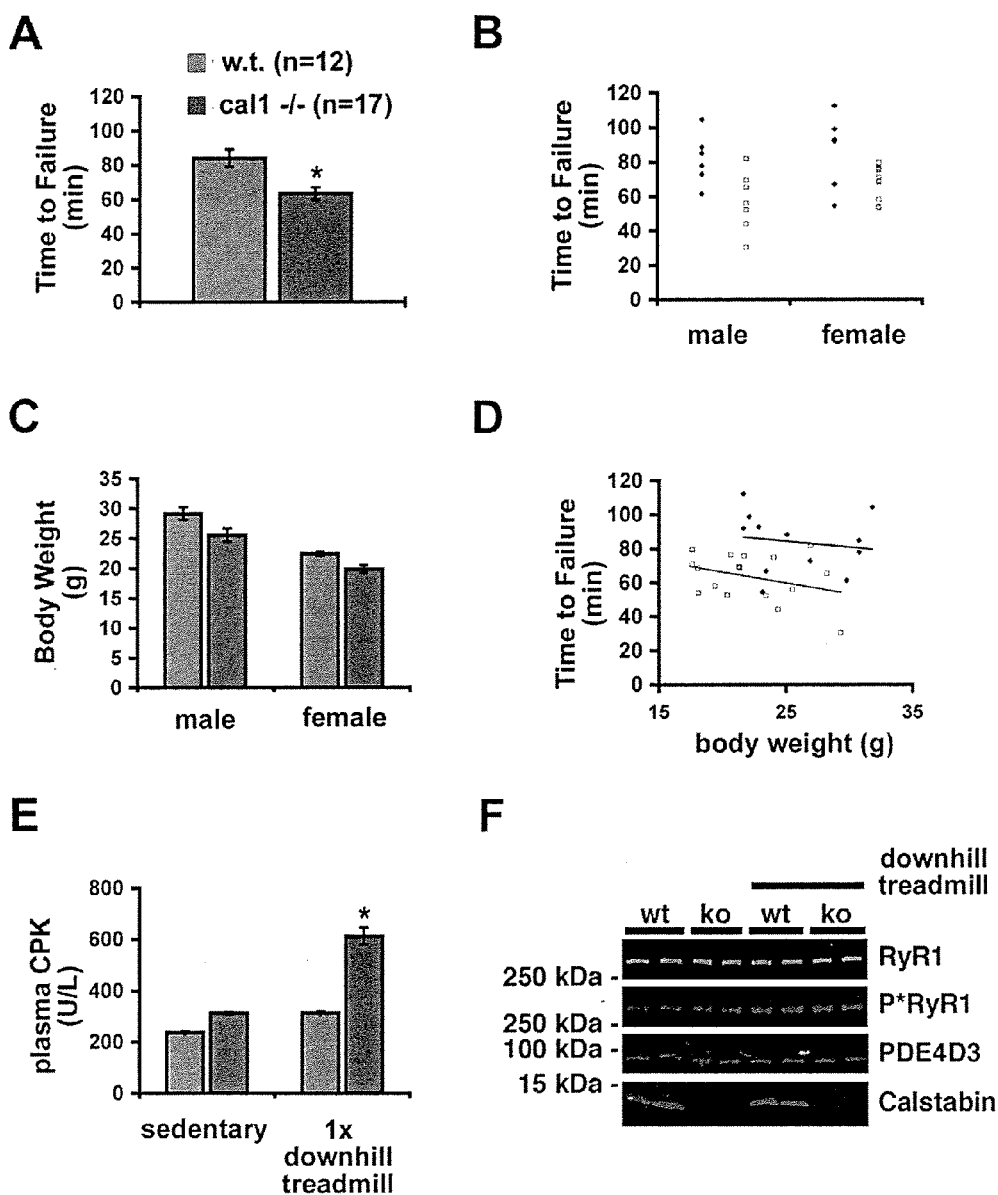
FIG. 45 shows that Muscle-specific Cal1−/− Mice Have a High Intensity Exercise Defect. A) Time to failure during a single level treadmill assay on 2 month-old cal1−/− mice and w.t. littermates. B) Individual treadmill failure times for each mouse separated by gender. C) Body weights of the cal1−/− mice were reduced. D) Scatter plot of failure time versus body weight shows no correlation in either group of mice. E) Plasma creatine kinase (CPK) levels at baseline and following a single downhill eccentric treadmill run. F) RyR1 immunoprecipitated from EDL and immunoblotted for RyR1, RyR1-pS2844, PDE4D3, and calstabin1. *, $p<0.01$, Wilcoxon rank-sum test.
Figure 46:
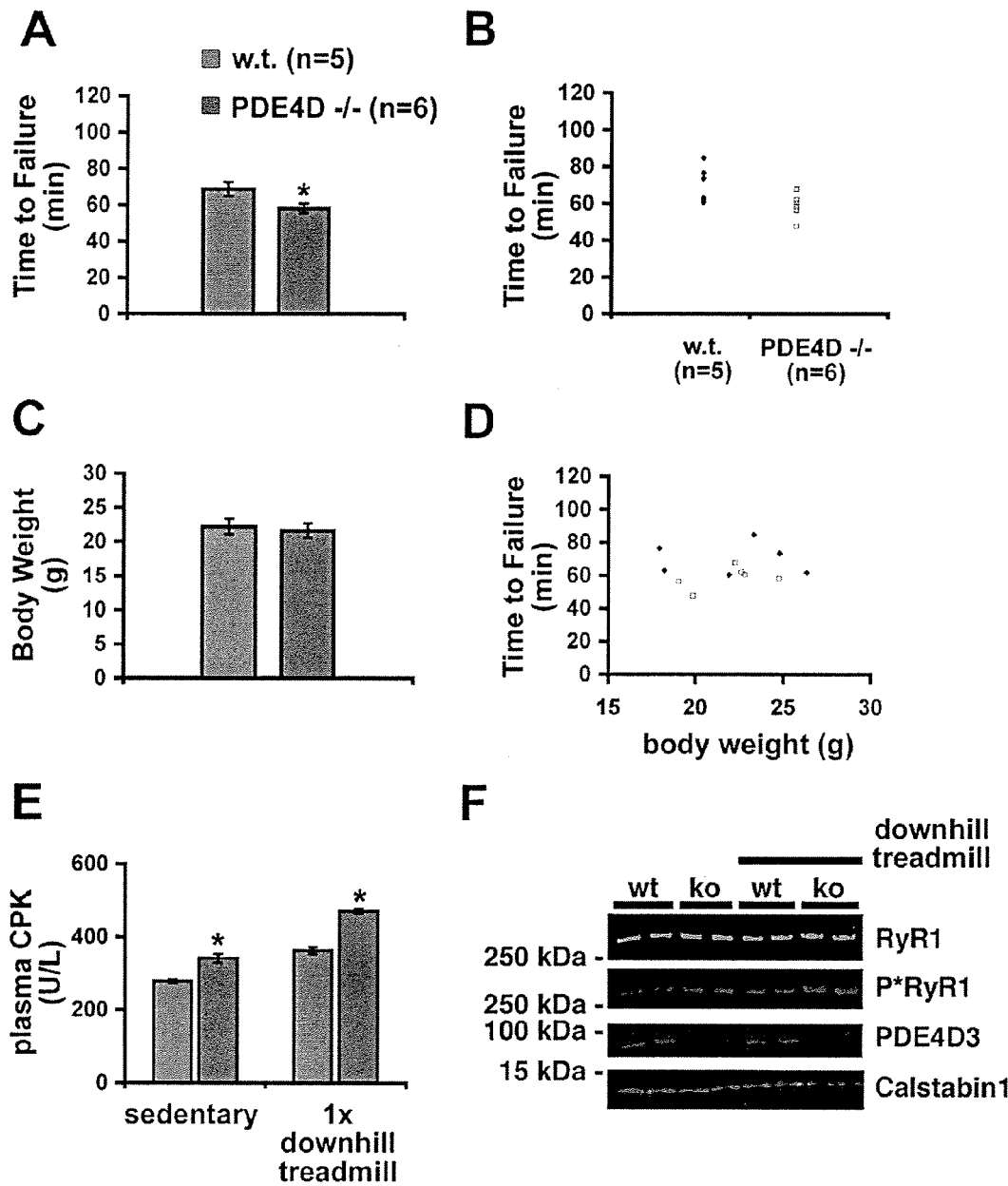
FIG. 46 shows that PDE4D−/− mice have an exercise defect. A) Time to failure during a single level treadmill assay on 2 month-old PDE4D−/− mice and w.t. littermates. B) Individual treadmill failure times for each mouse. C) Body weights of the PDE4D−/− mice. D) Scatter plot of failure time versus body weight shows no correlation in either group of mice. E) Plasma creatine kinase (CPK) levels at baseline and following a single downhill eccentric treadmill run. F) RyR1 immunoprecipitated from EDL and immunoblotted for RyR1, RyR1-pS2844, PDE4D3, and calstabin1. *, $p<0.05$, Wilcoxon rank-sum test.
Figure 47:
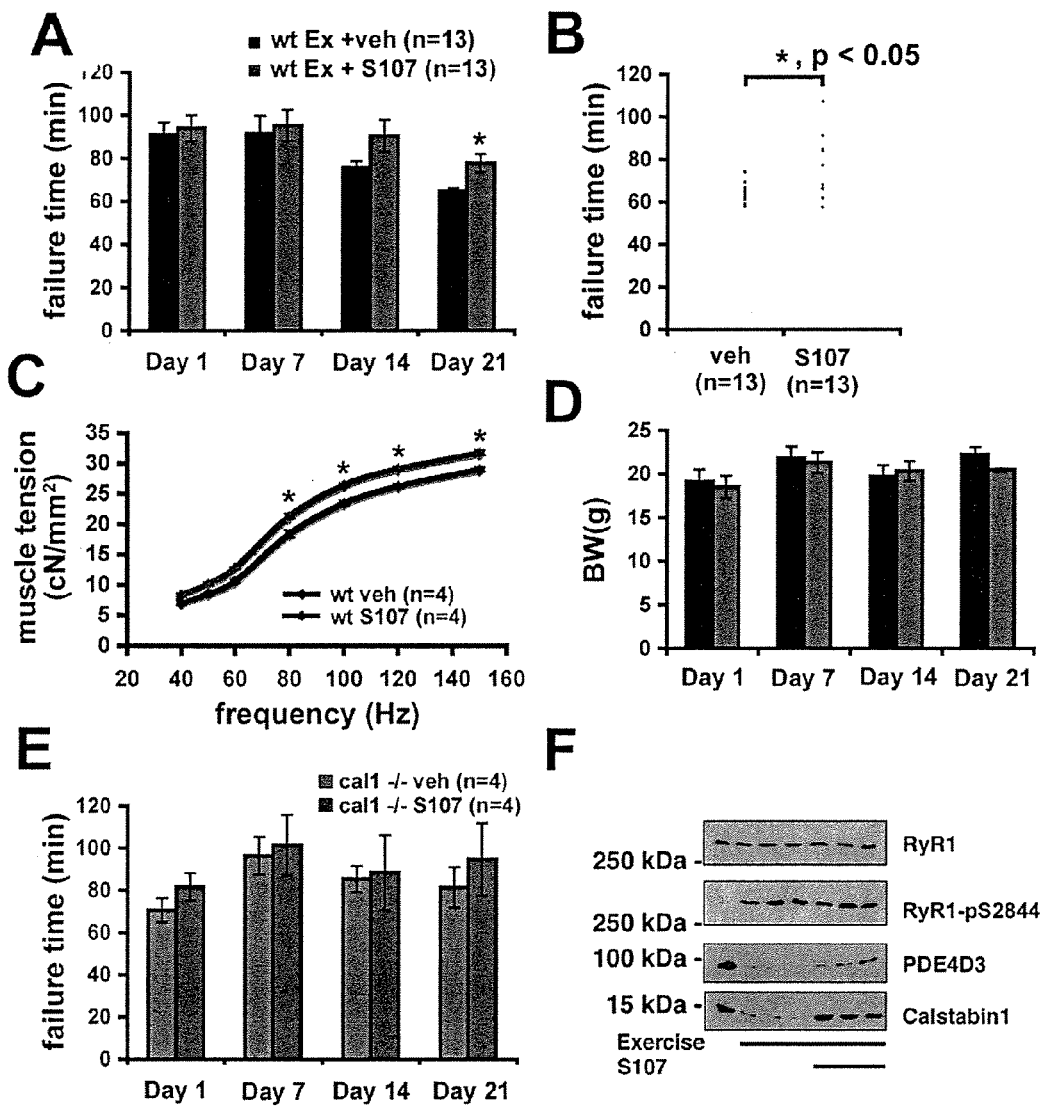
FIG. 47 shows that pharmacologic rebinding of calstabin1 to RyR1 improves in vivo exercise performance. A) Time to failure during treadmill assays on indicated days of a 28 day treatment trial with S107. B) Individual treadmill failure times for each mouse on Day 21. C) Force-frequency curves of EDL muscle isolated immediately following the 21st day of exercise and isometrically stimulated in an oxygenated muscle bath. Forces (cN) are normalized to muscle cross sectional area. D) Body weights throughout the trial showed no treatment effect. E) Treadmill failure times from a parallel experiment in muscle-specific cal1−/− mice. F) RyR1 immunoprecipitated from EDL and immunoblotted for RyR1, RyR1-pS2844, PDE4D3, and calstabin1. *, $p<0.01$, Wilcoxon rank-sum test.

In addition, the RyR1 macromolecular complex from extensor digitorum longus (EDL) muscle underwent remodeling, including depletion of calstabin1 and PDE4D3 from the channel by day 14 (FIGS. 43A and 43B). An identical pattern of biochemical changes was seen in all other hind limb skeletal muscles isolated from the same mice, including soleus, tibialis anterior, and gastrocnemius. RyR1 PKA hyperphosphorylation and depletion of calstabin1 and PDE4D3 were dependent on the intensity of the exercise, with only relatively high intensity exercise resulting in significant channel modifications (FIGS. 43C and 43D). Furthermore, the remodeling of the RyR1 channel complex persisted after exercise and recovered only partially following three days of rest after chronic exercise (FIG. 51A). PKA hyperphosphorylation of RyR1 was not due to changes in the amount of PKA and PP1 bound the RyR1 complex, as these levels were not affected by exercise conditions (FIGS. 51A and 51B). Calstabin 1 levels in whole muscle homogenate, measured by immunoblot, were not altered during exercise (FIG. 51C). Thus, intense daily exercise, over weeks causes remodeling of the RyR1 channel complex manifested by depletion of the phosphodiesterase PDE4D3 from the channel, PKA hyperphosphorylation, and depletion of the stabilizing subunit calstabin1 from the RyR1 channel complex.

RyR1 channel defects occur during human exercise: To assess whether the remodeling of the RyR1 channel macromolecular complex observed in exercised mice is relevant to human physiology, human thigh muscle biopsies were obtained from trained athletes before and after exercise on Days 1 and 3 of a high-intensity exercise protocol (cycling 3 hr/day at 57% of VO$_2$max) (Nieman, Henson et al. 2006). The human RyR1 macromolecular complex was immunoprecipitated from muscle homogenate, size fractionated by SDS-PAGE, and immunoblotted to assess RyR1 PKA phosphorylation and levels of calstabin1 and PDE4D3 in the RyR1 complex. High intensity exercise resulted in PKA hyperphosphorylation of RyR1 and calstabin1 depletion compared to controls who did not exercise (FIG. 44). Prior to exercise on Day 3, PKA phosphorylation of RyR1 in the trained cyclists was at or near resting levels and no significant calstabin1 depletion from the RyR1 complex was observed, however, PDE4D3 was stably depleted from the RyR1 complex by the beginning of the third day of the high intensity exercise (FIG. 44B). Thus, the same remodeling of the RyR1 channel complex observed in chronically exercised mice occurs in highly trained athletes subjected to intense exercise.

Muscle-specific calstabin1−/− mice have a high-intensity exercise defect: Muscle-specific deficiency of calstabin1 has been previously shown to be associated with alterations in the force-frequency relationships of isolated muscle preparations and a reduction in Cav1.1 current (Tang, Ingalls et al. 2004). To determine if calstabin1 binding to RyR1 has an effect on exercise performance, we assessed treadmill run to exhaustion times in mice with muscle-specific deficiency of calstabin1 (cal1−/−). There was a significant defect in the high intensity exercise capacity of cal1−/− mice compared to WT littermate controls (FIG. 45A). The exercise defect was similar in both males and females (FIG. 45B), and despite a small reduction in the body weights of the cal1−/− mice (FIG. 45C), there was no correlation between failure time and reduced body weight (FIG. 45D). The exercise defect was most apparent in high intensity exercise (treadmill speeds equal to or greater than 24 m/min) or in eccentric exercise such as 14 degree downhill treadmill runs. 0/2 cal1−/− mice were able to complete a 30 min downhill treadmill exercise protocol while 2/2 WT littermates were able to complete the protocol.

Twenty-four hours following a downhill exercise regimen (as described herein), plasma creatine kinase (CPK), was elevated consistent with increased muscle damage in the cal1−/− mice compared to WT littermate controls (FIG. 45E). Following several weeks of daily exercise training, the exercise capacity of WT mice approached that of cal1−/− presumably because of the progressive depletion of calstabin1 from the RyR1 complex that occurs with chronic exercise in WT mice (FIG. 43) resulting in an exercised-induced depletion of calstabin1 from the RyR1 channel complex that is comparable to that observed prior to exercise in the cal1−/− mice (FIG. 45F). Thus, muscle-specific calstabin1 deficient mice exhibit enhanced fatigue consistent with depletion of calstabin1 from the RyR1 complex playing a role in muscle fatigue.

PDE4D−/− mice exhibit an exercise defect: Global deficiency of PDE4D results in an age-dependent progressive cardiomyopathy (Lehnart, Wehrens et al. 2005). Prior to the age of three months, however, PDE4D−/− mice exhibit no cardiac defect as determined by echocardiogram or cardiac catheterization. The exercise capacity of 2 month-old PDE4D−/− mice was compared with their WT littermates. A significant reduction in exercise capacity was observed (FIG. 46A) without any correlation with body weight (FIG. 46B,C, D). Remarkably, CPK levels were increased, consistent with muscle damage at rest, in PDE4D−/− mice relative to WT littermate controls, and there was a significant increase in CPK levels 24 hours following a single episode of eccentric exercise consisting of thirty minutes of downhill treadmill running (FIG. 46E) in PDE4D−/− mice. PDE4D−/− mice exhibited an absence of RyR1 bound PDE4D3, a small increase in basal RyR1 PKA phosphorylation, and a significant increase in calstabin1 depletion following only a single day of mild exercise (FIG. 46F). These data show that PDE4D3 plays a significant role in the RyR1 complex by regulating the extent of PKA phosphorylation of RyR1 and that depletion of PDE4D3 from the channel complex during exercise promotes PKA phosphorylation of RyR1 which in turn contributes to muscle damage and skeletal muscle fatigue during exercise.

Pharmacologic rebinding of calstabin1 to RyR1 improves chronic exercise performance: Having demonstrated that a deficiency of calstabin1 is associated with an exercise defect and that chronic or high intensity exercise can result in calstabin1 depletion from RyR1, the effect on chronic or high intensity exercise performance of pharmacologic rebinding of calstabin1 to RyR1 was determined. 1,4-benzothiazepine derivatives, RyCal compounds, were screened to identify compounds with increased target activity, improved specificity (absence of activity against other known ion channels) and in vivo efficacy in terms of improved exercise capacity. Compound S107 at a concentration of 500 nM was found not to affect L-type calcium channel current or hERG potassium current.

Age and sex-matched WT mice were randomized to receive osmotic pumps containing either S107 or vehicle. Dosing with S107 at 2.5 ug/hr or vehicle was initiated four days prior to the beginning of a 21-day forced swimming exercise protocol. Exercise capacity was assessed once a week by a level treadmill run to exhaustion during the nocturnal cycle of the mouse. The mice were not exercised on the same day as treadmill assessments. FIG. 47A shows that calstabin1 rebinding with S107 had no acute effect on WT exercise performance, but that over time the S107 treated WT mice were relatively protected against a decline in treadmill exercise capacity that occurred in vehicle treated mice (p<0.05 Wilcoxon rank test, S107 vs. vehicle at Day 21). These studies are complicated by the training effect of repeated exercise which leads to improved performance due to enhanced musculature. Individual treadmill failure times on Day 21 are shown in FIG. 47B. Isometric force production was measured in EDL muscles in a tissue bath during field stimulation.

EDL muscles from S107 treated mice showed increased force production at stimulation frequencies greater than 80 Hz consistent with a left-shift of the force-frequency relationship (FIG. 47C). Drug treatment did not result in a change in body weight (FIG. 47D) or muscle weight. In parallel chronic exercise trials with mice deficient in calstabin1, S107 failed to improve treadmill performance (FIG. 47E). The chronic exercise protocol resulted in substantial PKA phosphorylation of RyR1 and calstabin1 depletion from immunoprecipitated RyR1. Calstabin1 depletion from RyR1 was nearly entirely reversed by S107 treatment (FIG. 47F). Taken together these data show that preventing the SR $Ca^{2+}$ leak due to PKA hyperphosphorylated RyR1 channel with a drug that enhances calstabin1 binding to the channel can protect against muscle damage, muscle fatigue, enhance muscle function and improve exercise performance during fatigue protocols.

Reduced fatiguability in calstabin1 rebound FDB muscle fibers: Flexor digitorum brevis (FDB) muscle fibers were enzymatically dissociated from mice following the chronic exercise protocol and loaded with the calcium indicator fluo-4. Individual muscle fibers were imaged on a Zeiss Live5 confocal microscope during field stimulation at 1 Hz and during a fatiguing protocol consisting of repeated 300 ms long 120 Hz tetani every 2 seconds for 400 seconds. Representative F/F0 traces during the fatigue protocol are shown for a FDB fiber isolated from a vehicle treated mouse (FIG. 48A) and a S107 treated mouse (FIG. 48B). FDB fibers from S107 treated mice exhibited a delayed decline in peak tetanic calcium transients (FIG. 48C). It is known that muscle fibers with slower kinetics of $Ca^{2+}$ release and reuptake are less prone to fatigue. The kinetics of $Ca^{2+}$ release and reuptake during single twitches at 1 Hz were assessed. The distribution of 50% reuptake times (tau) showed no significant differences between vehicle and S107 treatment (FIG. 52), indicating no shift in the calcium reuptake kinetics of the FDB fibers. These data indicate that treatment with S107 improves $Ca^{2+}$ handling in muscle fibers during fatigue protocols.

Figure 49A:
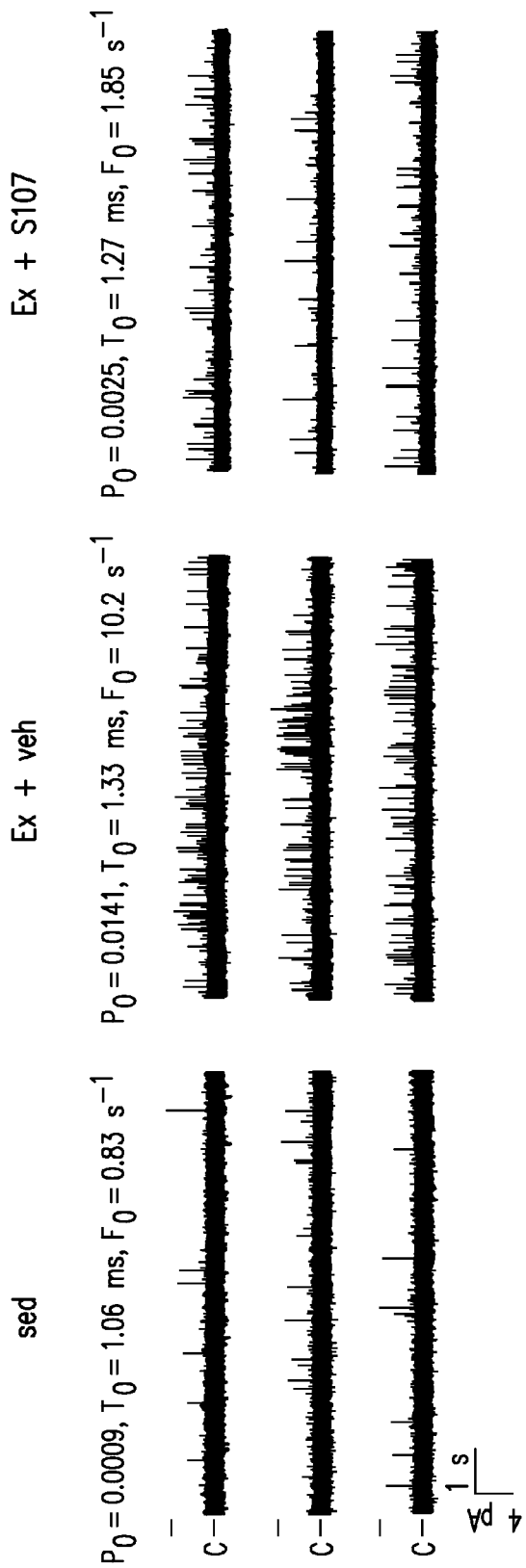
FIG. 49 shows that RyR1 from exercised muscle is leaky, with increased Po at resting calcium. (A) Representative traces of RyR1 channel activity at 90 nM [Ca2+]cis from sedentary mice (sed, left column), mice chronically exercised and treated with vehicle (Ex+veh, middle column) and with S107 (Ex+S107, right column). Single channel openings are plotted as upward deflections; the open and closed (c) states of the channel are indicated by horizontal bars at the beginning of the traces. Corresponding channel open probability (Po), mean open time (To) and frequency of openings (Fo) are shown above each group of traces and represent average values from all experiments. (B) Average values of open probability (left), mean open times (middle) and frequency of openings (right) of RyR1 activity from sedentary mice (sed, n=9) and mice chronically exercised treated either with vehicle (Ex+veh, n=9) or S107 (Ex+S107, n=12). Error bars indicate SEM; *, p<0.005 compared to sed; #, p<0.005 compared to Ex+S107.
Figure 51:
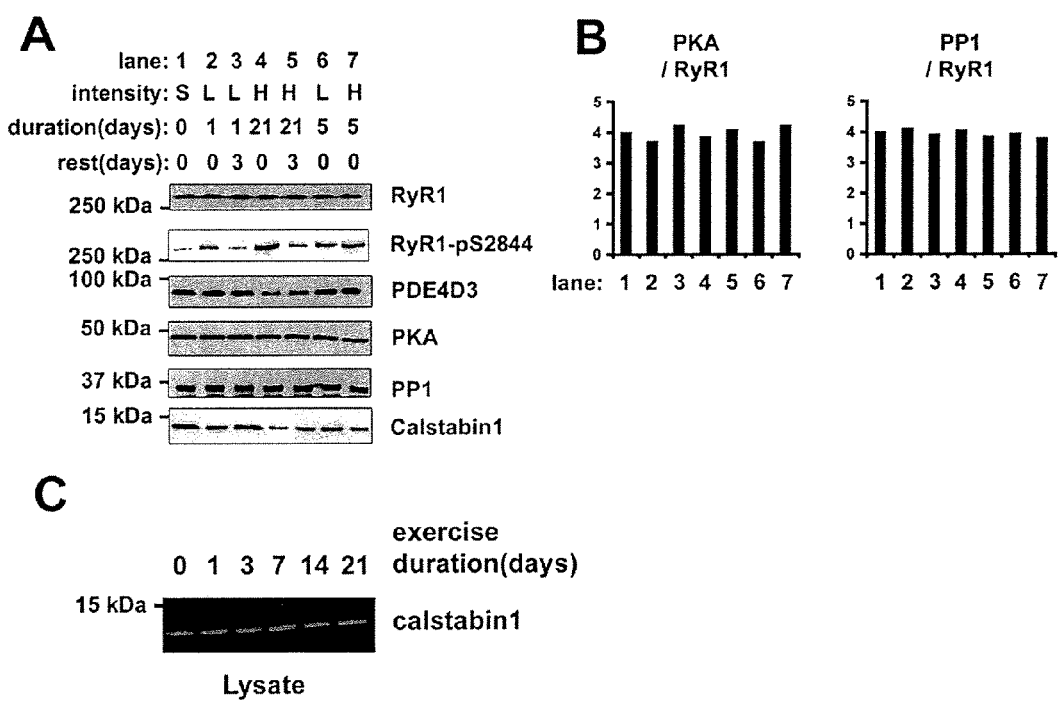
FIG. 51 shows the effect of exercise on the composition of the RyR1 complex.
Figure 52:
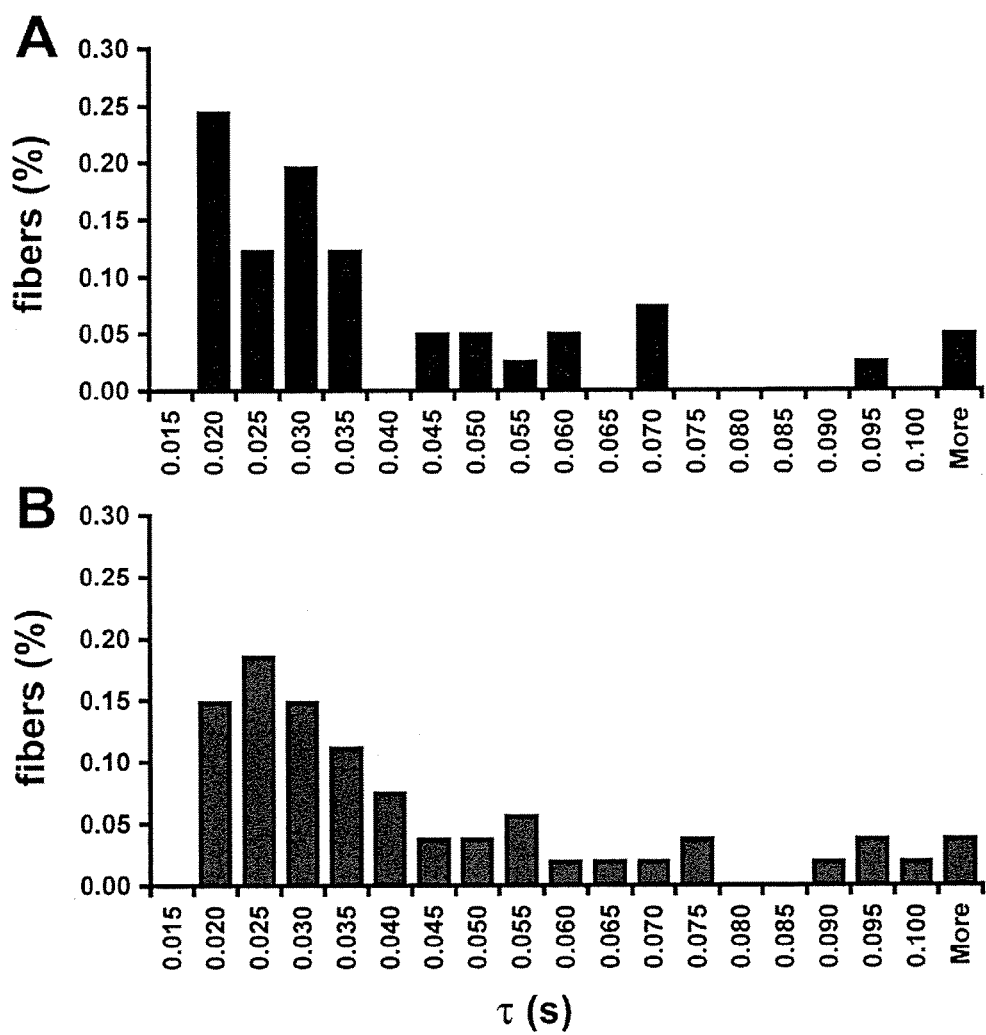
FIG. 52 shows the distribution of 50% reuptake times (tau) in muscle fibers in the presence or absence of S107 treatment.
Figure 53:
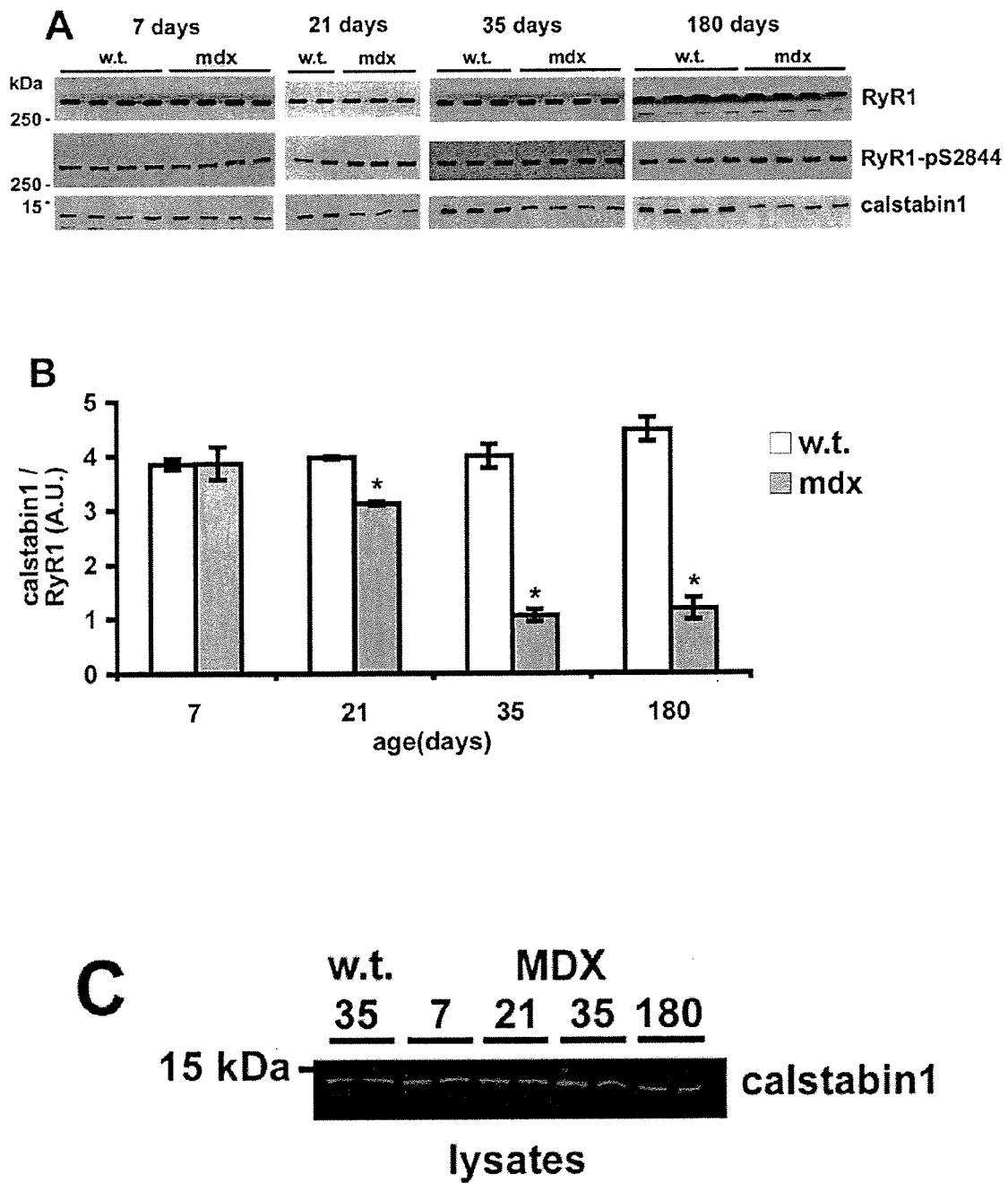
FIG. 53 shows the progressive phosphorylation of RyR1 and calstabin 1 depletion from the RyR1 complex in an mdx mouse model as a factor of time.
Figure 54:
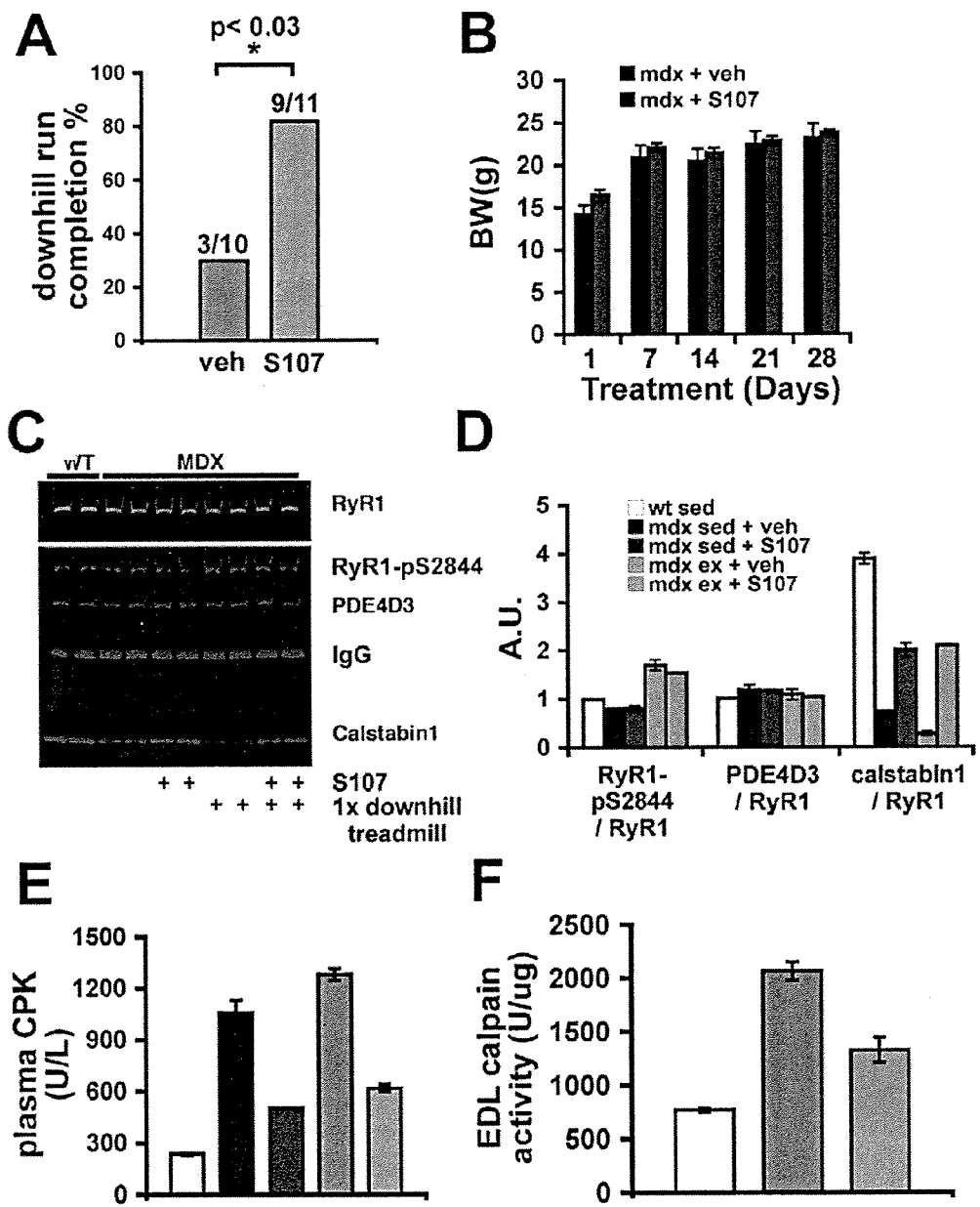
FIG. 54 shows the effect of S107 on exercise tolerance, body weight, CPK and calpain levels in wt (unaffected) and mdx mice.
Figure 55:
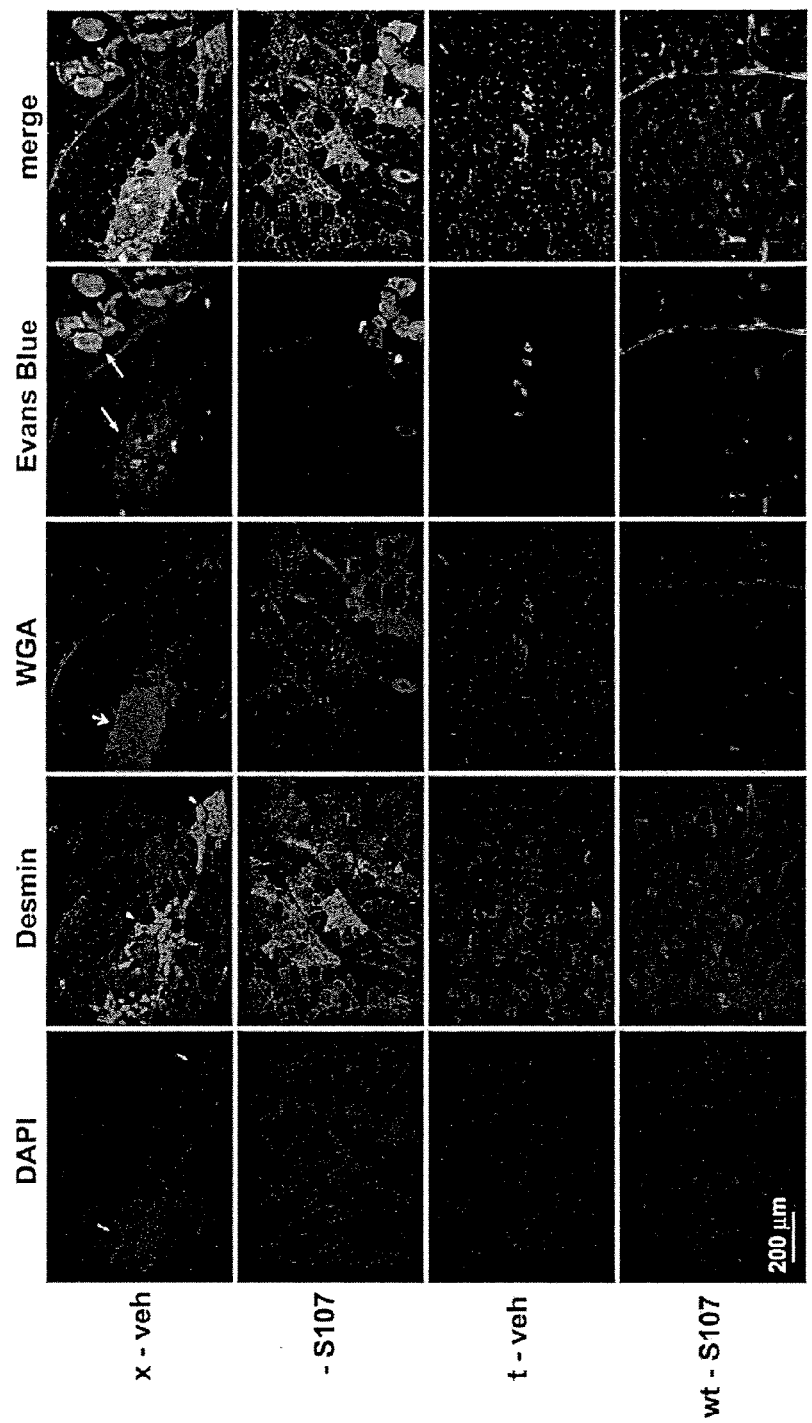
FIG. 55 shows histological slides of wt (unaffected) and mdx mice which are untreated or treated with S107.

Chronic exercise results in leaky RyR1 Channels which can be reversed by calstabin1 rebinding: A critical issue is whether the biochemical changes in the RyR1 macromolecular complex identified during exercise result in changes in RyR1 channel activity. To address this directly, SR microsomes were prepared from the hind limb muscle of sedentary mice, mice chronically exercised and treated with vehicle, and mice chronically exercised and treated with S107. Using standard techniques, vesicles were fused to planar lipid bilayers and the single channel activity of incorporated RyR1 channels was continuously measured for at least 10 minutes at 90 nM $[Ca^{2+}]_{cis}$ (FIG. 49A). In agreement with previously published data (Meissner, 1994, Reiken, 2003), the activity of RyR1 from sedentary mice at resting calcium concentrations was very low resulting in a small number of openings over long period of time (in some experiments as long as 20 min of recording was necessary to calculate an open probability for the channel). In contrast, RyR1 channels from mice chronically exercised and treated with vehicle displayed increased activity with significantly higher open probabilities ($p<0.005$, Ex+veh, n=9 vs sedentary, n=9) due to an increased frequency of openings (FIG. 49B). Administration of S107 caused a significant decrease of RyR1 open probability ($p<0.005$, Ex+S107, n=12 vs Ex+veh, n=9) to a level comparable to that observed in channels from sedentary mice. Neither chronic exercise nor S107 had any effect on the duration of the channel dwell times meaning that observed changes in open probability were due to changes in the number of opening events (FIG. 49B). These data show that RyR1 channels from exercised animals exhibit "leaky" channel behavior (increased open probability) and that channels from animals treated with S107 were not Reduced calpain activation in muscle tissue and reduced muscle tissue damage due to calstabin1 rebinding: One possible mechanism by which calcium released by leaky RyR1 channels impairs exercise performance is the activation of a member of the calpain family of $Ca^{2+}$-dependent neutral proteases, which are known to be responsible for muscle damage in a number of pathophysiological states. (Belcastro 1993; Berchtold, Brinkmeier et al. 2000). Calpain activity in muscle homogenates was assessed by means of the degradation of the synthetic calpain substrate Suc-LLVY-AMC, which fluoresces upon cleavage by calpain. Chronically exercised EDL muscle exhibited elevated calpain activity compared to sedentary controls. Calpain activity was significantly reduced in S107 treated and chronically exercised mice (FIG. 50A). Evidence of a protection from muscle damage was further provided by measurement of plasma CPK activity levels which were elevated in the chronically exercised mice, but reduced close to the levels observed in sedentary controls in the S107 treated mice (FIG. 50B). Muscle histology showed evidence of muscle hypertrophy with some inflammation and scattered loci of damaged fibers in the chronically exercise mice, without evidence of extensive necrosis in either treatment group.

Example 9

Muscular Dystrophy and Effects of S107

RyR1 calcium release channels become PKA hyperphosphorylated and depleted of the stabilizing protein calstabin1 during exercise. The compounds of the invention increase the binding affinity of calstabin1 to PKA hyperphosphorylated RyR1. These compounds (referred to as called "calcium channel stabilizers" or "rycal") are 1,4-benzothiazepines and derivatives thereof. Treatment with these compounds improves exercise performance of mice running on a treadmill. A calcium leak via PKA hyperphoshorylated RyR1 channels causes muscle damage due to activation of calcium-dependent proteases and rycals prevent the calcium leak and inhibit muscle damage during chronic exercise. Rycals can be used to improve muscle fatigue in chronic diseases including heart failure, AIDS, cancer, renal failure, and can also be used to treat muscular dystrophies.

Duchenne muscular dystrophy (DMD) is an X-linked muscle disease characterized by mutations in the dystrophin gene. Increased calcium-activated calpain proteolysis in the sarcolemma membrane is thought to be a primary mechanism in the pathophysiology of DMD. The mdx mouse, carrying a stop codon inside exon 23 of the dystrophin gene, provides a useful system to study the effectiveness of different therapeutic strategies for the cure of this disease.

A RyCal compound, S107, reduces calpain activity in mdx mice during exercise. FIGS. 42, 53, 54, 55 provide data from these studies. This indicates that RyCals may be useful for treating muscle related diseases, including, but not limited to, muscular dystrophies.

Animal Model: Mdx mice (21 days old) were treated with S107 (0.125 mg/kg/h) or vehicle using implantable, osmotic pumps for 28 days. After treatment, the mice were subjected to downhill (14° angel) treadmill running for 30 min at 18 m/min. Immediately after the exercise, the animals were sacrificed and the skeletal muscles were harvested.

Preparation of EDL Homogenates: EDL muscles homogenates were prepared in 0.5 ml of homogenization buffer (20 mM NaF, 10 mM Tris-maleate, pH7.2+protease inhibitors). Cardiac sarcoplasmic reticulum (CSR) fractions were obtained by centrifuging the homogenates at 50,000×g for 30 min. Homogenates were centrifuged at 4000×g for 20 min and the supernatants were centrifuged for 20 min at 10000×g. Aliquots of the homogenates were assayed for protein concentration and stored at −80° C.

Calpain Activity Assay: Calpain activity of EDL homogenates (30 µg) were measured using a Calpain Activity Assay kit (Calbiochem). The assay utilizes a synthetic calpain substrate, suc-LLVY-AMC. AMC is released upon cleavage with calpain and is measured fluorometrically. Assays are performed with both an activation and an inhibition buffer to determine specific calpain activity in the sample.

Serum Creatine Kinase: Serum (10 µl) proteins were separated using 4-20% PAGE. After transferring the proteins to nitrocellulose, the immunoblots were developed using an anti-creatine kinase Antibody (Research Diagnostics, 1:1000 dilution). Bands were quantified by densitometry.

Immunoprecipitation of Ryanodine Receptor: The ryanodine receptor (RyR1) was immunoprecipitated from samples by incubating 250 µg of EDL homogenate with anti-RyR antibody (2 µl 5029 Ab) in 0.5 ml of as modified RIPA buffer (50 mM Tris-HCl (pH 7.4), 0.9% NaCl, 5.0 mM NaF, 1.0 mM $Na_3VO_4$, 0.5% Triton-X100, and protease inhibitors) 1 hr at 4° C. The samples were incubated with Protein A sepharose beads (Ammersham Pharmacia Biotech, Piscatawy, N.J.) at 4° C. for 1 hour, after which, the beads were washed three times with RIPA. Samples were heated to 95° C. and size fractionated by PAGE.

Western Analysis: Samples (immunoprecipitates or 10 µg CSR) were heated to 95° C. and the proteins were size fractionated on 6% SDS PAGE for RYR and 15% PAGE for calstabin. Immunoblots were developed using antibodies against RyR (5029, 1:5000 dilution), PKA phosphorylated RyR (1:10000), or Calstabin (1:2000). Dilutions are made in 5% milk in TBS-T.

Example 10

Preparation of Tissue Lysates

Tissue lysates were prepared by homogenizing the tissue (e.g., brain, cardiac, muscle) with Tissuemiser in 0.7 ml lysis buffer (pH 7.4, 10 mM HEPES, 1 mM EDTA, 20 mM NaF, 2 mM $Na_3\ VO_4$, 320 mM sucrose, and protease inhibitors) and centrifuged for 15 min at 4,000×g at 4° C. The supernatant was then centrifuged for 15 min at 10,000×g at 4° C. For brain homogenates, the supernatant was centrifuged at 50,000×g at 4° C. for 30 minutes, and the pellet (microsomes) was resuspended in homogenization buffer which was supplemented with 0.9% NaCl. For brain tissue, the resuspended pellet was used for immunoprecipitation of RyR. For cardiac and muscle tissue homogenates, the supernatant of the 10,000×g spin was used for immunoprecipitation of the RyR. Protein concentrations were measured by Bradford protein assay. The sample was frozen at −80° C. until use.

Example 11

Immunoprecipitation of Ryanodine Receptors (RyRs)

100 µg of microsomes were brought to a volume of 500 µl with modified RIP A buffer (50 mM Tris-HCl (PH 7.4), 0.9% NaCl, 5.0 mM NaF, 1.0 mM $Na_3VO_4$, 0.5% TritonX100, and protease inhibitors). The ryanodine receptor was immunoprecipitated by adding 2 µl of anti-RyR antibody (5209) and rotating the sample for 1 hr at 4° C. The sample was incubated with 40 µl of Protein A Sepharose beads and rotated for 1 hr at 4° C. After washing the beads with 500 µl RIP A buffer three times, the resulted pellet was resuspended in 15 µl of 2×SDS sample buffer and boiled for 5 min.

For Western Blot Analysis, proteins were size fractionated on SDS-PAGE 4-20% gradient (BioRad). Immunoblots were developed with anti-FKBP and anti-RyR antibody or anti-phosphorylated FKBP.

Example 12

Effects of S107 on Spatial Learning and Cognitive Function

Figure 56:
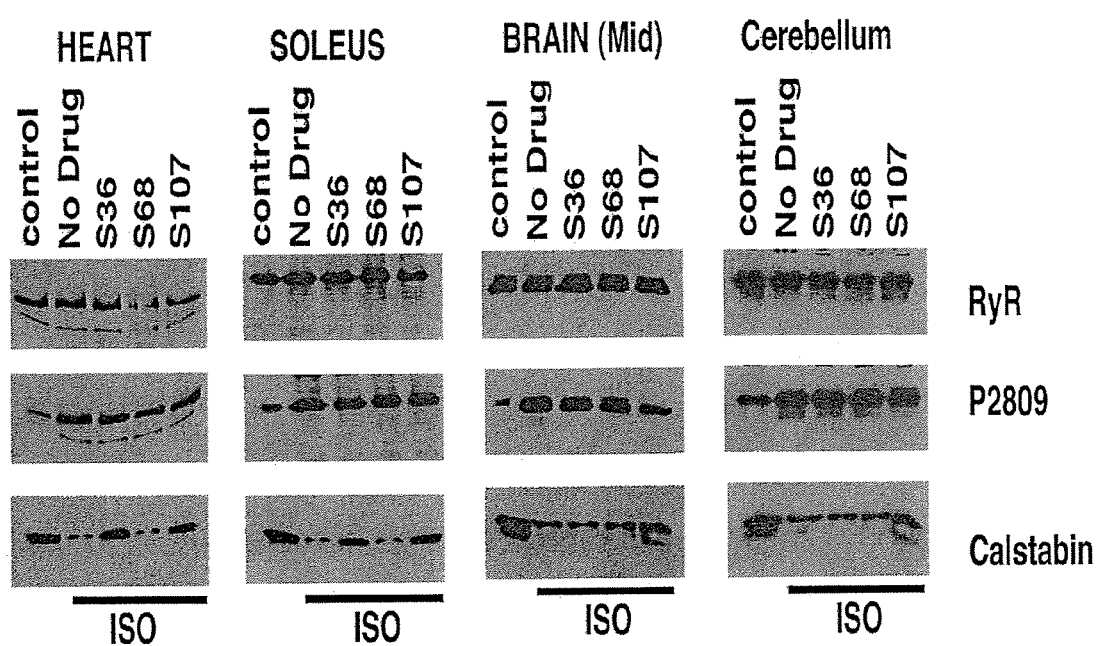
FIG. 56 provides data illustrating that the compound S107 crosses the blood brain barrier and enhances binding of calstabin to a RyR in the brain (mid-section and cerebellum) in vivo. Data from heart and soleus muscle are also illustrated.

Experiments were performed to determine whether the compounds described herein cross the blood brain barrier and enhance binding of cal stab in to ryanodine receptors in the brain. FIG. 56 shows the results of Western blots performed on RyR immunoprecipitated from the tissue samples indicated (i.e. heart, soleus muscle, mid-brain, and cerebellum). As illustrated in FIG. 56, the compound S107 crosses the blood brain barrier and restores in vivo binding of calstabin to RyR in both the mid-brain and the cerebellum, following depletion of calstabin from the RyR complex by treatment of the mice with isoproterenol ("ISO") by chronic infusion for 5 days. RyR was immunoprecipitated using an antibody to RyR, and the presence of calstabin in the immunoprecipitates was detected using an antibody to calstabin. The figure shows that the compound S107 penetrates the brain and restores in vivo binding of calstabin to RyR. Thus, S107 has calstabin rebinding activity in the brain.

Figure 57:
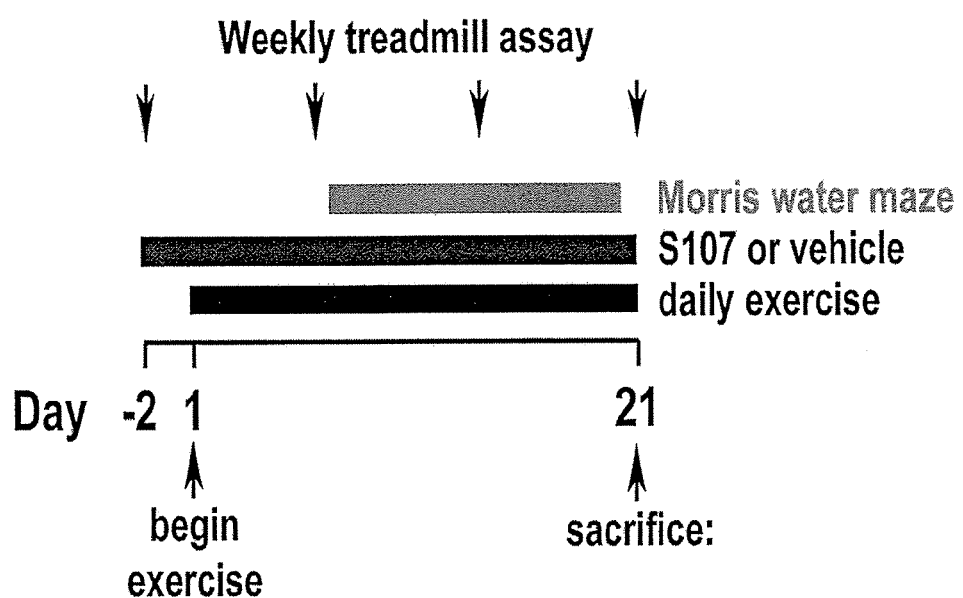
FIG. 57 provides a schematic representation of an experimental protocol used to test the effect of S107 on exercise performance and spatial learning in mice.

FIG. 57 provides a schematic representation of in vivo experiments used to test the effect of S107 on cognitive function in mice, using the Morris water maze system (described below in FIG. 58). 16 wild type C57BL/6J 3-month-old mice, pairwise-matched for sex, age, and body weight, were randomized to either S 107 treatment (10 mg/ml; 0.25 µl/hr subcutaneous osmotic pump) or "vehicle" (25% DMSO in $dH_2O$) treatment groups.

Two days after initiation of treatment, mice were subject to an exercise regimen for 21 days, and effect of S107 treatment was assayed by the weekly protocol as described below. Mice were sacrificed after 21 days for performing biochemistry, calcium imaging and ex vivo function studies.

FIG. 58 (A) provides a schematic representation of in vivo experiments used to test the effect of S107 on learning in the Morris water maze system. The layout of the water maze system consists of a circular water tank divided into four quadrants (labeled 1 thru 4 in FIG. 58, with four hidden platforms (labeled 5 to 8 in FIG. 58). The following protocol was followed: Day 1: mice trained to find "hidden" platform with visible marker on platform from random starting location. On days 2-4, the visible cue was removed, and mice were repeatedly challenged to find hidden platform at target 5 in quadrant 1. The time taken for each mouse to reach the target, i.e. the "latency," was recorded. On day 5, the previous day's protocol was repeated, then the hidden platform was removed, and each mouse's movements recorded to quantify time in various target regions. The protocol was repeated in week 2. The bar graphs at the bottom of FIG. 3 show the latency to target(s) (panel B) and mean velocity (cm/s) (panel C) for the vehicle and S107 treated groups at the end of the 21-day testing period.

The platform was then removed, and the swimming pattern of the mice was assessed at the end of the 21-day testing period. FIG. 59 shows a trend towards improved learning or increased persistence in S107-treated mice as compared to vehicle. FIG. 60 provides graphical data from the above experiments and shows a trend towards altered behavior consistent with improved learning and persistence in the S107-treated mice. p was approximately 0.2 vs. control (n=8 in both groups). The difference in permanence times between S107-treated and vehicle-treated mice does not appear to be due to swimming differences during the 2-minute probe learning assay.

Figure 61:
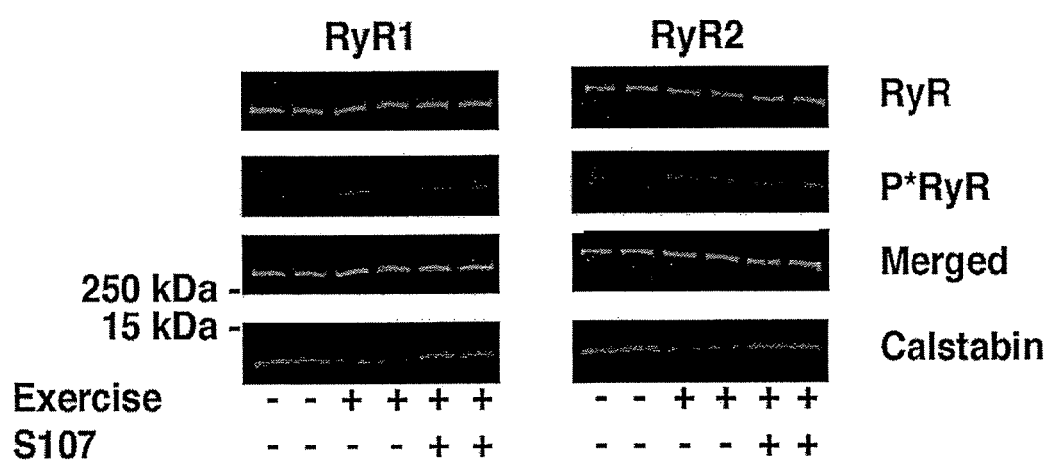
FIG. 61 is an immunoblot showing total RyR (types 1 and 2), phosphorylated RyR and calstabin (types 1 and 2) in control mice and mice subjected to an exercise regimen, with or without treatment with S 107. Whole brain microsomes were obtained. Immunoprecipitates were separated by 4-20% PAGE and analyzed for total RyR, PKA phosphorylated RyR, and calstabin.

FIG. 61 shows biochemical data for mice subjected to an exercise regimen in the absence and presence of S107 at the end of the 21-day testing period. Ryanodine receptor (types 1 and 2) was immunoprecipitated from whole brain microsomes. Immunoprecipitates were separated by 4-20% PAGE and analyzed for total RyR, PKA phosphorylated RyR, and calstabin. The figure shows exercised-induced RyR1 and RyR2 phosphorylation, accompanied with reduction in calstabin 1 or 2 binding. Treatment with S107 restores the binding of calstabin to RyR in exercised mice.

Example 13

Effects of Restraint Stress on PKA Phosphorylation at Different Stress Periods

Figure 62:
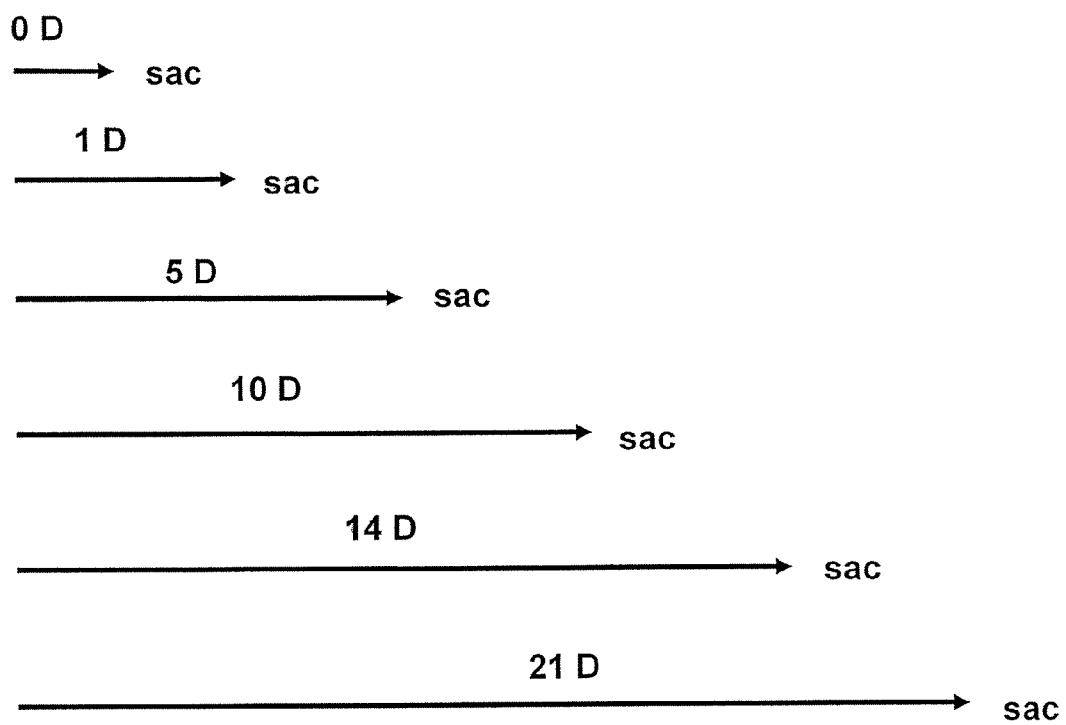
FIG. 62 provides a schematic representation of a protocol for evaluating the effects of restraint stress on PKA phosphorylation at different stress periods.

FIGS. 62-65 illustrate the effect of restraint stress on PKA phosphorylation at different stress periods. Restraint Stress Model: Chronic stress has been found to induce PKA phosphorylation of ryanodine receptors (RyRs) in cardiac (RyR2) and skeletal (RyR1) muscle cells. The effects of chronic stress on PKA phosphorylation of RyRs in the brain, however, have not been explored. The Restraint Stress Model is designed to investigate whether chronic stress induces PKA phosphorylation of neuronal RyRs. As shown in FIG. 62, twelve C57BL/6J wild type male mice were assigned to different stress groups (n=2/group), generating 6 groups. Five of the 6 groups were stressed and sacrificed at the end of each stress period: 1, 5, 10, 14, and 21 days of stress (respectively 1 D, 5 D, 10 D, 14D and 21 D). The remaining group served as control (0 D) that was not restrained, and was sacrificed together with the 1 D group. Subjects in each stress group were restraint stressed in Plexiglas restrainer tubes (10×2½×3¾ cm) 2 hr in the morning and 2 hr in the afternoon of each stress period. The two nonstressed control subjects were handled in their home cage. At the end of each stress period, subjects were sacrificed (sac) by $CO_2$ and their brains were immediately removed and frozen for later immunoblot analysis. RyR2 was immunoprecipitated from whole brain microsomes.

Figure 63:
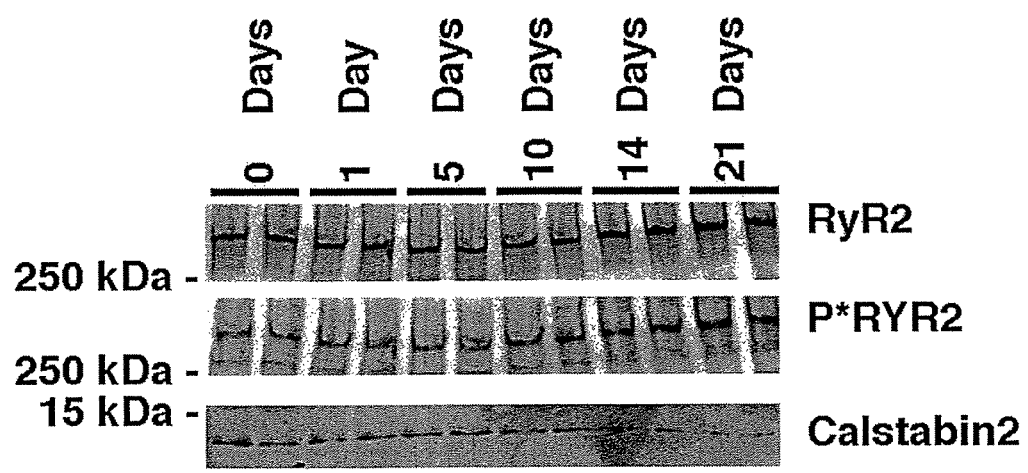
FIG. 63 shows PKA phosphorylation of RyR2 channels in brain following restraint induced stress in mice. Mice were restrained for time periods indicated. Ryanodine receptor (type2) was immunoprecipitated from whole brain microsomes. Immunoprecipitates were separated by 4-20% PAGE and analyzed for total RyR2, PKA phosphorylated RyR2, and calstabin2.

FIG. 63 shows the results of PKA phosphorylation of RyR2 channels in brain following restraint induced stress in mice. The mice were restrained for time periods as indicated. Ryanodine Receptor (type2) was immunoprecipitated from whole brain microsomes. Immunoprecipitates were separated by 4-20% PAGE and analyzed for total RyR2, PKA Phosphorylated RyR2, and calstabin2. FIG. 63 shows stress-induced RyR2 phosphorylation, accompanied with reduction in calstabin 2 binding.

Figure 64:
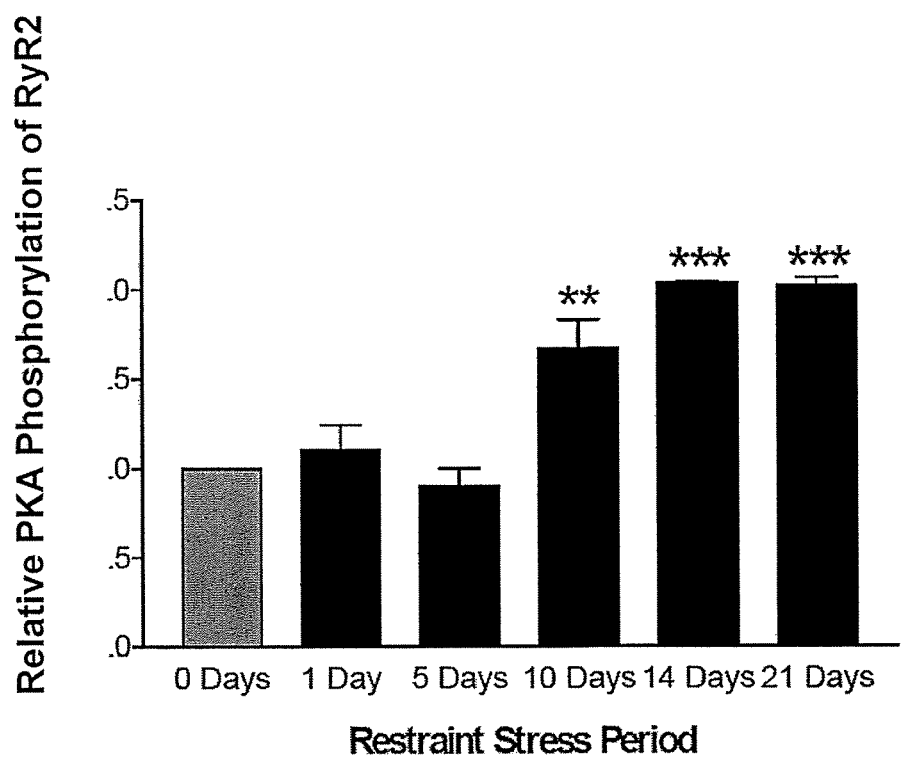
FIG. 64 shows the effect of chronic restraint stress (CRS) on relative PKA phosphorylation of RyR2 in brain. Total RyR2 and PKA phosphorylated RyR2 were quantified by densitometry of the immunoblot shown in FIG. 63. The bar graphs represent the relative PKA phosphorylation of the RyR2 channel, as determined by dividing the phosphorylation signal by the RyR2 signal. (* $P<0.001$;  $P<0.01$).
Figure 65:
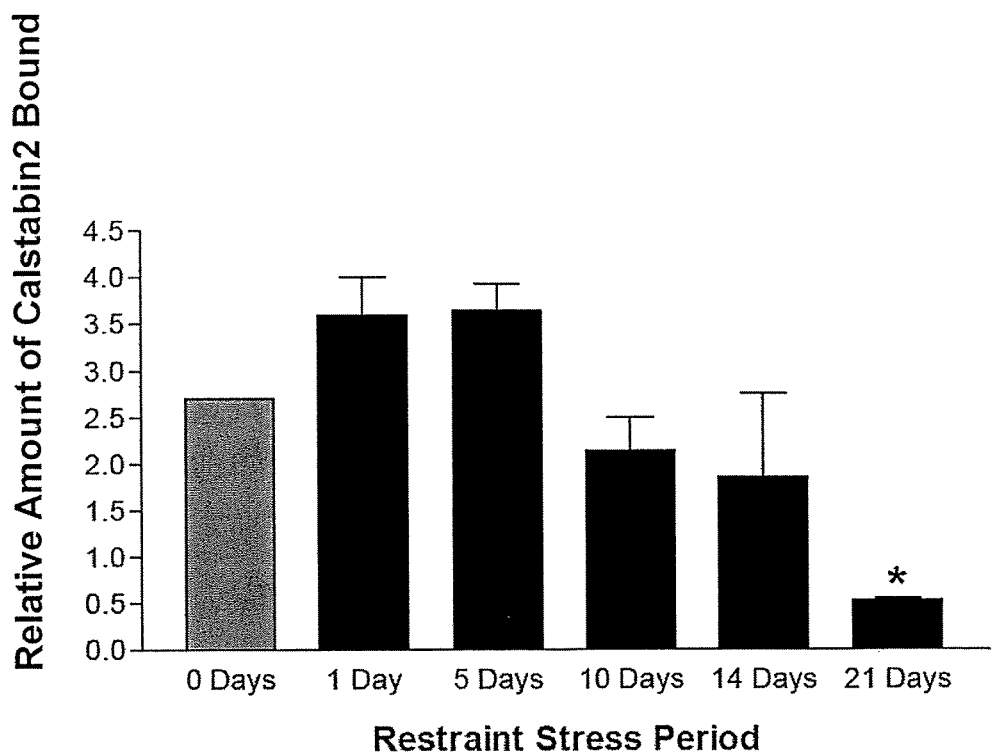
FIG. 65 shows the effects of chronic restraint stress (CRS) on calstabin2 binding to RyR2 in the brain. Total RyR2 and calstabin2 were quantified by densitometry of the immunoblot shown in FIG. 63. The bar graphs represent the relative amount of calstabin2 in the immunoprecipitates and were determined by dividing the calstabin signal by the RyR2 signal. (* $P<0.05$).

FIG. 64 is a bar graph summarizing the relative amounts of PKA phosphorylation of RyR2 from FIG. 63. The relative phosphorylation of RyR2 is represented using arbitrary units. A one-way ANOVA shows that there was a significant difference between groups [T(5,6)=27.58, P<0.0005]. Fisher's LSD post hoc test reveals that 14 and 21 days of chronic restraint stress (CRS) induced the highest PKA phosphorylation of RyR2 in the brain, where * (P<0.001) and  (P<0.01) compared with nonstressed controls (0 days). FIG. 65 is a bar graph summarizing the relative amounts of calstabin2 bound to RyR2 from FIG. 63. A one-way ANOVA also shows a group difference between the stress periods [T(5,6)= 5.91, P<0.037]. Fisher's LSD post hoc test reveals that only the 21 days of CRS showed the lowest calstabin2 binding to the RyR2 where * (P<0.05) compared with nonstressed controls (0 days).

All publications, references, patents and patent applications cited herein are incorporated by reference in their entirety to the same extent as if each individual application, patent or patent application was specifically and individually indicated to be incorporated by reference in its entirety.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A compound which is selected from the group consisting of formula I-g, I-h, I-k-1, I-l-1, or I-m-1: wherein
   (a) the compound of formula I-g or I-h is:

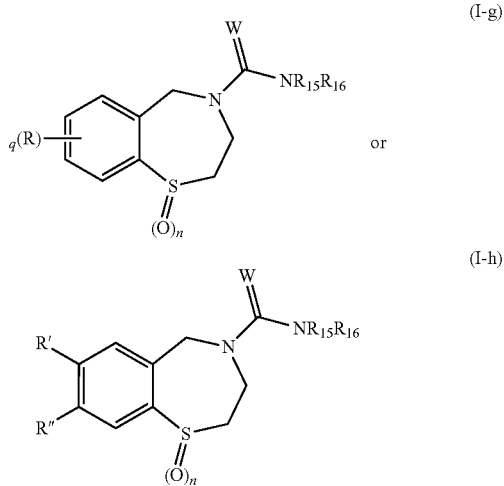

wherein W is S or O;

n is 0, 1, or 2;

q is 0, 1, 2, 3, or 4;

each R is located at position 6, 7, 8 or 9 on the benzothiazepine ring;

each R is independently selected from the group consisting of halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino; wherein each acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino may be substituted or unsubstituted;

R$_{15}$ and R$_{16}$ independently are selected from the group consisting of H, acyl, alkenyl, alkoxyl, OH, NH$_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally R$_{15}$ and R$_{16}$ together with the N to which they are bonded may form a heterocycle which may be substituted or unsubstituted; and R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heteroaryl, heterocyclyl, heterocyclylalkyl, alkenyl, alkynyl, (hetero-)arylthio, and (hetero-)arylamino; wherein each acyl, alkyl, alkoxyl, alkylamino, cycloalkyl, aryl, heteroaryl, heterocyclyl, heterocyclylalkyl, alkenyl, alkynyl, and (hetero-)arylthio may be substituted or unsubstituted;

provided that when q is 0 and n is 0, then —C(=W)NR$_{15}$R$_{16}$ is not —C(=O)NH$_2$, —C(=O)NHPh, —C(=S)NH-nButyl, or —C(=O)NHC(=O)CH$_2$Cl;

when q is 0, n is 0 or 2, then —C(=W)NR$_{15}$R$_{16}$ is not —C=ONHPh, —C=ONHCOCH$_2$Cl, —C=ONH$_2$, —C=ONH(n-Bu), —C=S(NHPh), —C=S(NHCOCH$_2$Cl), —C=S(NH$_2$), or —C=SNH(n-Bu);

(b) the compound of formula I-k-1 is:

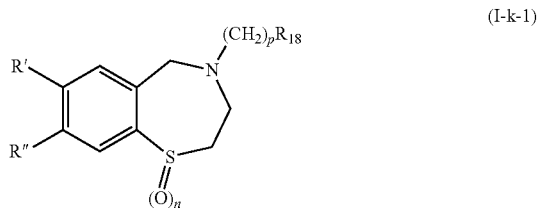

wherein n is 0, 1, or 2;

R$_{18}$ is selected from the group consisting of —NR$_{15}$R$_{16}$, —C(=O)—NR$_{15}$R$_{16}$, —OR$_{15}$, —C(=O)—OR$_{15}$, alkyl, aryl, cycloalkyl and heterocyclyl, wherein each alkyl, aryl, cycloalkyl and heterocyclyl may be unsubstituted or substituted;

R$_{15}$ and R$_{16}$ independently are selected from the group consisting of H, acyl, alkenyl, alkoxyl, OH, NH$_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally R$_{15}$ and R$_{16}$ together with the N to which they are bonded may form a heterocycle which may be substituted or unsubstituted;

p is 1, 2, 3, 4, 5, 6, 7, 8, 9 or 10;

R' is selected from the group consisting of halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heteroaryl, heterocyclyl, heterocyclylalkyl, alkenyl, alkynyl, (hetero-)arylthio, and (hetero-)arylamino; wherein each acyl, alkyl, alkoxyl, alkylamino, cycloalkyl, aryl, heteroaryl, heterocyclyl, heterocyclylalkyl, alkenyl, alkynyl, and (hetero-)arylthio may be substituted or unsubstituted; and R" is H;

provided that when n is 0, and R' is OH or C$_1$-C$_3$ alkoxyl, then —(CH$_2$)$_p$—R$_{18}$ is not —(CH$_2$)$_{3-4}$-benzylpiperidine;

(c) the compound of formula I-l-1 is:

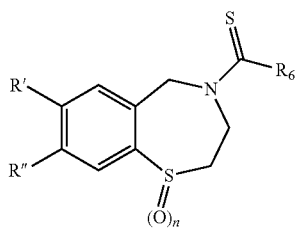

(I-l-1)

wherein n is 0, 1, or 2;

$R_6$ is selected from the group consisting of —$OR_{15}$, —$NHNR_{15}R_{16}$, —NHOH, —$CH_2X$, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted or unsubstituted;

$R_{15}$ and $R_{16}$ independently are selected from the group consisting of H, acyl, alkenyl, alkoxyl, OH, $NH_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally $R_{15}$ and $R_{16}$ together with the N to which they are bonded may form a heterocycle which may be substituted or unsubstituted;

X is selected from the group consisting of halogen, —CN, —$CO_2R_{15}$, —$C(=O)NR_{15}R_{16}$, —$NR_{15}R_{16}$, —$OR_{15}$, —$SO_2R_7$, and —$P(=O)R_8R_9$;

$R_7$ is selected from the group consisting of —$OR_{15}$, —$NR_{15}R_{16}$, —$NHNR_{15}R_{16}$, —NHOH, alkyl, alkenyl, alkynyl, aryl, cycloalkyl, cycloalkylalkyl, heterocyclyl, and heterocyclylalkyl; wherein each alkyl, alkenyl, alkynyl, aryl, cycloalkyl, cycloalkylalkyl, heterocyclyl, and heterocyclylalkyl may be substituted or unsubstituted;

$R_8$ and $R_9$ independently are selected from the group consisting of OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and R' and R" are independently selected from the group consisting of H, halogen, —OH, —$NH_2$, —$NO_2$, —CN, —$CF_3$, —$OCF_3$, —$N_3$, —$SO_3H$, —$S(=O)_2$alkyl, —$S(=O)$alkyl, —$OS(=O)_2CF_3$, acyl, alkyl, alkoxyl, alkylamino, alkylthio, cycloalkyl, aryl, heteroaryl, heterocyclyl, heterocyclylalkyl, alkenyl, alkynyl, (hetero-)arylthio, and (hetero-)arylamino; wherein each acyl, alkyl, alkoxyl, alkylamino, cycloalkyl, aryl, heteroaryl, heterocyclyl, heterocyclylalkyl, alkenyl, alkynyl, and (hetero-) arylthio may be substituted or unsubstituted; or (d) the compound of formula I-m-1 is:

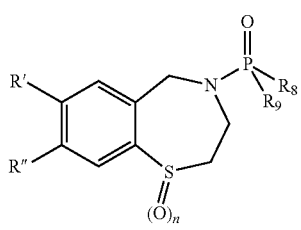

(I-m-1)

wherein n is 0, 1, or 2;

$R_8$ and $R_9$ independently are selected from the group consisting of OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted;

R' and R" are independently selected from the group consisting of H, halogen, —OH, —$NH_2$, —$NO_2$, —CN, —$CF_3$, —$OCF_3$, —$N_3$, —$SO_3H$, —$S(=O)_2$alkyl, —$S(=O)$alkyl, —$OS(=O)_2CF_3$, acyl, alkyl, alkoxyl, alkylamino, alkylthio, cycloalkyl, aryl, heteroaryl, heterocyclyl, heterocyclylalkyl, alkenyl, alkynyl, (hetero-)arylthio, and (hetero-) arylamino; wherein each acyl, alkyl, alkoxyl, alkylamino, cycloalkyl, aryl, heteroaryl, heterocyclyl, heterocyclylalkyl, alkenyl, alkynyl, and (hetero-) arylthio may be substituted or unsubstituted.

2. The compound of claim 1 having the formula of I-g or I-h:

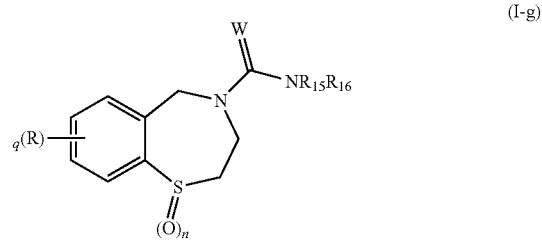

(I-g)

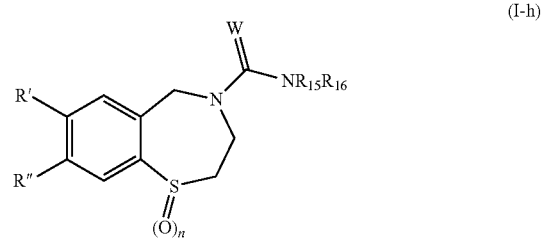

(I-h)

wherein W is S or O;

n is 0, 1, or 2;

q is 0, 1, 2, 3, or 4;

each R is located at position 6, 7, 8 or 9 on the benzothiazepine ring;

each R is independently selected from the group consisting of halogen, —OH, —$NH_2$—$NO_2$, —CN, —$CF_3$—$OCF_3$, —$N_3$—$SO_3H$, —$S(=O)_2$alkyl, —$S(=O)$alkyl, —$OS(=O)_2CF_3$, acyl, alkyl, alkoxyl, alkylamino, alkylthio, cycloalkyl, aryl, heterocyclyl, heterocyclylalkyl, alkenyl, alkynyl, (hetero-) aryl, (hetero-)arylthio, and (hetero-)arylamino; wherein each acyl, alkyl, alkoxyl, alkylamino, alkylthio, cycloalkyl, aryl, heterocyclyl, heterocyclylalkyl, alkenyl, alkynyl, (hetero-)aryl, (hetero-)arylthio, and (hetero-)arylamino may be substituted or unsubstituted;

$R_{15}$ and $R_{16}$ independently are selected from the group consisting of H, acyl, alkenyl, alkoxyl, OH, $NH_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally $R_{15}$ and $R_{16}$ together with the N to which they are bonded may form a heterocycle which may be substituted or unsubstituted; and R' and R" are independently selected from the group consisting of H, halogen, —OH, —NH$_2$, —NO$_2$, —CN, —CF$_3$, —OCF$_3$, —N$_3$, —SO$_3$H, —S(═O)$_2$alkyl, —S(═O)alkyl, —OS(═O)$_2$CF$_3$, acyl, alkyl, alkoxyl, alkylamino, alkylthio, cycloalkyl, aryl, heteroaryl, heterocyclyl, heterocyclylalkyl, alkenyl, alkynyl, (hetero-)arylthio, and (hetero-) arylamino; wherein each acyl, alkyl, alkoxyl, alkylamino, cycloalkyl, aryl, heteroaryl, heterocyclyl, heterocyclylalkyl, alkenyl, alkynyl, and (hetero-) arylthio may be substituted or unsubstituted.

3. The compound of claim 2, wherein W is O.

4. The compound of claim 3, wherein R$_{15}$ and R$_{16}$ independently are selected from the group consisting of H, OH, NH$_2$, alkyl, alkylamino, aryl, cycloalkyl, cycloalkylalkyl, heterocyclyl, and heterocyclylalkyl; wherein each alkyl, alkylamino, aryl, cycloalkyl, cycloalkylalkyl, heterocyclyl, and heterocyclylalkyl may be substituted; and optionally R$_{15}$ and R$_{16}$ together with the N to which they are bonded may form a heterocycle which may be substituted.

5. The compound of claim 1, having the formula I-k-1:

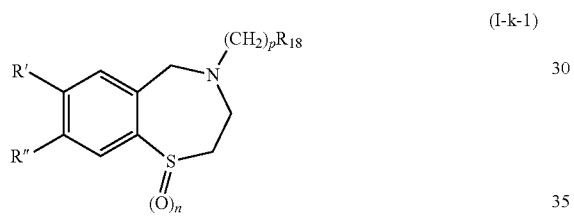

(I-k-1)

wherein n is 0, 1, or 2;

R$_{18}$ is selected from the group consisting of —NR$_{15}$R$_{16}$, —C(═O)—NR$_{15}$R$_{16}$, —OR$_{15}$, —C(═O)—OR$_{15}$, alkyl, aryl, cycloalkyl and heterocyclyl, wherein each alkyl, aryl, cycloalkyl and heterocyclyl may be unsubstituted or substituted;

R$_{15}$ and R$_{16}$ independently are selected from the group consisting of H, acyl, alkenyl, alkoxyl, OH, NH$_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally R$_{15}$ and R$_{16}$ together with the N to which they are bonded may form a heterocycle which may be substituted or unsubstituted;

p is 1, 2, 3, 4, 5, 6, 7, 8, 9 or 10;

R' is selected from the group consisting of halogen, —OH, —NH$_2$, —NO$_2$, —CN, —CF$_3$, —OCF$_3$, —N$_3$, —SO$_3$H, —S(═O)$_2$alkyl, —S(═O)alkyl, —OS(═O)$_2$CF$_3$, acyl, alkyl, alkoxyl, alkylamino, alkylthio, cycloalkyl, aryl, heteroaryl, heterocyclyl, heterocyclylalkyl, alkenyl, alkynyl, (hetero-)arylthio, and (hetero-) arylamino; wherein each acyl, alkyl, alkoxyl, alkylamino, cycloalkyl, aryl, heteroaryl, heterocyclyl, heterocyclylalkyl, alkenyl, alkynyl, and (hetero-) arylthio may be substituted or unsubstituted; and R" is H.

6. The compound of claim 1 having the formula I-l-1:

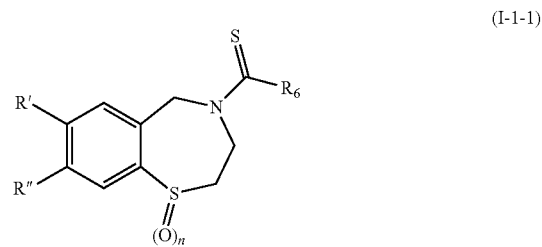

(I-1-1)

wherein n is 0, 1, or 2;

R$_6$ is selected from the group consisting of —OR$_{15}$, —NHNR$_{15}$R$_{16}$, —NHOH, —CH$_2$X, acyl, alkenyl, alkyl, aryl, cycloalkyl, cycloalkylalkyl, heterocyclyl, and heterocyclylalkyl; wherein each acyl, alkenyl, alkyl, aryl, cycloalkyl, cycloalkylalkyl, heterocyclyl, and heterocyclylalkyl may be substituted or unsubstituted;

R$_{15}$ and R$_{16}$ independently are selected from the group consisting of H, acyl, alkenyl, alkoxyl, OH, NH$_2$, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and optionally R$_{15}$ and R$_{16}$ together with the N to which they are bonded may form a heterocycle which may be substituted or unsubstituted;

X is selected from the group consisting of halogen, —CN, —CO$_2$R$_{15}$, —C(═O)NR$_{15}$R$_{16}$, —NR$_{15}$R$_{16}$, —OR$_{15}$, —SO$_2$R$_7$, and —P(═O)R$_8$R$_9$;

R$_7$ is selected from the group consisting of —OR$_{15}$, —NR$_{15}$R$_{16}$, —NHNR$_{15}$R$_{16}$, —NHOH, alkyl, alkenyl, alkynyl, aryl, cycloalkyl, cycloalkylalkyl, heterocyclyl, and heterocyclylalkyl; wherein each alkyl, alkenyl, alkynyl, aryl, cycloalkyl, cycloalkylalkyl, heterocyclyl, and heterocyclylalkyl may be substituted or unsubstituted;

R$_8$ and R$_9$ independently are selected from the group consisting of OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted; and R' and R" are independently selected from the group consisting of H, halogen, —OH, —NH$_2$, —NO$_2$, —CN, —CF$_3$, —OCF$_3$, —N$_3$, —SO$_3$H, —S(═O)$_2$alkyl, —S(═O)alkyl, —OS(═O)$_2$CF$_3$, acyl, alkyl, alkoxyl, alkylamino, alkylthio, cycloalkyl, aryl, heteroaryl, heterocyclyl, heterocyclylalkyl, alkenyl, alkynyl, (hetero-)arylthio, and (hetero-)arylamino; wherein each acyl, alkyl, alkoxyl, alkylamino, cycloalkyl, aryl, heteroaryl, heterocyclyl, heterocyclylalkyl, alkenyl, alkynyl, and (hetero-) arylthio may be substituted or unsubstituted.

7. The compound of claim 1 having the formula I-m-1:

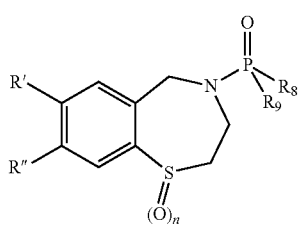

(I-m-1)

wherein
n is 0, 1, or 2;
R$_8$ and R$_9$ independently are selected from the group consisting of OH, acyl, alkenyl, alkoxyl, alkyl, alkylamino, aryl, cycloalkyl, cycloalkylalkyl, heterocyclyl, and heterocyclylalkyl; wherein each acyl, alkenyl, alkoxyl, alkyl, alkylamino, aryl, cycloalkyl, cycloalkylalkyl, heterocyclyl, and heterocyclylalkyl may be substituted or unsubstituted;

R' and R" are independently selected from the group consisting of H, halogen, —OH, —NH$_2$, —NO$_2$, —CN, —CF$_3$, —OCF$_3$, —N$_3$, —SO$_3$H, —S(=O)$_2$alkyl, —S(=O)alkyl, —OS(=O)$_2$CF$_3$, acyl, alkyl, alkoxyl, alkylamino, alkylthio, cycloalkyl, aryl, heteroaryl, heterocyclyl, heterocyclylalkyl, alkenyl, alkynyl, (hetero-)arylthio, and (hetero-) arylamino; wherein each acyl, alkyl, alkoxyl, alkylamino, cycloalkyl, aryl, heteroaryl, heterocyclyl, heterocyclylalkyl, alkenyl, alkynyl, and (hetero-) arylthio may be substituted or unsubstituted.

8. A compound selected from the group consisting of:

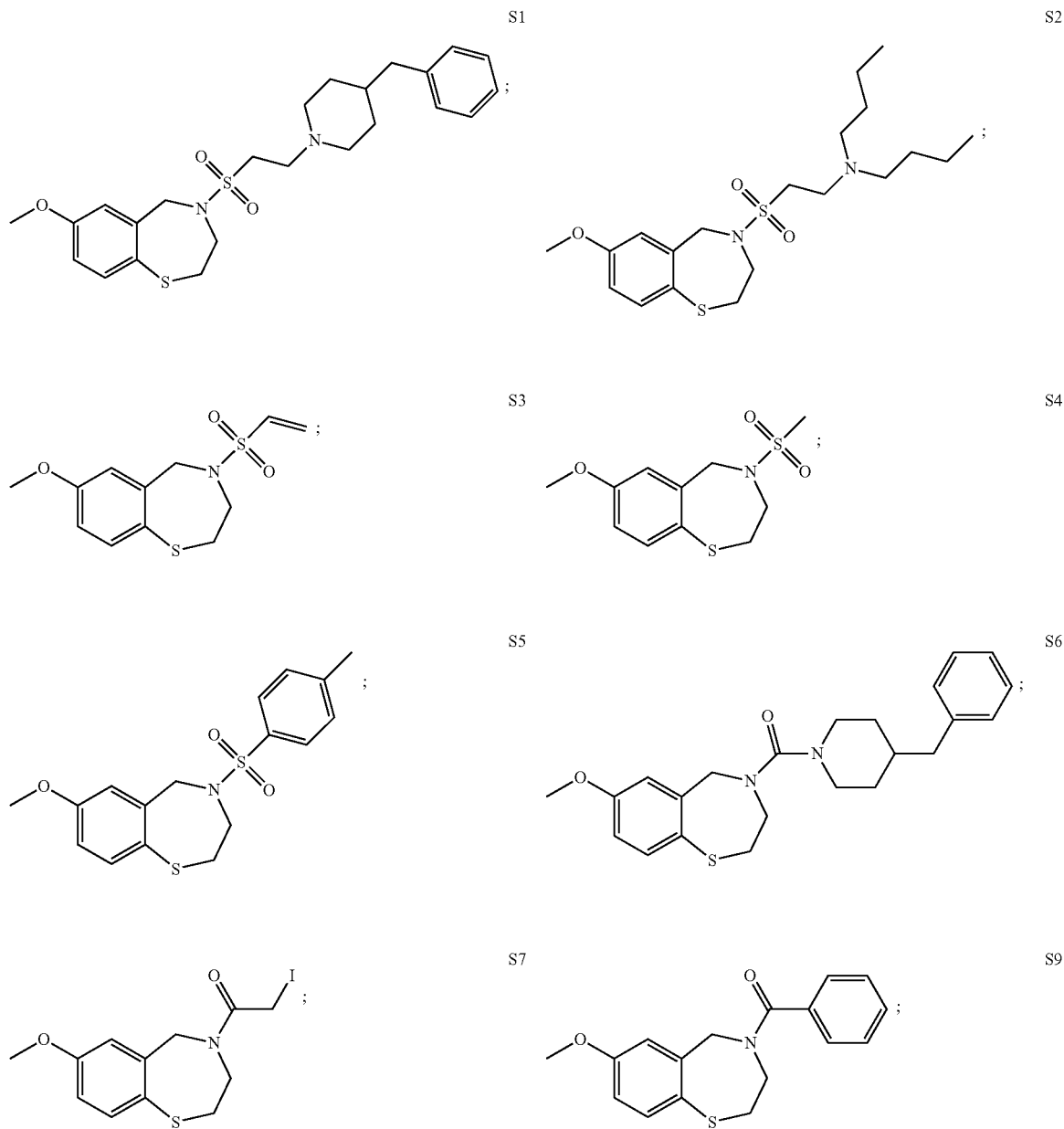

-continued
S11
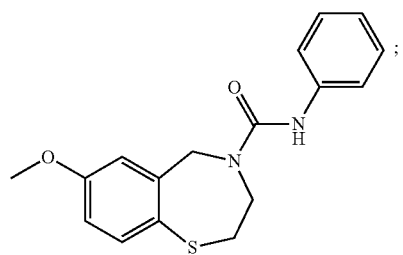
S12
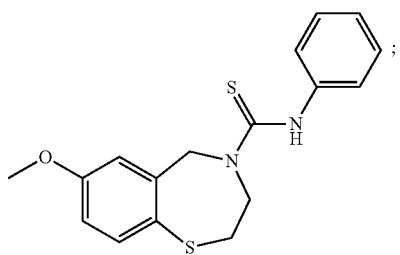
S13
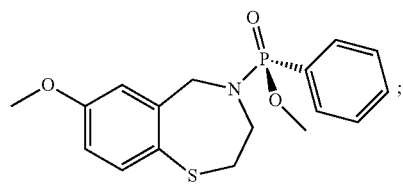
S14
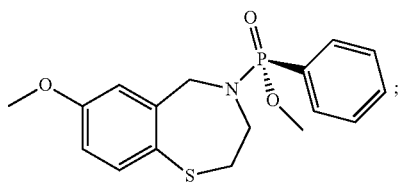
S19
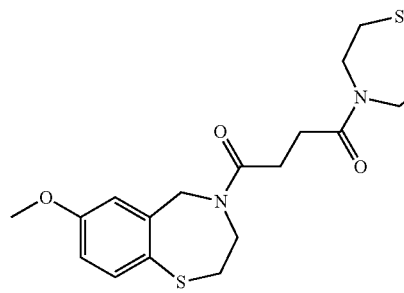
S20
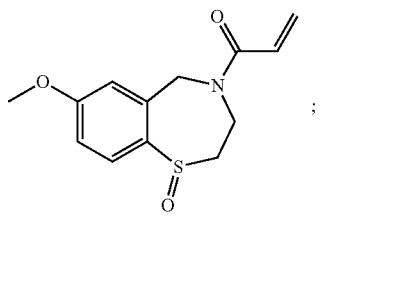
S22
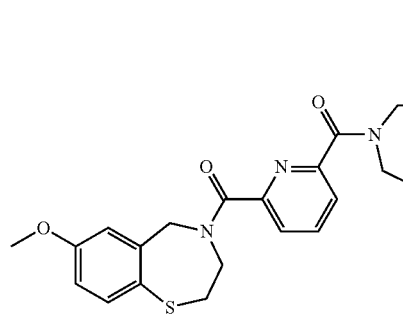
S23
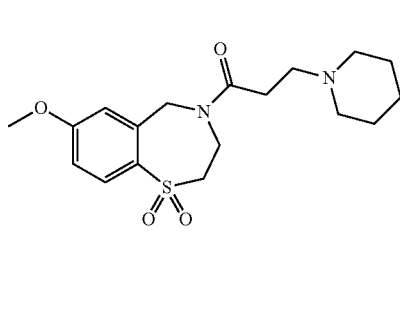
S36
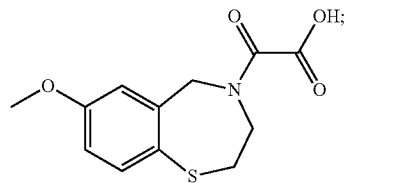
S37
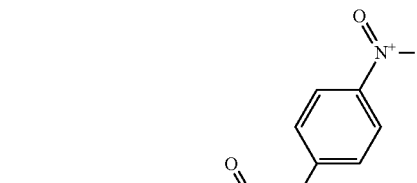

-continued
S38
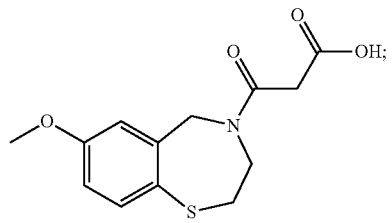
S40
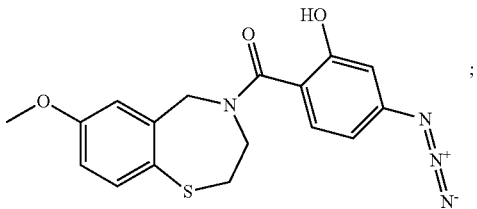
S43
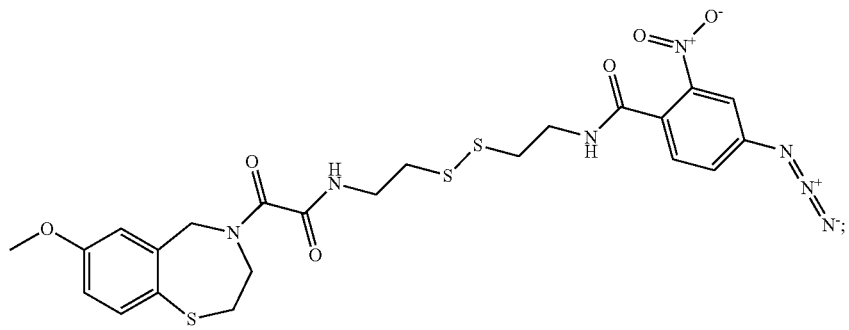
S44
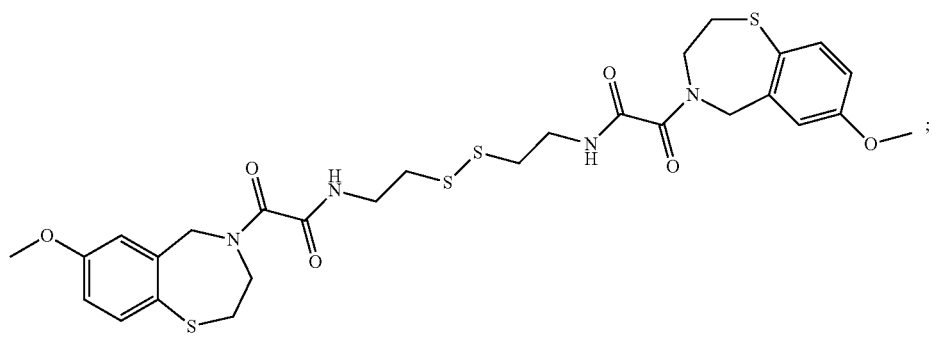
S45
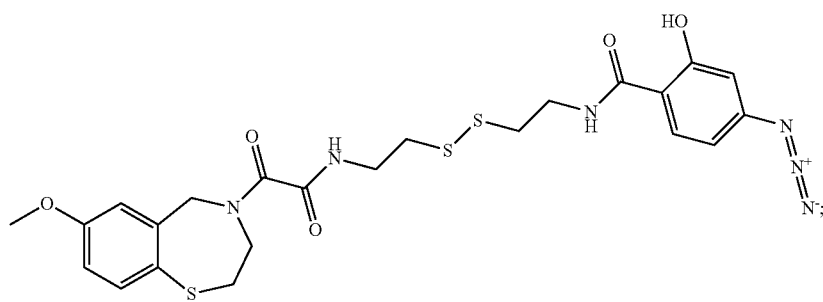
S46
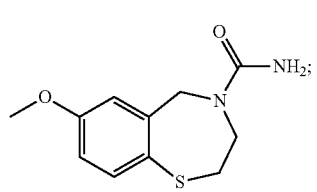
S47
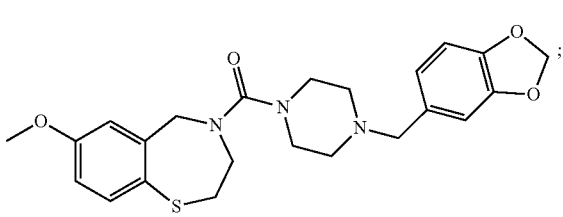
S48
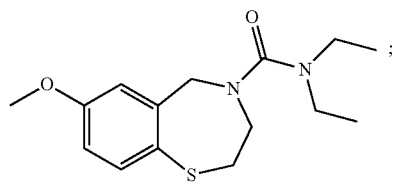
S49
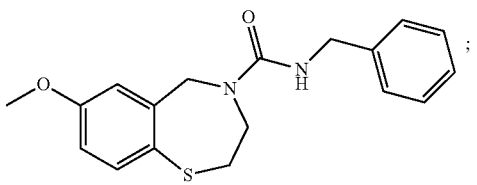

-continued
S50
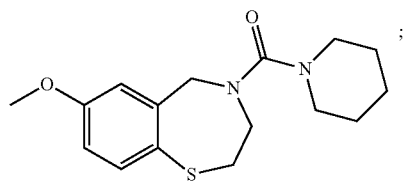
S51
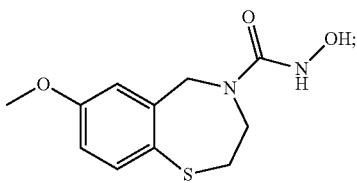
S52
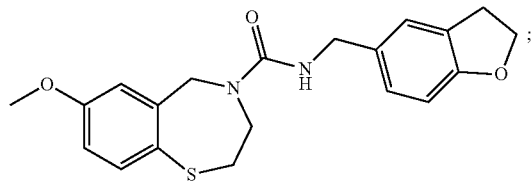
S53
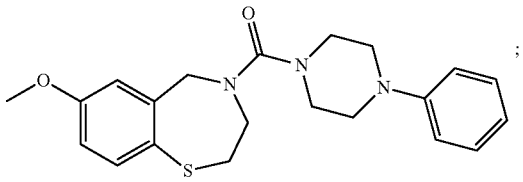
S54
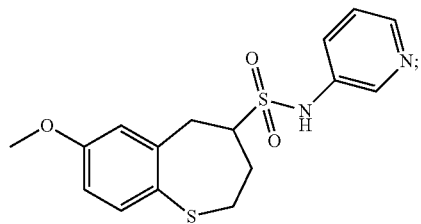
S55
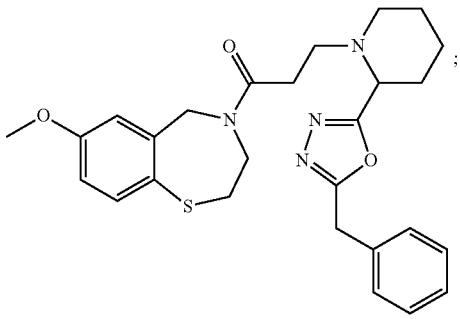
S56
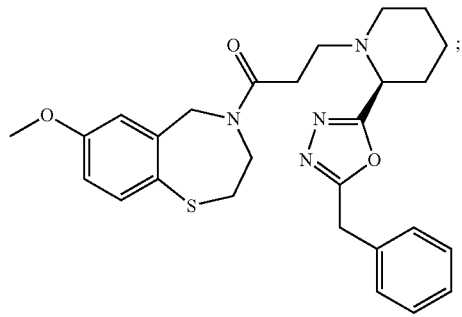
S57
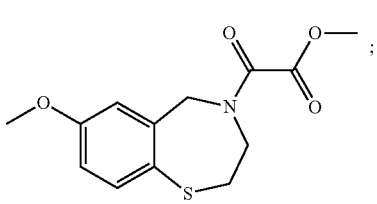
S58
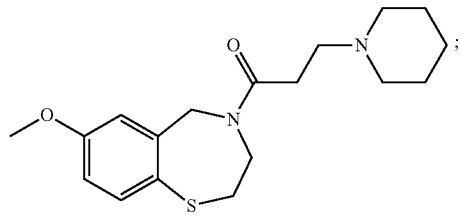
S59
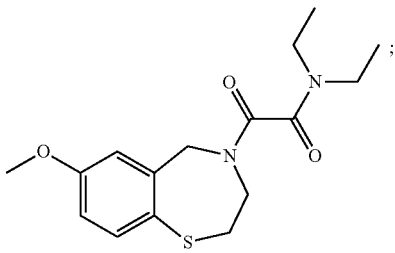
S60
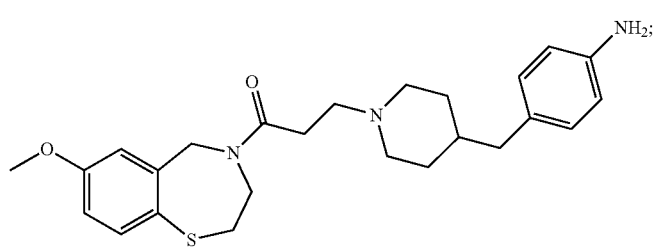

-continued
S61
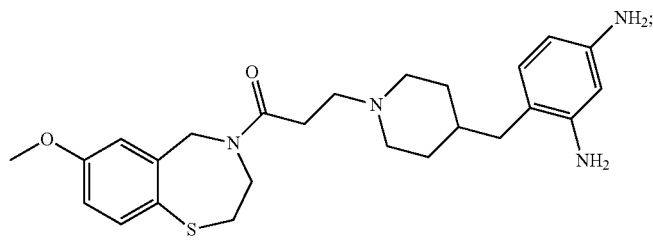
S62
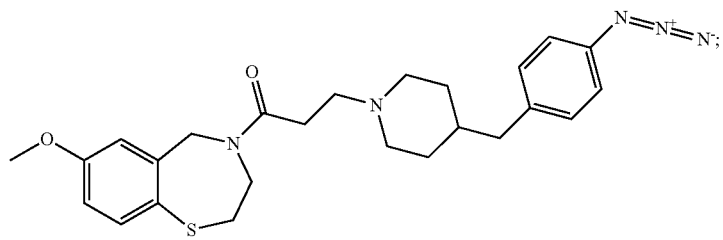
S63
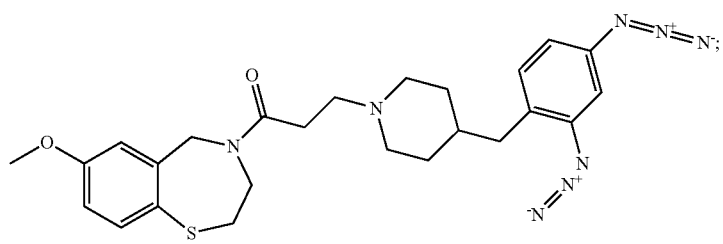
S64
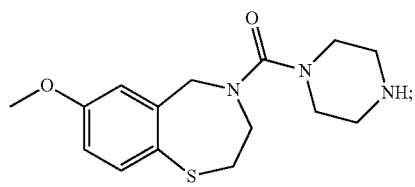
S66
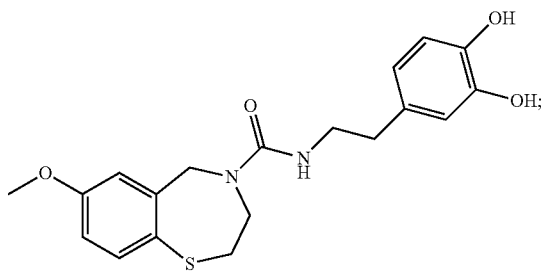
S67
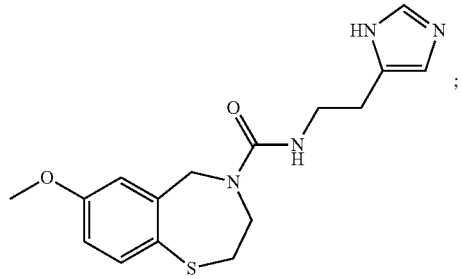
S69
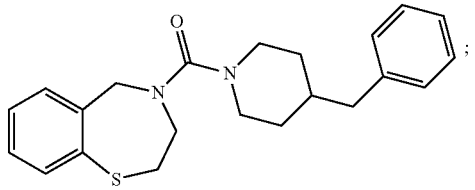
S71
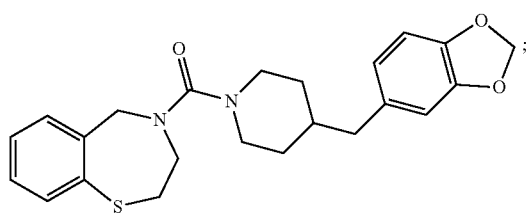
S72
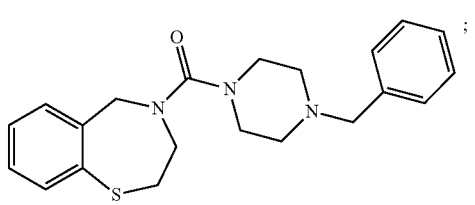

-continued
| | |
|---|---|
| S73 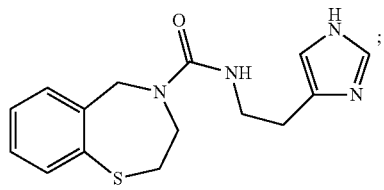 | S74 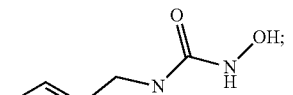 |
| S75 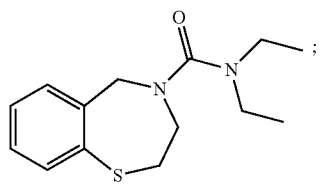 | S76 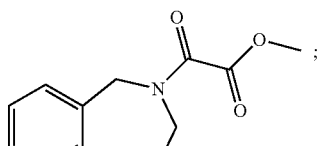 |
| S77 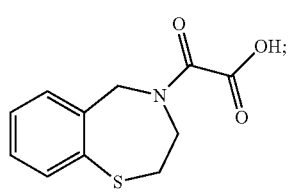 | S78 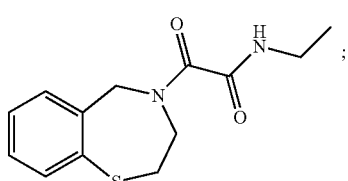 |
| S79 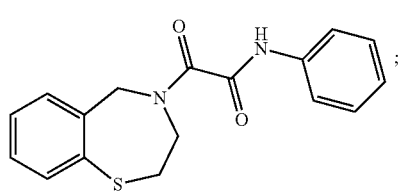 | S80 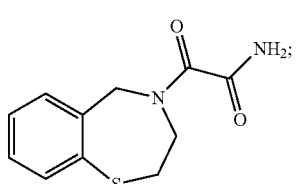 |
| S81 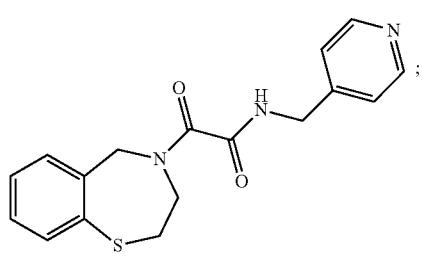 | S82 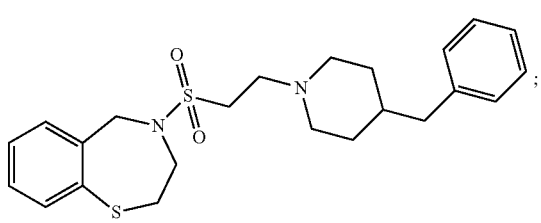 |
| S83 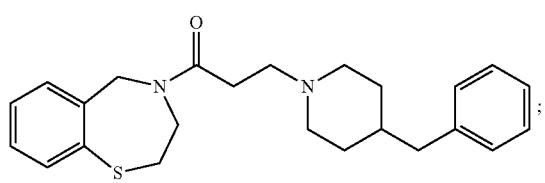 | S84 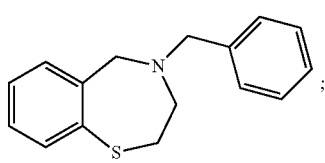 |
| S85 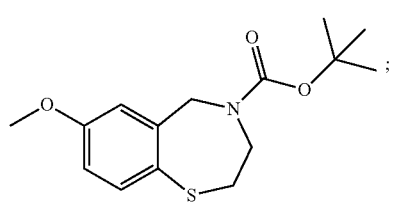 | S86 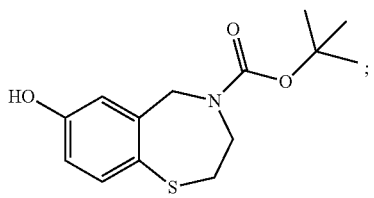 |
| S87 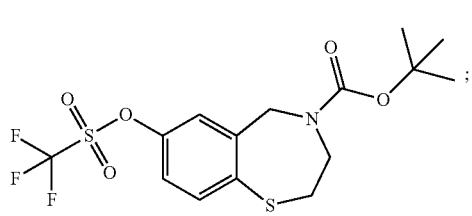 | S88 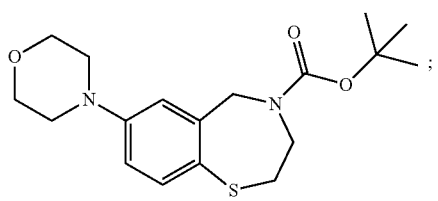 |

-continued
S89
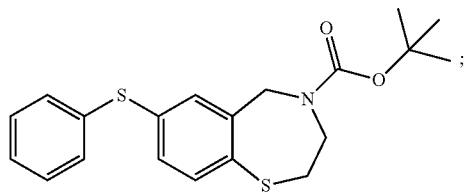
S90
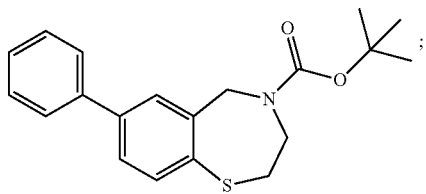
S91
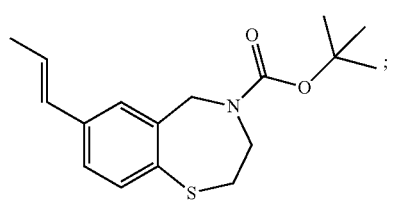
S92
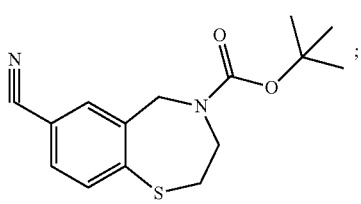
S93
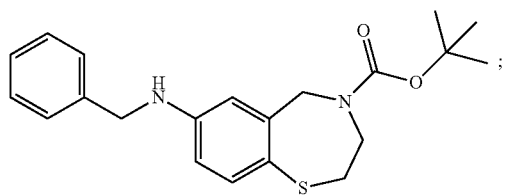
S94
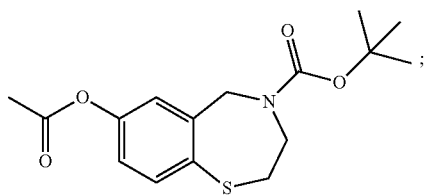
S95
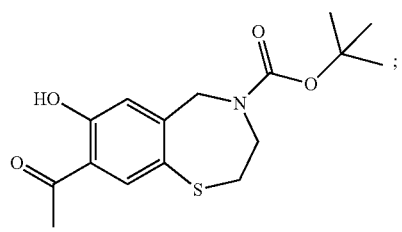
S96
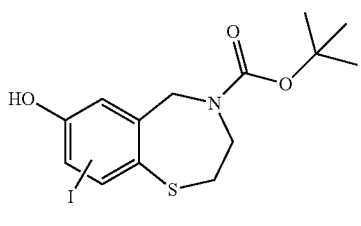
S97
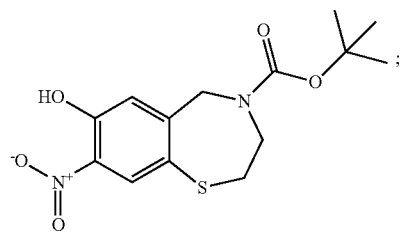
S98
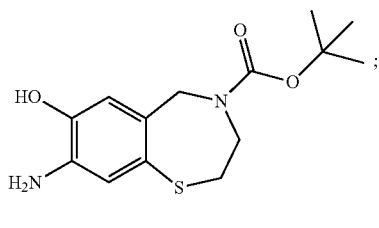
S99
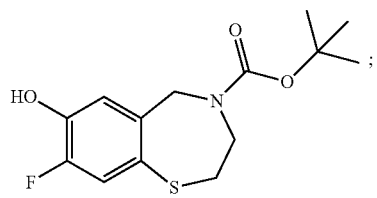
S100
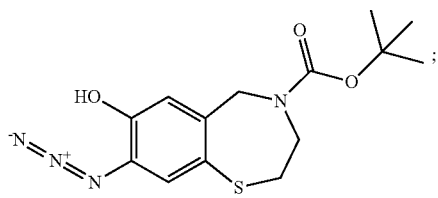
S101
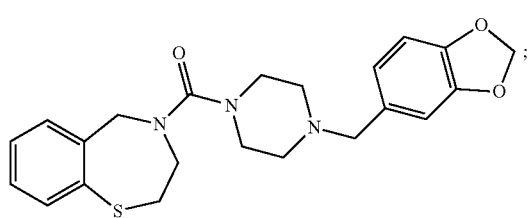
S102
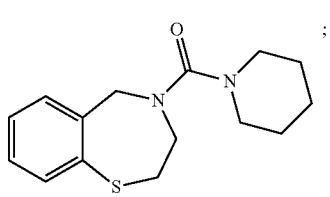

149 150
-continued
S103 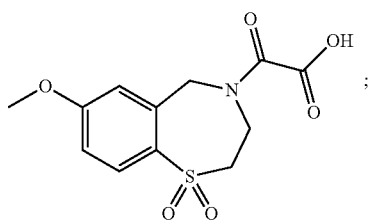 S104
S107 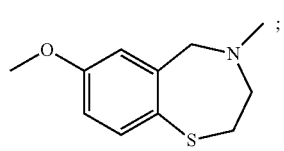 S108 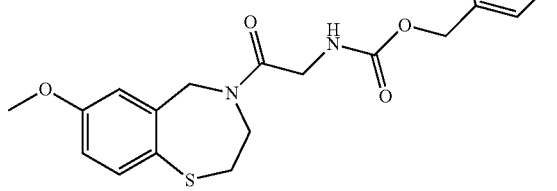
S109 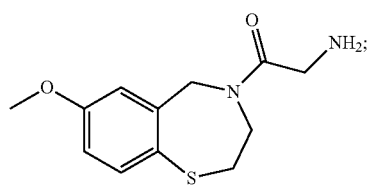 S110 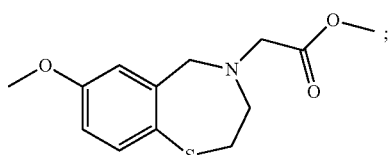
S111 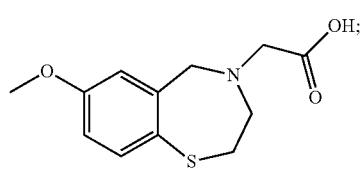 S112 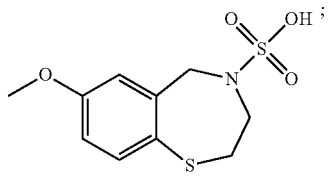
S113 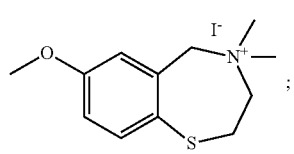 S114 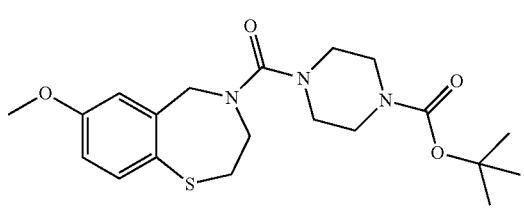
S117 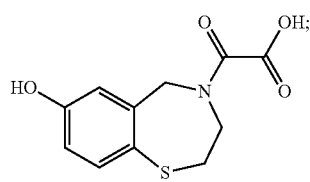 S118 
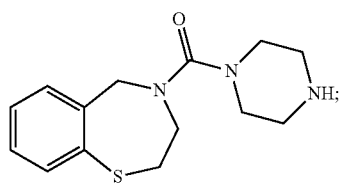
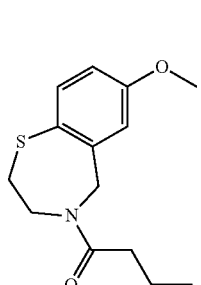
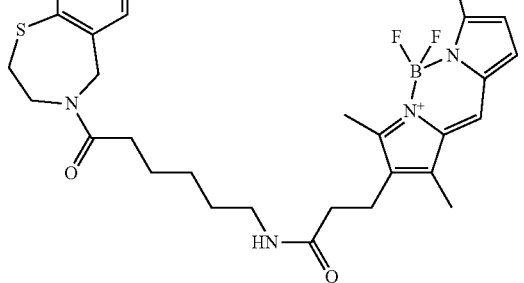

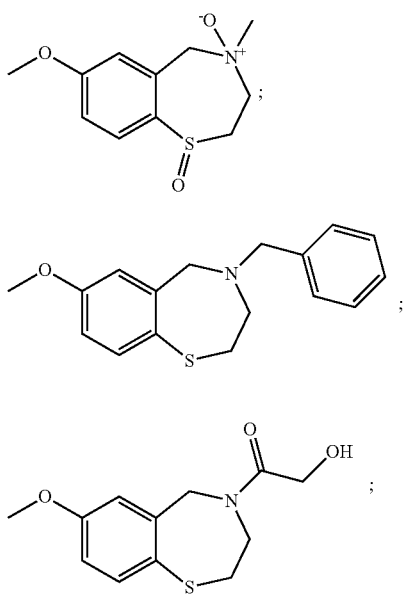

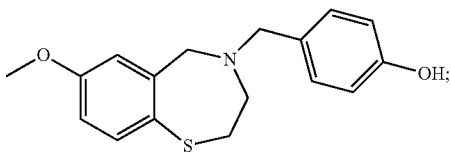

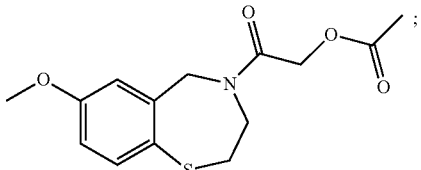

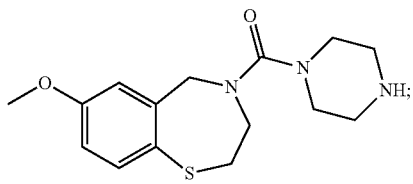

and a salt thereof.

9. The compound of claim 1, wherein the compound is S64

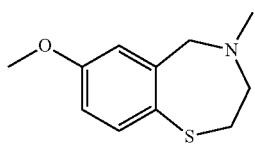

or its HCl salt.

10. The compound of claim 8, wherein the compound is S107

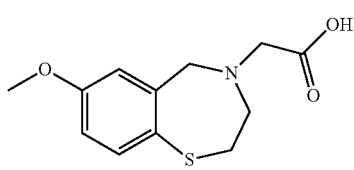 [SMILES: COc1ccc2c(c1)CN(CC(=O)O)CCS2]

or its pharmaceutically acceptable salt.

11. The compound of claim 10, wherein the salt is the HCl salt.

12. The compound of claim 1, wherein the compound is S111

13. The compound of claim 12, wherein the salt is the HCl salt.

14. A pharmaceutical composition comprising a compound according to claim 1, and a pharmaceutically acceptable carrier.

15. A pharmaceutical composition comprising one of the compounds according to claim 8, and a pharmaceutically acceptable carrier.

16. A method of treating a disorder or a disease in a subject, or reducing the risk of sudden cardiac death in a subject who is considered to be subject to such risk, comprising administering to the subject a therapeutically effective amount of a compound according to claim 1 to effectuate the treatment, wherein the disorder or disease is selected from the group consisting of cardiac disorders and diseases, skeletal muscular disorders and diseases, cognitive disorders and diseases, malignant hyperthermia, diabetes, and sudden infant death syndrome; wherein the cardiac disorders and diseases are selected from the group consisting of irregular heartbeat disorders and diseases; exercise-induced irregular heartbeat disorders and diseases; heart failure, congestive heart failure; chronic obstructive pulmonary disease; and high blood pressure; wherein the skeletal muscular disorders and diseases are selected from the group consisting of skeletal muscle fatigue, exercise-induced skeletal muscle fatigue, muscular dystrophy, bladder disorders, and incontinence; and wherein the cognitive disorders and diseases are selected from the group consisting of Alzheimer's Disease, forms of memory loss, and age-dependent memory loss.

17. The method of claim 16, wherein the compound is administered to the subject to treat cardiac disorders and diseases selected from the group consisting of irregular heartbeat disorders and diseases; exercise-induced irregular heartbeat disorders and diseases; congestive heart failure; chronic obstructive pulmonary disease; and high blood pressure.

18. The method of claim 17, wherein the irregular heartbeat disorders and diseases and exercise-induced irregular heartbeat disorders and diseases are selected from the group consisting of atrial and ventricular arrhythmia; atrial and ventricular fibrillation; atrial and ventricular tachyarrhythmia;

atrial and ventricular tachycardia; catecholaminergic polymorphic ventricular tachycardia (CPVT); and exercise-induced variants thereof.

19. The method of claim 16, wherein the compound is administered to the subject to treat skeletal muscular disorders and diseases selected from the group consisting of skeletal muscle fatigue, exercise-induced skeletal muscle fatigue, muscular dystrophy, bladder disorders, and incontinence.

20. The method of claim 16, wherein the compound is administered to the subject to treat cognitive disorders and diseases selected from the group consisting of Alzheimer's Disease, forms of memory loss, and age-dependent memory loss.

* * * * *

UNITED STATES PATENT AND TRADEMARK OFFICE
CERTIFICATE OF CORRECTION

PATENT NO.         : 8,710,045 B2
APPLICATION NO.    : 12/938098
DATED              : April 29, 2014
INVENTOR(S)        : Marks et al.

Page 1 of 1

It is certified that error appears in the above-identified patent and that said Letters Patent is hereby corrected as shown below:

In the Claims

Column 141:
Delete formula S54 and insert the following:

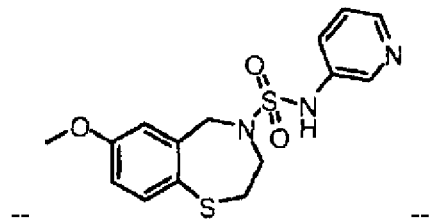

-- --

Signed and Sealed this
Twenty-third Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,710,045 B2
APPLICATION NO. : 12/938098
DATED : April 29, 2014
INVENTOR(S) : Andrew R. Marks, Donald W. Landry and Shixian Deng It is certified that error appears in the above-identified patent and that said Letters Patent is hereby corrected as shown below:

In the Specification

Column 1, Line 26:
"This invention was made with government support under grant number ARMY W911NF-05-1-0462 awarded by Defense Advanced Research Projects Agency (DARPA), Department of Defense. The government has certain rights in the invention." should read --This invention was made with government support under HL061503, and HL067849 awarded by the National Institutes of Health, and W911NF-05-1-0462 awarded by the Army Research Laboratory - Army Research Office. The government has certain rights in the invention.--

Signed and Sealed this
Seventeenth Day of October, 2023

*Katherine Kelly Vidal*

Katherine Kelly Vidal
*Director of the United States Patent and Trademark Office*